US008785915B2

(12) United States Patent  
Nakano et al.

(10) Patent No.: US 8,785,915 B2
(45) Date of Patent: Jul. 22, 2014

(54) COMPOUND FOR ORGANIC THIN FILM TRANSISTOR AND ORGANIC THIN FILM TRANSISTOR USING THE SAME

(75) Inventors: Yuki Nakano, Chiba (JP); Masatoshi Saito, Chiba (JP); Hiroaki Nakamura, Chiba (JP); Hirofumi Kondo, Chiba (JP)

(73) Assignee: Idemitsu Kosan Co., Ltd., Tokyo (JP)

( * ) Notice: Subject to any disclaimer, the term of this patent is extended or adjusted under 35 U.S.C. 154(b) by 643 days.

(21) Appl. No.: 13/060,780

(22) PCT Filed: Aug. 28, 2009

(86) PCT No.: PCT/JP2009/065076
§ 371 (c)(1),
(2), (4) Date: May 20, 2011

(87) PCT Pub. No.: WO2010/024388
PCT Pub. Date: Mar. 4, 2010

(65) Prior Publication Data
US 2011/0210319 A1 Sep. 1, 2011

(30) Foreign Application Priority Data

Aug. 29, 2008 (JP) ................................. 2008-222308

(51) Int. Cl.
| | | |
|---|---|---|
| H01L 51/52 | (2006.01) |
| H01L 51/10 | (2006.01) |
| C07C 43/20 | (2006.01) |
| C07D 495/04 | (2006.01) |
| C07C 13/66 | (2006.01) |
| C07C 25/22 | (2006.01) |
| C07F 7/08 | (2006.01) |
| C07C 255/52 | (2006.01) |
| C07D 207/06 | (2006.01) |
| C07C 211/61 | (2006.01) |
| C07C 317/14 | (2006.01) |
| C07C 22/08 | (2006.01) |
| C07C 15/20 | (2006.01) |
| C07C 321/28 | (2006.01) |
| H01L 51/05 | (2006.01) |
| H01L 51/00 | (2006.01) |

(52) U.S. Cl.
CPC ......... *H01L 51/0074* (2013.01); *H01L 51/0541* (2013.01); *H01L 51/0076* (2013.01); *C07C 2103/54* (2013.01); *C07C 25/22* (2013.01); *C07C 43/20* (2013.01); *H01L 51/0072* (2013.01); *H01L 51/0545* (2013.01); *C07F 7/0809* (2013.01); *C07C 255/52* (2013.01); *C07F 7/0812* (2013.01); *C07D 207/06* (2013.01); *C07C 211/61* (2013.01); *C07C 2103/24* (2013.01); *C07F 7/0814* (2013.01); *C07C 317/14* (2013.01); *C07D 495/04* (2013.01); *C07C 22/08* (2013.01); *C07C 15/20*

(2013.01); *C07F 7/0807* (2013.01); *H01L 51/0056* (2013.01); *C07C 321/28* (2013.01)
USPC .............. 257/40; 257/E51.006; 257/E51.018; 568/633; 549/41; 585/26

(58) Field of Classification Search
None
See application file for complete search history.

(56) References Cited

U.S. PATENT DOCUMENTS

2005/0258417 A1* 11/2005 Minakata ........................ 257/40
2009/0256145 A1 10/2009 Saito et al.

FOREIGN PATENT DOCUMENTS

| JP | 5-55568 A | 3/1993 |
| JP | 2001-94107 A | 4/2001 |
| JP | 2009218333 A | 9/2009 |
| JP | 2010034456 A | 2/2010 |
| WO | 2008/059816 A1 | 5/2008 |

OTHER PUBLICATIONS

Tian et al. "Electronic Structure of Helicenes, C2S Helicenes, and Thiaheterohelicenes" Chem. Mater. 2008, 20, 3266-3277. Date of web publication: Apr. 24, 2008.*
Office Action for related Japanese Patent Application No. 2010 526788 dated Sep. 24, 2013.
Mitsui Chemicals Inc., "Organic Transistor," Patent Abstract of Japan, Publication Date: Sep. 24, 2009; English Abstract of JP-2009 218333.

(Continued)

*Primary Examiner* — Andrew K Bohaty
(74) *Attorney, Agent, or Firm* — Millen, White, Zelano & Branigan, P.C.

(57) ABSTRACT

A compound for an organic thin film transistor represented by the following formula (1):

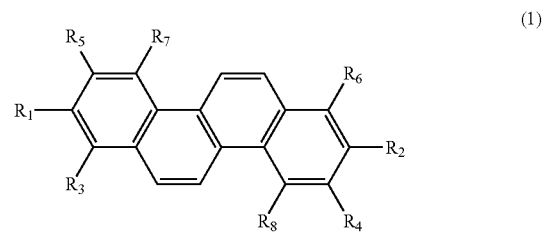

(1)

wherein at least one pair of adjacent two groups of $R_1$, $R_3$, $R_5$ and $R_7$ is bonded to each other to form a substituted or unsubstituted aromatic hydrocarbon ring having 6 to 60 carbon atoms or a substituted or unsubstituted aromatic heterocyclic ring having 3 to 60 carbon atoms, the ring being fused to the ring to which the groups are bonded; and at least one pair of adjacent two groups of $R_2$, $R_4$, $R_6$ and $R_8$ is bonded to each other to form a substituted or unsubstituted aromatic hydrocarbon ring having 6 to 60 carbon atoms or a substituted or unsubstituted aromatic heterocyclic ring having 3 to 60 carbon atoms, the ring being fused to the ring to which the groups are bonded.

12 Claims, 2 Drawing Sheets

(56) References Cited

OTHER PUBLICATIONS

Mitsui Chemicals Inc., "Organic Transistor," Patent Abstract of Japan, Publication Date: Feb. 12, 2010; English Abstract of JP-2010 034456.

Machine Translation of JP-2009 218333, Publication Date: Sep. 24, 2009.

Machine Translation of JP-2010 034456, Publication Date: Feb. 12, 2010.

Biermann, D. et al., "Diels-Alder Reactivity of Polycyclic Aromatic Hydrocarbons. 2. Phenes and Starphenes," Journal of the American Chemical Society, Apr. 23, 1980, vol. 102, No. 2, pp. 3173-3181.

English Translation of Office Action for related Chinese Patent Application No. 200980133843.6 dated Jan. 7, 2013.

Lehoullier, C. S. et al., "Twin annulation of naphthalene via a 1,5-Naphthodiyne Synthon. New Syntheses of Chrysene and Dibenzo [b,k]chrysene," J. Org. Chem., 1983, vol. 48, pp. 1682-1685.

Office Action for related Chinese Patent Application No. 200980133843.6 dated Jan. 7, 2013.

Sander, L. C. et al., "Shape discrimination in Liquid Chromatography Using Charge-transfer phases," Anal. Chem., 1991, vol. 63, pp. 2589-2597.

Okamoto, H. et al., "Air-assisted High-performance Field-effect Transistor with Thin Films of Picene," J. Am. Chem. Soc., 2008, vol. 130, pp. 10470-10471.

Chen, J. et al., "Structural Characterzation of Aromatic Fractions of Some Typical Solvent Refined Coals Using Mass Spectrometric Techniques," Fuel Science & Technology Int'l, vol. 6, No. 6, pp. 687-722; Cited in ISR, dated Nov. 2, 2009, issued in corresponding PCT/JP2009/065076.

Ma, H., et al., "Theoretical Study of Very High Spin Organic pi-Conjugated Polyradicals," J. Phys. Chem A, 2007, vol. 111, No. 38, pp. 9471-9478; Cited in ISR, dated Nov. 2, 2009, issued in corresponding PCT/JP2009/065076.

LeHoullier, C.S. et al., "Twin Annulation of Naphthalene via a 1,5-Naphthodiyne Synthon. New Synthesis of Chrysene and Dibenzo [b,k] chrysene," J. Org. Chem., 1983, vol. 48, No. 10, pp. 1682-1685; Cited in ISR, dated Nov. 2, 2009, issued in corresponding PCT/JP2009/065076.

Registry (STN) [online], Nov. 16, 1984, [retrieval date Oct. 15, 2009], CAS restry No. 222-73-1; Cited in ISR, dated Nov. 2, 2009, issued in corresponding PCT/JP2009/065076.

International Search Report, dated Nov. 2, 2009, issued in corresponding PCT/JP2009/065076.

Written Opinion, dated Nov. 2, 2009, issued in corresponding PCT/JP2009/065076.

\* cited by examiner

COMPOUND FOR ORGANIC THIN FILM TRANSISTOR AND ORGANIC THIN FILM TRANSISTOR USING THE SAME

TECHNICAL FIELD

The invention relates to a compound for an organic thin film transistor and an organic thin film transistor using it in an organic semiconductor layer.

BACKGROUND ART

A thin film transistor (TFT) has been used widely as a switching device for a display of a liquid crystal display apparatus or the like. A representative TFT comprises a gate electrode, an insulating layer and a semiconductor layer sequentially on a substrate, and a source electrode and a drain electrode formed on the semiconductor layer with a predetermined interval. The organic semiconductor layer constitutes a channel region, and a TFT performs an on-off operation by adjusting current flowing between the source electrode and the drain electrode by a voltage applied to the gate electrode.

Conventionally, a TFT was fabricated by using amorphous or polycrystalline silicon. However, a CVD apparatus which is used for fabricating a TFT using silicon is very expensive. Therefore, there was a problem that an increase in size of a display apparatus or the like using a TFT resulted in a significant increase in production cost. Further, since forming an amorphous or polycrystalline silicon into a film is conducted at a significantly high temperature, kind of materials which can be used as a substrate is limited, which makes the use of a light-weight resin substrate or the like impossible.

In order to solve such problem, a TFT which uses an organic substance instead of amorphous or polycrystalline silicon (hereinafter often abbreviated as an organic TFT) has been proposed. As the film-formation method when a TFT is fabricated by using an organic substance, a vacuum vapor deposition method, a coating method or the like are known. According to these film-formation methods, a device can be increased in size while suppressing an increase in production cost, and the process temperature necessary for film formation can be suppressed to a relatively low temperature. Therefore, an organic TFT has advantages that less restriction is imposed on the selection of materials used in a substrate. As a result, practical application of an organic TFT is expected, and intensive studies have been made thereon.

As for the organic semiconductor used in an organic TFT, as the material for a p-type FET (field effect transistor), a polymer such as a conjugated polymer and thiophene, a metal phthalocyanine compound, a fused aromatic hydrocarbon such as pentacene or the like are used singly or in the form of a mixture with other compounds. As the material for an n-type FET, 1,4,5,8-naphthalene tetracarboxylic dianhydride (NTCDA), 11,11,12,12-tetracyanonaphtho-2,6-quinodimethane (TCNNQD), 1,4,5,8-naphthalene tetracarboxylic diimide (NTCDI) or fluorinated phthalocyanine are known, for example.

On the other hand, as the device which similarly utilizes electric conductance, an organic electroluminescence (EL) device is known. In an organic EL device, generally, electric charge is flown forcibly by applying a strong electric field of $10^5$ V/cm or more in the film thickness direction of an ultrathin film of 100 nm or less. In the case of an organic TFT, electric charge is required to be flown at a high speed in an electric field of $10^5$ V/cm or less for a distance of several μm or more. Therefore, an organic substance itself used in an organic TFT is required to be further conductive. However, the above-mentioned compounds used in conventional organic TFTs have a small field effect mobility and a slow response speed, and hence, the high-speed responsiveness thereof as a transistor is not satisfactory. In addition, it has a small on-off ratio.

The "on-off ratio" as referred to herein means a value obtained by dividing current flowing between a source and a drain when applying a gate voltage (ON state) by current flowing between a source and a drain when applying no gate voltage (OFF state). The ON current normally means a current value (saturation current) at the time when current flowing between a source and a drain is saturated when the gate voltage is increased.

In order to obtain a TFT having a high electric field effect mobility and a high response speed, a compound having an arylethynylene group is disclosed in Patent Document 1, for example. In this document, in the fabrication of a device, a high mobility is obtained by forming a monolayer on the substrate, and conducting vapor deposition while heating the substrate. However, this method had a problem that the processing is complicated.

As the representative example of the material for this organic TFT, pentacene can be given. In Patent Documents 1 and 2, an organic TFT in which pentacene is used in an organic semiconductor layer is fabricated. Since pentacene had a defect that its stability in the atmosphere is low, although the mobility of a device was significantly high immediately after the device fabrication, it fell with the passage of time. Organic TFTs using picene which is a fused aromatic ring are reported in Non-Patent Document 1. This document states that, since picene has a lower ionization potential than pentacene, it has superior oxidation stability in the air. However, when picene was used, although a device showed a mobility of 1.0 cm²/Vs, the use of picene had such defects that a high driving voltage of −67 V, is required to be applied.

RELATED ART DOCUMENTS

Patent Documents

Patent Document 1: JP-A-H05-55568
Patent Document 2: JP-A-2001-94107

Non-Patent Documents

Non-Patent Document 1: H. Okamoto et al., Journal of the American Chemical Society, Vol. 130, page 10470, 2008

SUMMARY OF THE INVENTION

The invention is aimed at providing an organic thin film transistor which has a high mobility and a low driving voltage or can be applied to a coating method, and also aimed at providing a compound for an organic thin film transistor used for producing the organic thin film transistor.

As a result of intensive studies in order to achieve the above-mentioned object, the inventors have found that an organic compound represented by the following formula (1) in which the π conjunction system is enlarged by allowing an aromatic ring to be further fused to the picene structure is preferable as a material of an organic thin film transistor having a high mobility and a low driving voltage. The invention has been made on this finding.

That is, the invention is a compound for an organic thin film transistor represented by the following formula (1).

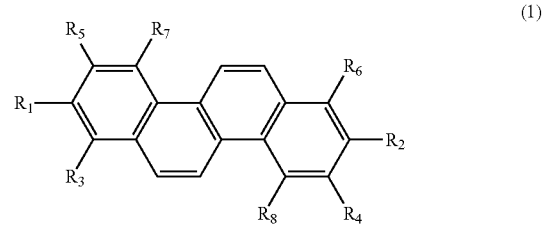

wherein at least one pair of adjacent two groups of $R_1$, $R_3$, $R_5$ and $R_7$ is bonded to each other to form a substituted or unsubstituted aromatic hydrocarbon ring having 6 to 60 carbon atoms or a substituted or unsubstituted aromatic heterocyclic ring having 3 to 60 carbon atoms, the ring being fused to the ring to which the groups are bonded; at least one pair of adjacent two groups of $R_2$, $R_4$, $R_6$ and $R_8$ is bonded to each other to form a substituted or unsubstituted aromatic hydrocarbon ring having 6 to 60 carbon atoms or a substituted or unsubstituted aromatic heterocyclic ring having 3 to 60 carbon atoms, the ring being fused to the ring to which the groups are bonded; and, the groups of $R_1$ to $R_8$ that do not form the aromatic hydrocarbon ring or the aromatic heterocyclic ring are independently a hydrogen atom, a halogen atom, an alkyl group having 1 to 30 carbon atoms, a haloalkyl group having 1 to 30 carbon atoms, an alkoxyl group having 1 to 30 carbon atoms, a haloalkoxyl group having 1 to 30 carbon atoms, an alkylthio group having 1 to 30 carbon atoms, a haloalkylthio group having 1 to 30 carbon atoms, an alkylamino group having 1 to 30 carbon atoms, a dialkylamino group having 2 to 60 carbon atoms (the alkyl groups may be combined with each other to form a ring structure containing the nitrogen atom), an alkylsulfonyl group having 1 to 30 carbon atoms, a haloalkylsulfonyl group having 1 to 30 carbon atoms, an aromatic hydrocarbon group having 6 to 60 carbon atoms, an aromatic heterocyclic group having 3 to 60 carbon atoms, an alkylsilyl group having 3 to 20 carbon atoms, an alkylsilylacetylene group having 5 to 60 carbon atoms or a cyano group. Each of these groups may have a substituent.

The invention is a compound for an organic thin film transistor which can be used in an organic phase of an organic thin film transistor.

Further, an organic thin film transistor can be produced by using the above-mentioned compound for an organic thin film transistor.

The invention also provides an organic thin film transistor comprising: a substrate and three terminals of a gate electrode, a source electrode and a drain electrode, an insulator layer and an organic semiconductor layer being provided on the substrate, source-drain current being controlled by applying a voltage to the gate electrode, the organic semiconductor layer comprising the organic compound represented by the formula (1).

The invention provides a benzopicene compound represented by the following formula (2).

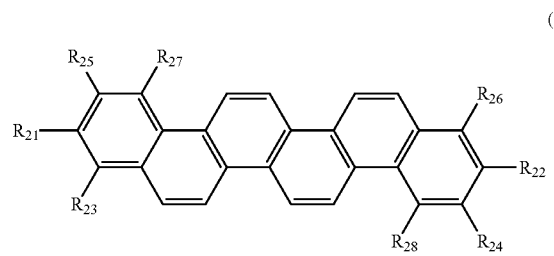

(2)

wherein $R_{21}$ to $R_{28}$ are independently a hydrogen atom, a halogen atom, an alkyl group having 2 to 30 carbon atoms, a haloalkyl group having 1 to 30 carbon atoms, an alkoxyl group having 1 to 30 carbon atoms, a haloalkoxyl group having 1 to 30 carbon atoms, an alkylthio group having 1 to 30 carbon atoms, a haloalkylthio group having 1 to 30 carbon atoms, an alkylamino group having 1 to 30 carbon atoms, a dialkylamino group having 2 to 60 carbon atoms (the alkyl groups may be combined with each other to form a ring structure containing the nitrogen atom), an alkylsulfonyl group having 1 to 30 carbon atoms, a haloalkylsulfonyl group having 1 to 30 carbon atoms, an aromatic hydrocarbon group having 6 to 60 carbon atoms, an aromatic heterocyclic group having 3 to 60 carbon atoms, an alkylsilyl group having 3 to 20 carbon atoms, an alkylsilylacetylene group having 5 to 60 carbon atoms or a cyano group. Each of these groups may have a substituent. However, the compound in which all of $R_{21}$ to $R_{28}$ are a hydrogen atom is excluded.

The invention provides a dibenzochrysene compound represented by the following formula (3):

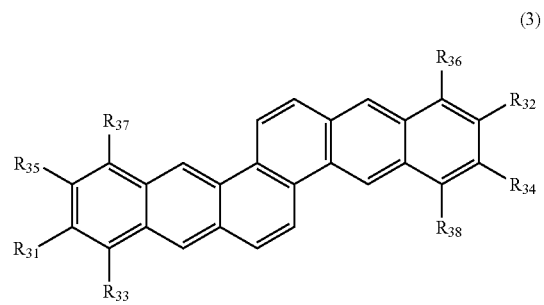

(3)

In the formula (3), $R_{31}$ to $R_{38}$ are independently a hydrogen atom, a halogen atom, an alkyl group having 2 to 30 carbon atoms, a haloalkyl group having 1 to 30 carbon atoms, an alkoxyl group having 1 to 30 carbon atoms, a haloalkoxyl group having 1 to 30 carbon atoms, an alkylthio group having 1 to 30 carbon atoms, a haloalkylthio group having 1 to 30 carbon atoms, an alkylamino group having 1 to 30 carbon atoms, a dialkylamino group having 2 to 60 carbon atoms (the alkyl groups may be combined with each other to form a ring structure containing the nitrogen atom), an alkylsulfonyl group having 1 to 30 carbon atoms, a haloalkylsulfonyl group having 1 to 30 carbon atoms, an aromatic hydrocarbon group having 6 to 60 carbon atoms, an aromatic heterocyclic group having 3 to 60 carbon atoms, an alkylsilyl group having 3 to 20 carbon atoms, an alkylsilylacetylene group having 5 to 60 carbon atoms or a cyano group. Each of these groups may have a substituent. However, the compound in which all of $R_{31}$ to $R_{38}$ are a hydrogen atom is excluded.

The invention provides an organic compound represented by the following formula (4):

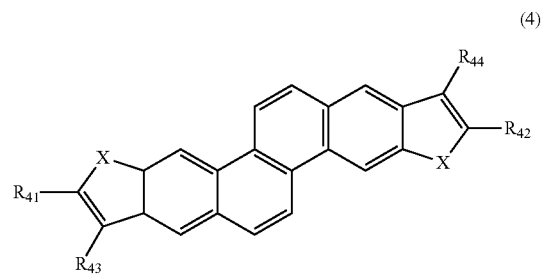

(4)

In the formula (4), X is independently O, S or N—Z.

$R_{41}$ to $R_{44}$ and Z are independently a hydrogen atom, a halogen atom, an alkyl group having 2 to 30 carbon atoms, a haloalkyl group having 1 to 30 carbon atoms, an alkoxyl group having 1 to 30 carbon atoms, a haloalkoxyl group having 1 to 30 carbon atoms, an alkylthio group having 1 to 30 carbon atoms, a haloalkylthio group having 1 to 30 carbon atoms, an alkylamino group having 1 to 30 carbon atoms, a dialkylamino group having 2 to 60 carbon atoms (the alkyl groups may be combined with each other to form a ring structure containing the nitrogen atom), an alkylsulfonyl group having 1 to 30 carbon atoms, a haloalkylsulfonyl group having 1 to 30 carbon atoms, an aromatic hydrocarbon group having 6 to 60 carbon atoms, an aromatic heterocyclic group having 3 to 60 carbon atoms, an alkylsilyl group having 3 to 20 carbon atoms, an alkylsilylacetylene group having 5 to 60 carbon atoms or a cyano group. Each of these groups may have a substituent. However, the compound in which all of $R_{41}$ to $R_{44}$ are a hydrogen atom is excluded.

$R_{41}$ and $R_{43}$, or $R_{42}$ and $R_{44}$ may be bonded to each other to form a substituted or unsubstituted aromatic hydrocarbon ring having 6 to 60 carbon atoms or a substituted or unsubstituted aromatic heterocyclic ring having 3 to 60 carbon atoms which is fused to the ring to which the groups are bonded.

The invention also provides an organic compound represented by the following formula (5):

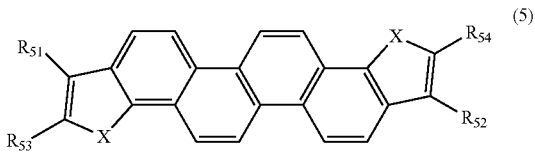

(5)

In the formula (5), X is independently O, S or N—Z.

$R_{51}$ to $R_{54}$ and Z are independently a hydrogen atom, a halogen atom, an alkyl group having 2 to 30 carbon atoms, a haloalkyl group having 1 to 30 carbon atoms, an alkoxyl group having 1 to 30 carbon atoms, a haloalkoxyl group having 1 to 30 carbon atoms, an alkylthio group having 1 to 30 carbon atoms, a haloalkylthio group having 1 to 30 carbon atoms, an alkylamino group having 1 to 30 carbon atoms, a dialkylamino group having 2 to 60 carbon atoms (the alkyl groups may be combined with each other to form a ring structure containing the nitrogen atom), an alkylsulfonyl group having 1 to 30 carbon atoms, a haloalkylsulfonyl group having 1 to 30 carbon atoms, an aromatic hydrocarbon group having 6 to 60 carbon atoms, an aromatic heterocyclic group having 3 to 60 carbon atoms, an alkylsilyl group having 3 to 20 carbon atoms, an alkylsilylacetylene group having 5 to 60 carbon atoms or a cyano group. Each of these groups may have a substituent. However, the compound in which all of $R_{51}$ to $R_{54}$ are a hydrogen atom is excluded.

$R_{51}$ and $R_{53}$, or $R_{52}$ and $R_{55}$ may be bonded to each other to form a substituted or unsubstituted aromatic hydrocarbon ring having 6 to 60 carbon atoms or a substituted or unsubstituted aromatic heterocyclic ring having 3 to 60 carbon atoms which is fused to the ring to which the groups are bonded.

The invention provides an organic compound represented by the following formula (6):

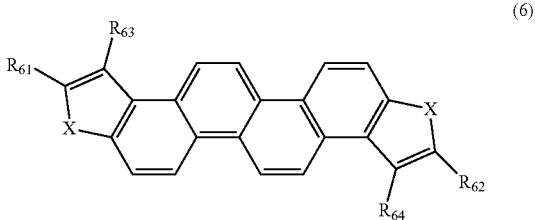

(6)

In the formula (6), X is independently O, S or N—Z.

$R_{61}$ to $R_{64}$ and Z are independently a hydrogen atom, a halogen atom, an alkyl group having 1 to 30 carbon atoms, a haloalkyl group having 1 to 30 carbon atoms, an alkoxyl group having 1 to 30 carbon atoms, a haloalkoxyl group having 1 to 30 carbon atoms, an alkylthio group having 1 to 30 carbon atoms, a haloalkylthio group having 1 to 30 carbon atoms, an alkylamino group having 1 to 30 carbon atoms, a dialkylamino group having 2 to 60 carbon atoms (the alkyl groups may be combined with each other to form a ring structure containing the nitrogen atom), an alkylsulfonyl group having 1 to 30 carbon atoms, a haloalkylsulfonyl group having 1 to 30 carbon atoms, an aromatic hydrocarbon group having 6 to 60 carbon atoms, an aromatic heterocyclic group having 3 to 60 carbon atoms, an alkylsilyl group having 3 to 20 carbon atoms, an alkylsilylacetylene group having 5 to 60 carbon atoms or a cyano group. Each of these groups may have a substituent.

$R_{61}$ and $R_{63}$, or $R_{62}$ and $R_{64}$ may be bonded to each other to form a substituted or unsubstituted aromatic hydrocarbon ring having 6 to 60 carbon atoms or a substituted or unsubstituted aromatic heterocyclic ring having 3 to 60 carbon atoms which is fused to the ring to which the groups are bonded.

The invention provides an organic compound represented by the following formula (7):

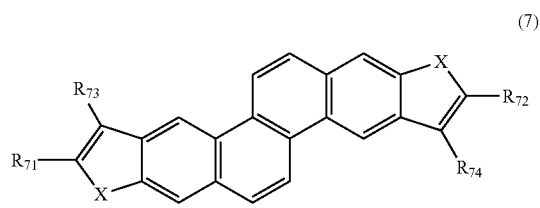

(7)

In the formula (7), X is independently O, S or N—Z.

$R_{71}$ to $R_{74}$ and Z are independently a hydrogen atom, a halogen atom, an alkyl group having 1 to 30 carbon atoms, a haloalkyl group having 1 to 30 carbon atoms, an alkoxyl group having 1 to 30 carbon atoms, a haloalkoxyl group having 1 to 30 carbon atoms, an alkylthio group having 1 to 30 carbon atoms, a haloalkylthio group having 1 to 30 carbon atoms, an alkylamino group having 1 to 30 carbon atoms, a dialkylamino group having 2 to 60 carbon atoms (the alkyl groups may be combined with each other to form a ring structure containing the nitrogen atom), an alkylsulfonyl group having 1 to 30 carbon atoms, a haloalkylsulfonyl group having 1 to 30 carbon atoms, an aromatic hydrocarbon group having 6 to 60 carbon atoms, an aromatic heterocyclic group having 3 to 60 carbon atoms, an alkylsilyl group having 3 to 20 carbon atoms, an alkylsilylacetylene group having 5 to 60 carbon atoms or a cyano group. Each of these groups may have a substituent.

$R_{71}$ and $R_{73}$, or $R_{72}$ and $R_{74}$ may be bonded to each other to form a substituted or unsubstituted aromatic hydrocarbon ring having 6 to 60 carbon atoms or a substituted or unsubstituted aromatic heterocyclic ring having 3 to 60 carbon atoms which is fused to the ring to which the groups are bonded.

The invention provides an organic thin film transistor having a high mobility and a low driving voltage or can be applied to a coating process, and a compound for an organic thin film transistor used for producing the organic thin film transistor.

MODE FOR CARRYING OUT THE INVENTION

Figure 1:
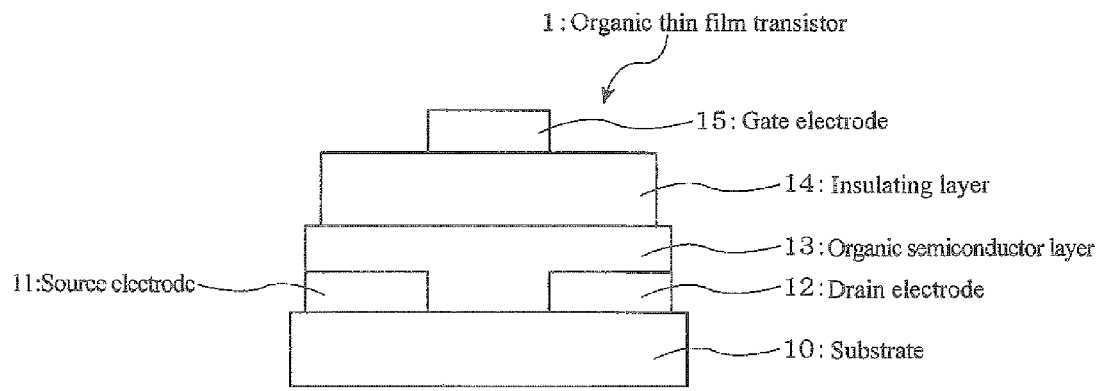
FIG. 1 is a view showing one example of the device structure of the organic thin film transistor of the invention.

The compound for an organic thin film transistor according to the invention is represented by the following formula (1):

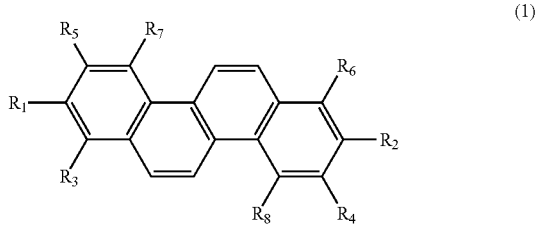

(1)

in the formula (1), at least one pair of adjacent two groups of $R_1$, $R_3$, $R_5$ and $R_7$ is bonded to each other to form a substituted or unsubstituted aromatic hydrocarbon ring having 6 to 60 carbon atoms or a substituted or unsubstituted aromatic heterocyclic ring having 3 to 60 carbon atoms, the ring being fused to the ring to which the groups are bonded; at least one pair of adjacent two groups of $R_2$, $R_4$, $R_6$ and $R_8$ is bonded to each other to form a substituted or unsubstituted aromatic hydrocarbon ring having 6 to 60 carbon atoms or a substituted or unsubstituted aromatic heterocyclic ring having 3 to 60 carbon atoms, the ring being fused to the ring to which the groups are bonded; and, the groups of $R_1$ to $R_8$ that do not form the aromatic hydrocarbon ring or the aromatic heterocyclic ring are independently a hydrogen atom, a halogen atom, an alkyl group having 1 to 30 carbon atoms, a haloalkyl group having 1 to 30 carbon atoms, an alkoxyl group having 1 to 30 carbon atoms, a haloalkoxyl group having 1 to 30 carbon atoms, an alkylthio group having 1 to 30 carbon atoms, a haloalkylthio group having 1 to 30 carbon atoms, an alkylamino group having 1 to 30 carbon atoms, a dialkylamino group having 2 to 60 carbon atoms (the alkyl groups may be combined with each other to form a ring structure containing the nitrogen atom), an alkylsulfonyl group having 1 to 30 carbon atoms, a haloalkylsulfonyl group having 1 to 30 carbon atoms, an aromatic hydrocarbon group having 6 to 60 carbon atoms, an aromatic heterocyclic group having 3 to 60 carbon atoms, an alkylsilyl group having 3 to 20 carbon atoms, an alkylsilylacetylene group having 5 to 60 carbon atoms or a cyano group. Each of these groups may have a substituent.

When two adjacent groups are bonded to form a substituted or unsubstituted aromatic hydrocarbon ring having 6 to 60 carbon atoms which is fused to a ring to which these groups are bonded, the 6 to 60 carbons include two carbons of the ring to which these groups are bonded. When two adjacent groups are bonded to form a substituted or unsubstituted aromatic heterocyclic ring having 3 to 60 carbon atoms which is fused to the ring to which these groups are bonded, the 3 to 60 carbons include two carbons of the ring to which these groups are bonded.

In the formula (1), it is preferred that 6 to 12 aromatic rings be fused, more preferably 6 aromatic rings be fused.

In the formula (1), it is particularly preferred that the compound (1) have a skeleton in which 6 to 12 aromatic rings are fused in a curved manner. It is further preferred that the compound (1) have a structure in which 6 aromatic rings are fused in a curved manner. The curved skeleten means a skeleten in which benzene rings are fused in a curved manner unlike a fused aromatic ring like pentacene in which benzene rings are fused linearly.

In the formula (1), it is preferred that at least one pair of adjacent two groups of $R_1$, $R_3$, $R_5$ and $R_7$ be bonded to each other to form a substituted or unsubstituted aromatic hydrocarbon ring having 6 to 60 carbon atoms which is fused to the ring to which these groups are bonded, and that at least one pair of adjacent two groups of $R_2$, $R_4$, $R_6$ and $R_8$ be bonded to each other to form a substituted or unsubstituted aromatic hydrocarbon ring having 6 to 60 carbon atoms which is fused to the ring to which these groups are bonded.

In the formula (1), it is preferred that at least one pair of adjacent two groups of $R_1$, $R_3$, $R_5$ and $R_7$ be bonded to each other to form a substituted or unsubstituted aromatic heterocyclic ring having 3 to 60 carbon atoms which is fused to the ring to which these groups are bonded, and that at least one pair of adjacent two groups of $R_2$, $R_4$, $R_6$ and $R_8$ be bonded to each other to form a substituted or unsubstituted aromatic heterocyclic ring having 3 to 60 carbon atoms which is fused to the ring to which these groups are bonded.

Further, it is preferred that the compound represented by the formula (1) have a symmetrical structure with respect to the black point as shown below, since the molecules tend to align in an orderly manner in such a structure.

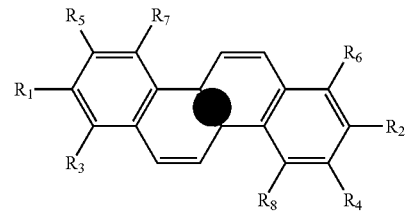

The fused ring compound of the invention is represented by the following formulas (2) to (7). These compounds are included in the compound represented by the formula (1).

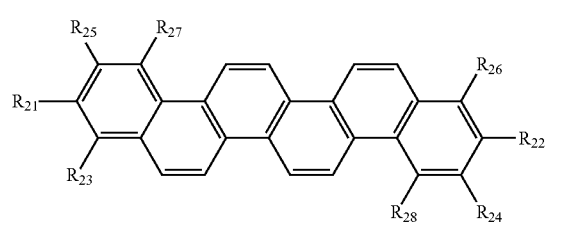

(2)

In the formula (2), $R_{21}$ to $R_{28}$ are independently a hydrogen atom, a halogen atom, an alkyl group having 2 to 30 carbon atoms, a haloalkyl group having 1 to 30 carbon atoms, an alkoxyl group having 1 to 30 carbon atoms, a haloalkoxyl group having 1 to 30 carbon atoms, an alkylthio group having 1 to 30 carbon atoms, a haloalkylthio group having 1 to 30 carbon atoms, an alkylamino group having 1 to 30 carbon atoms, a dialkylamino group having 2 to 60 carbon atoms (the alkyl groups may be combined with each other to form a ring structure containing the nitrogen atom), an alkylsulfonyl group having 1 to 30 carbon atoms, a haloalkylsulfonyl group having 1 to 30 carbon atoms, an aromatic hydrocarbon group having 6 to 60 carbon atoms, an aromatic heterocyclic group having 3 to 60 carbon atoms, an alkylsilyl group having 3 to 20 carbon atoms, an alkylsilylacetylene group having 5 to 60 carbon atoms or a cyano group. Each of these groups may have a substituent. However, the compound in which all of $R_{21}$ to $R_{28}$ are a hydrogen atom is excluded.

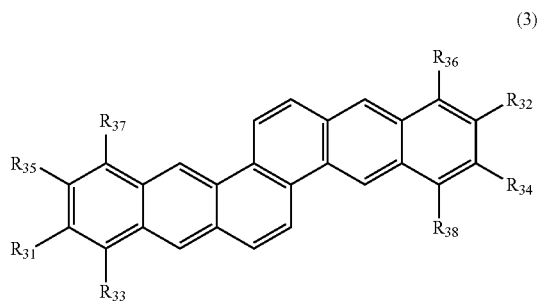

(3)

In the formula (3), $R_{31}$ to $R_{38}$ are independently a hydrogen atom, a halogen atom, an alkyl group having 2 to 30 carbon atoms, a haloalkyl group having 1 to 30 carbon atoms, an alkoxyl group having 1 to 30 carbon atoms, a haloalkoxyl group having 1 to 30 carbon atoms, an alkylthio group having 1 to 30 carbon atoms, a haloalkylthio group having 1 to 30 carbon atoms, an alkylamino group having 1 to 30 carbon atoms, a dialkylamino group having 2 to 60 carbon atoms (the alkyl groups may be combined with each other to form a ring structure containing the nitrogen atom), an alkylsulfonyl group having 1 to 30 carbon atoms, a haloalkylsulfonyl group having 1 to 30 carbon atoms, an aromatic hydrocarbon group having 6 to 60 carbon atoms, an aromatic heterocyclic group having 3 to 60 carbon atoms, an alkylsilyl group having 3 to 20 carbon atoms, an alkylsilylacetylene group having 5 to 60 carbon atoms or a cyano group. Each of these groups may have a substituent. However, the compound in which all of $R_{31}$ to $R_{38}$ are a hydrogen atom is excluded.

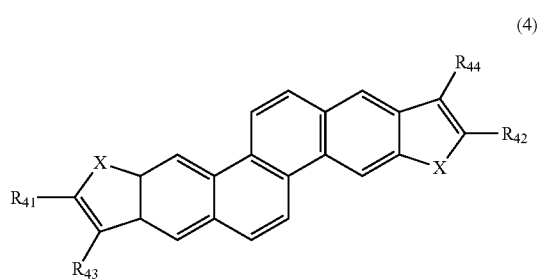

(4)

In the formula (4), X is independently O, S or N—Z. $R_{41}$ to $R_{44}$ and Z are independently a hydrogen atom, a halogen atom, an alkyl group having 2 to 30 carbon atoms, a haloalkyl group having 1 to 30 carbon atoms, an alkoxyl group having 1 to 30 carbon atoms, a haloalkoxyl group having 1 to 30 carbon atoms, an alkylthio group having 1 to 30 carbon atoms, a haloalkylthio group having 1 to 30 carbon atoms, an alkylamino group having 1 to 30 carbon atoms, a dialkylamino group having 2 to 60 carbon atoms (the alkyl groups may be combined with each other to form a ring structure containing the nitrogen atom), an alkylsulfonyl group having 1 to 30 carbon atoms, a haloalkylsulfonyl group having 1 to 30 carbon atoms, an aromatic hydrocarbon group having 6 to 60 carbon atoms, an aromatic heterocyclic group having 3 to 60 carbon atoms, an alkylsilyl group having 3 to 20 carbon atoms, an alkylsilylacetylene group having 5 to 60 carbon atoms or a cyano group. Each of these groups may have a substituent. However, the compound in which all of $R_{41}$ to $R_{44}$ are a hydrogen atom is excluded.

$R_{41}$ and $R_{43}$, or $R_{42}$ and $R_{44}$ may be bonded to each other to form a substituted or unsubstituted aromatic hydrocarbon ring having 6 to 60 carbon atoms or a substituted or unsubstituted aromatic heterocyclic ring having 3 to 60 carbon atoms which is fused to the ring to which the groups are bonded.

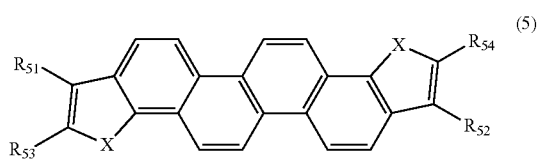

(5)

In the formula (5), X is independently O, S or N—Z. $R_{51}$ to $R_{54}$ and Z are independently a hydrogen atom, a halogen atom, an alkyl group having 2 to 30 carbon atoms, a haloalkyl group having 1 to 30 carbon atoms, an alkoxyl group having 1 to 30 carbon atoms, a haloalkoxyl group having 1 to 30 carbon atoms, an alkylthio group having 1 to 30 carbon atoms, a haloalkylthio group having 1 to 30 carbon atoms, an alkylamino group having 1 to 30 carbon atoms, a dialkylamino group having 2 to 60 carbon atoms (the alkyl groups may be combined with each other to form a ring structure containing the nitrogen atom), an alkylsulfonyl group having 1 to 30 carbon atoms, a haloalkylsulfonyl group having 1 to 30 carbon atoms, an aromatic hydrocarbon group having 6 to 60 carbon atoms, an aromatic heterocyclic group having 3 to 60 carbon atoms, an alkylsilyl group having 3 to 20 carbon atoms, an alkylsilylacetylene group having 5 to 60 carbon atoms or a cyano group. Each of these groups may have a substituent. However, the compound in which all of $R_{51}$ to $R_{54}$ are a hydrogen atom is excluded.

$R_{51}$ and $R_{53}$, or $R_{52}$ and $R_{55}$ may be bonded to each other to form a substituted or unsubstituted aromatic hydrocarbon ring having 6 to 60 carbon atoms or a substituted or unsubstituted aromatic heterocyclic ring having 3 to 60 carbon atoms which is fused to the ring to which the groups are bonded.

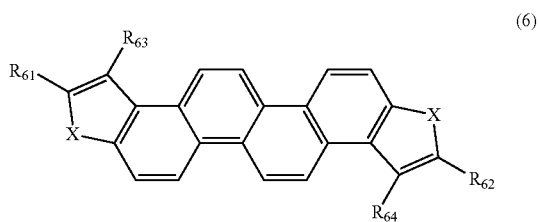

(6)

In the formula (6), X is independently O, S or N—Z.

$R_{61}$ to $R_{64}$ and Z are independently a hydrogen atom, a halogen atom, an alkyl group having 1 to 30 carbon atoms, a haloalkyl group having 1 to 30 carbon atoms, an alkoxyl group having 1 to 30 carbon atoms, a haloalkoxyl group having 1 to 30 carbon atoms, an alkylthio group having 1 to 30 carbon atoms, a haloalkylthio group having 1 to 30 carbon atoms, an alkylamino group having 1 to 30 carbon atoms, a dialkylamino group having 2 to 60 carbon atoms (the alkyl groups may be combined with each other to form a ring structure containing the nitrogen atom), an alkylsulfonyl group having 1 to 30 carbon atoms, a haloalkylsulfonyl group having 1 to 30 carbon atoms, an aromatic hydrocarbon group having 6 to 60 carbon atoms, an aromatic heterocyclic group having 3 to 60 carbon atoms, an alkylsilyl group having 3 to 20 carbon atoms, an alkylsilylacetylene group having 5 to 60 carbon atoms or a cyano group. Each of these groups may have a substituent.

$R_{61}$ and $R_{63}$, or $R_{62}$ and $R_{64}$ may be bonded to each other to form a substituted or unsubstituted aromatic hydrocarbon ring having 6 to 60 carbon atoms or a substituted or unsubstituted aromatic heterocyclic ring having 3 to 60 carbon atoms which is fused to the ring to which the groups are bonded.

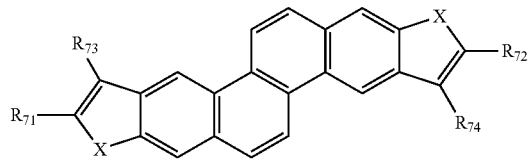

(7)

In the formula (7), X is independently O, S or N—Z.

$R_{71}$ to $R_{74}$ and Z are independently a hydrogen atom, a halogen atom, an alkyl group having 1 to 30 carbon atoms, a haloalkyl group having 1 to 30 carbon atoms, an alkoxyl group having 1 to 30 carbon atoms, a haloalkoxyl group having 1 to 30 carbon atoms, an alkylthio group having 1 to 30 carbon atoms, a haloalkylthio group having 1 to 30 carbon atoms, an alkylamino group having 1 to 30 carbon atoms, a dialkylamino group having 2 to 60 carbon atoms (the alkyl groups may be combined with each other to form a ring structure containing the nitrogen atom), an alkylsulfonyl group having 1 to 30 carbon atoms, a haloalkylsulfonyl group having 1 to 30 carbon atoms, an aromatic hydrocarbon group having 6 to 60 carbon atoms, an aromatic heterocyclic group having 3 to 60 carbon atoms, an alkylsilyl group having 3 to 20 carbon atoms, an alkylsilylacetylene group having 5 to 60 carbon atoms or a cyano group. Each of these groups may have a substituent.

$R_{71}$ and $R_{73}$, or $R_{72}$ and $R_{74}$ may be bonded to each other to form a substituted or unsubstituted aromatic hydrocarbon ring having 6 to 60 carbon atoms or a substituted or unsubstituted aromatic heterocyclic ring having 3 to 60 carbon atoms which is fused to the ring to which the groups are bonded.

$R_1$ to $R_6$, $R_{21}$ to $R_{28}$, $R_{31}$ to $R_{38}$, $R_{41}$ to $R_{44}$, $R_{51}$ to $R_{54}$, $R_{61}$ to $R_{64}$, $R_{71}$ to $R_{74}$ and Z which do not form a ring in the formulas (1) to (7) are preferably a hydrogen atom, a halogen atom, an alkyl group having 1 to 30 carbon atoms, a haloalkyl group having 1 to 30 carbon atoms, an alkoxyl group having 1 to 30 carbon atoms, a haloalkoxyl group having 1 to 30 carbon atoms, an alkylsilylacetylene group having 5 to 60 carbon atoms or a cyano group. Each of these groups may have a substituent.

Specific examples of each group represented by $R_1$ to $R_8$, $R_{21}$ to $R_{28}$, $R_{31}$ to $R_{38}$, $R_{41}$ to $R_{44}$, $R_{51}$ to $R_{54}$, $R_{61}$ to $R_{64}$, $R_{71}$ to $R_{74}$ and Z in the formulas (1) to (7) will be explained below.

Specific examples of the above-mentioned aromatic hydrocarbon ring include benzene, naphthalene, anthracene, phenanthrene, chrysene, phenanthrene and tetracene.

Examples of the above-mentioned aromatic heterocyclic group include pyridine, pyrazine, quinoline, naphthyridine, quinoxaline, phenazine, diazaanthracene, pyridoquinoline, pyrimidoquinazoline, pyrazinoquinoxaline, phenanthroline, carbazole, thiophene, benzothiophene, dibenzothiophene, benzodithiophene, [1]benzothieno[3,2-b]benzothiophene, thienothiophene, dithienothiophene, furan, benzofuran, dibenzofuran, benzodifuran, thiazole, benzothiazole, dithiaindacene, dithiaindenoindene, dibenzoselenophene, diselena-indacene, diselena-indenoindene and dibenzosilole.

Specific examples of the halogen atom include fluorine, chlorine, bromine and iodine atoms.

Examples of the alkyl group include methyl, ethyl, propyl, isopropyl, n-butyl, s-butyl, isobutyl, t-butyl, n-pentyl, n-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl, n-icosane, n-henicosane, n-docosane, n-tricosane, n-tetracosane, n-pentacosane, n-hexacosane, n-heptacosane, n-octacosane, n-nonacosane and n-triacontane.

Examples of the haloalkyl group include chloromethyl, 1-chloroethyl, 2-chloroethyl, 2-chloroisobutyl, 1,2-dichloroethyl, 1,3-dichloroisopropyl, 2,3-dichloro-t-butyl, 1,2,3-trichloropropyl, bromomethyl, 1-bromoethyl, 2-bromoethyl, 2-bromoisobutyl, 1,2-dibromoethyl, 1,3-dibromoisopropyl, 2,3-dibromo-t-butyl, 1,2,3-tribromopropyl, iodomethyl, 1-iodoethyl, 2-iodoethyl, 2-iodoisobutyl, 1,2-diiodoethyl, 1,3-diiodoisopropyl, 2,3-diiodo-t-butyl, 1,2,3-triiodopropyl, fluoromethyl, 1-fluoromethyl, 2-fluoromethyl, 2-fluoroisobutyl, 1,2-difluoroethyl, difluoromethyl, trifluoromethyl, pentafluoroethyl, perfluoroisopropyl, perfluorobutyl and perfluorocyclohexyl.

The alkoxyl group is a group shown by —$OY^1$. As examples of $Y^1$, the same examples as those given for the alkyl group can be given. The haloalkoxyl group is a group shown by —$OY^2$. As examples of $Y^2$, the same examples as those given for the haloalkyl group can be given.

The alkylthio group is a group shown by —$SY^1$. As examples of $Y^1$, the same examples as those given for the alkyl group can be given. The haloalkylthio group is a group shown by —$SY^2$. As examples of $Y^2$, the same examples as those given for the haloalkyl group can be given.

The alkylamino group is a group shown by —$NHY^1$. The dialkylamino group is a group shown by —$NY^1Y^3$. As examples of $Y^1$ and $Y^3$, the same examples as those given for the alkyl group can be given. The alkyl groups of the dialkylamino group may be combined with each other to form a ring structure containing the nitrogen atom. As the ring structure, pyrrolidine, piperidine or the like can be given, for example.

The alkylsulfonyl group is a group shown by —$SO_2Y^1$. As examples of $Y^1$, the same examples as those given for the alkyl group can be given. The haloalkylsulfonyl group is a group shown by —$SO_2Y^2$. As examples of $Y^2$, the same examples as those given for the haloalkyl group can be given.

As examples of the aromatic hydrocarbon group and the aromatic heterocyclic group mentioned above, the same examples as those given for the aromatic hydrocarbon group and the aromatic heterocyclic group can be given.

The alkylsilyl group is a group shown by —$SiY^1Y^3Y^4$, and as examples of $Y^1$, $Y^3$ and $Y^4$, the same examples as those given for the alkyl group can be given.

The alkylsilylacetylene group is a group obtained by connecting the above-mentioned alkylsilyl group with an ethylenylene group, and the examples thereof include a trimethylsilylacetylene group, a triethylacetylene group and a triisopropylsilylacetylene group.

The organic compound having a specific structure to be used in the organic thin film transistor of the invention is basically of bipolar type, showing both the p-type (hole conductance) and n-type (electron conductance) properties. Therefore, it can be driven both as a p-type device and an n-type device in combination with a source electrode and a drain electrode, which will be mentioned later.

By allowing the organic compound used in the organic thin film transistor of the invention to have an adequate substituent, it is possible to increase the solubility of the compound in an organic solvent. As a result, a device can be fabricated by a coating process.

By using an electron-accepting group as $R_1$ to $R_8$, $R_{21}$ to $R_{28}$, $R_{31}$ to $R_{38}$, $R_{41}$ to $R_{44}$, $R_{51}$ to $R_{54}$, $R_{61}$ to $R_{64}$, $R_{71}$ to $R_{74}$ and Z in the formulas (1) and (7), it is possible to lower the level of the lowest unoccupied molecular orbital (LUMO), thereby allowing the compound to function as an n-type semiconductor. Preferable electron-accepting groups include a hydrogen atom, a halogen atom, a cyano group, a haloalkyl group having 1 to 30 carbon atoms, a haloalkoxyl group having 1 to 30 carbon atoms and a haloalkylsulfonyl group having 1 to 30 carbon atoms. By using an electron-donating group as $R_1$ to $R_8$, $R_{21}$ to $R_{28}$, $R_{31}$ to $R_{38}$, $R_{41}$ to $R_{44}$, $R_{51}$ to $R_{54}$, $R_{61}$ to $R_{64}$, $R_{71}$ to $R_{74}$ and Z, it is possible to increase the level of the highest occupied molecular orbital (HOMO), thereby allowing the compound to function as a p-type semiconductor. Preferable examples of the electron-donating group include a hydrogen atom, an alkyl group having 1 to 30 carbon atoms, an alkoxyl group having 1 to 30 carbon atoms, an alkylamino group having 1 to 30 carbon atoms and a dialkylamino group having 2 to 60 carbon atoms (the amino groups may be combined with each other to form a ring structure containing the nitrogen atom).

As the substituent which may further substitute each group represented by $R_1$ to $R_8$, $R_{21}$ to $R_{28}$, $R_{31}$ to $R_{38}$, $R_{41}$ to $R_{44}$, $R_{51}$ to $R_{54}$, $R_{61}$ to $R_{64}$, $R_{71}$ to $R_{74}$ and Z in the formulas (1) to (7), an aromatic hydrocarbon group, an aromatic heterocyclic group, an alkyl group, an alkoxyl group, a haloalkyl group, an alkylthio group, an alkylsulfonyl group, an aryloxy group, an arylthio group, an alkoxycarbonyl group, an amino group, a halogen atom, a cyano group, a nitro group, a hydroxyl group and a carboxyl group can be given.

Specific examples of the compound for an organic thin film transistor of the invention will be given below. The invention is, however, not limited thereto.

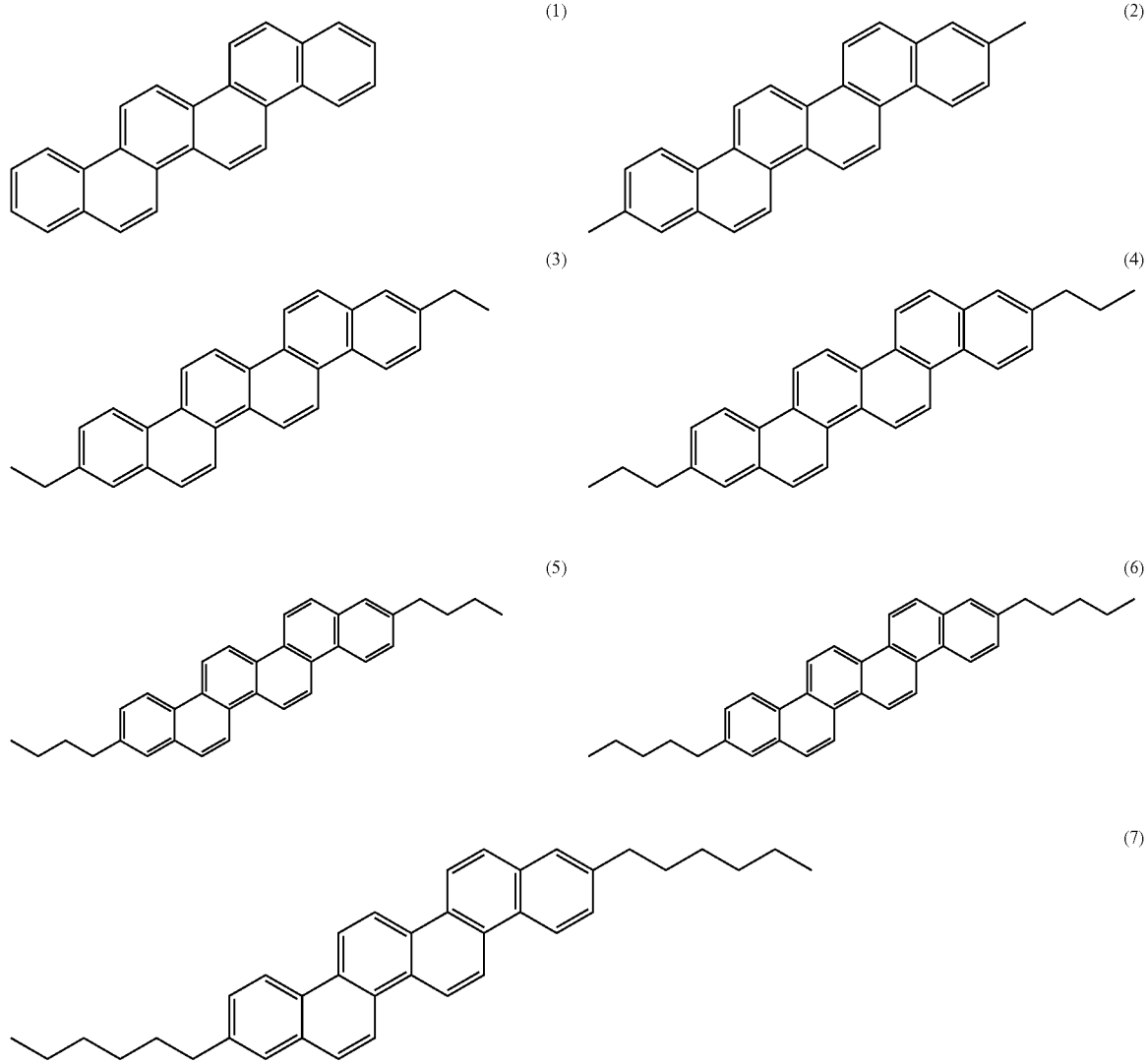

-continued
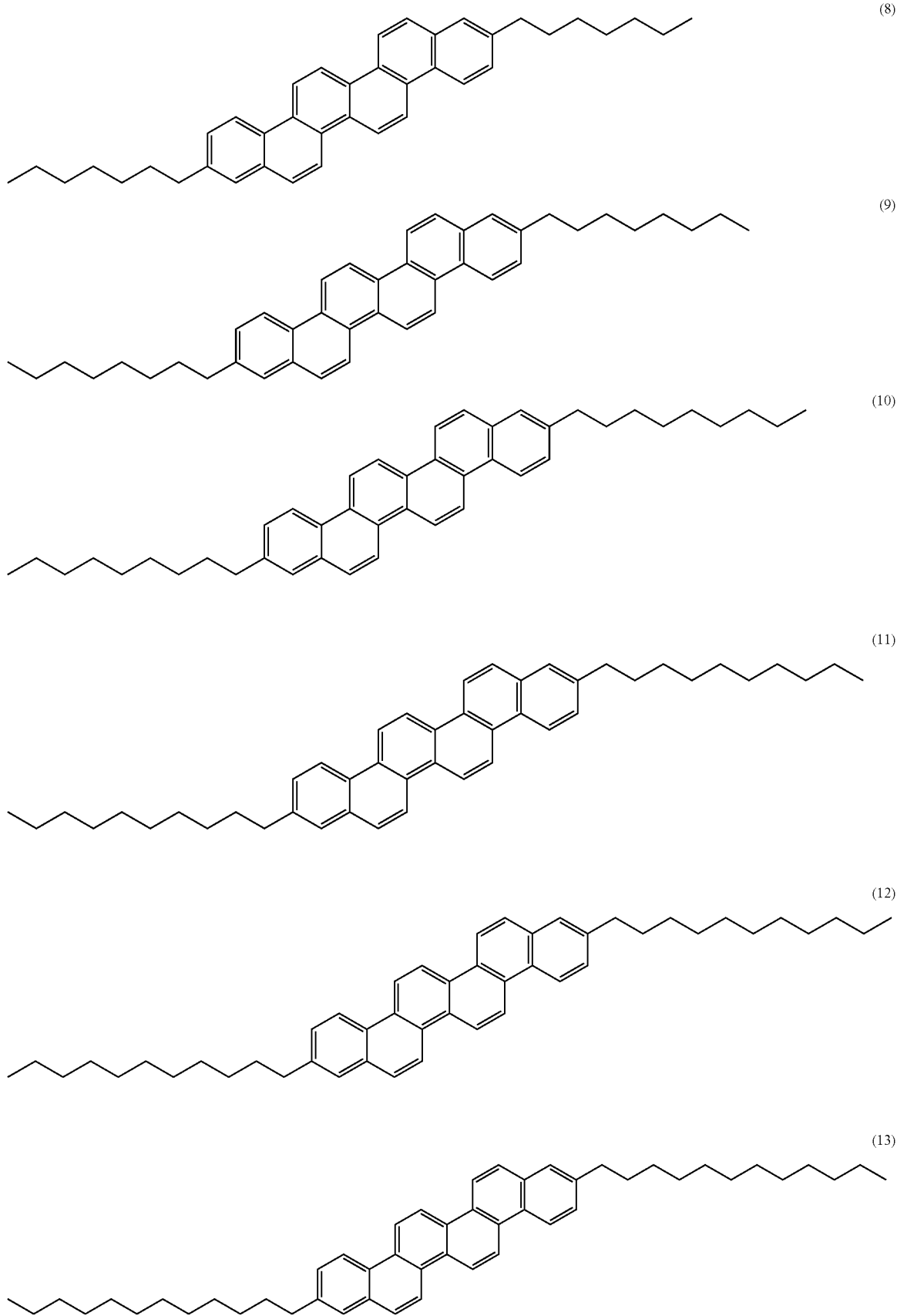

-continued
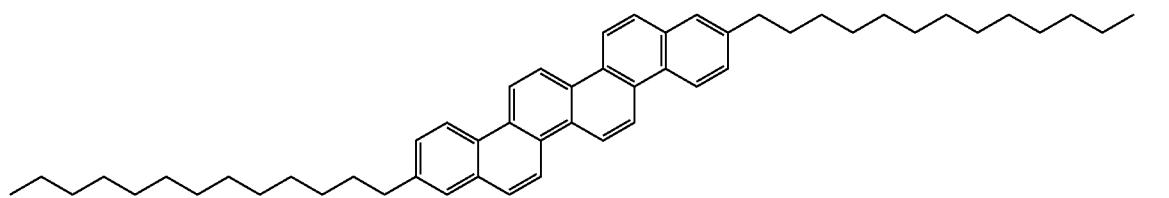
(14)
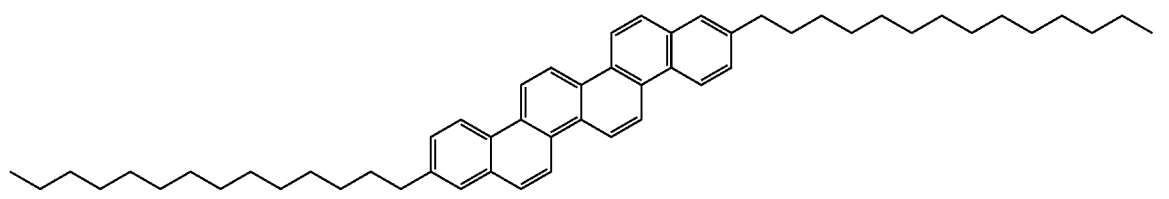
(15)
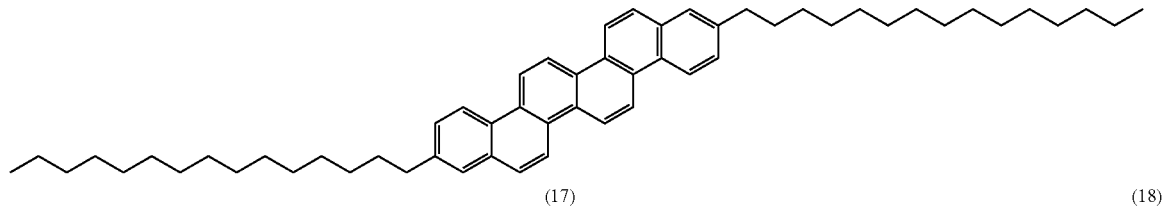
(16)
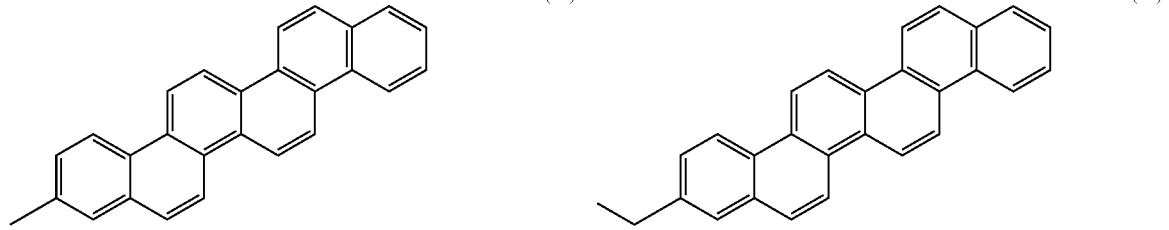
(17) (18)
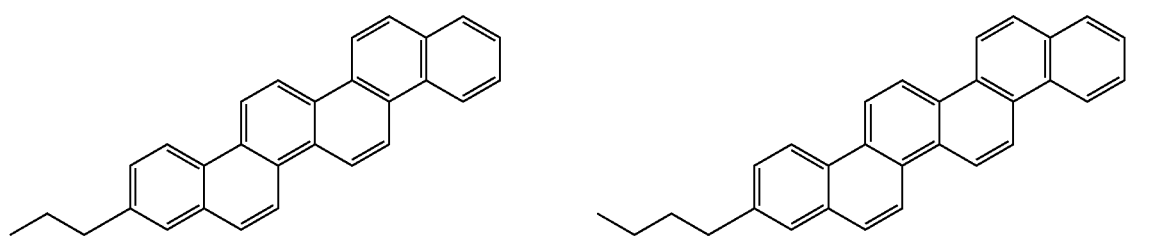
(19) (20)
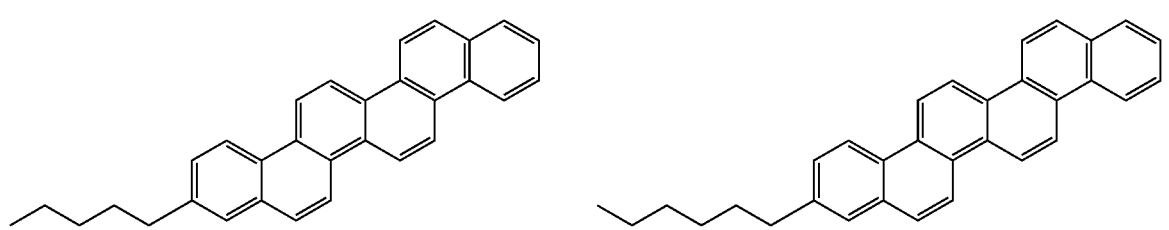
(21) (22)
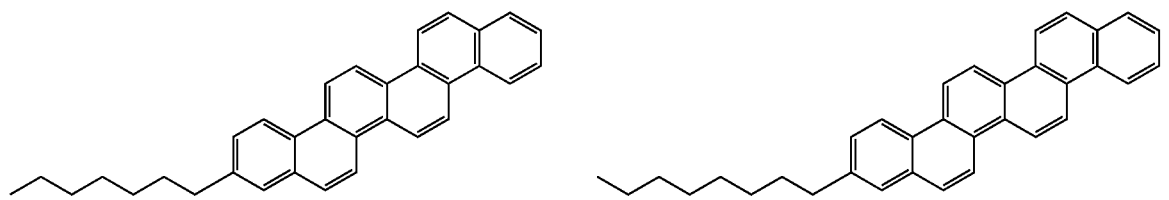
(23) (24)

-continued
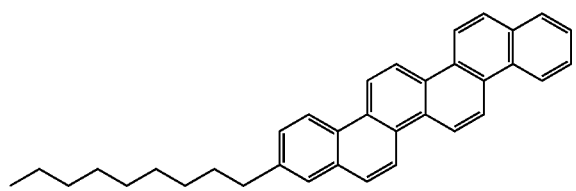
(25)
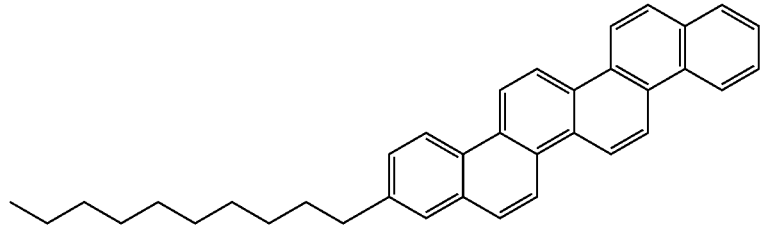
(26)
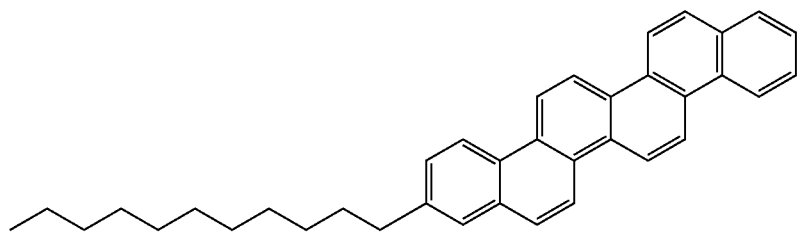
(27)
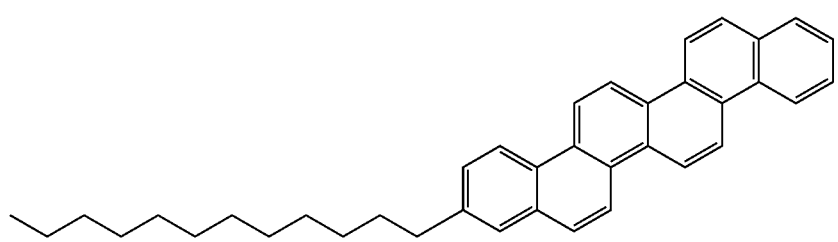
(28)
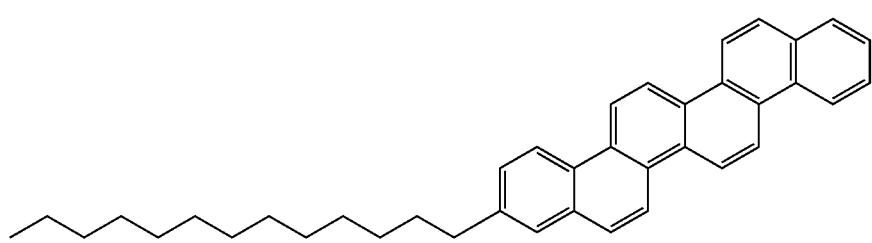
(29)
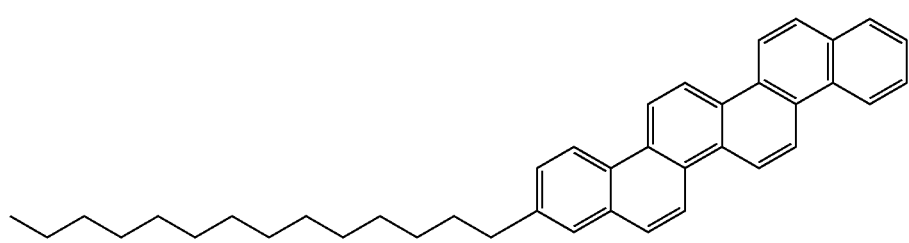
(30)
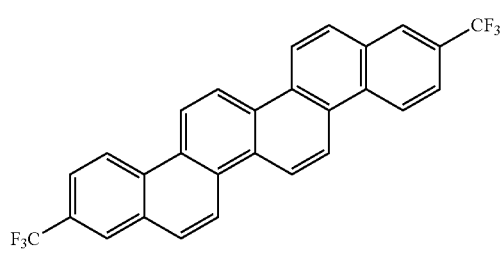
(31)
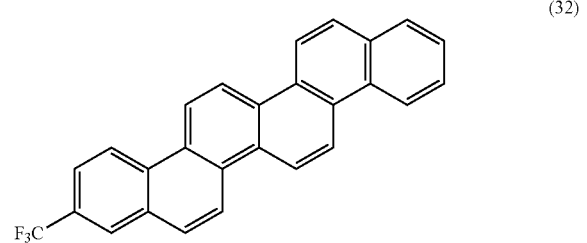
(32)

-continued
(33)
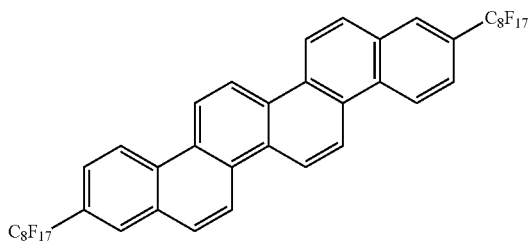
(34)
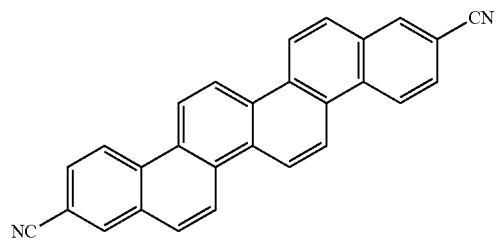
(35)
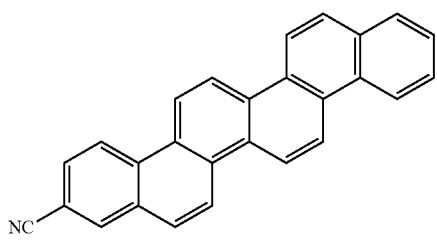
(36)
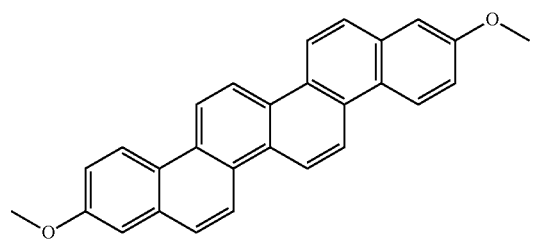
(37)
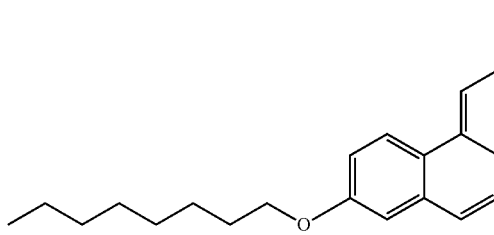
(38)
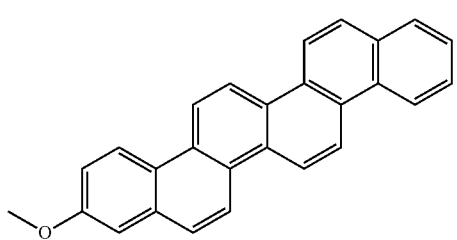
(39)
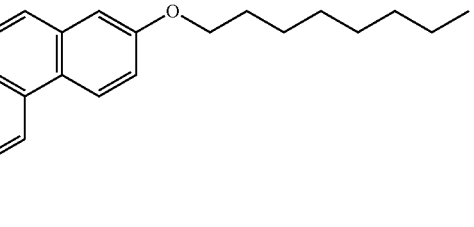
(40)
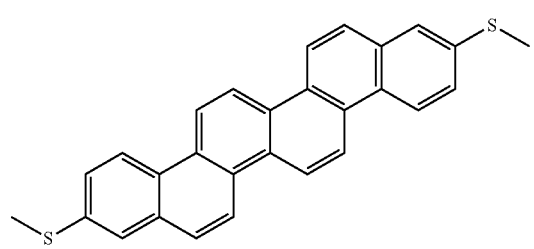
(41)
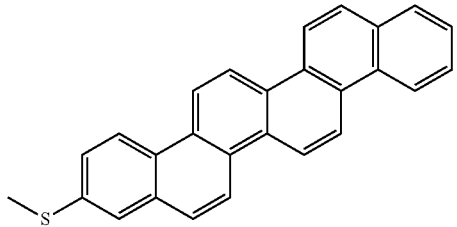
(42)
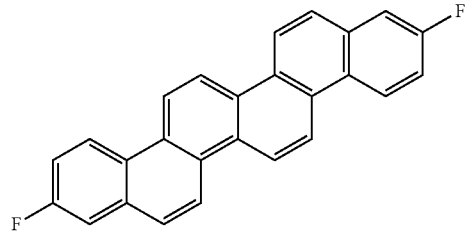

-continued
(43)
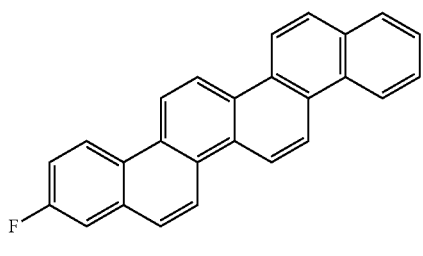
(44)
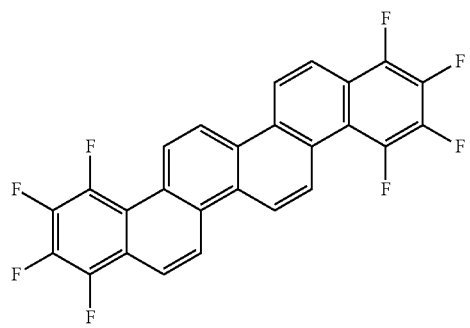
(45)
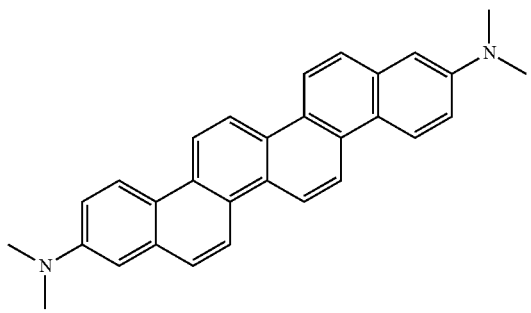
(46)
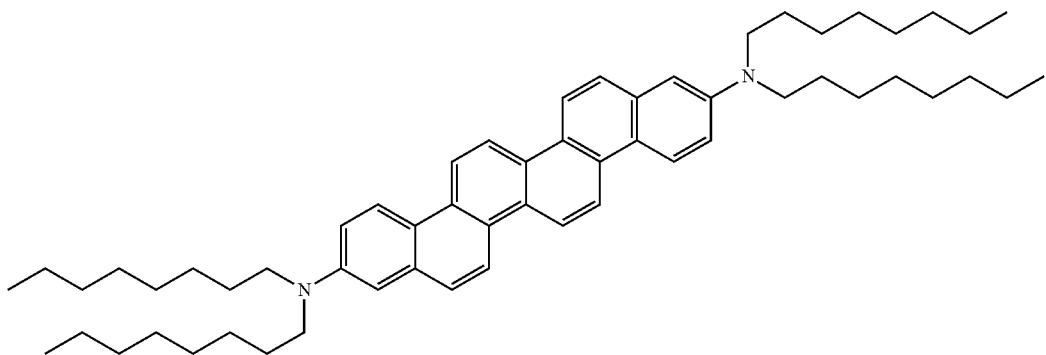
(47)
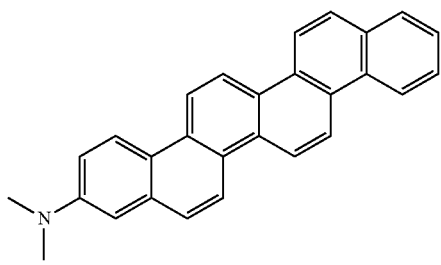
(48)
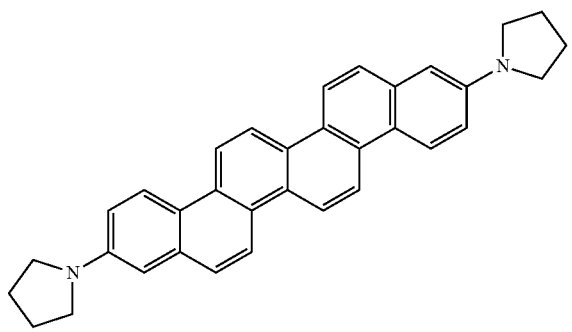

-continued
(49)
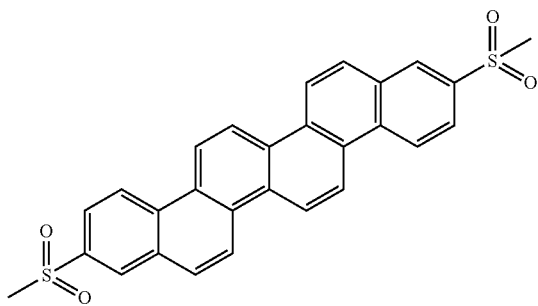
(50)
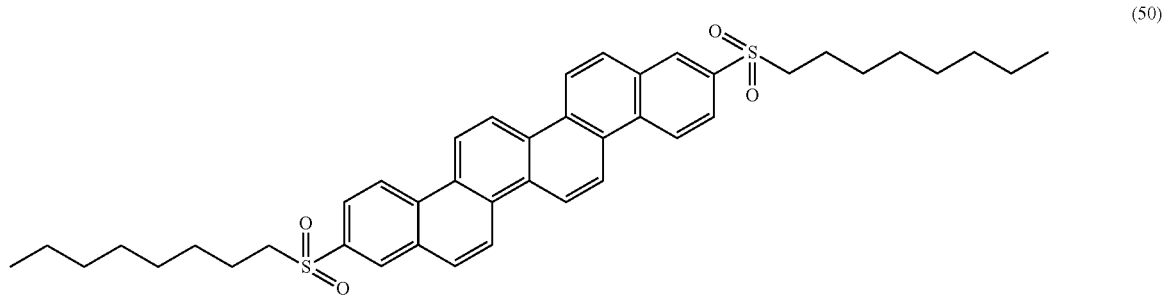
(51)
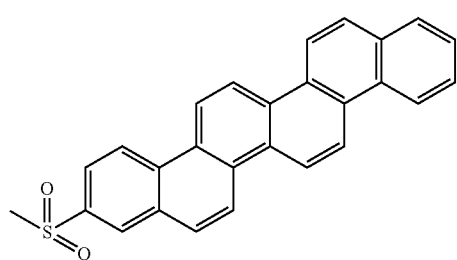
(52)
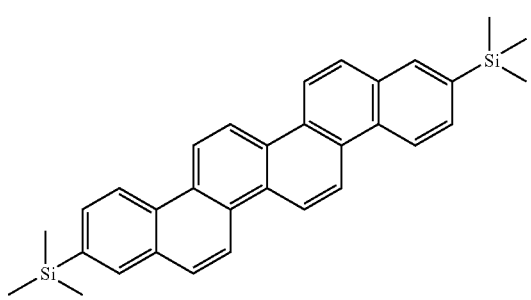
(53)
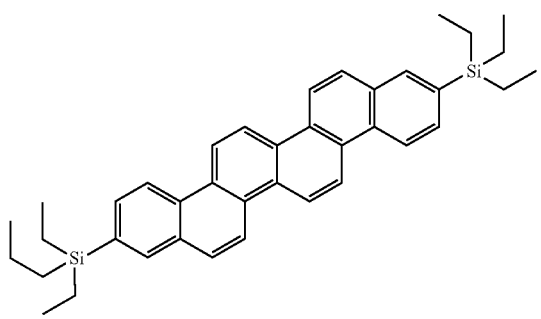
(54)
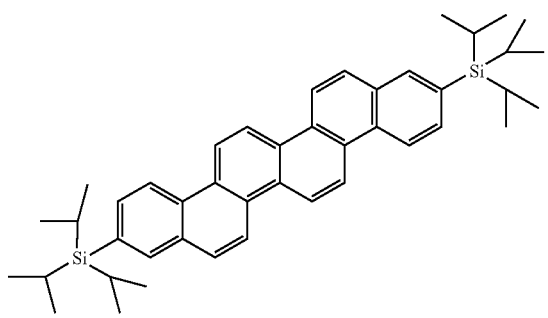
(55)
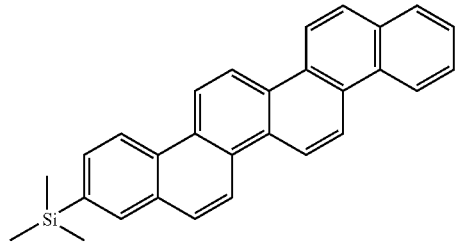
(56)
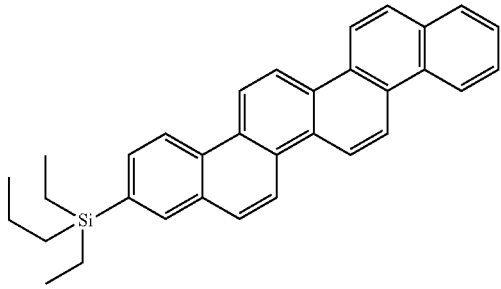

-continued
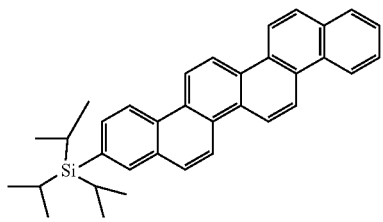
(57)
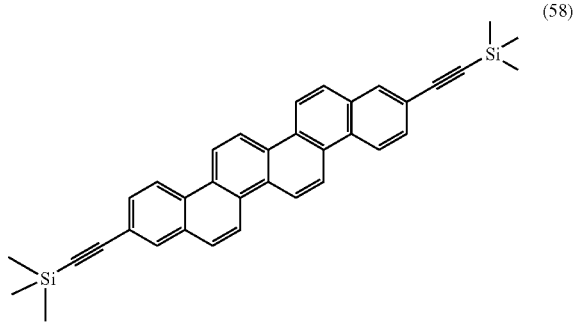
(58)
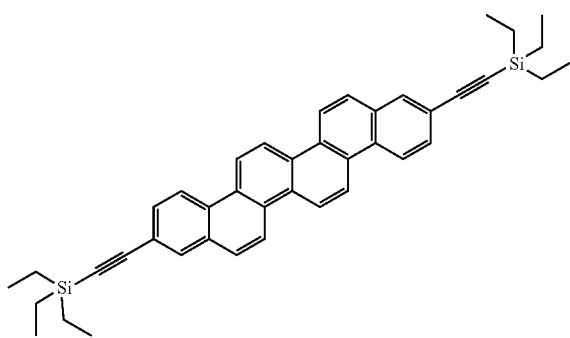
(59)
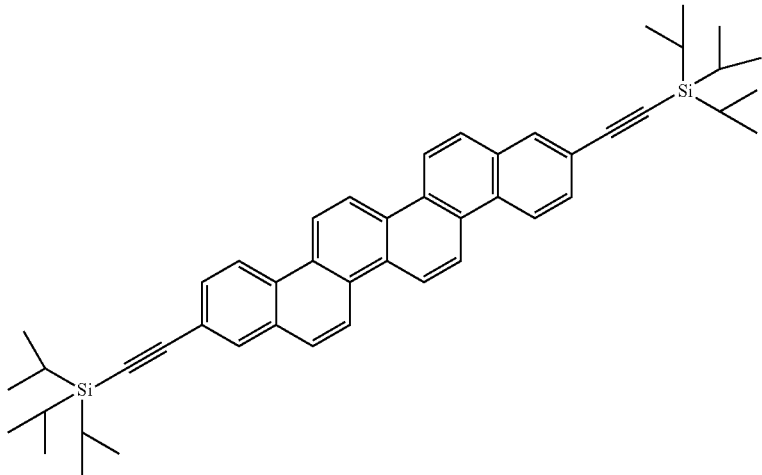
(60)
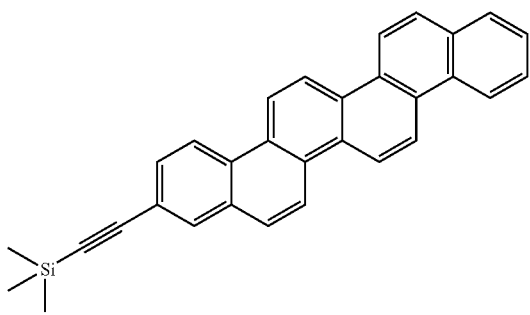
(61)
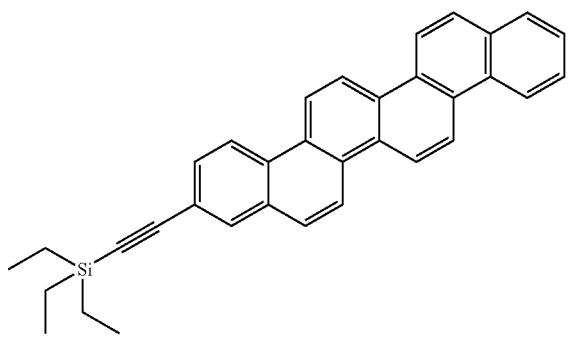
(62)

-continued
(63)
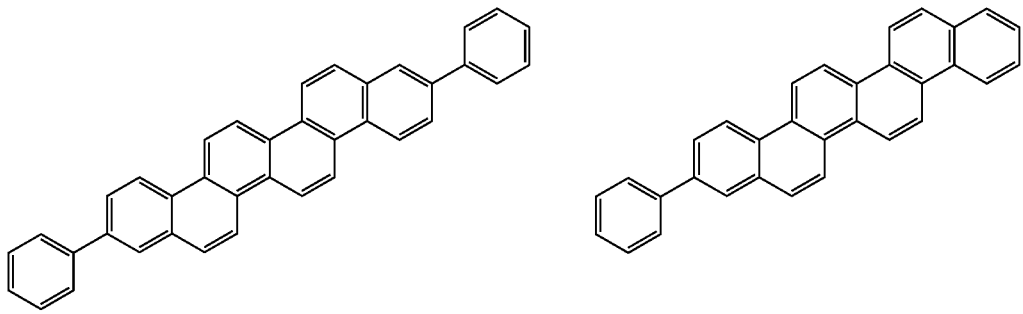
(64)
(65)
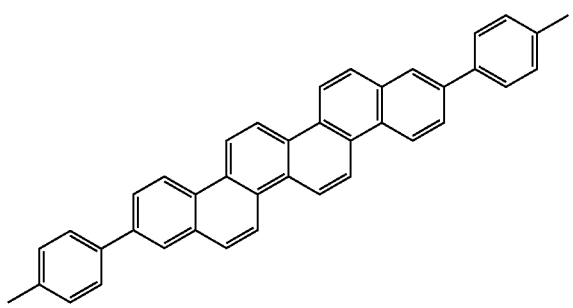
(66)
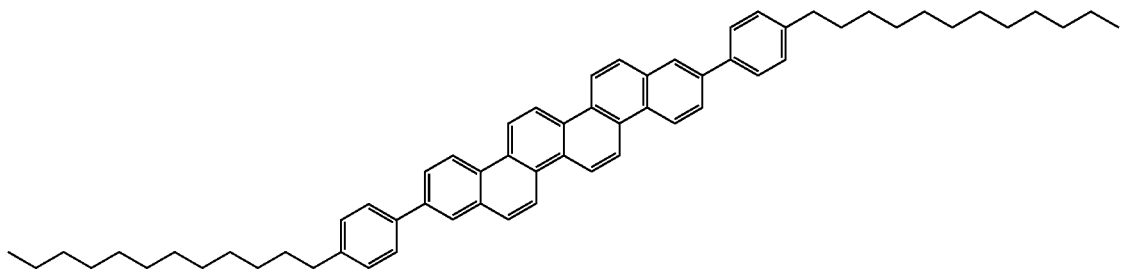
(67)
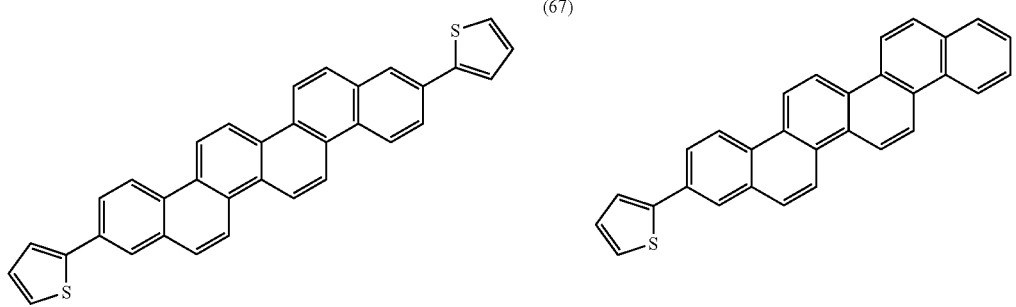
(68)
(69)
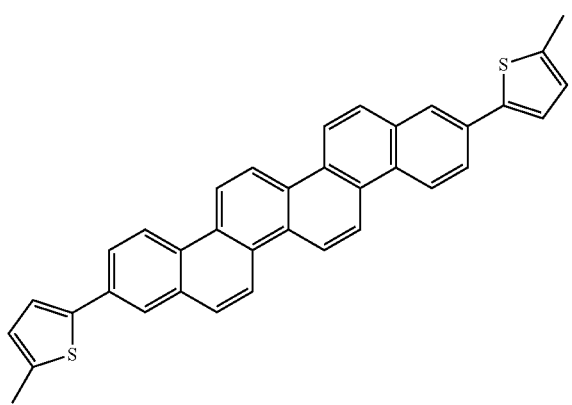

-continued
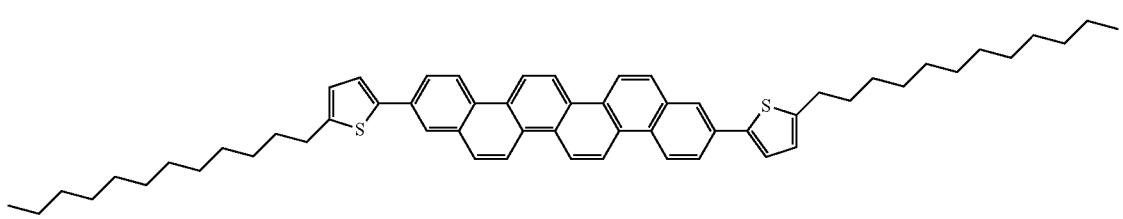
(70)
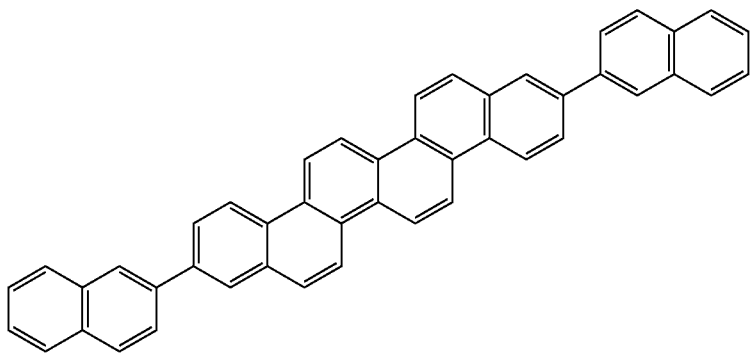
(71)
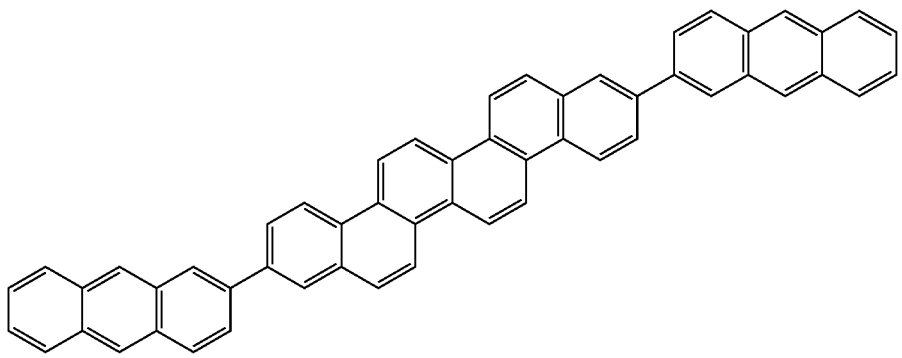
(72)
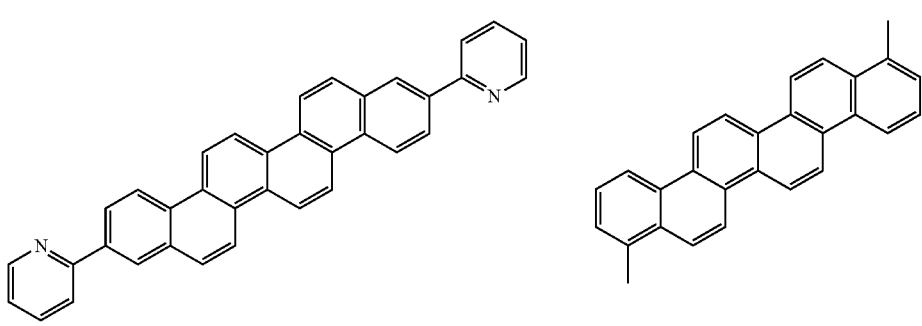
(73) (74)
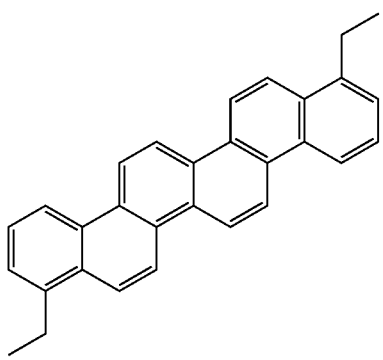
(75)

-continued
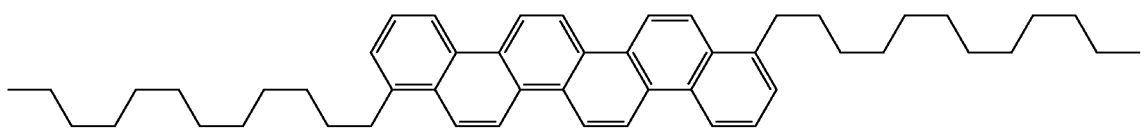
(76)
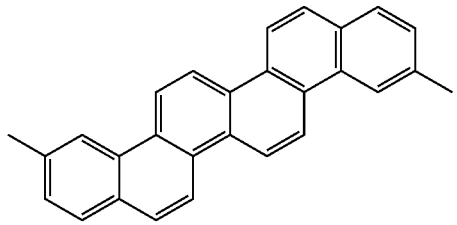
(77)
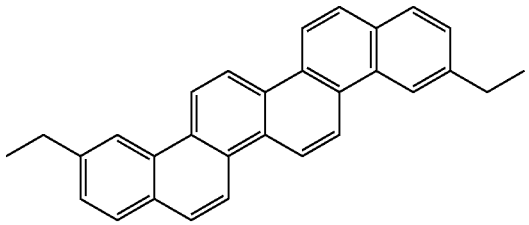
(78)
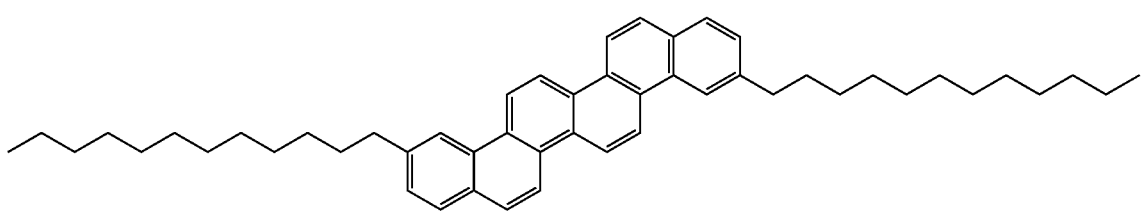
(79)
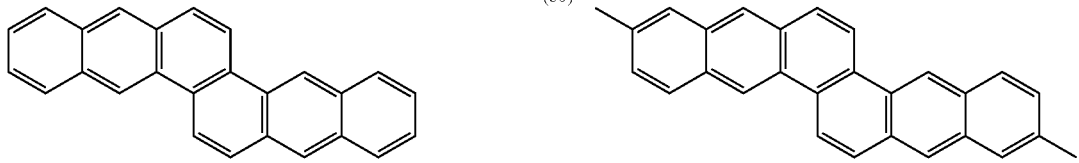
(80)
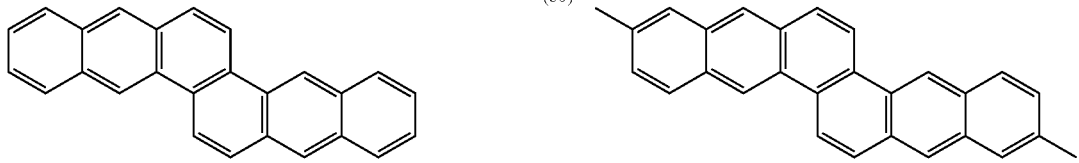
(81)
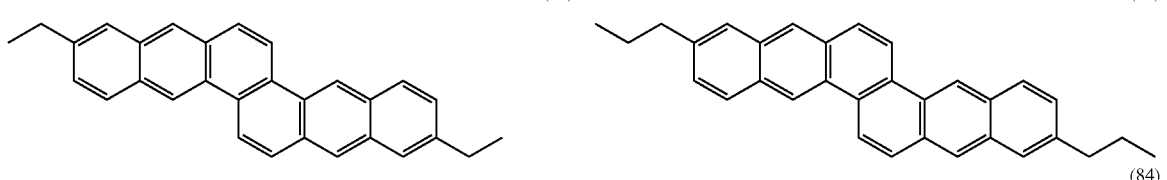
(82)
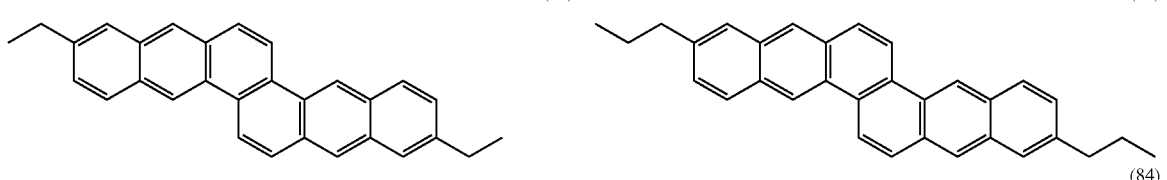
(83)
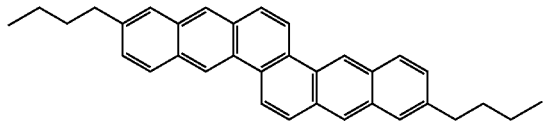
(84)
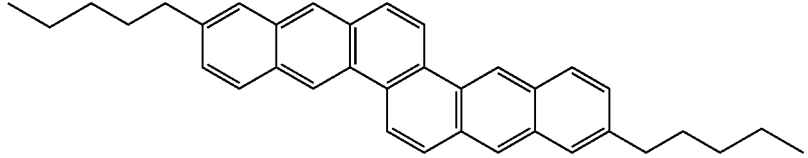
(85)
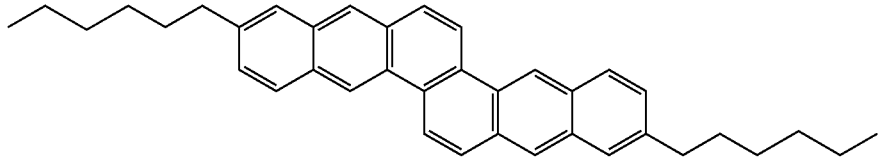
(86)
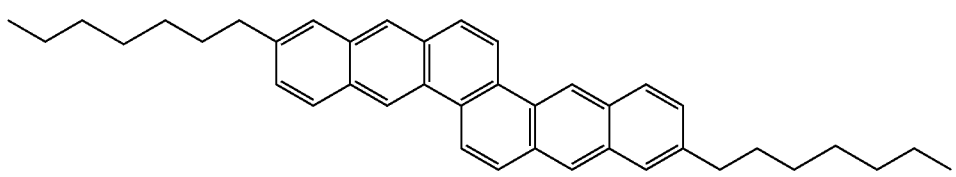
(87)

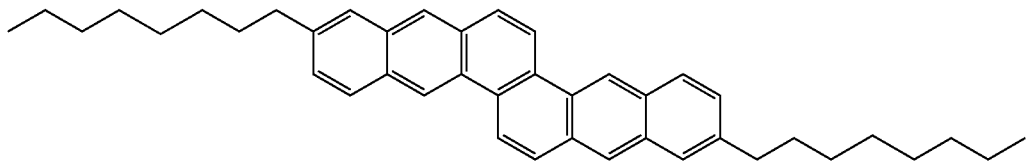
(88)
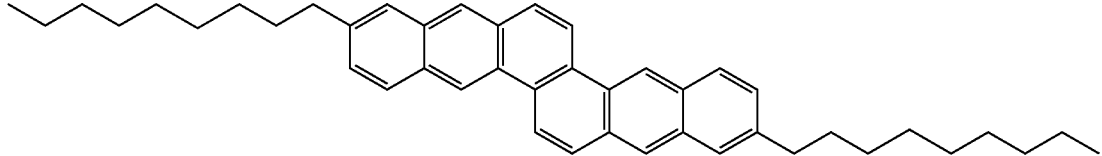
(89)
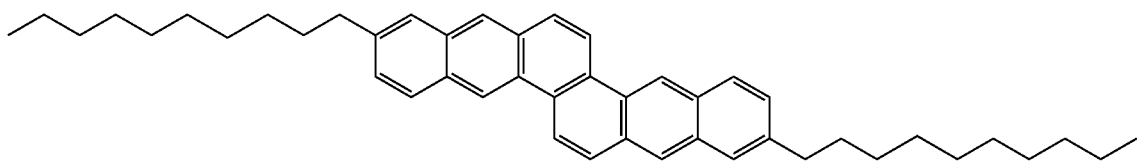
(90)
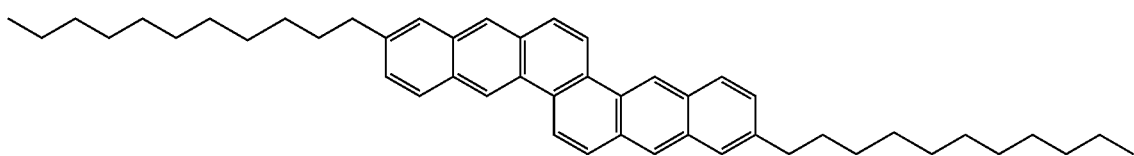
(91)
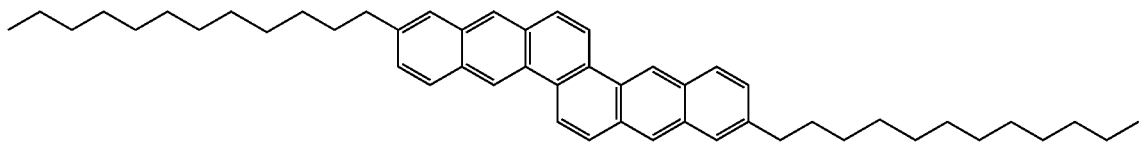
(92)
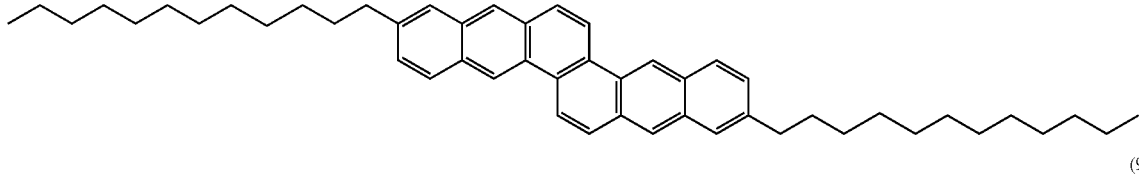
(93)
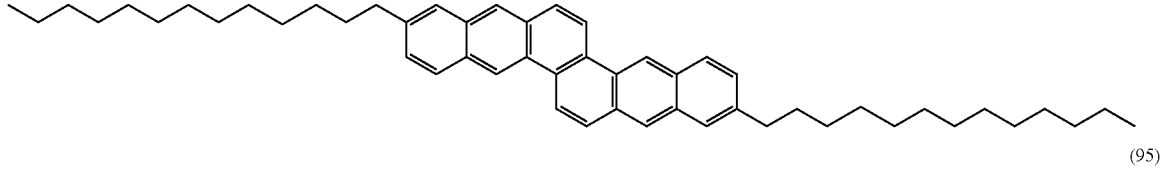
(94)
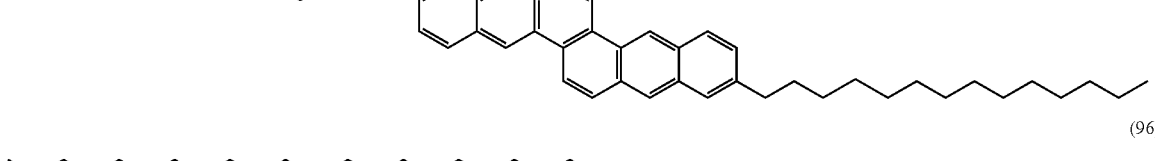
(95)
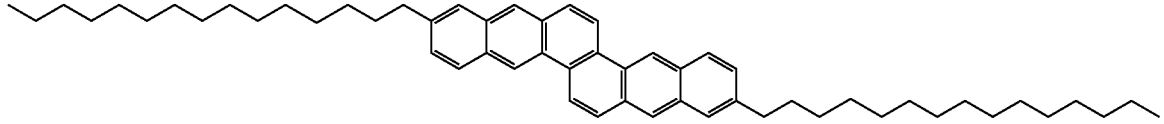
(96)

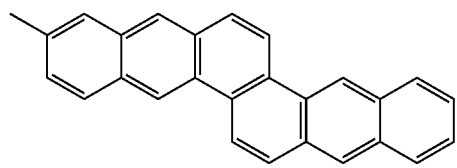
(97)
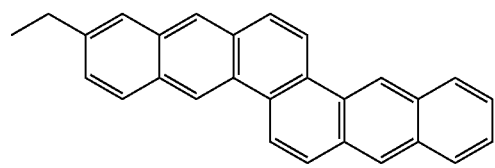
(98)
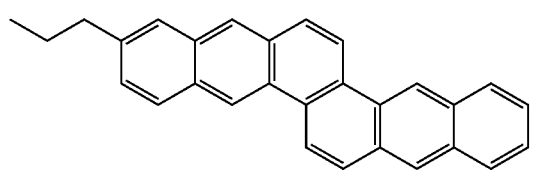
(99)
(100)
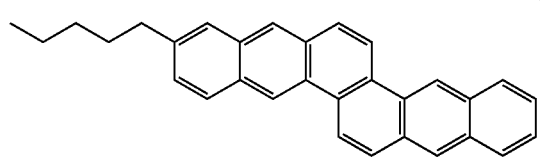
(101)
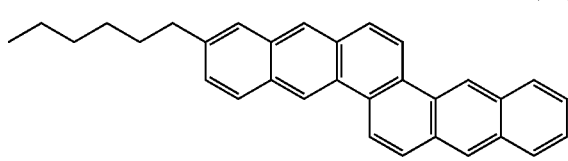
(102)
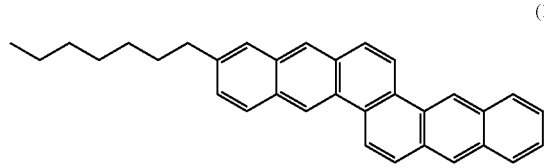
(103)
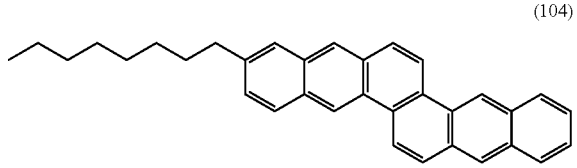
(104)
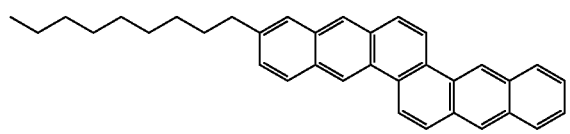
(105)
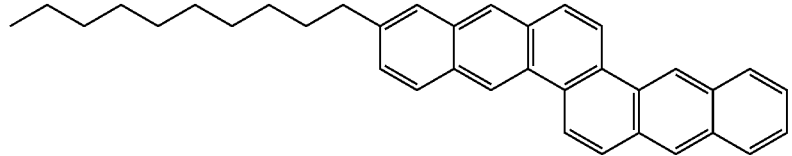
(106)
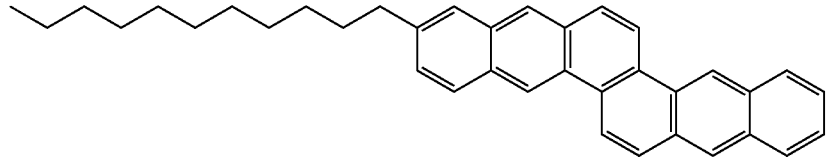
(107)
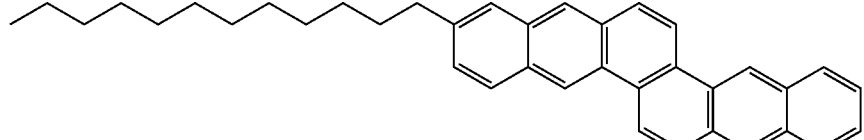
(108)
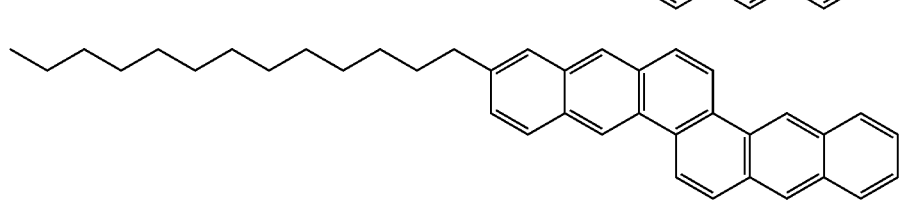
(109)

-continued
(110)
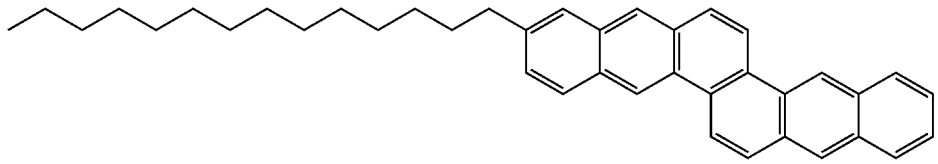
(111)
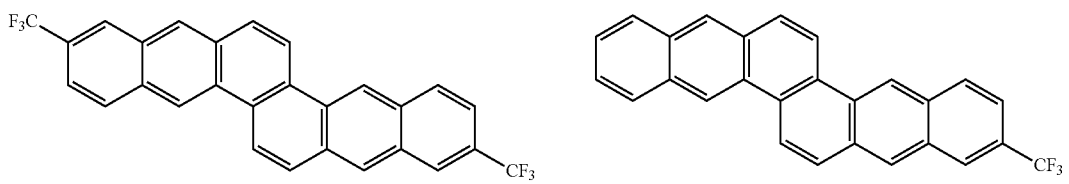
(112)
(113)
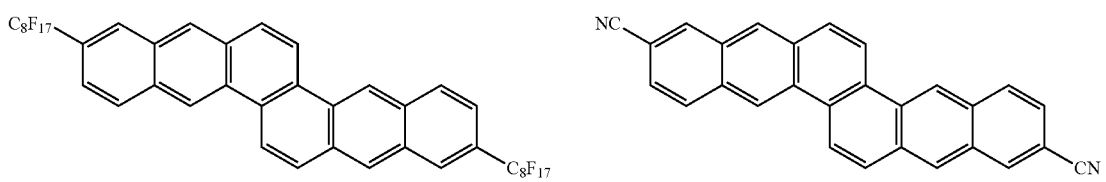
(114)
(115)
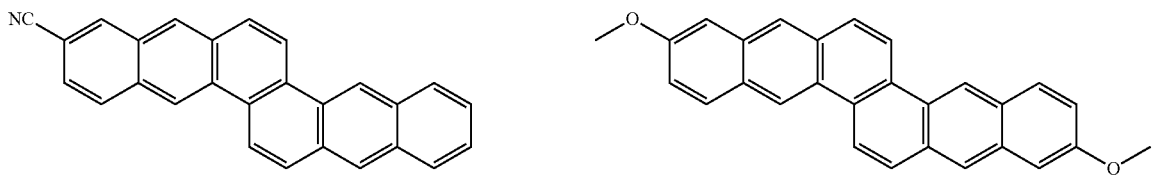
(116)
(117)
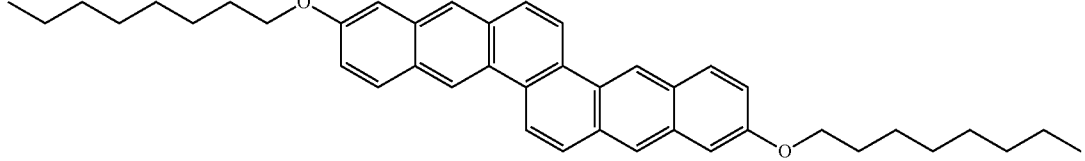
(118)
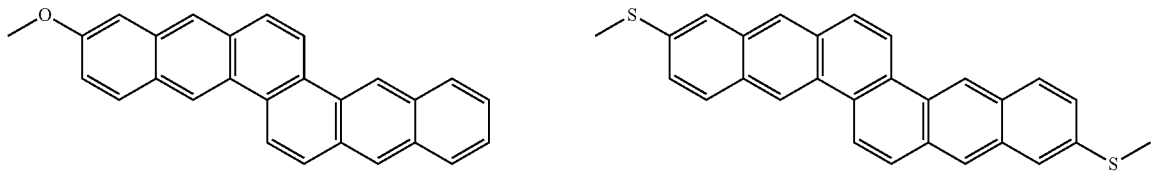
(119)
(120)
(121)
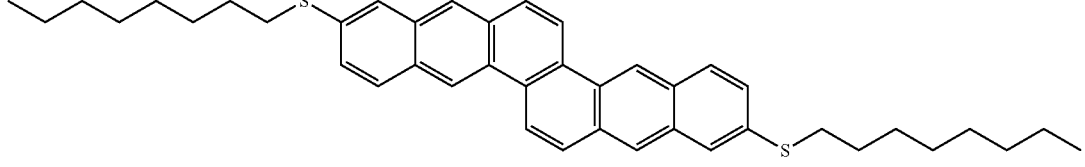
(122)

-continued
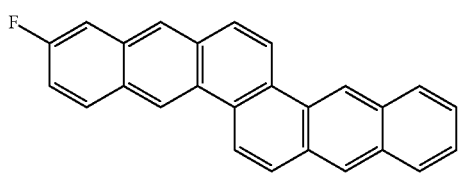
(123)
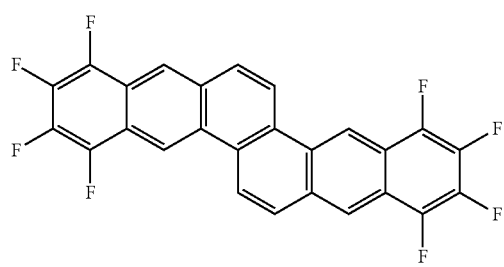
(124)
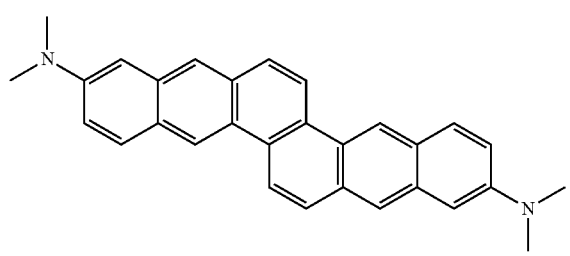
(125)
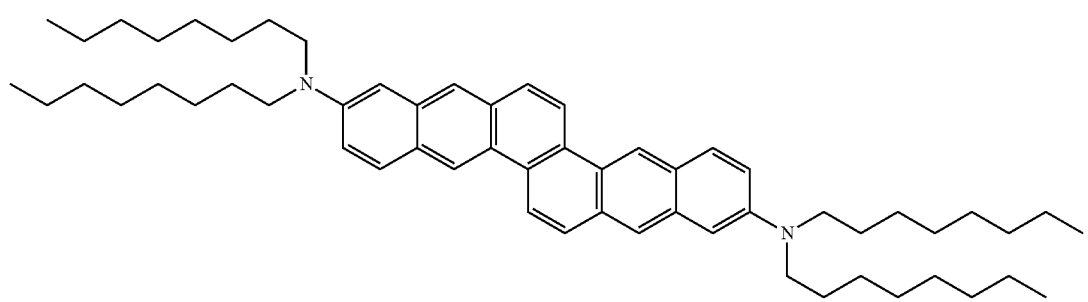
(126)
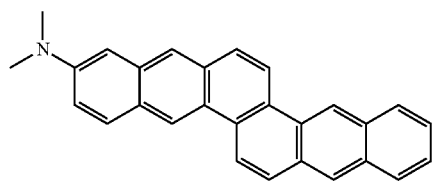
(127)
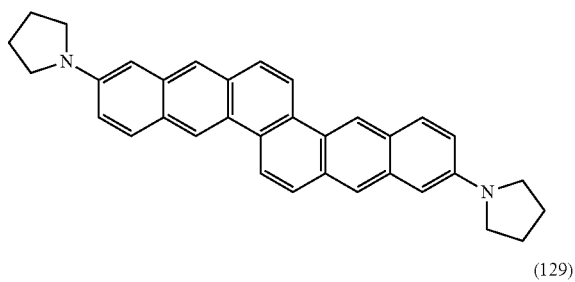
(128)
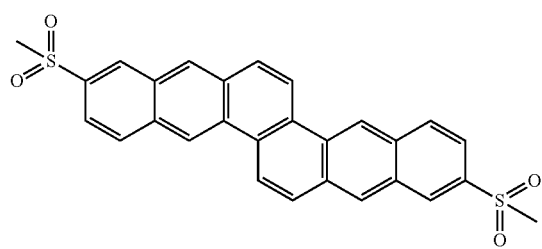
(129)
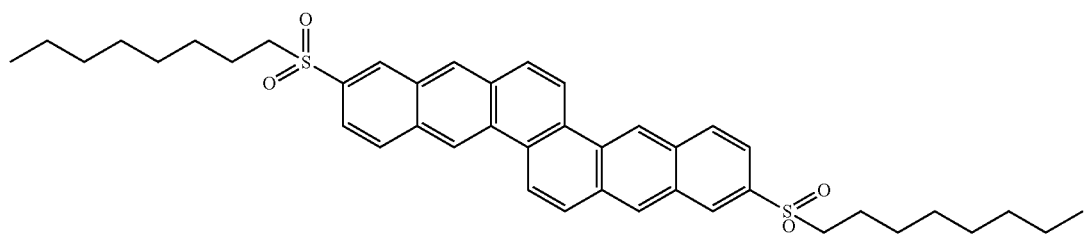
(130)

-continued
(131)
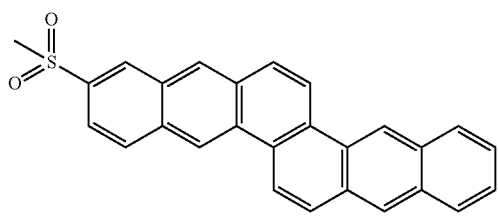
(132)
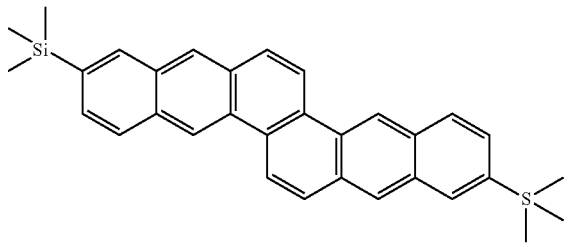
(133)
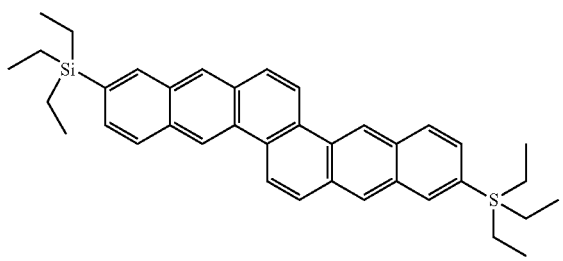
(134)
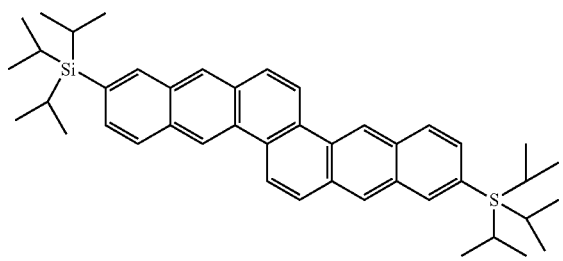
(135)
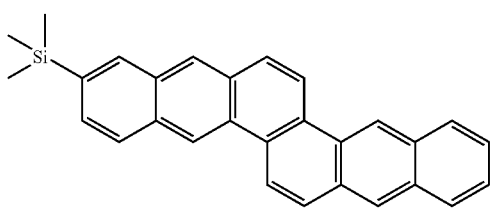
(136)
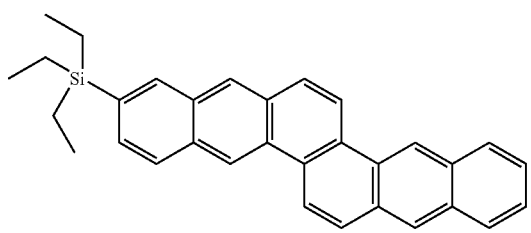
(137)
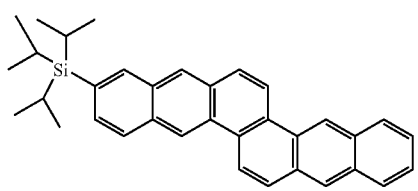
(138)
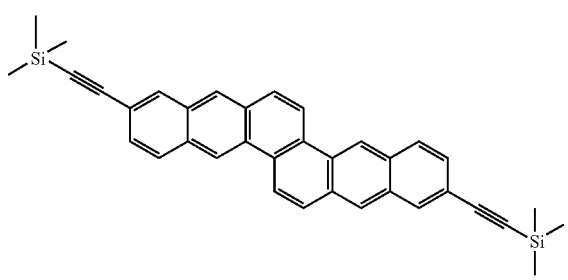
(139)
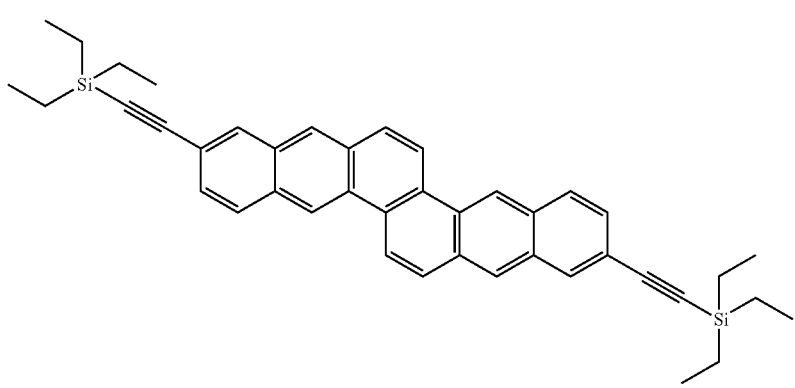

-continued
(140)
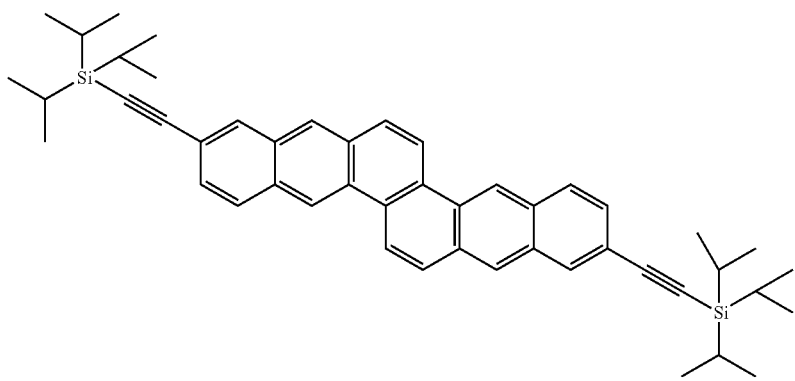
(141)
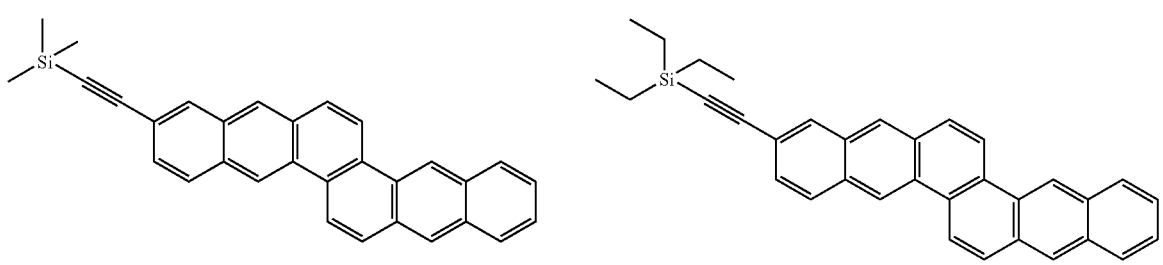
(142)
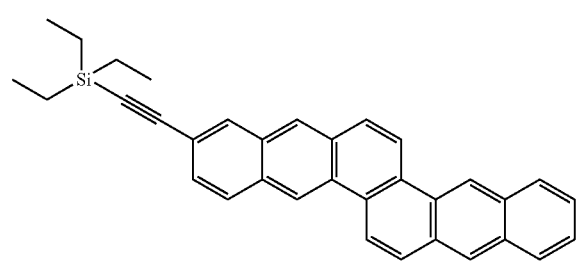
(143)
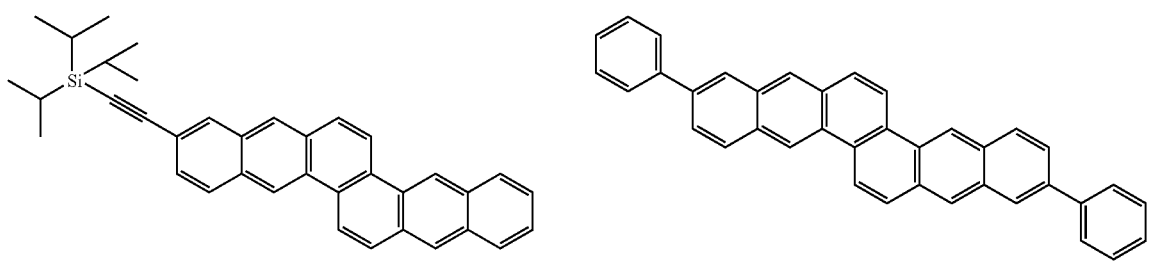
(144)
(145)
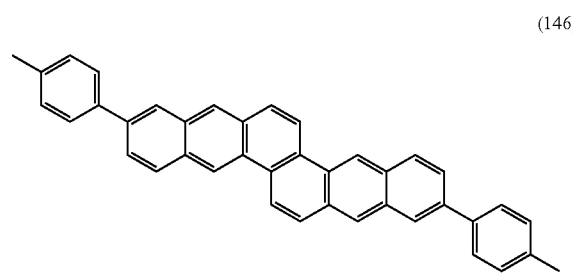
(146)
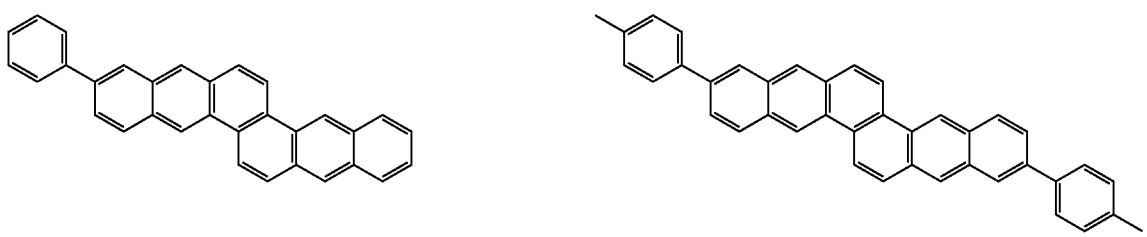
(147)
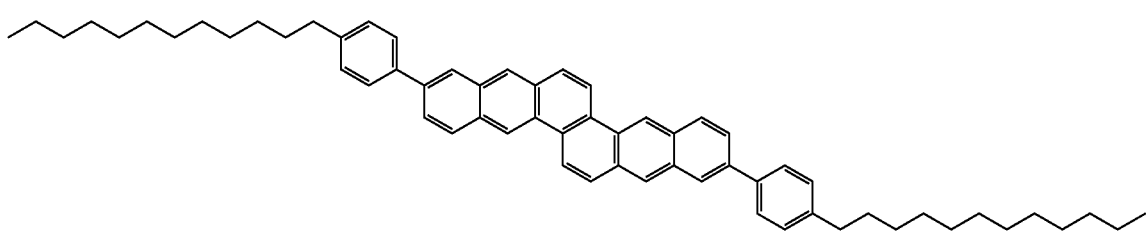

-continued
(148)
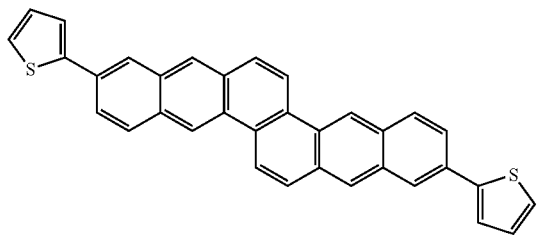
(149)
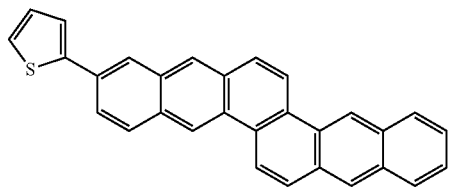
(150)
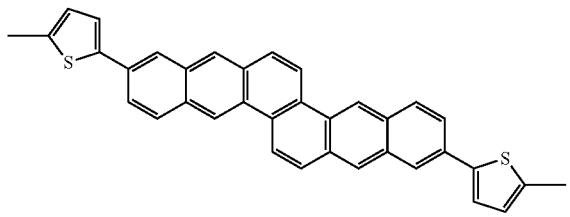
(151)
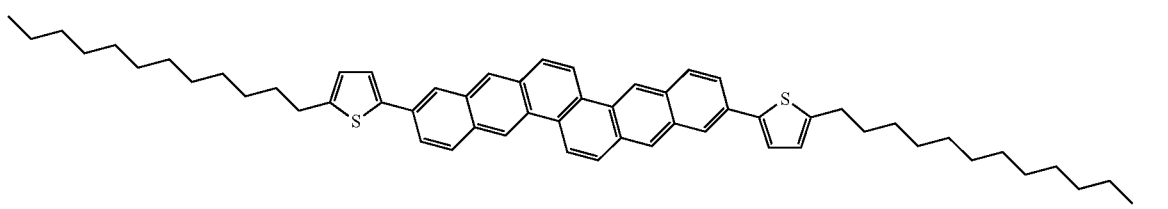
(152)
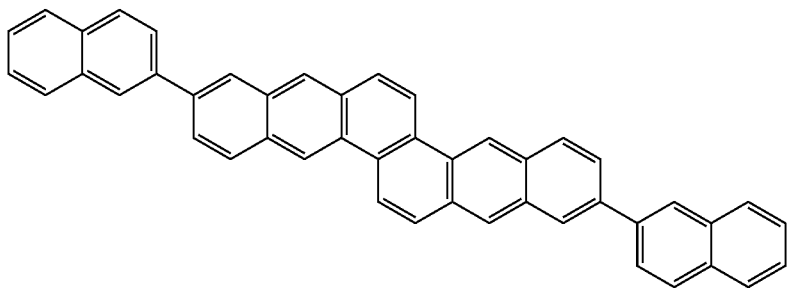
(153)
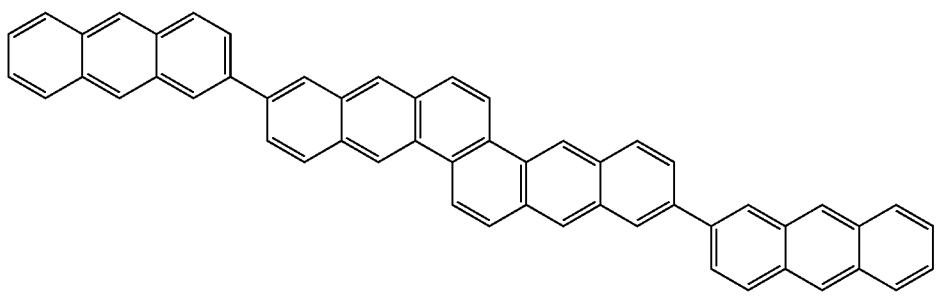
(154)
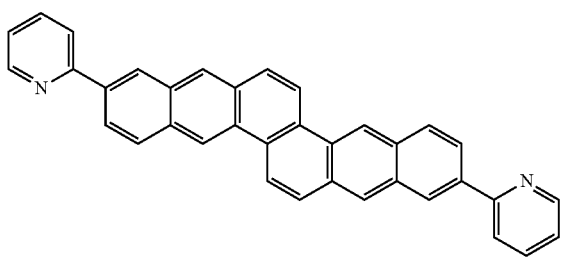
(155)
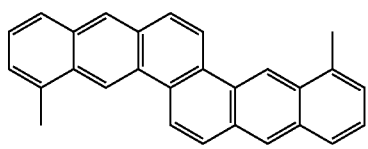

(156)
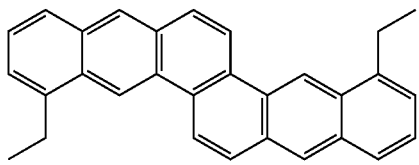
(157)
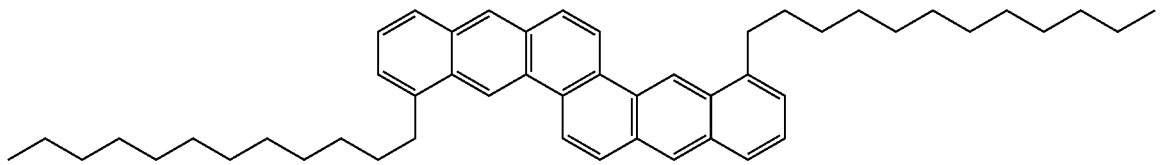
(161)
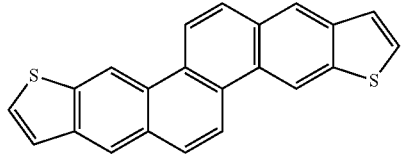
(162)
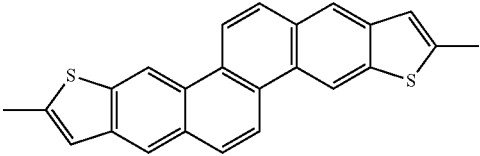
(163)
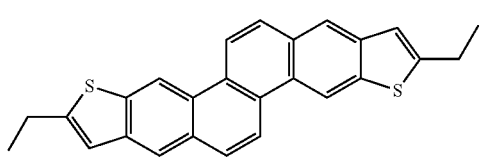
(164)
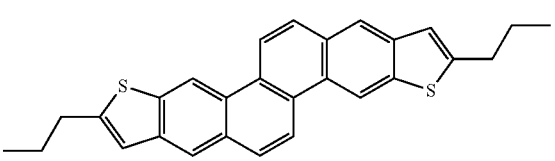
(165)
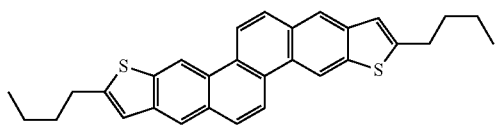
(166)
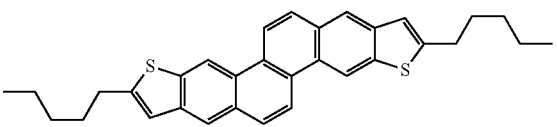
(167)
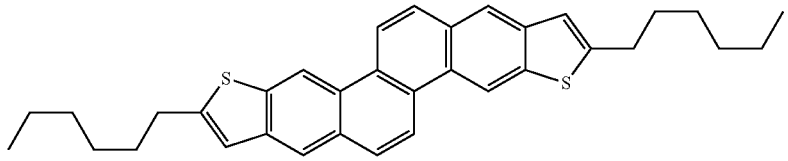
(168)
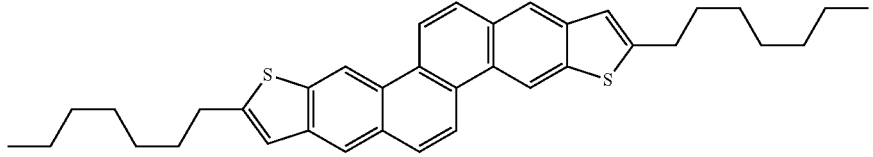
(169)
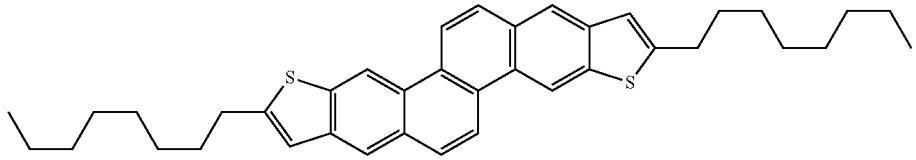
(170)
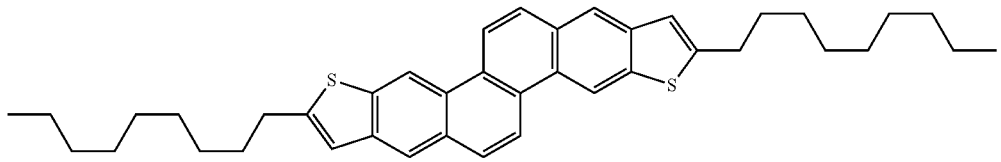

-continued
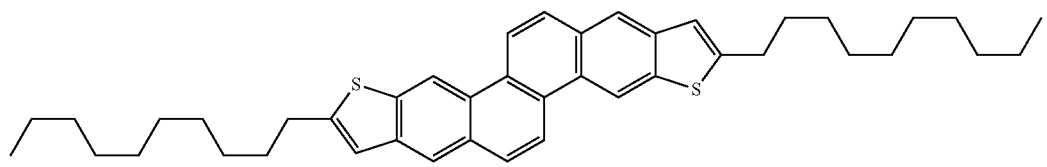
(171)
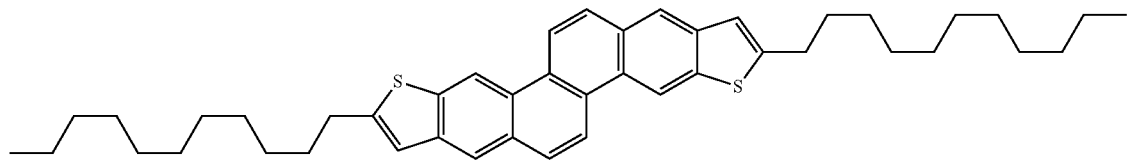
(172)
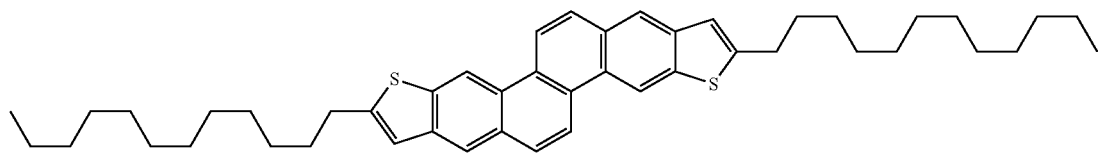
(173)
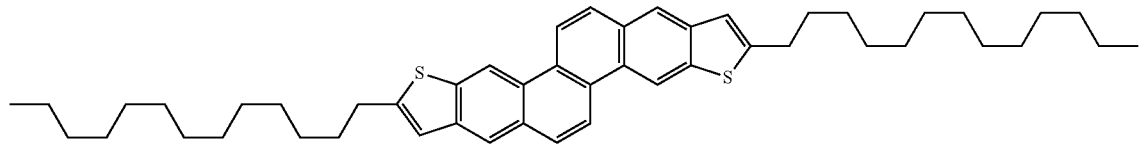
(174)
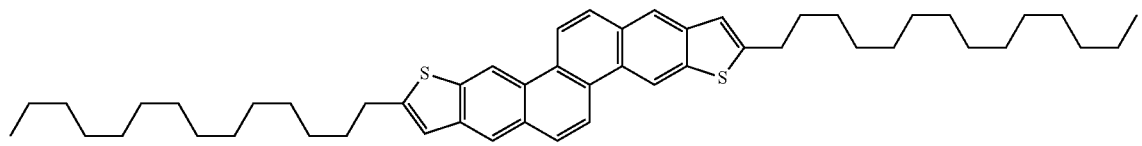
(175)
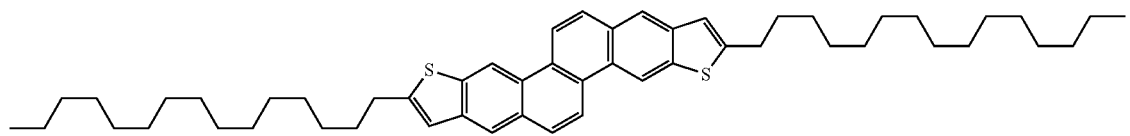
(176)
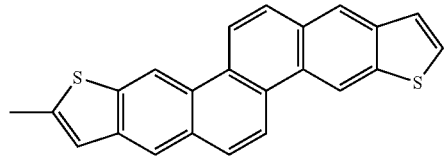
(177)
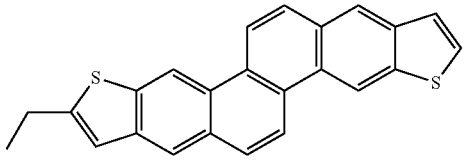
(178)
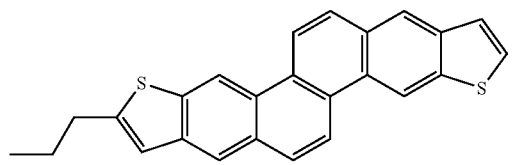
(179)
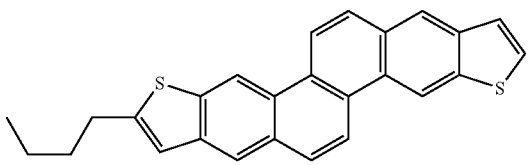
(180)
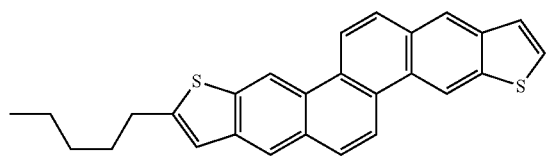
(181)
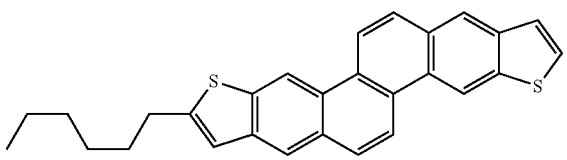
(182)

-continued
(183)
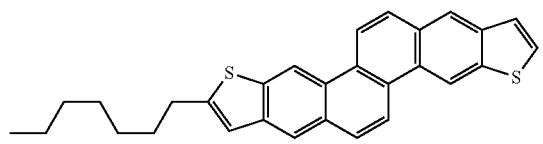
(184)
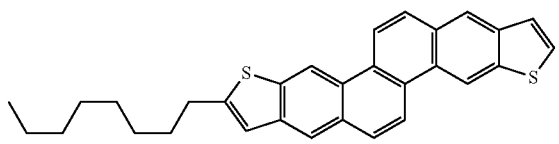
(185)
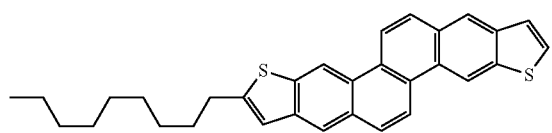
(186)
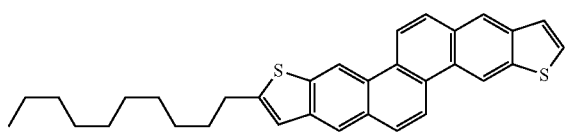
(187)
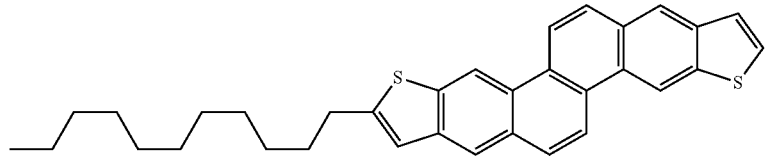
(188)
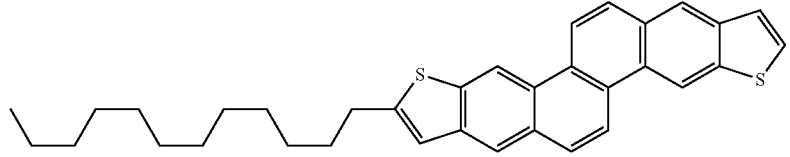
(189)
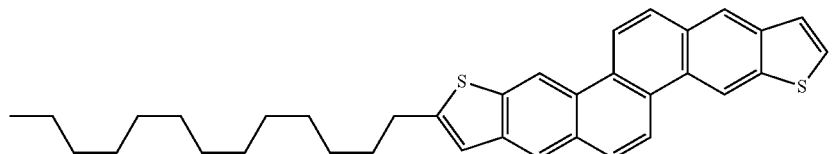
(190)
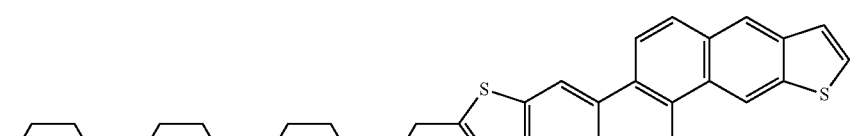
(191)
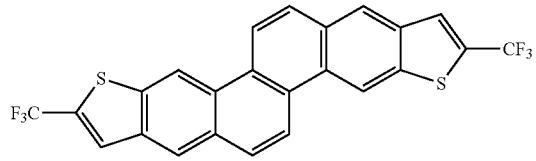
(192)
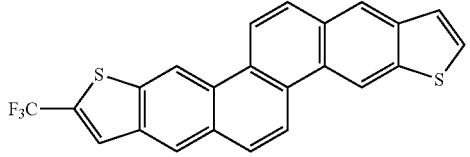
(193)
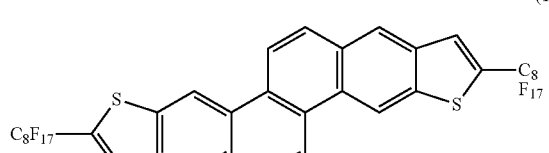
(194)
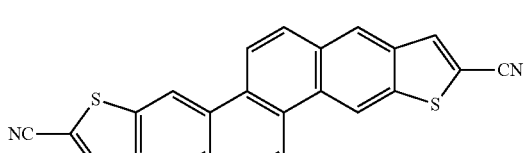
(195)
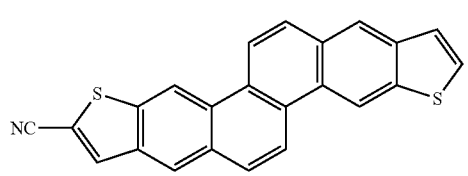
(196)
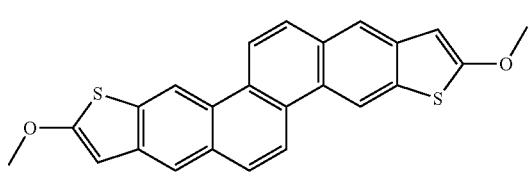

-continued
(197)
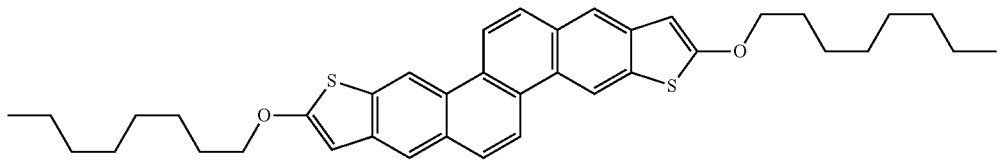
(198)
(199)
(200)
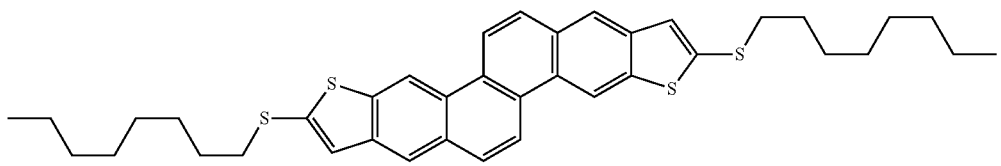
(201) (202)
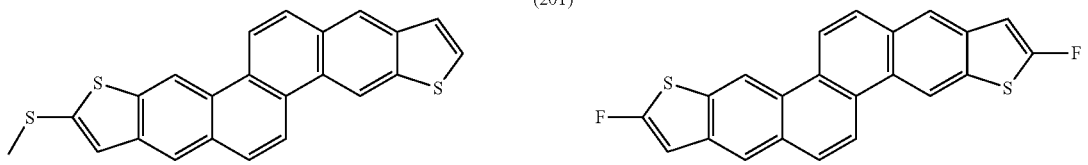
(203) (204)
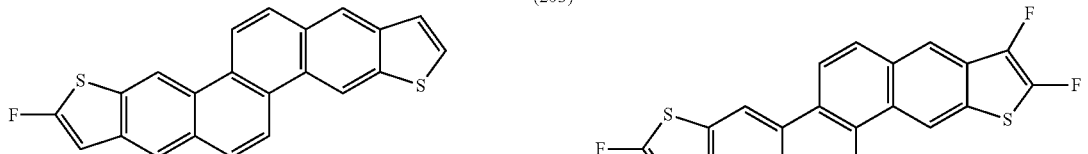
(205)
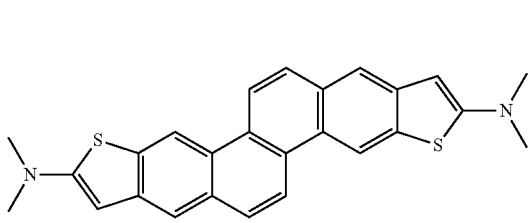
(206)
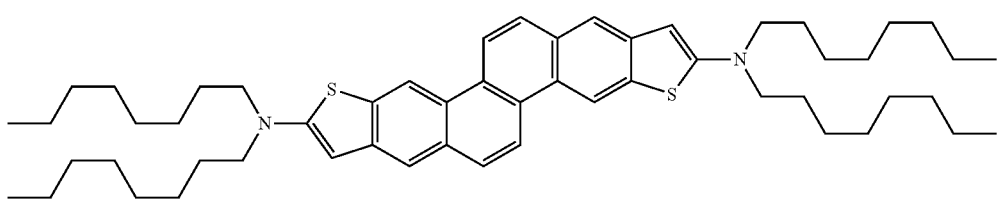
(207) (208)
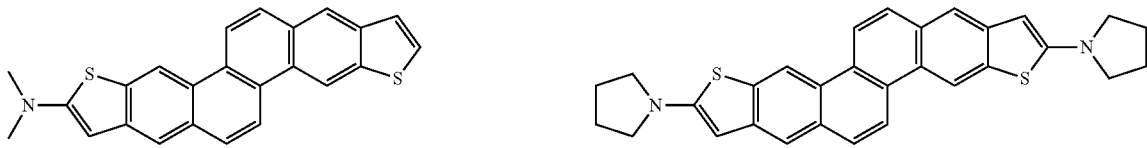

-continued
(209)
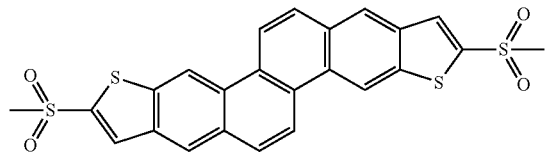
(210)
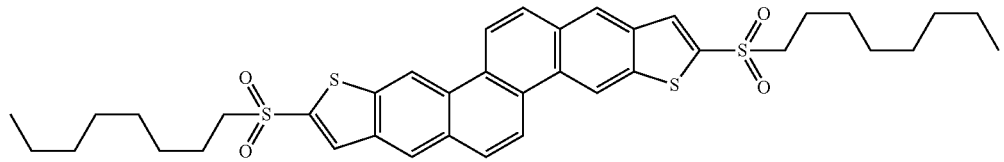
(211)
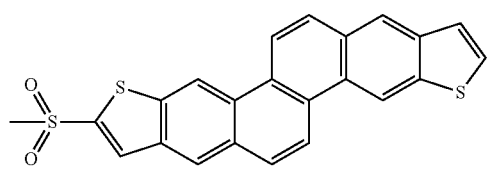
(212)
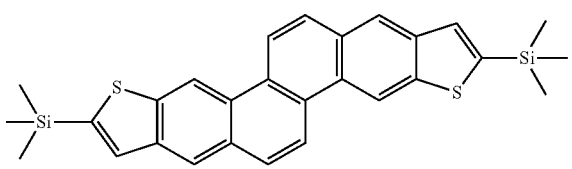
(213)
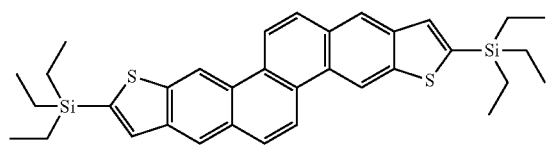
(214)
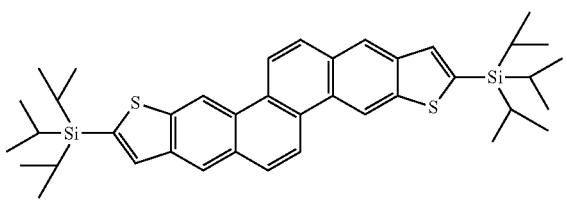
(215)
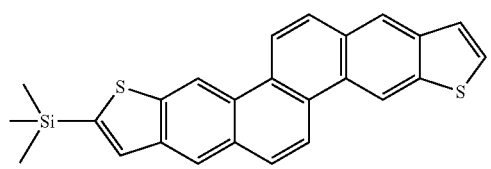
(216)
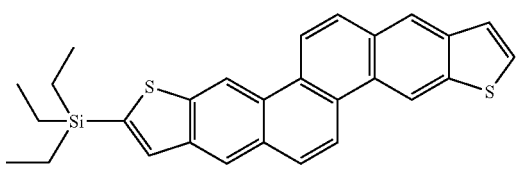
(217)
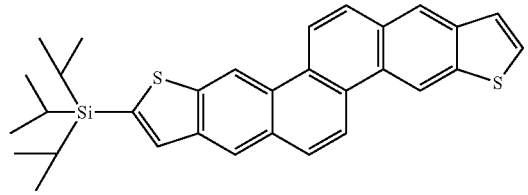
(218)
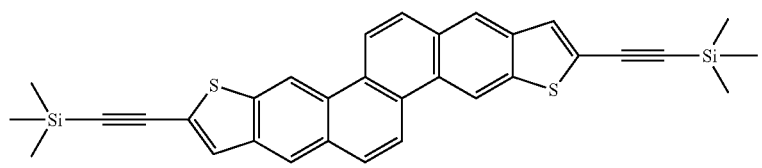
(219)
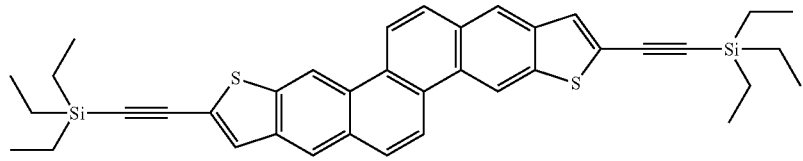

-continued
(220)
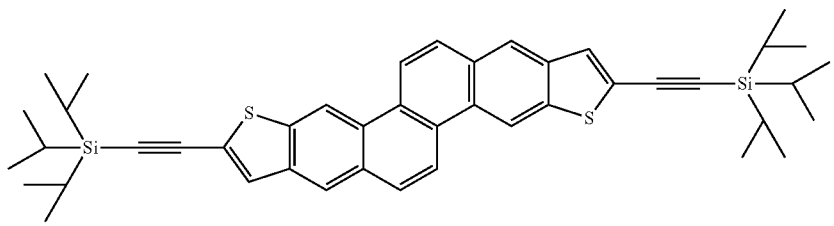
(221)
(222)
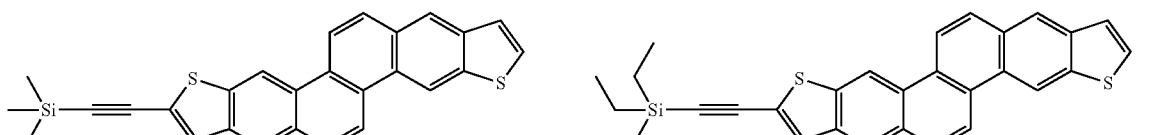
(223)
(224)
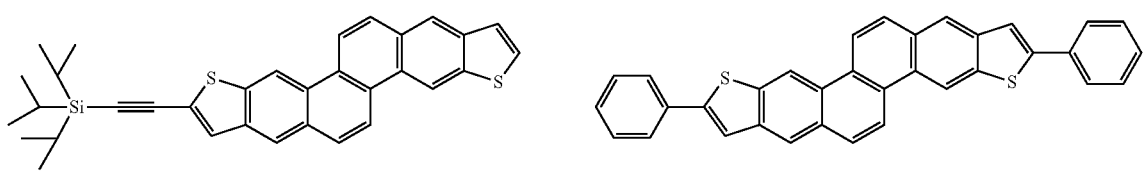
(225)
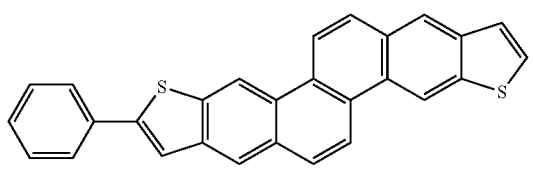
(226)
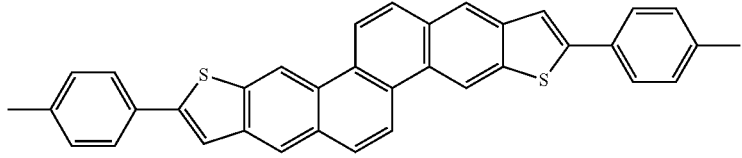
(227)
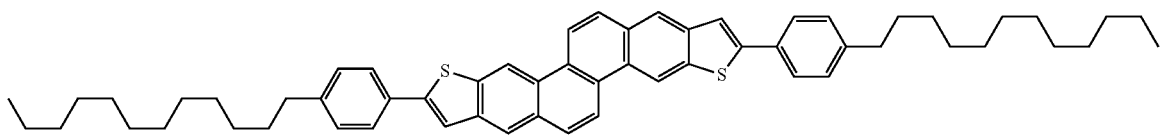
(228)
(229)
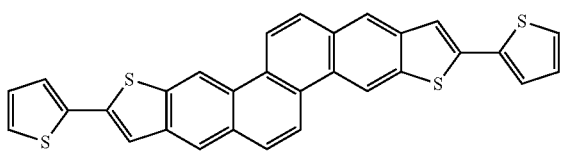
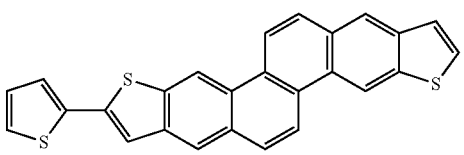
(230)
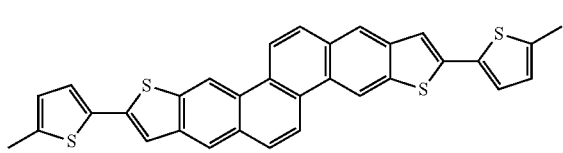

-continued
(231)
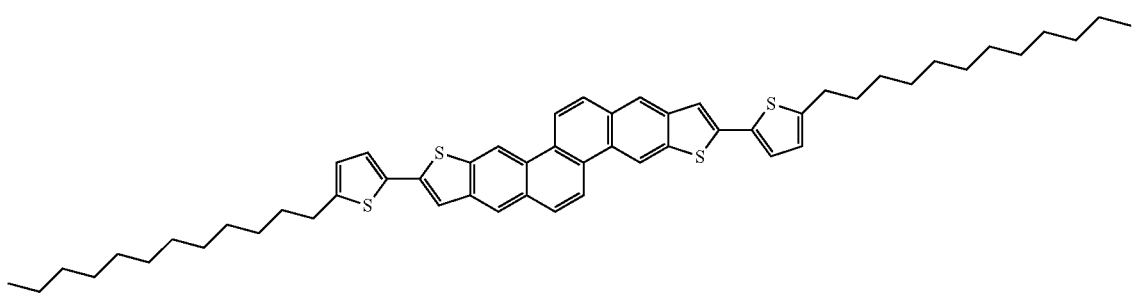
(232)
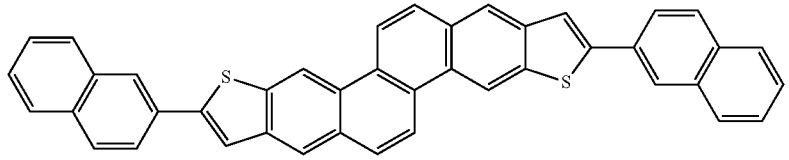
(233)
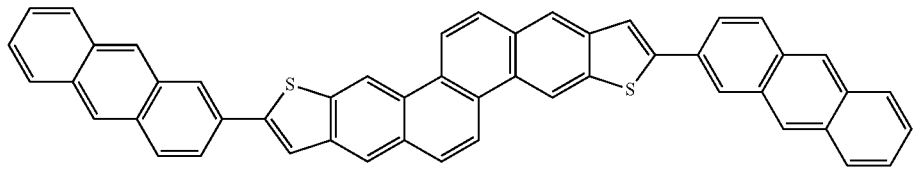
(234)
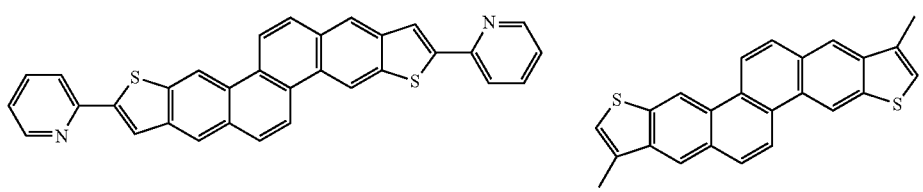
(235)
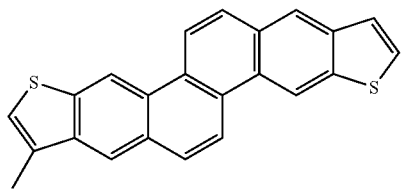
(236)
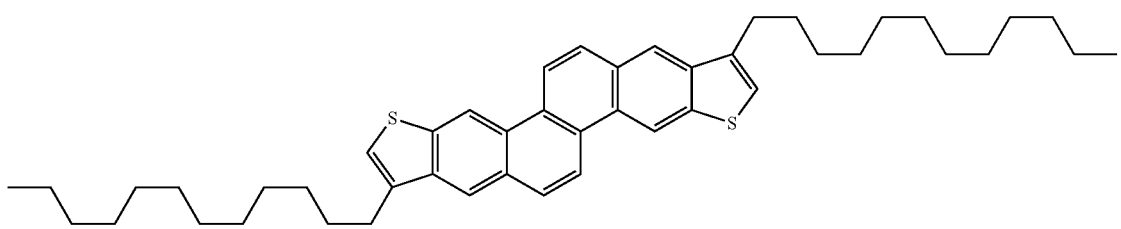
(237)
(238)
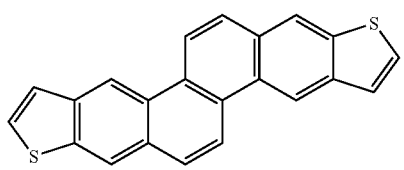
(239)
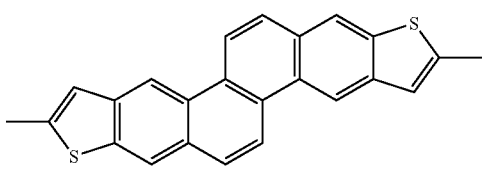

-continued
(240)
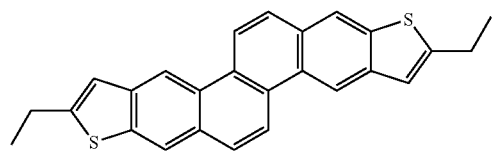
(241)
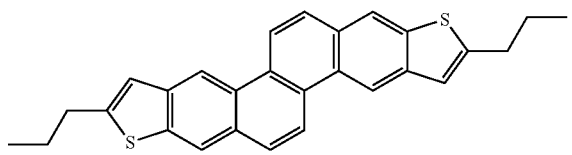
(242)
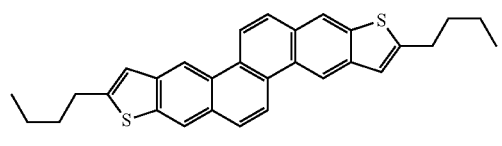
(243)
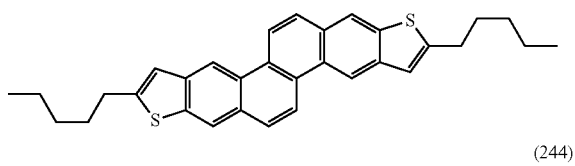
(244)
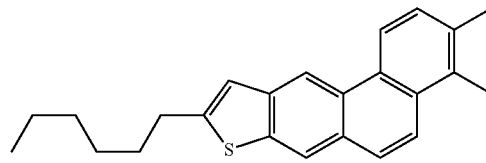
(245)
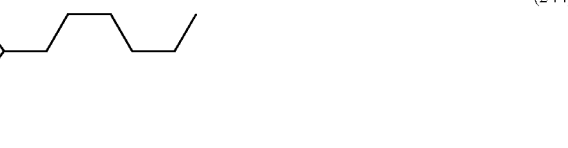
(246)
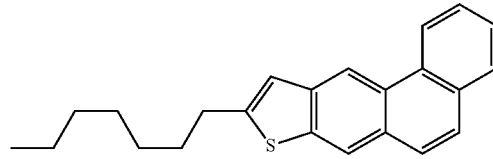
(247)
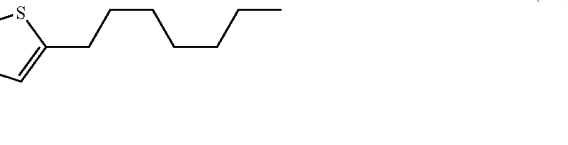
(248)
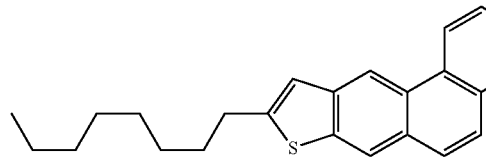
(249)
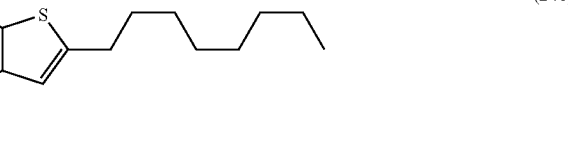
(250)
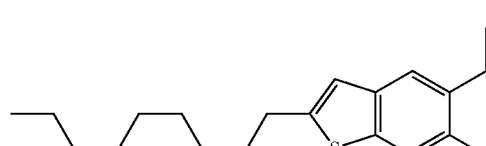

-continued
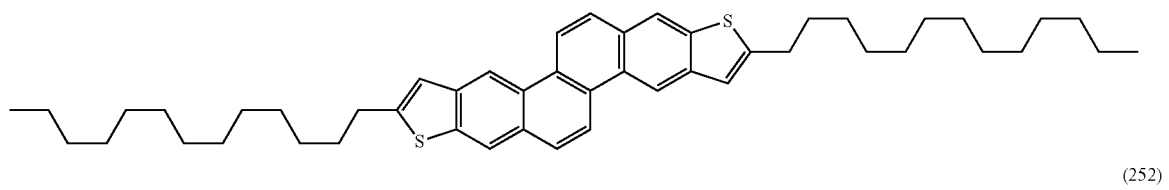
(251)
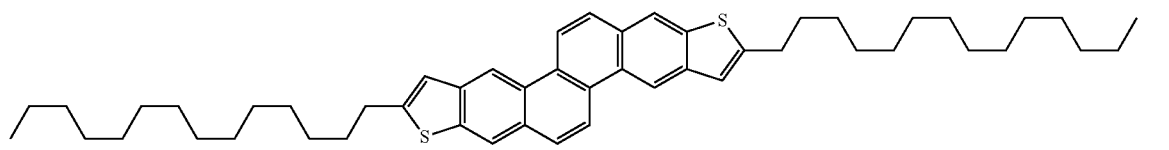
(252)
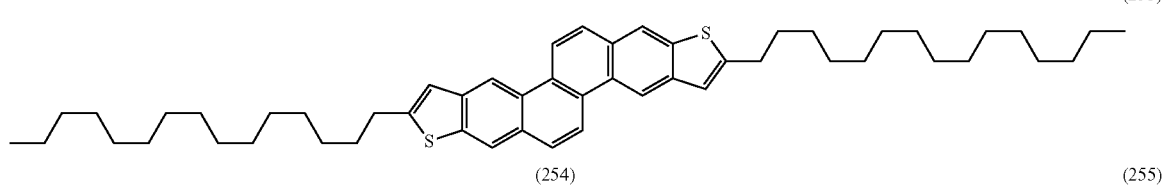
(253)
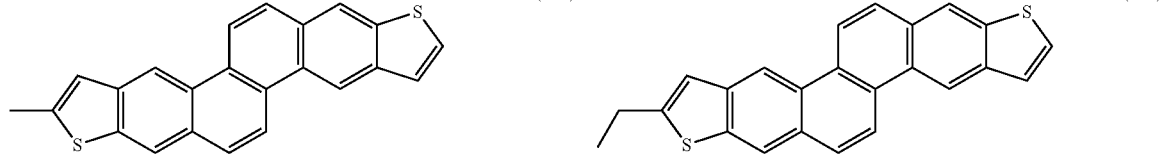
(254) (255)
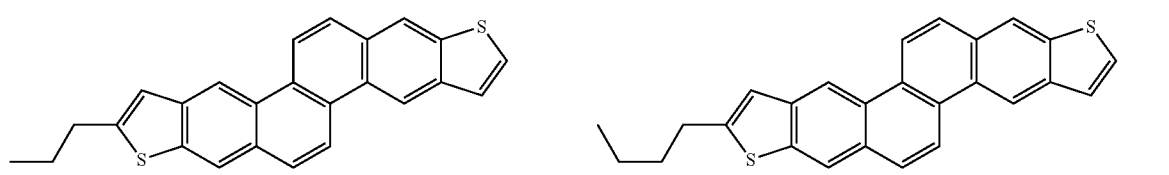
(256) (257)
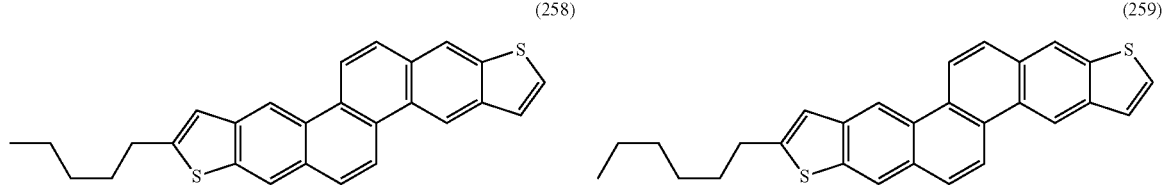
(258) (259)
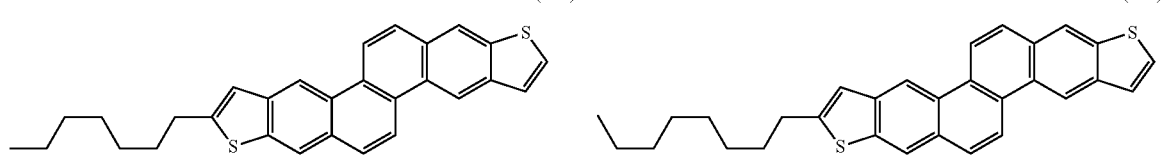
(260) (261)
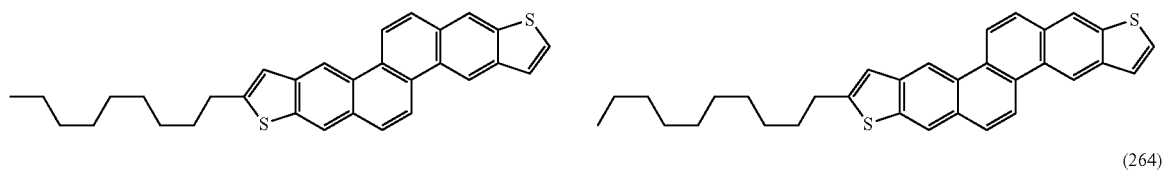
(262) (263)
(264)

-continued
(265)
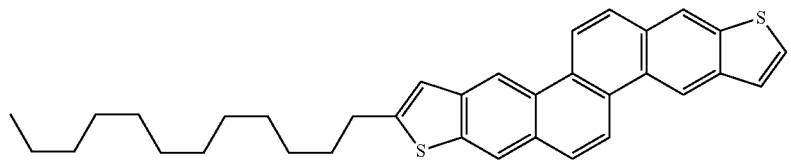
(266)
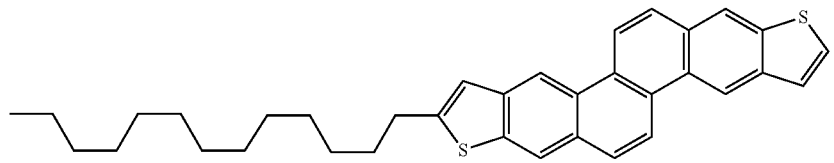
(267)
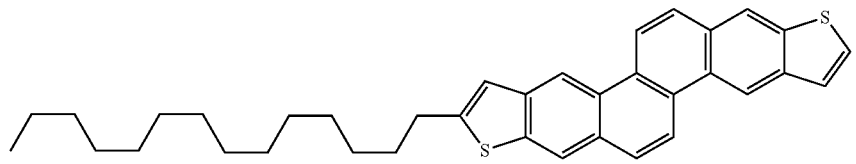
(268) (269)
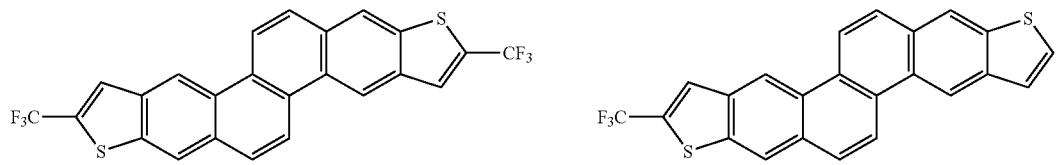
(270) (271)
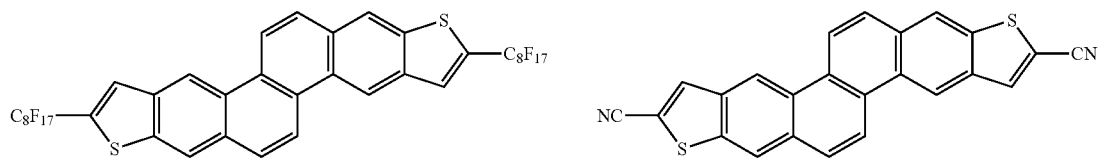
(272) (273)
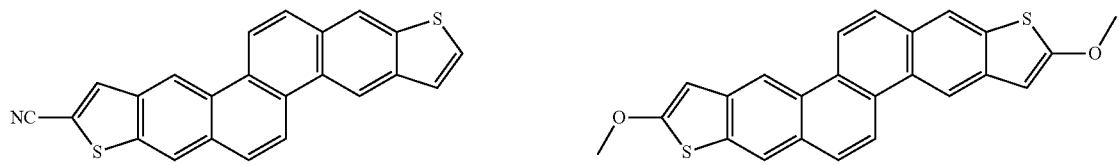
(274)
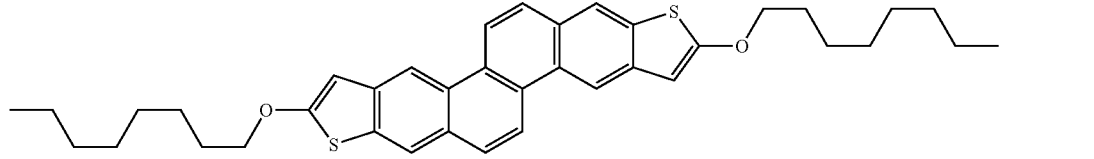
(275) (276)
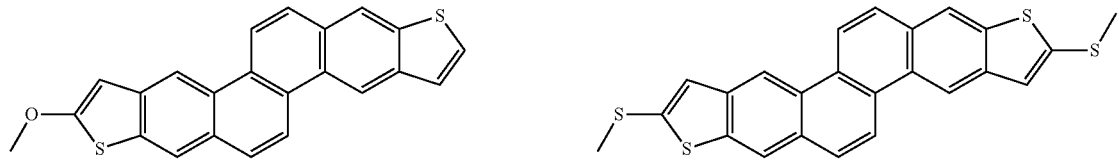
(277)
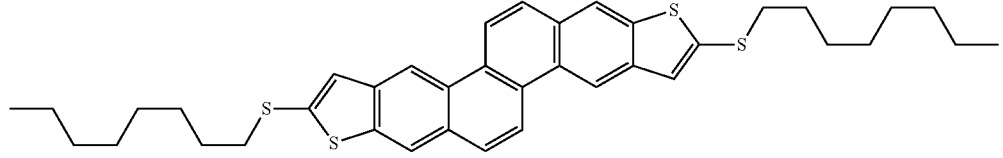

-continued
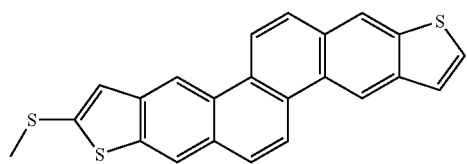
(278)
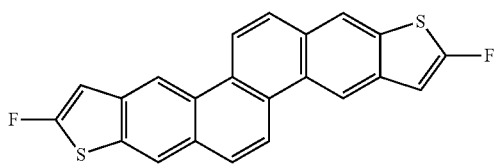
(279)
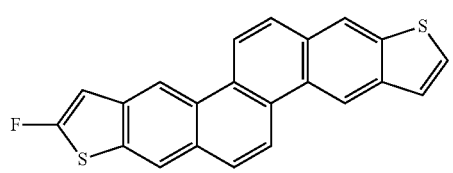
(280)
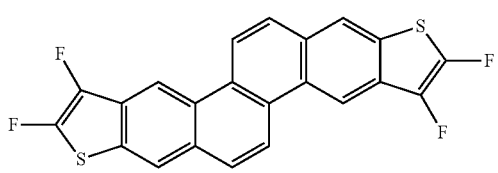
(281)
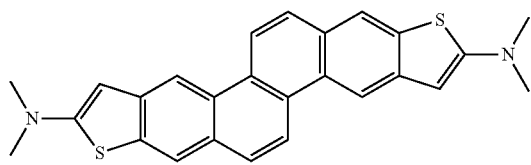
(282)
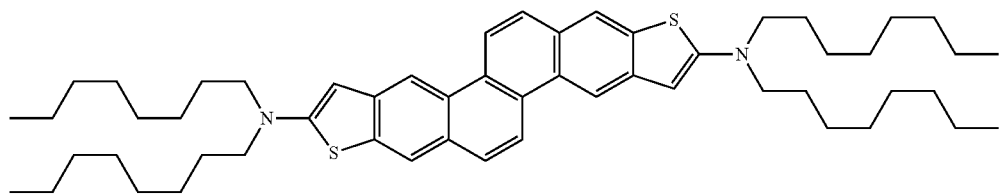
(283)
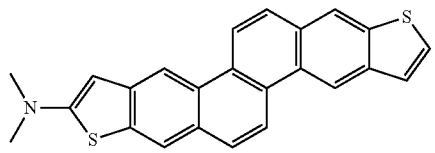
(284)
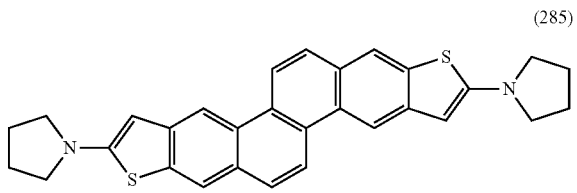
(285)
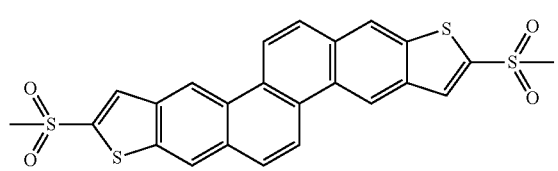
(286)
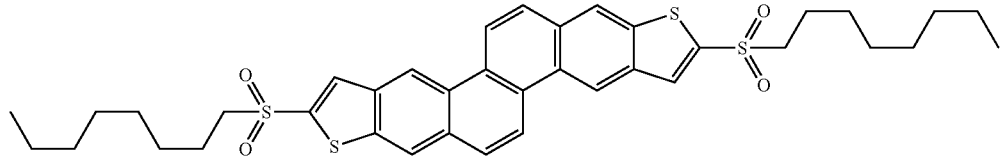
(287)
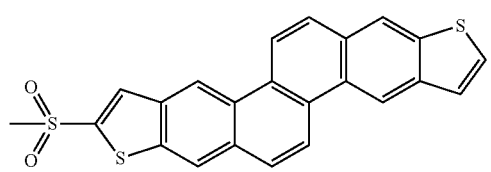
(288)
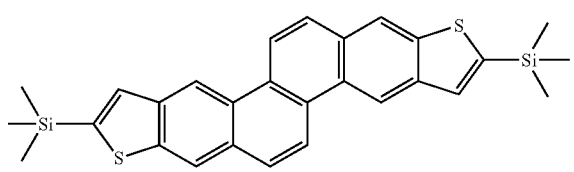
(289)

-continued
(290)
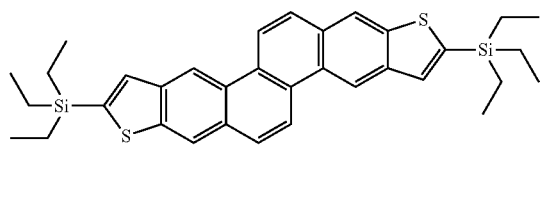
(291)
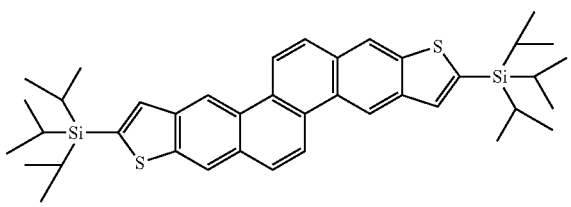
(292)
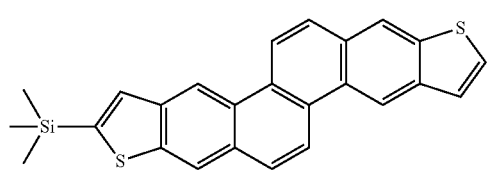
(293)
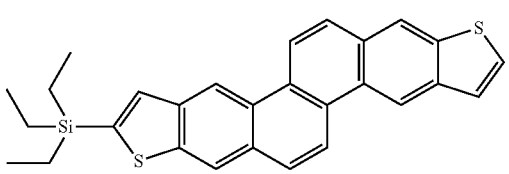
(294)
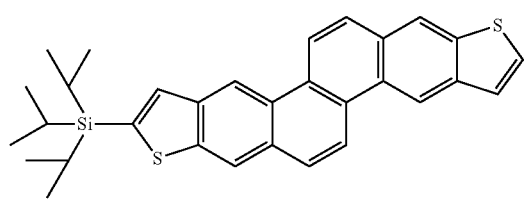
(295)
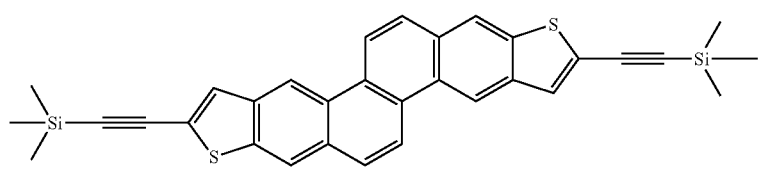
(296)
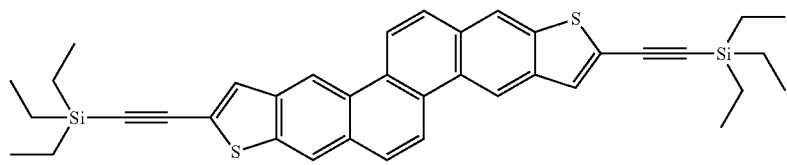
(297)
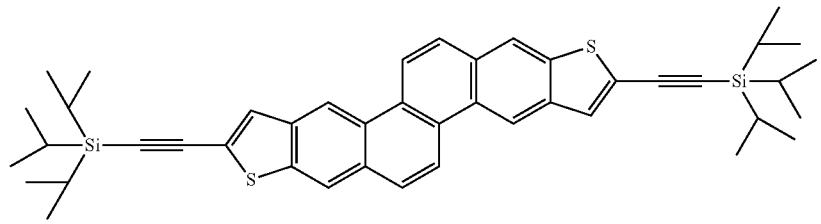
(298)
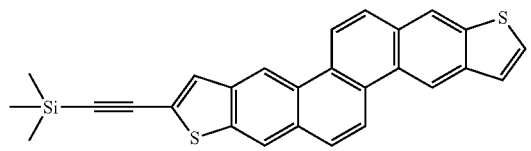
(299)
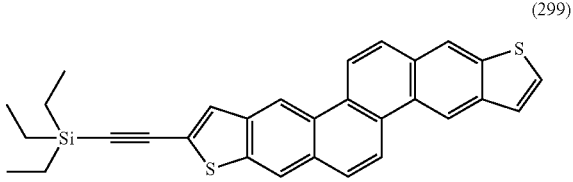
(300)
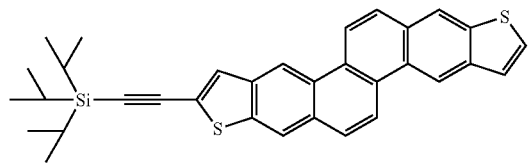
(301)
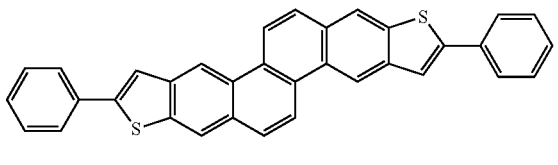

-continued
(302)
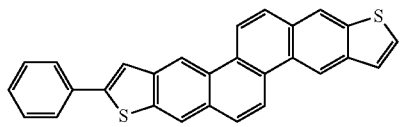
(303)
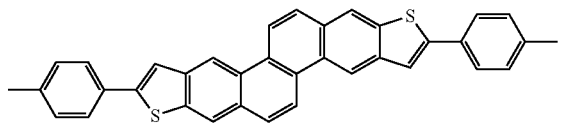
(304)
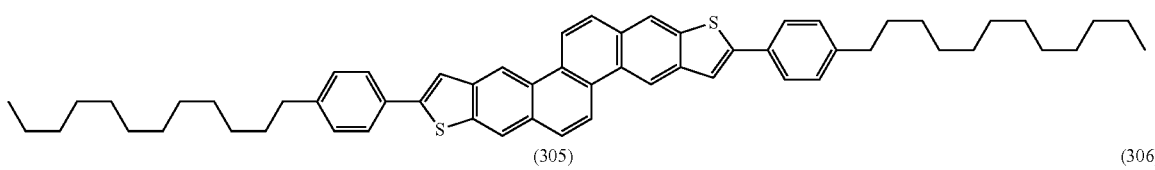
(305)
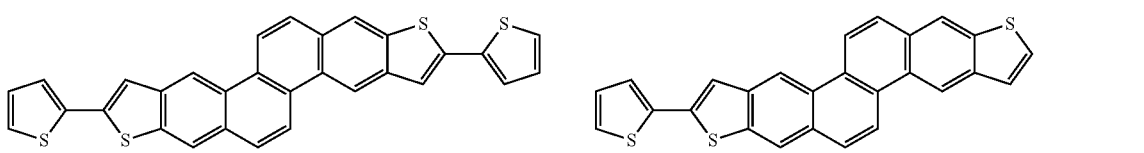
(306)
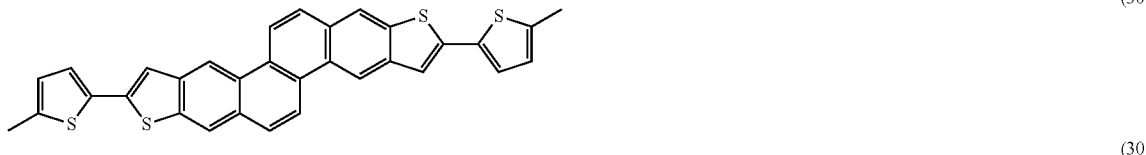
(307)
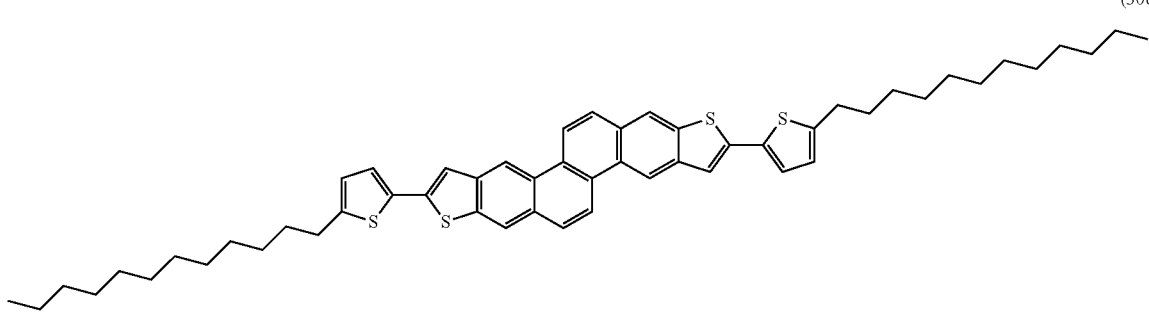
(308)
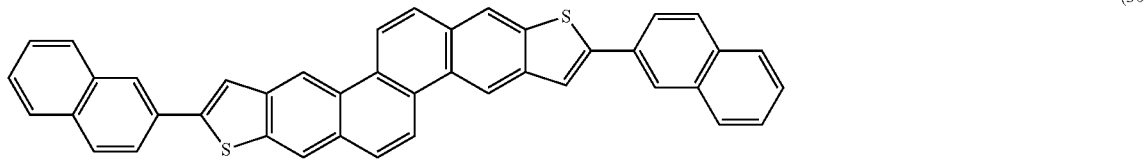
(309)
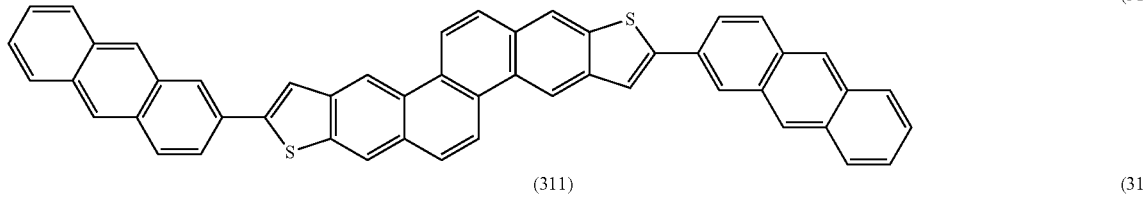
(310)
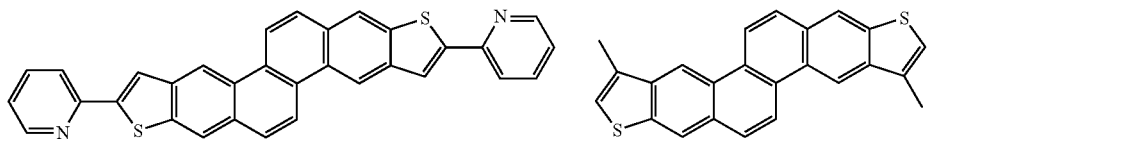
(311)
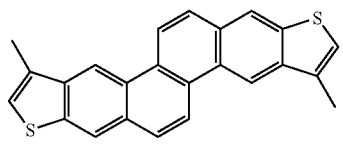
(312)
(313)

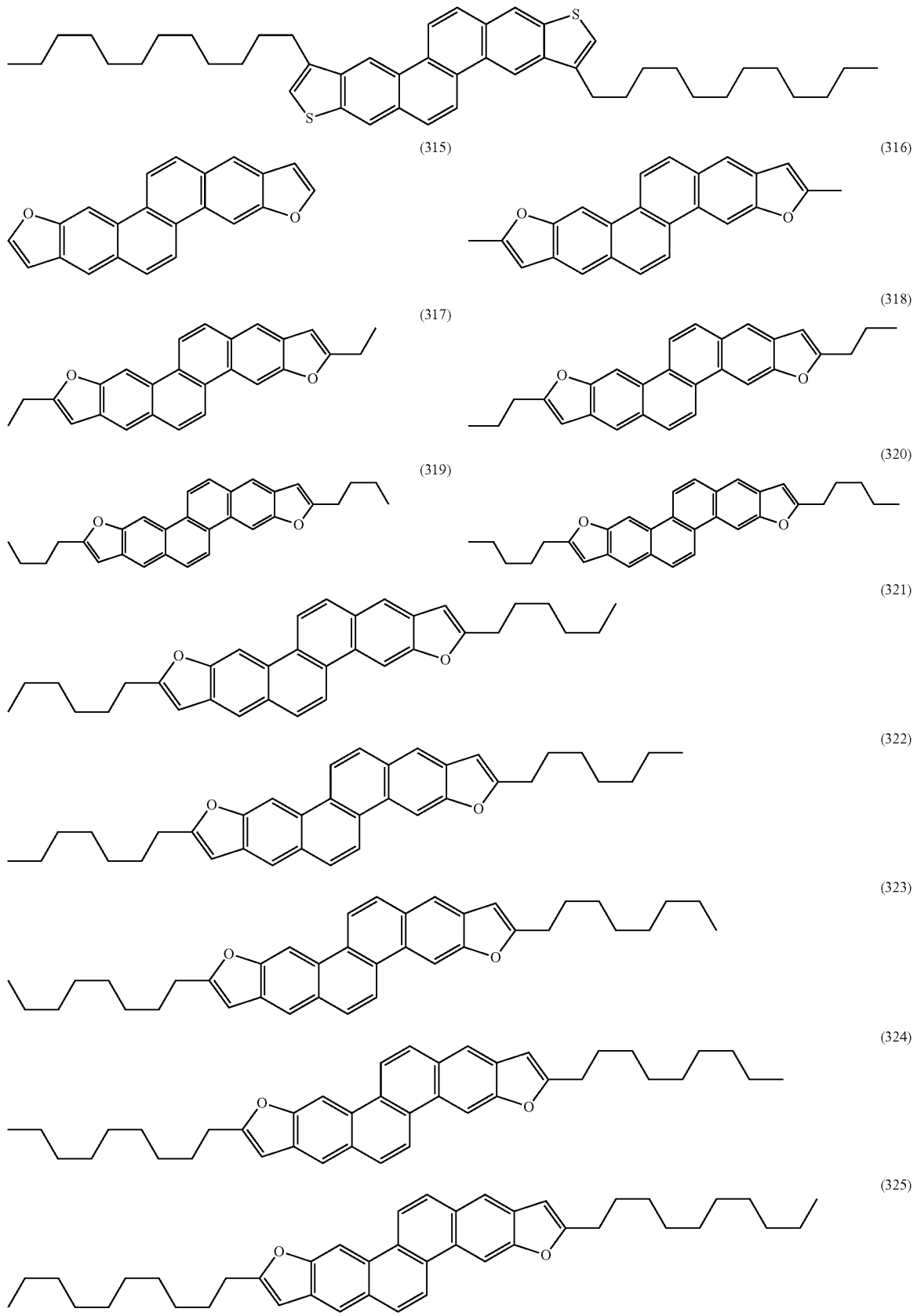

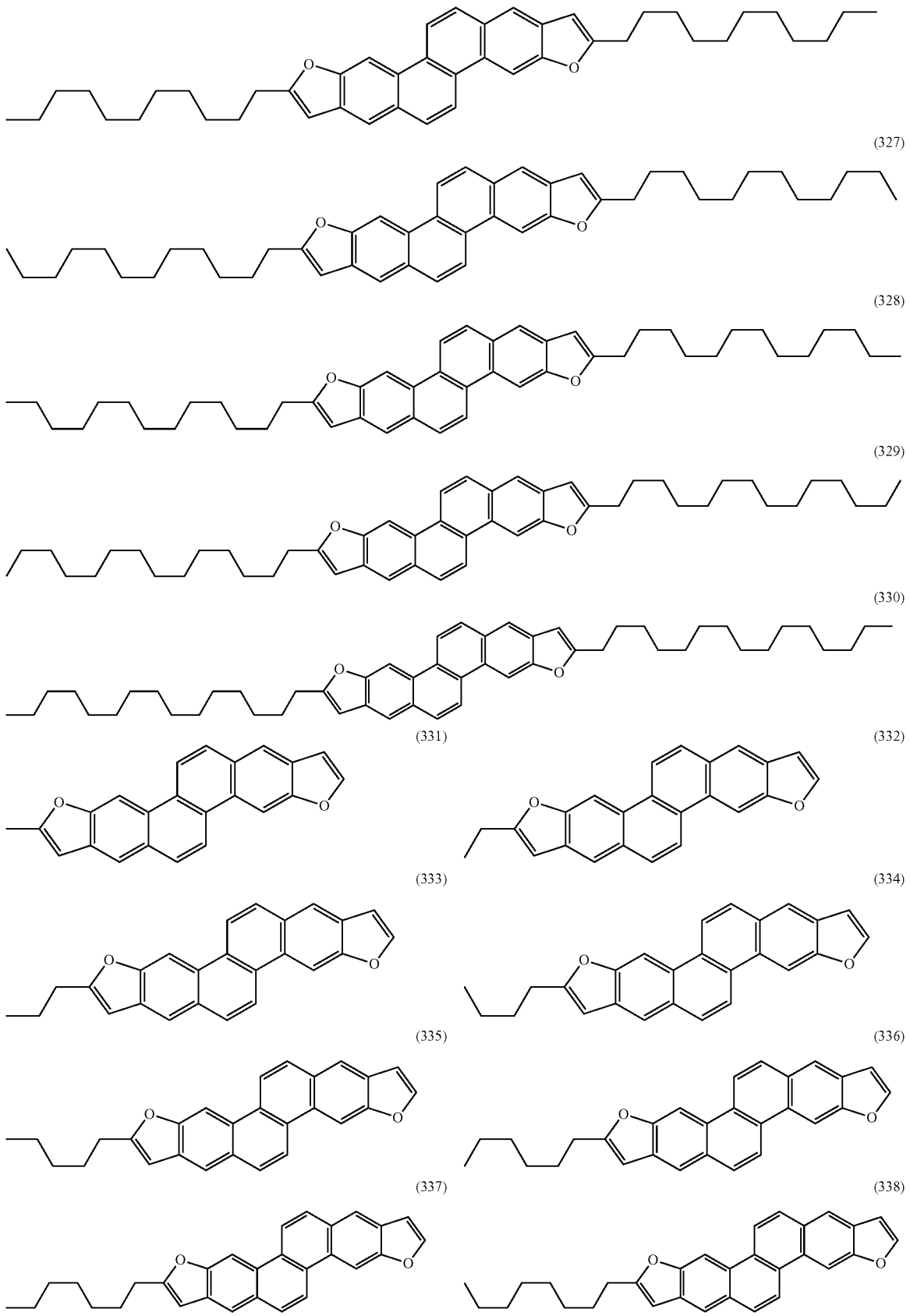

-continued
(339)
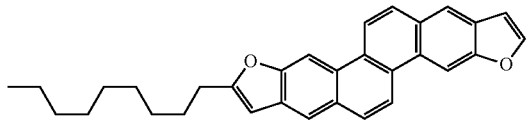
(340)
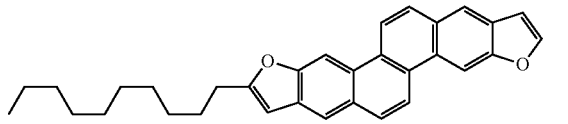
(341)
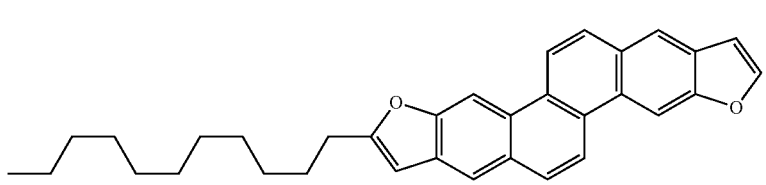
(342)
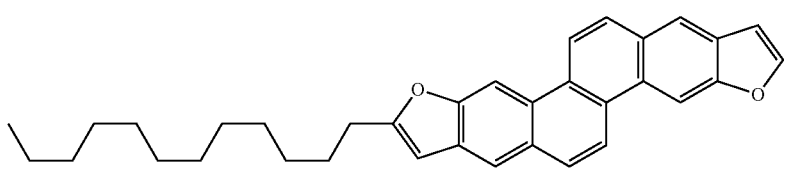
(343)
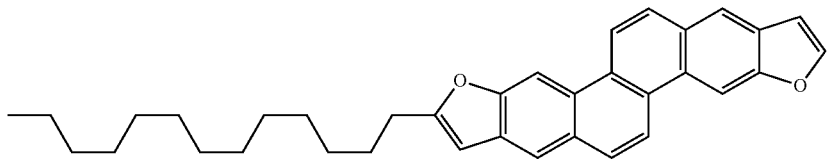
(344)
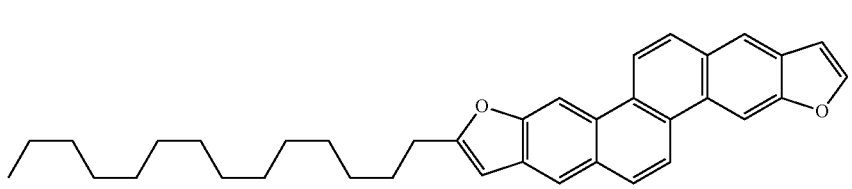
(345)
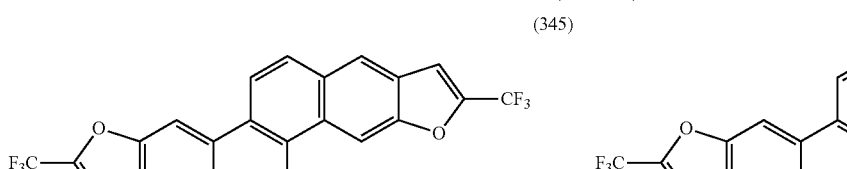
(346)
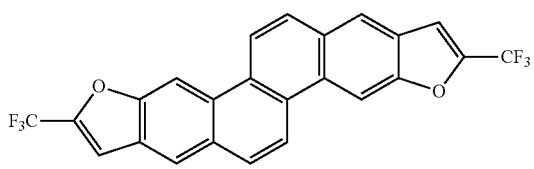
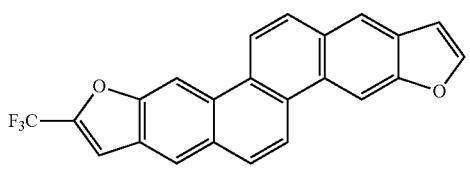
(347)
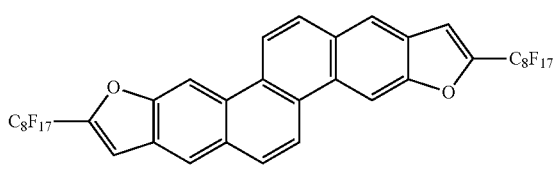
(348)
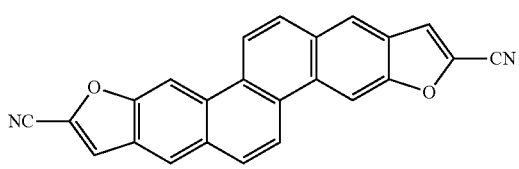
(349)
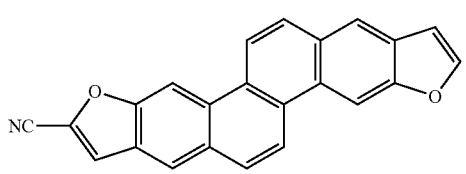
(350)
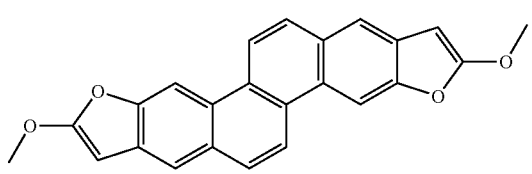
(351)
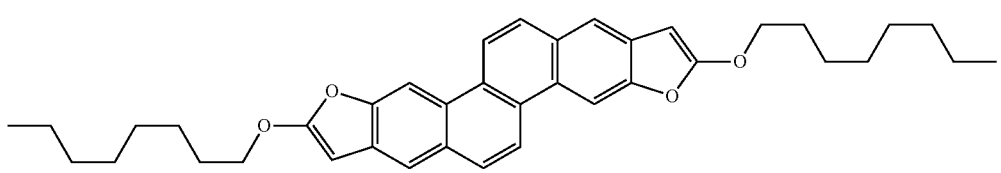

-continued
(352)
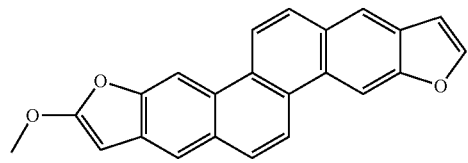
(353)
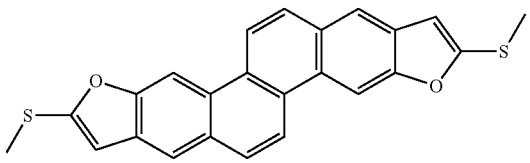
(354)
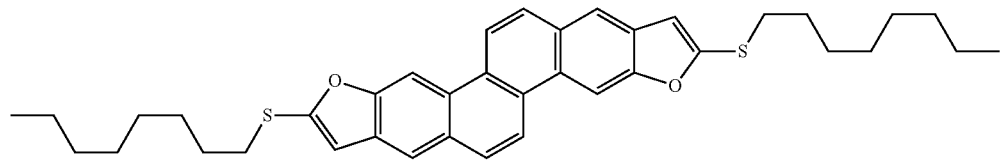
(355)
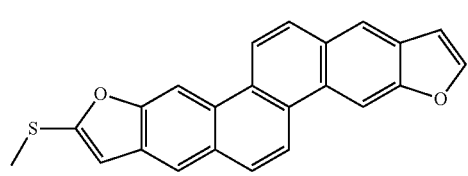
(356)
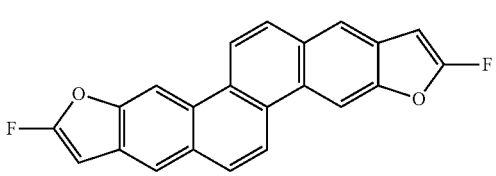
(357)
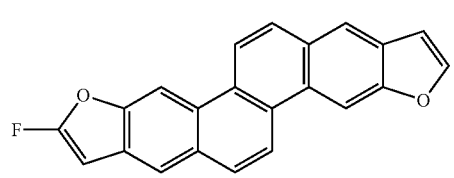
(358)
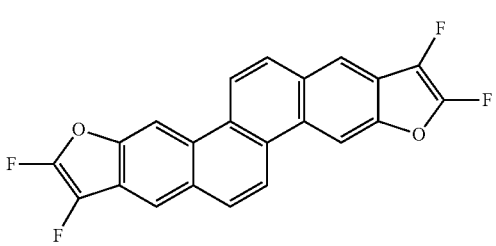
(359)
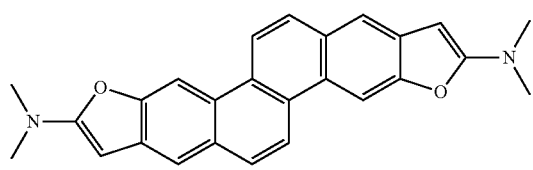
(360)
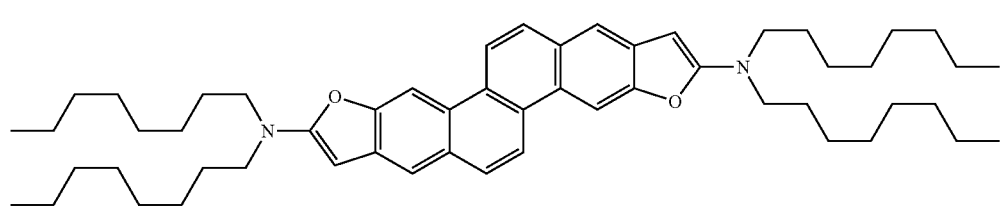
(361)
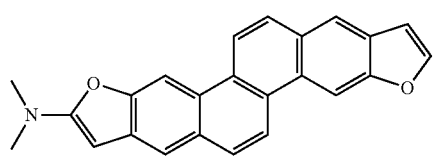
(362)
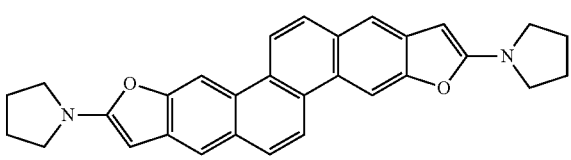
(363)
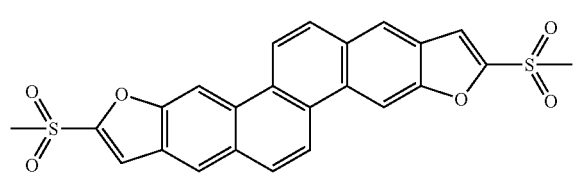

(364)
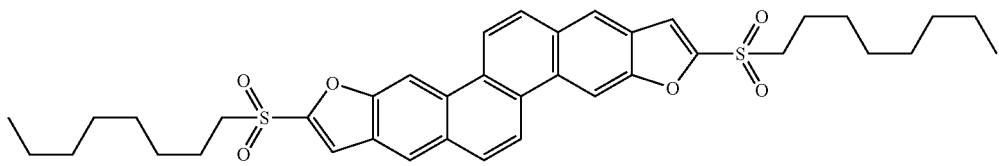
(365)
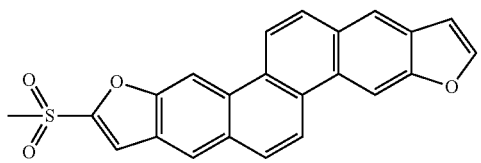
(366)
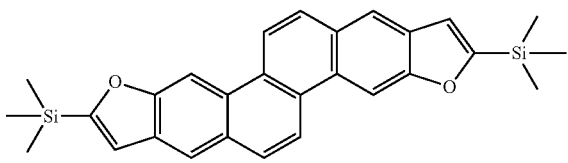
(367)
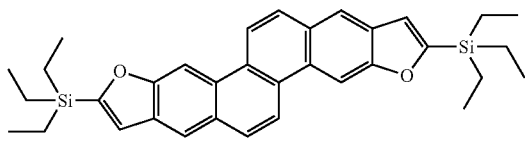
(368)
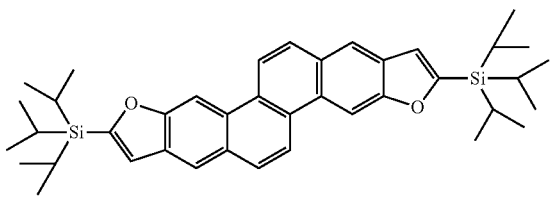
(369)
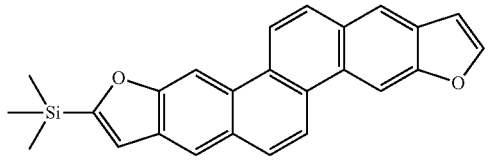
(370)
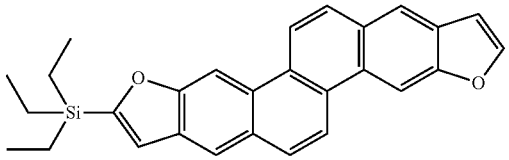
(371)
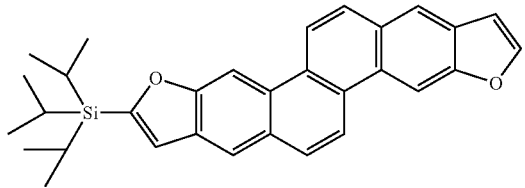
(372)
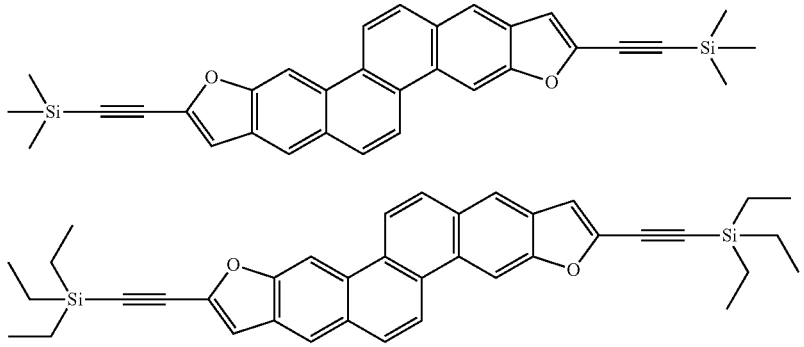
(373)
(374)
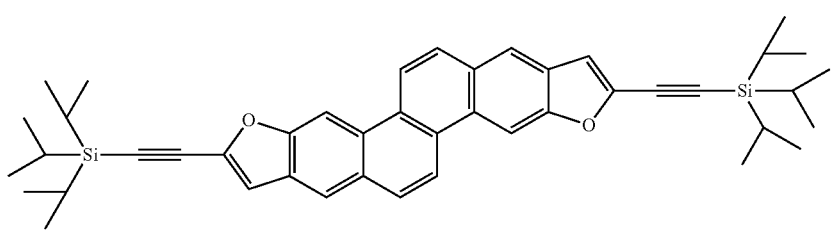

-continued
(375)
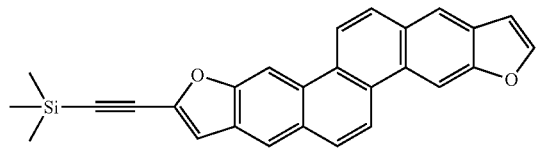
(376)
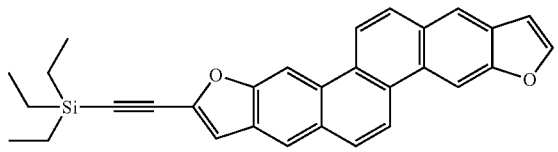
(377)
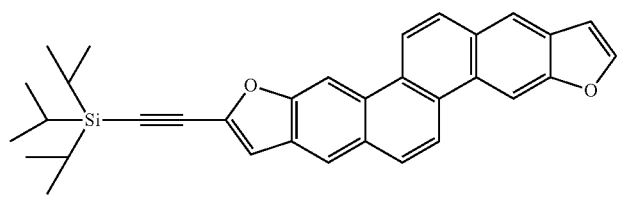
(378)
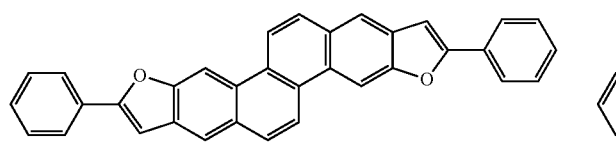
(379)
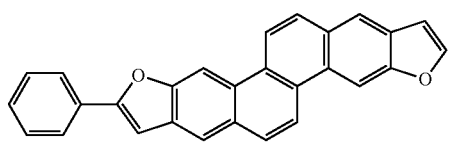
(380)
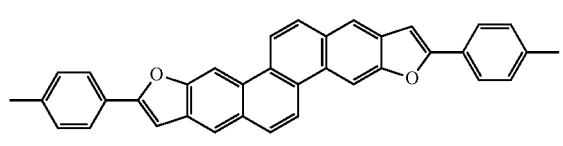
(381)
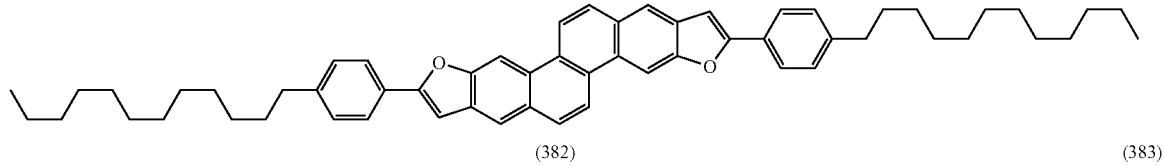
(382)
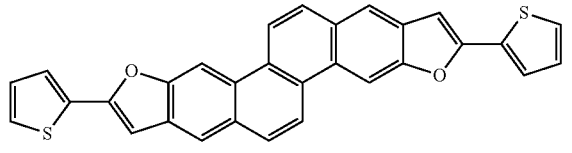
(383)
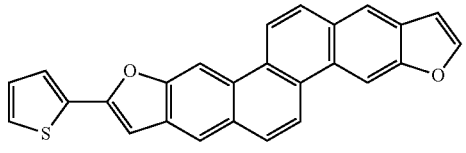
(384)
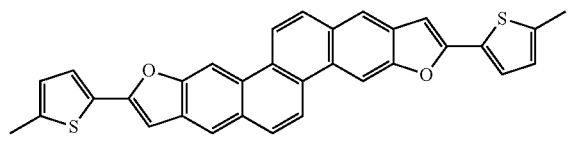
(385)
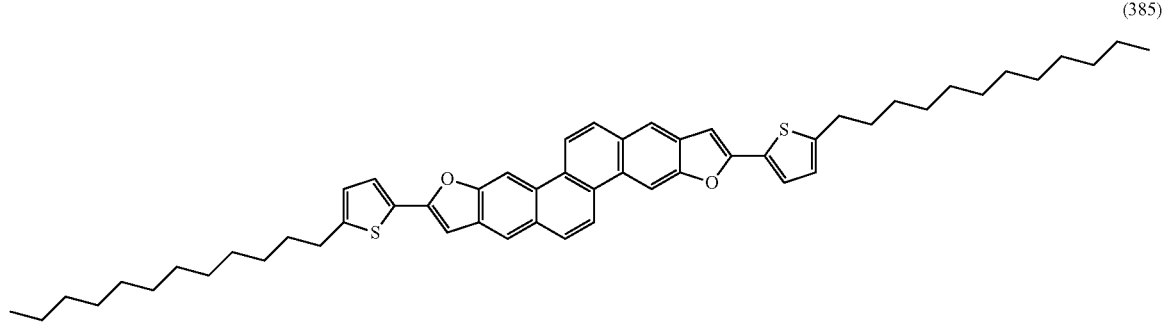

(386)
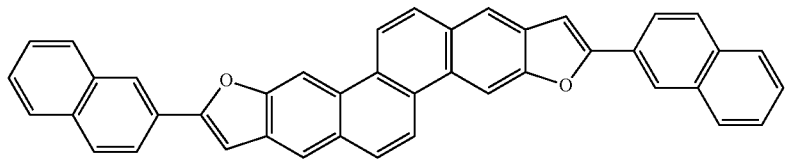
(387)
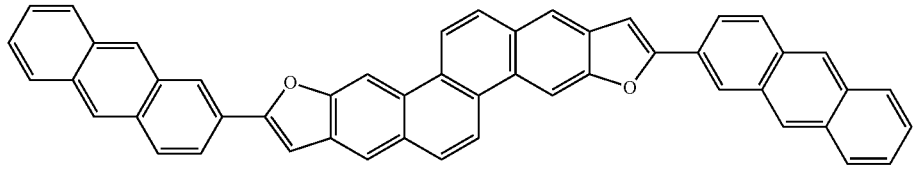
(388)
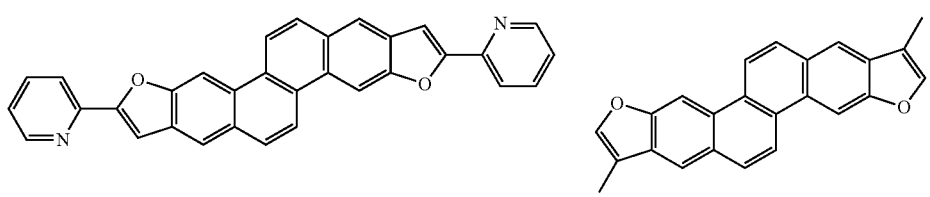
(389)
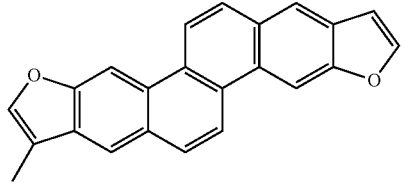
(390)
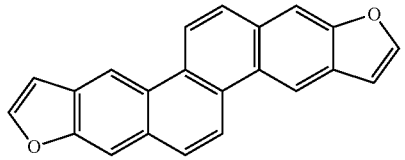
(391)
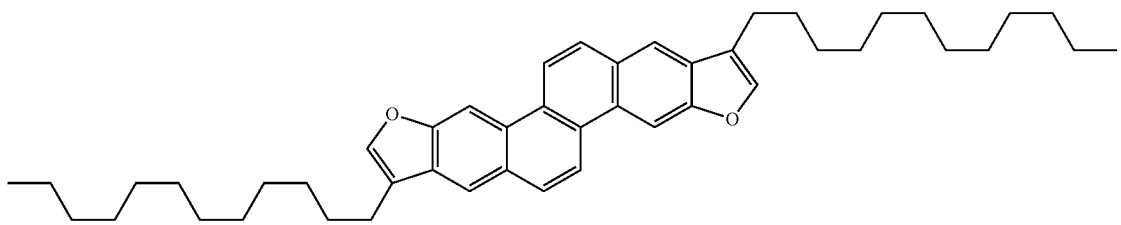
(392)
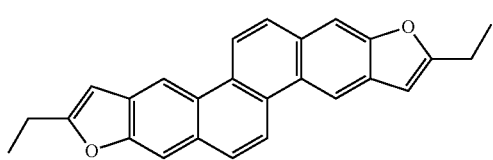
(393)
(394)
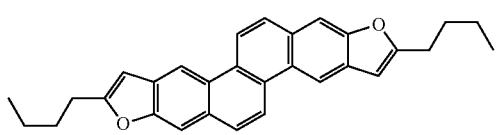
(395)
(396)
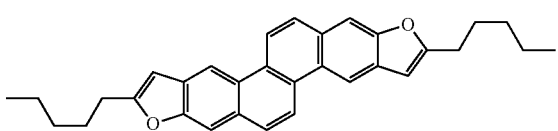
(397)

-continued
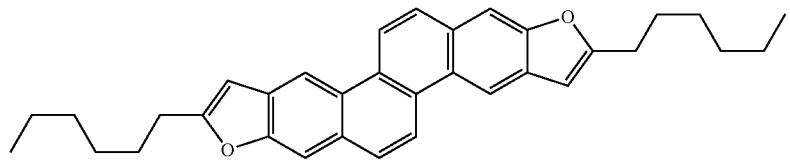
(398)
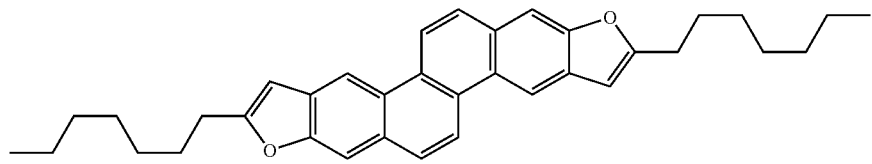
(399)
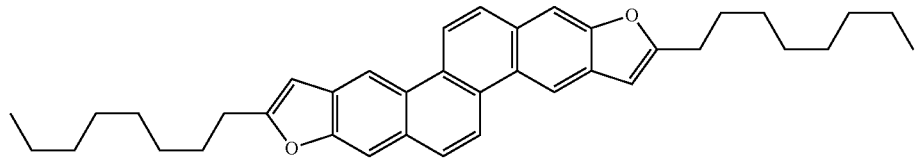
(400)
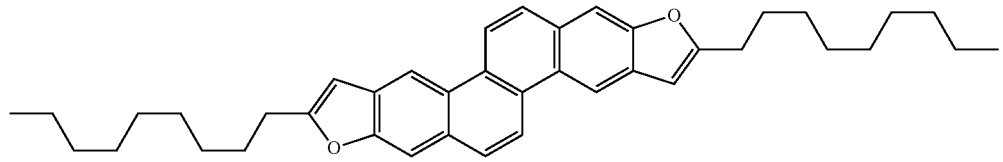
(401)
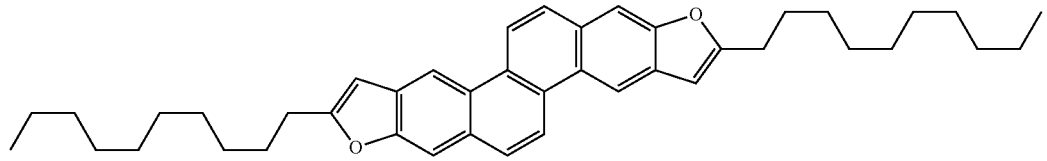
(402)
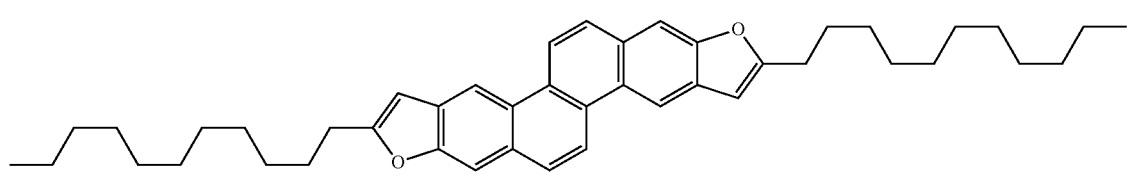
(403)
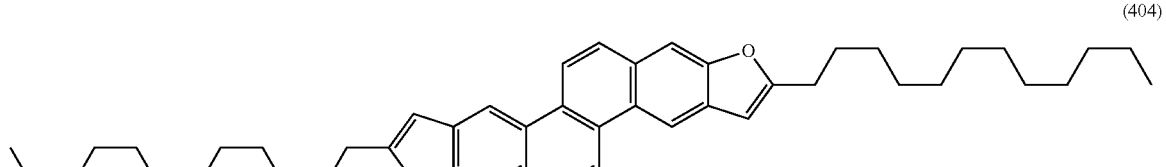
(404)
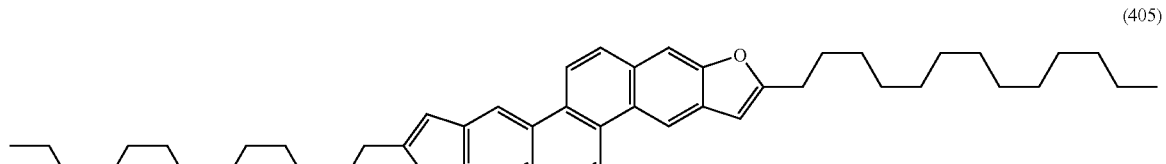
(405)
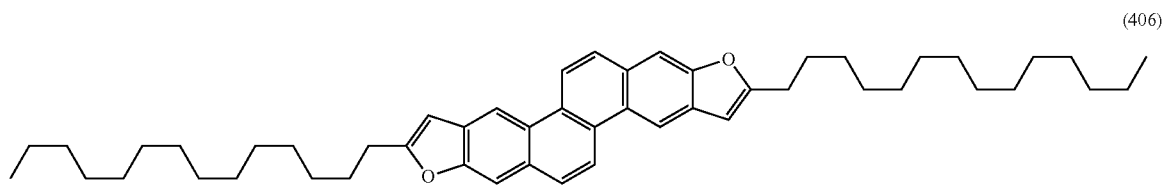
(406)

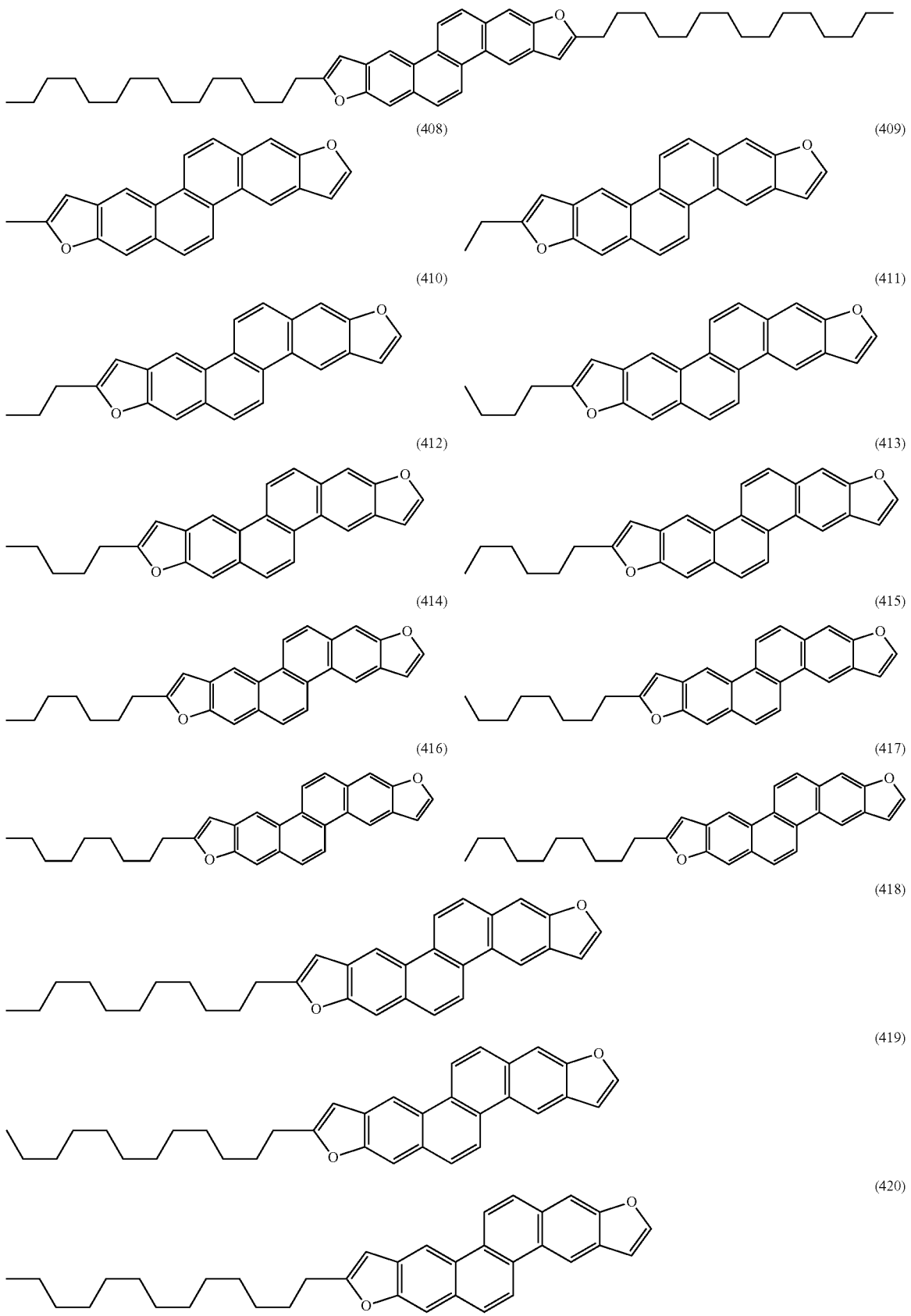

(421)
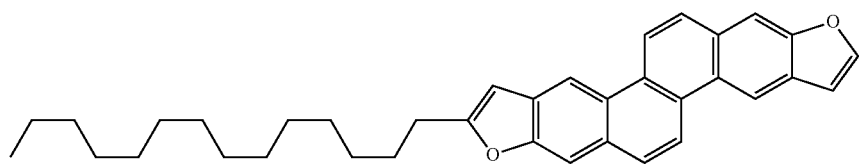
(422) 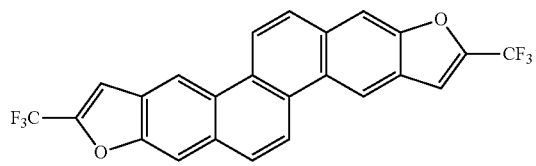 (423) 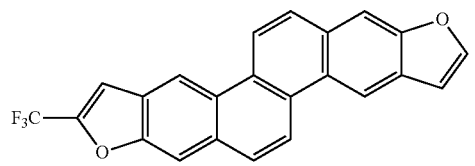
(424) 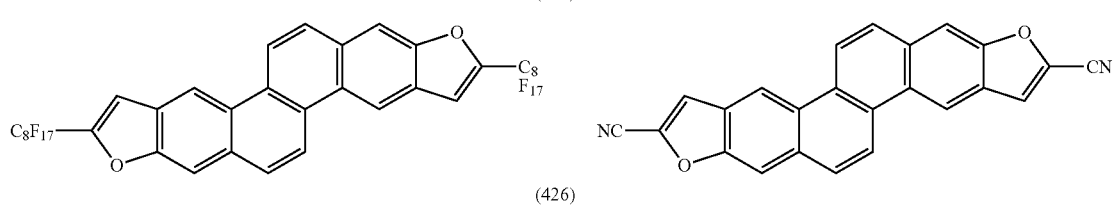 (425) 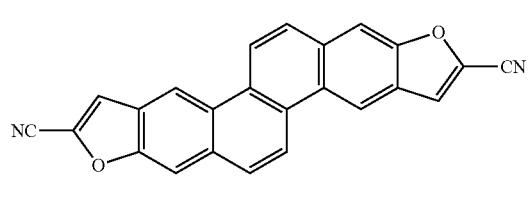
(426) (427)
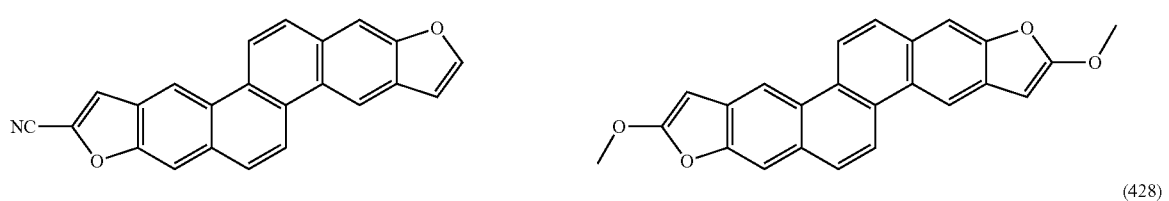
(428)
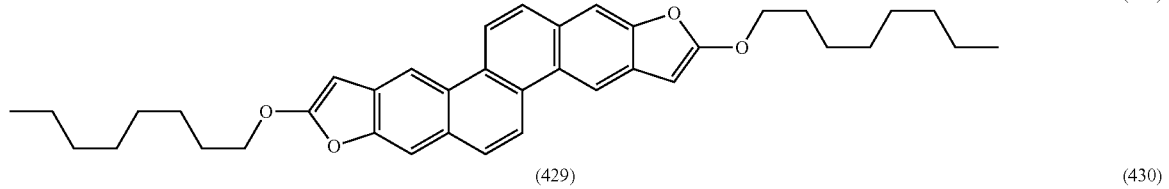
(429) (430)
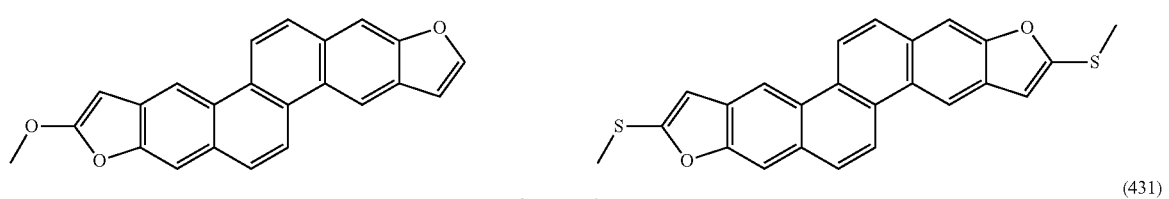
(431)
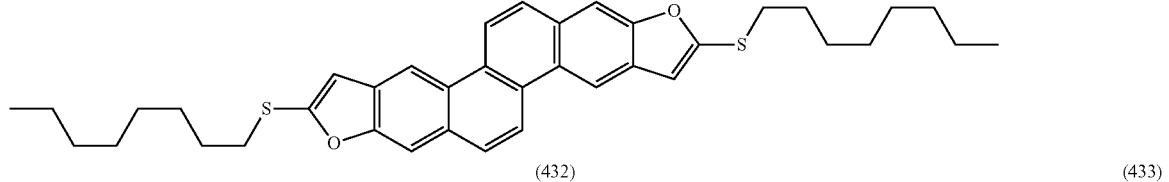
(432) (433)
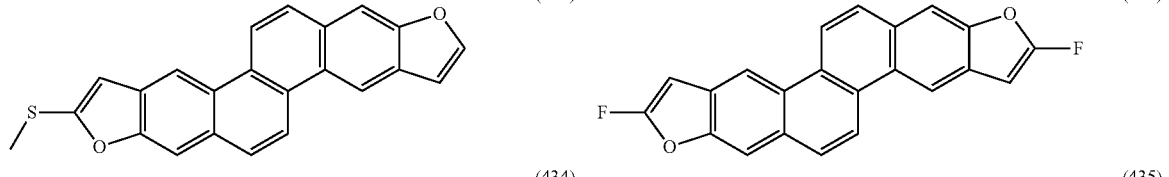
(434) (435)
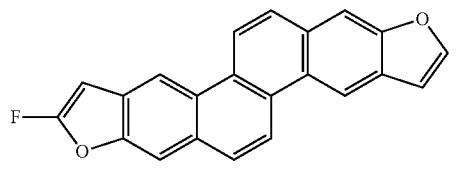 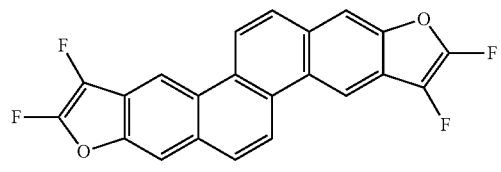

(436) 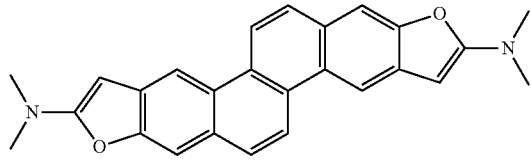
(437) 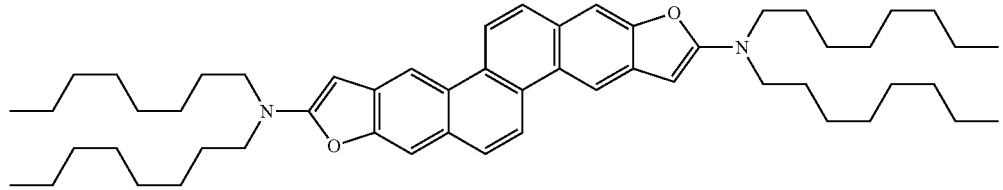
(438) 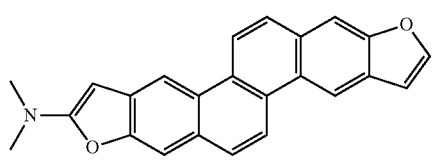
(439) 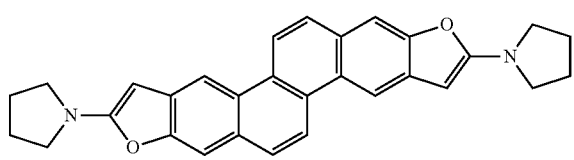
(440) 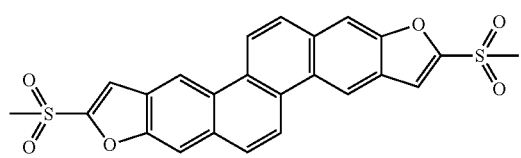
(441) 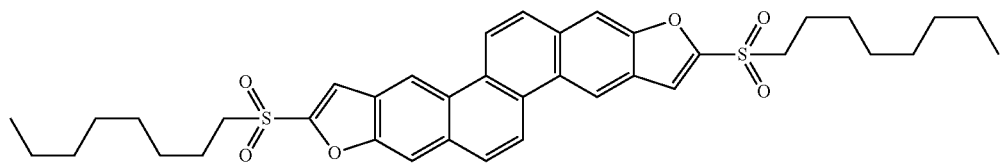
(442) 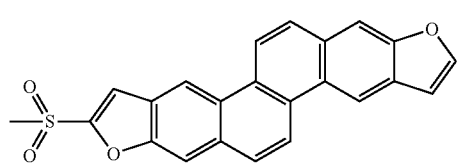
(443) 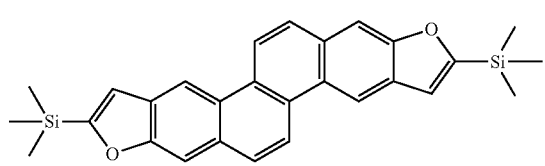
(444) 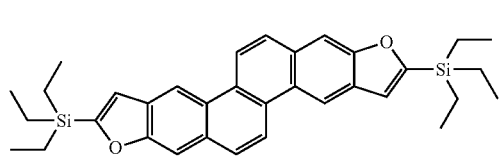
(445) 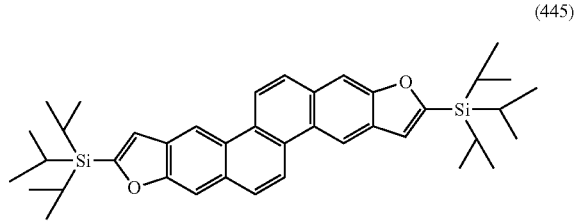
(446) 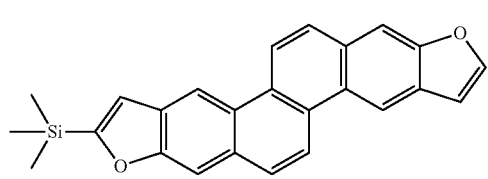
(447) 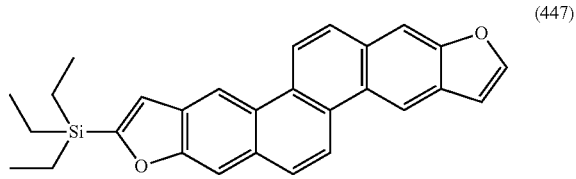

(448)
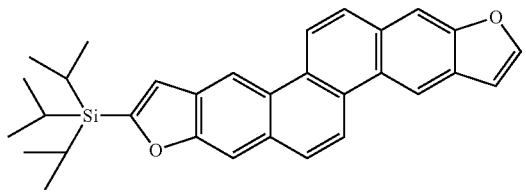
(449)
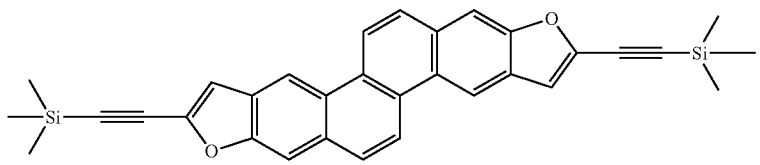
(450)
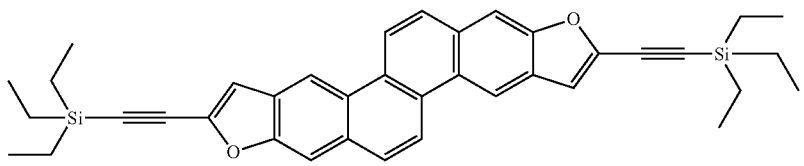
(451)
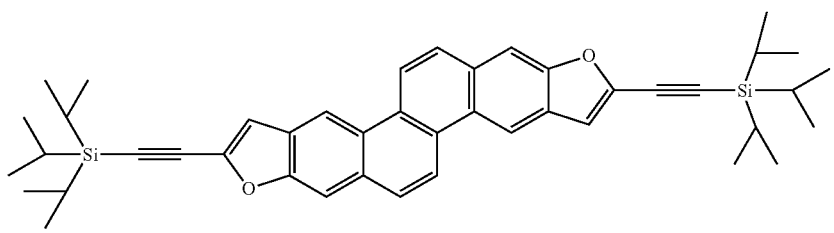
(452)
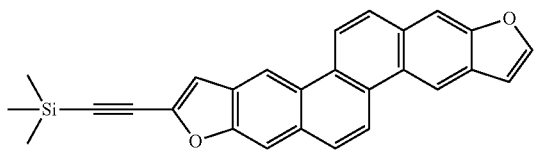
(453)
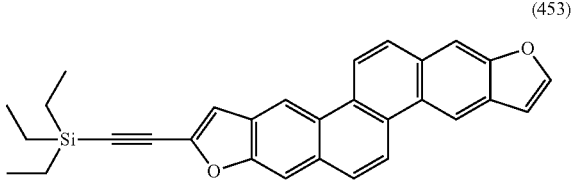
(454)
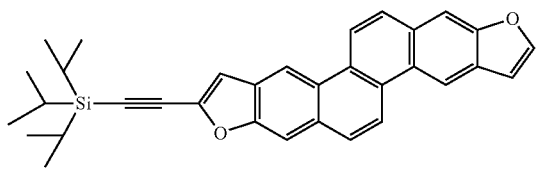
(455)
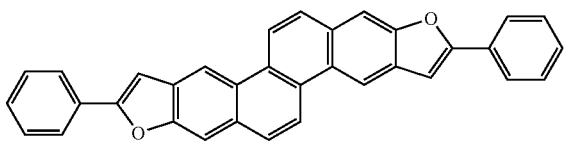
(456)
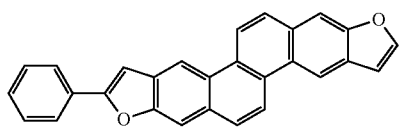
(457)
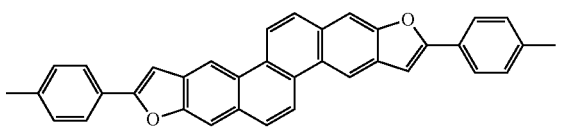
(458)
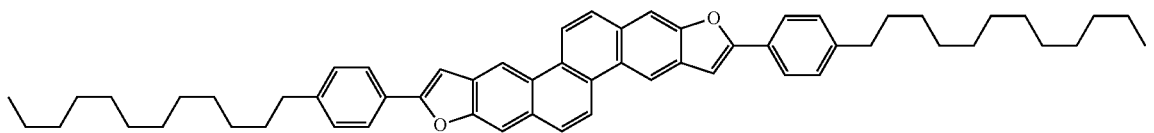

-continued
(459)
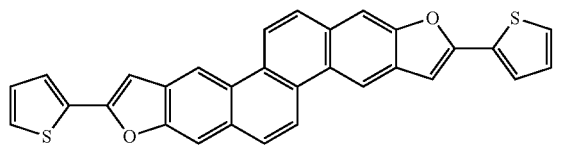
(460)
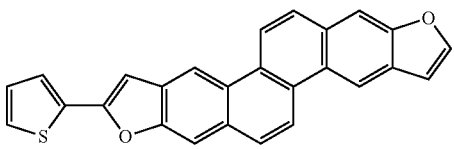
(461)
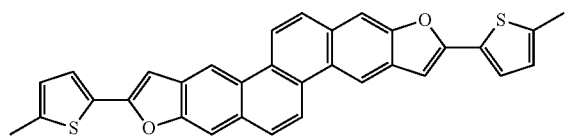
(462)
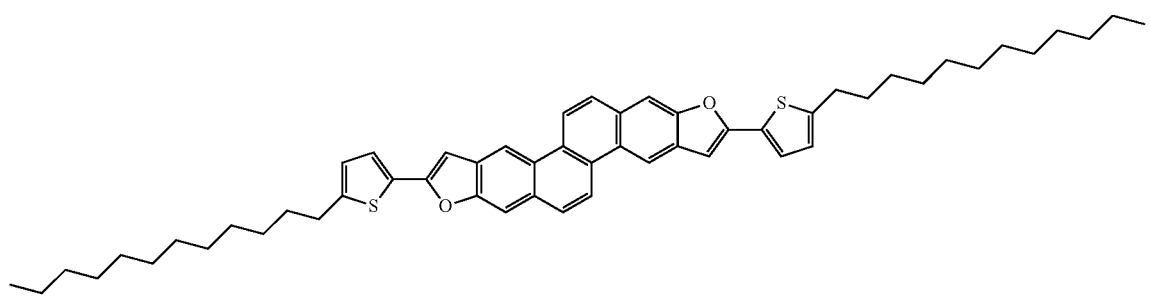
(463)
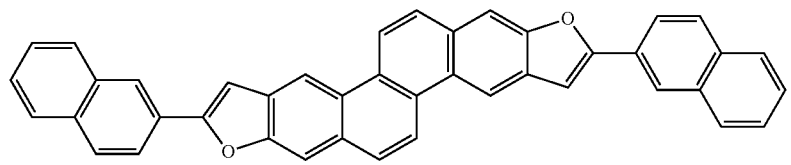
(464)
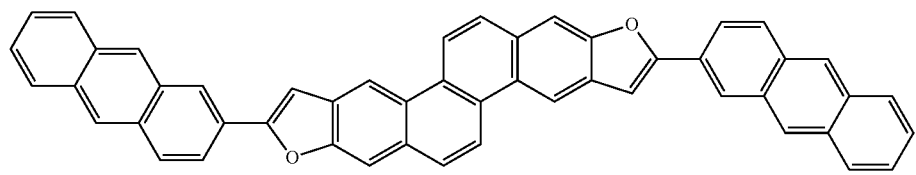
(465)
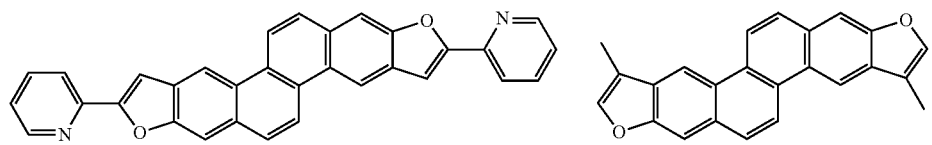
(466)
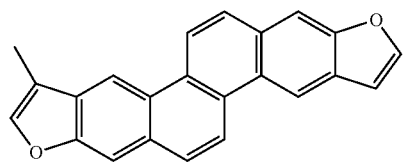
(467)
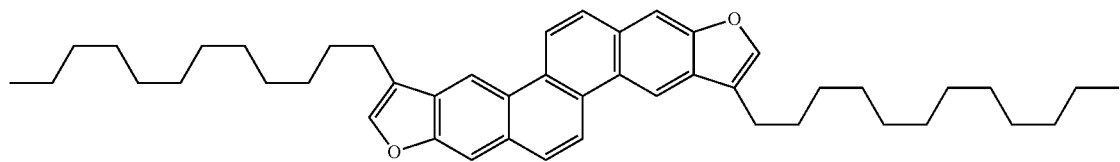
(468)

(469) 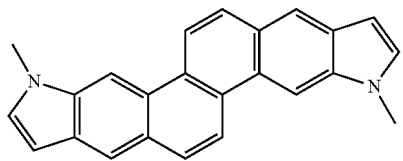
(470) 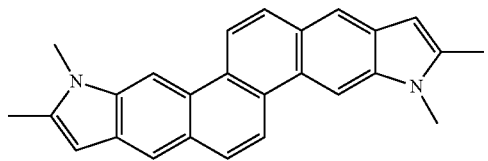
(471) 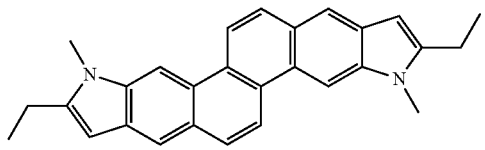
(472) 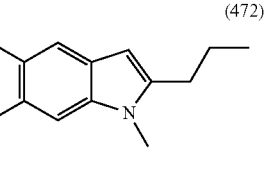
(473) 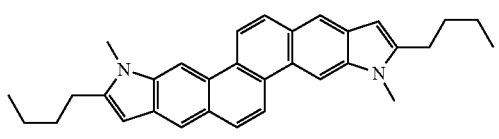
(474) 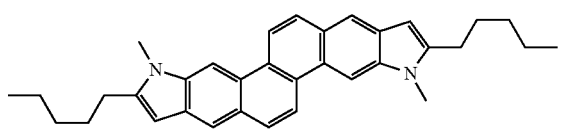
(475) 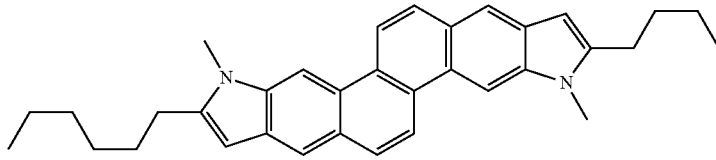
(476) 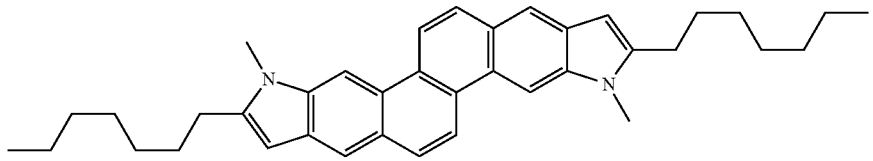
(477) 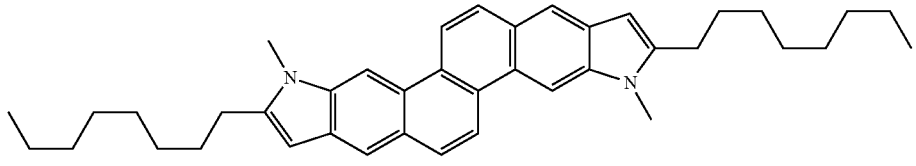
(478) 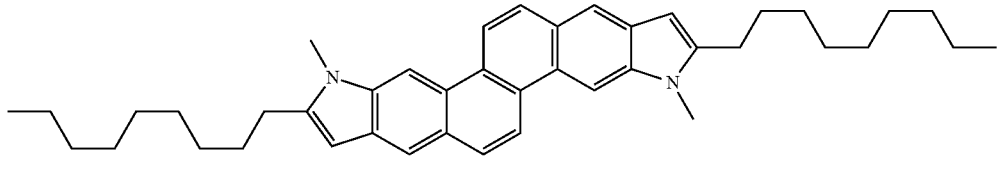
(479) 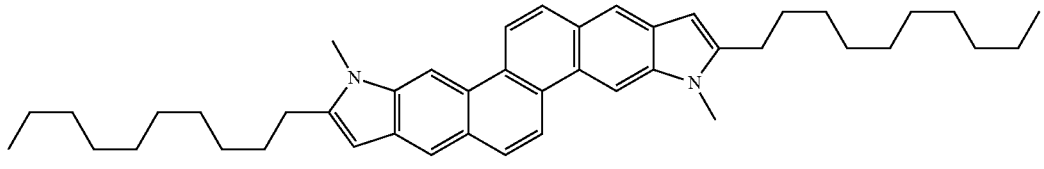
(480) 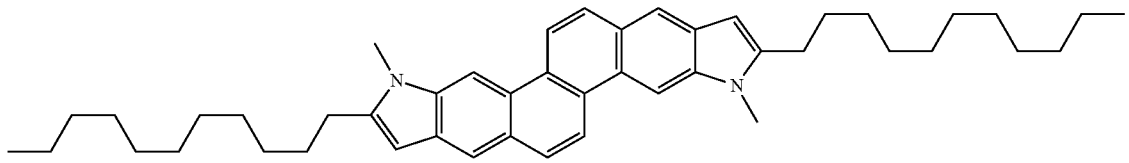

-continued
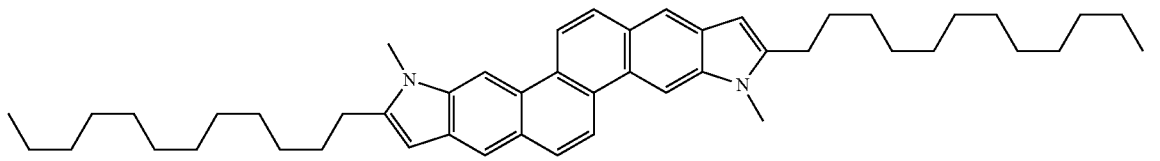
(481)
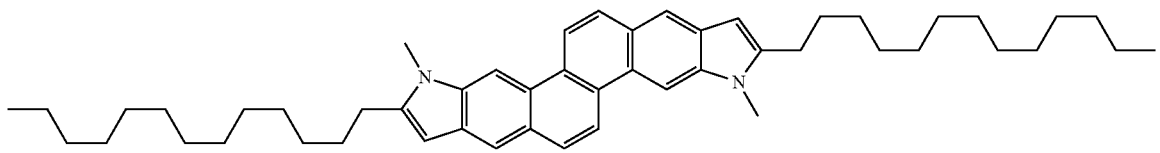
(482)
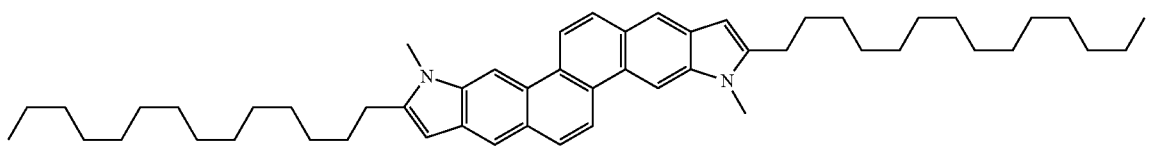
(483)
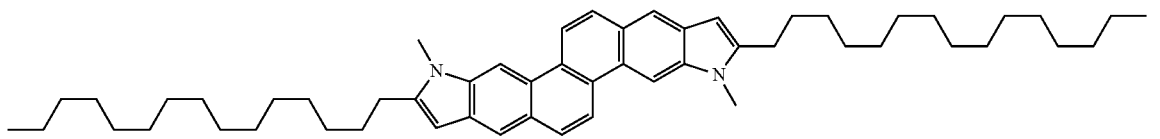
(484)
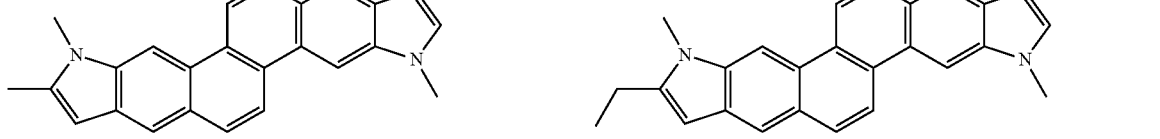
(485) (486)
(487) (488)
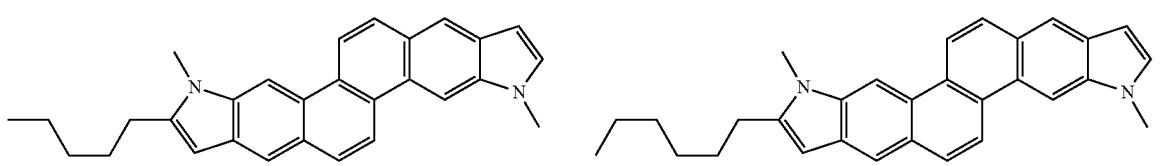
(489) (490)
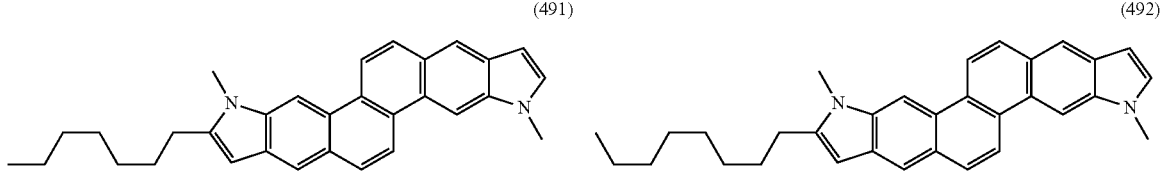
(491) (492)
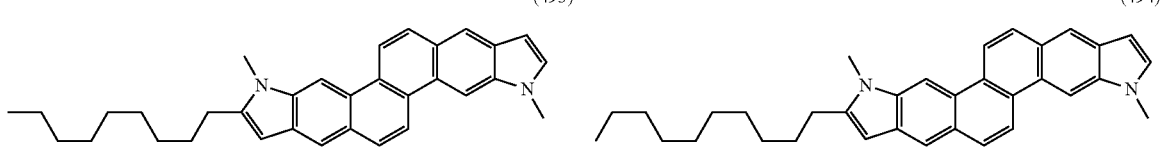
(493) (494)

-continued
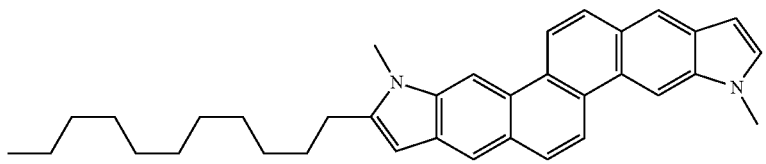
(495)
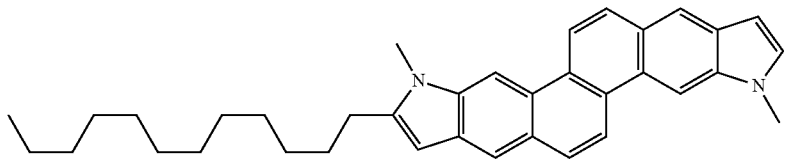
(496)
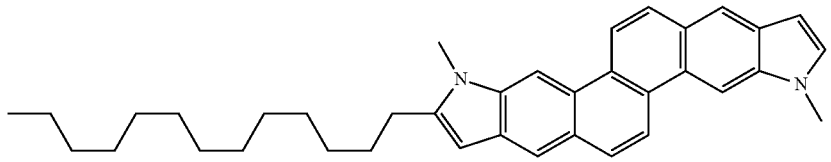
(497)
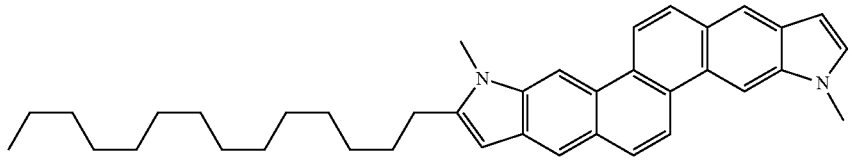
(498)
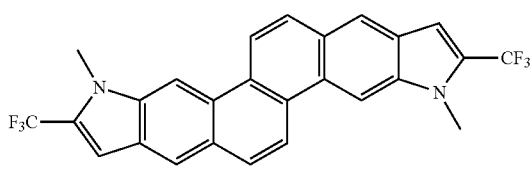
(499)
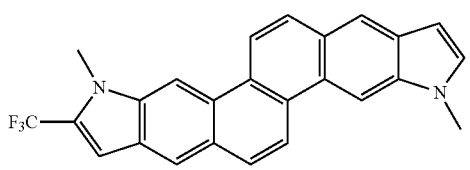
(500)
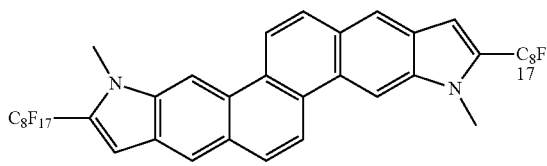
(501)
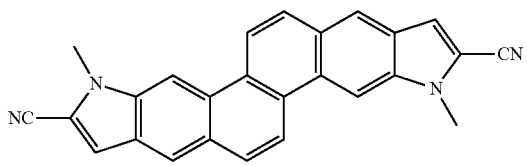
(502)
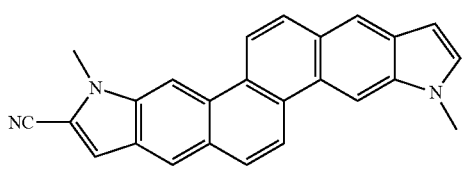
(503)
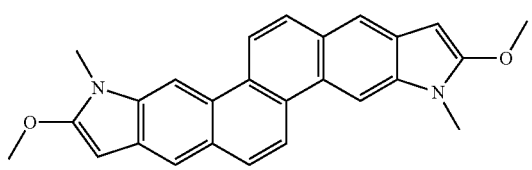
(504)
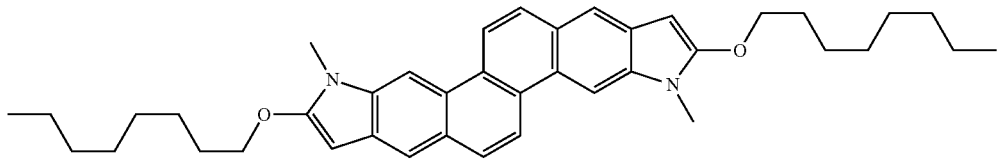
(505)
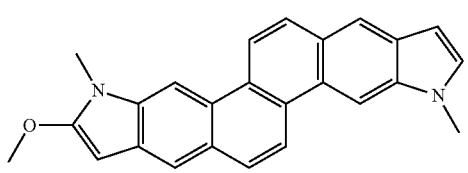
(506)
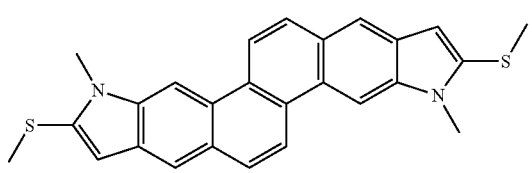
(507)

(508)
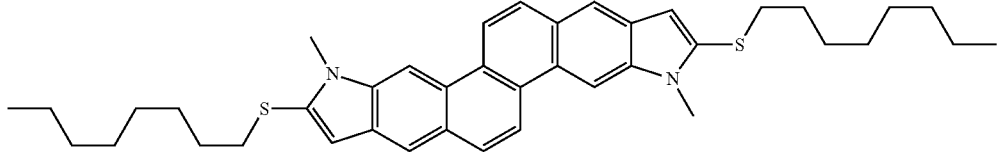
(509)
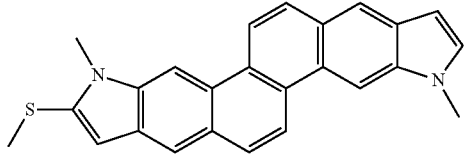
(510)
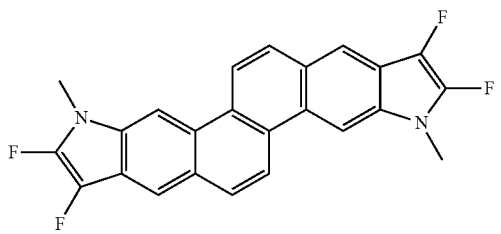
(511)
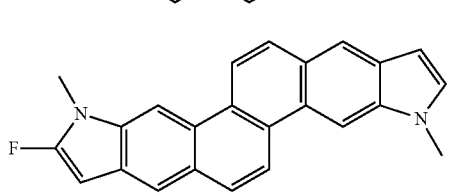
(512)
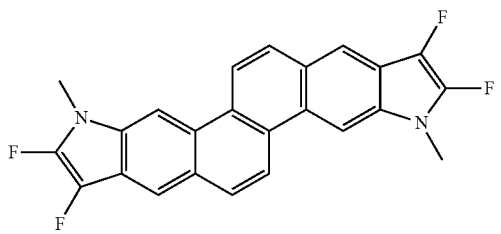
(513)
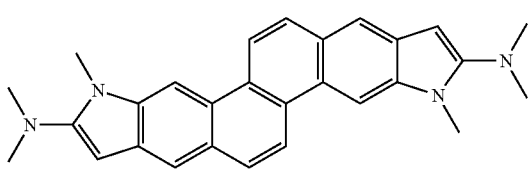
(514)
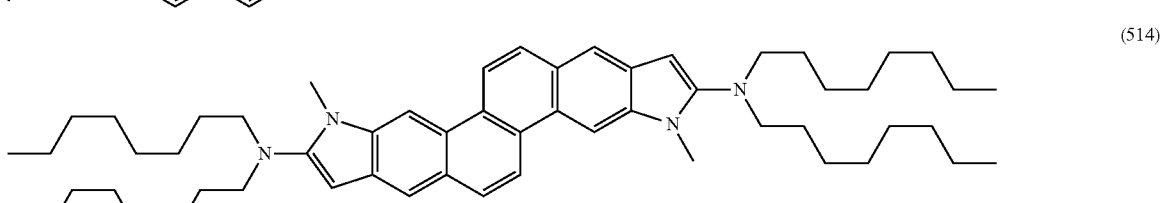
(515)
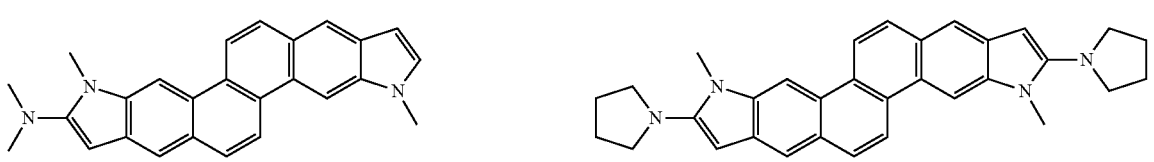
(516)
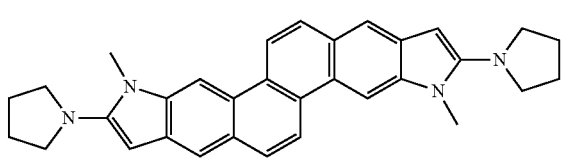
(517)
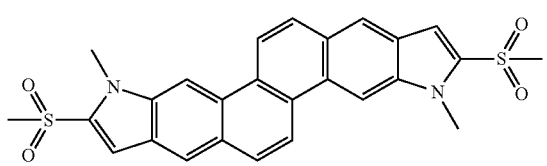
(518)
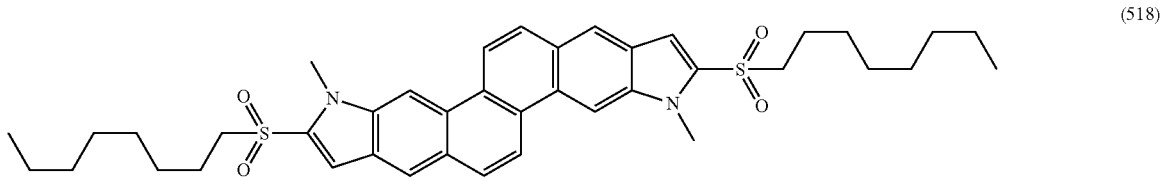

-continued
(519)
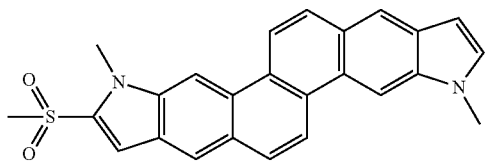
(520)
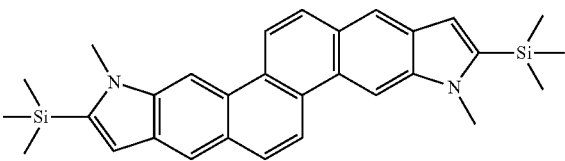
(521)
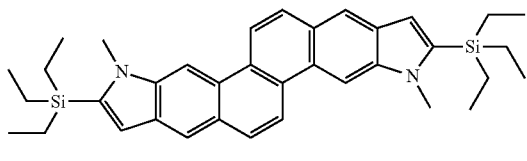
(522)
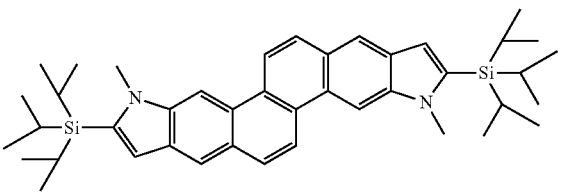
(523)
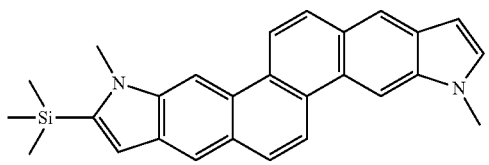
(524)
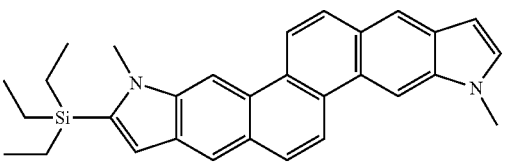
(525)
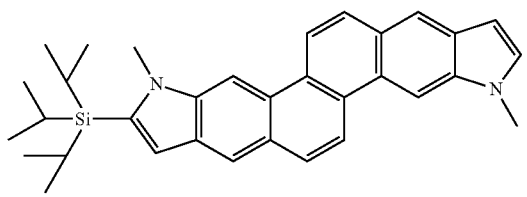
(526)
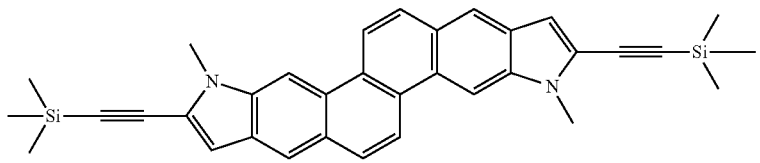
(527)
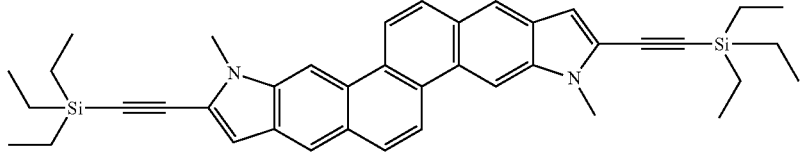
(528)
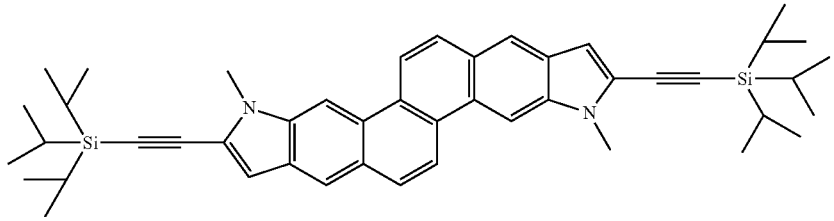
(529)
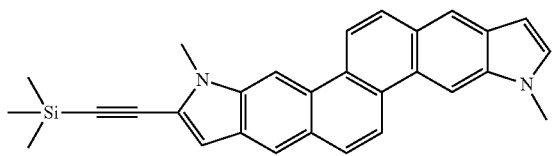
(530)
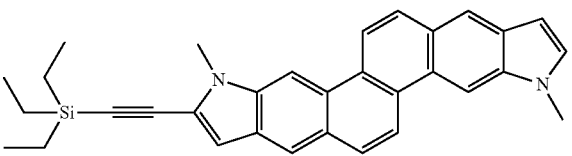

-continued
(531)
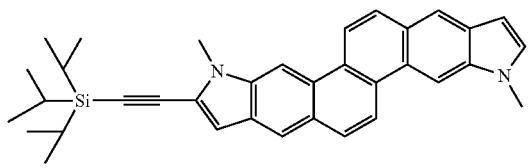
(532)
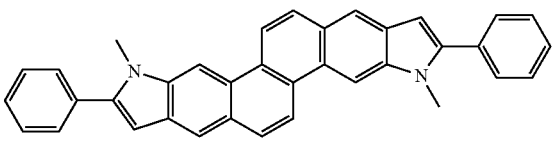
(533)
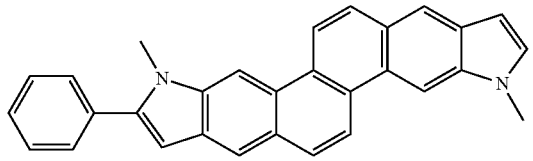
(534)
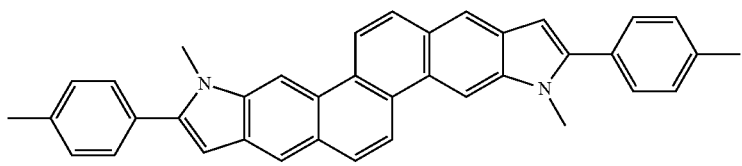
(535)
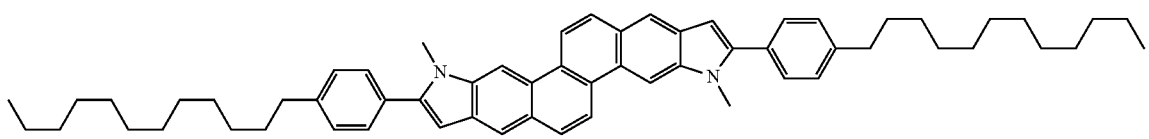
(536)
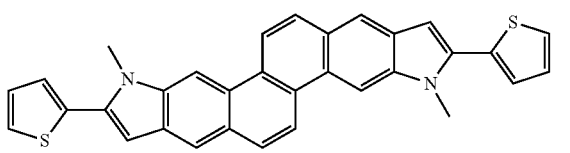
(537)
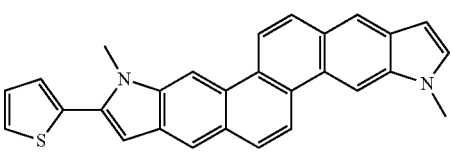
(538)
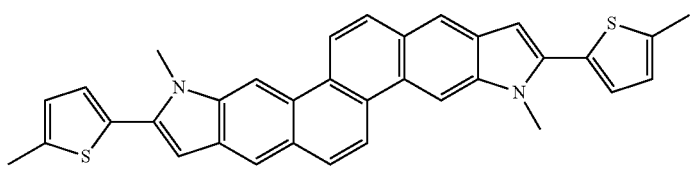
(539)
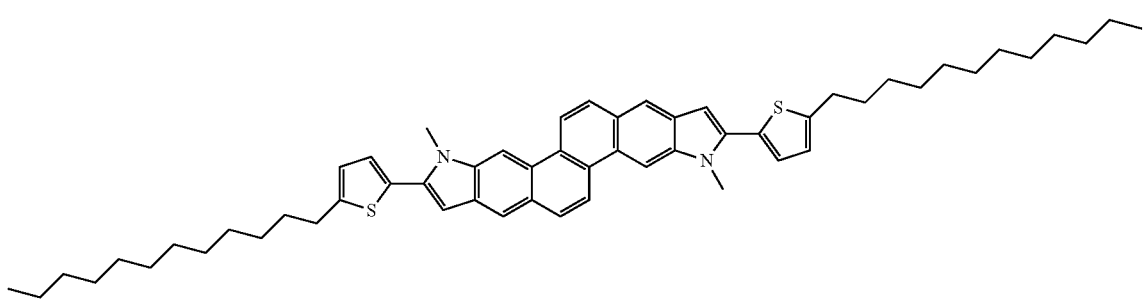
(540)
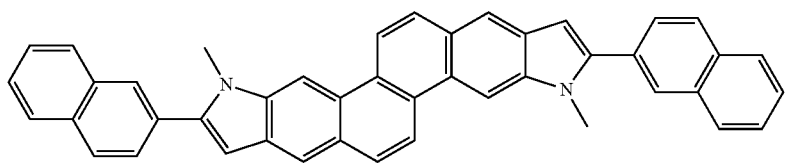

-continued
(541)
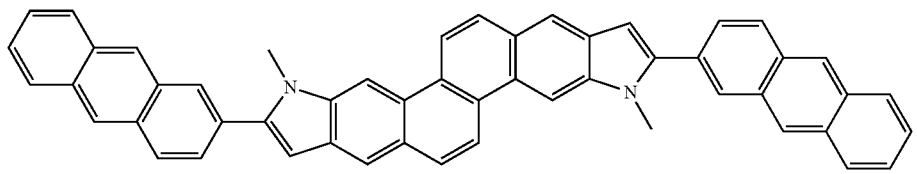
(542)
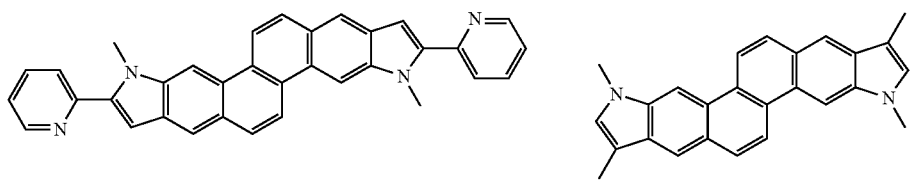
(543)
(544)
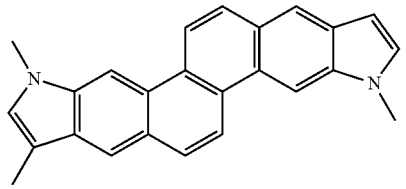
(545)
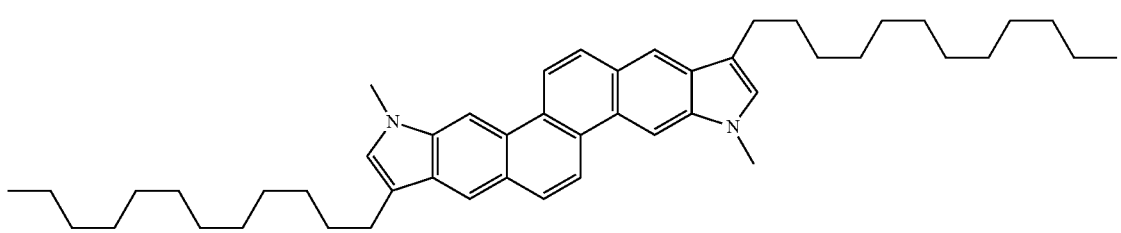
(546)
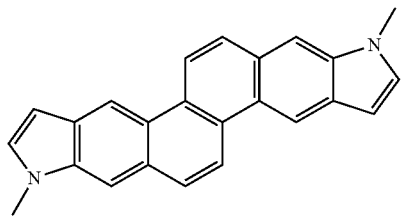
(547)
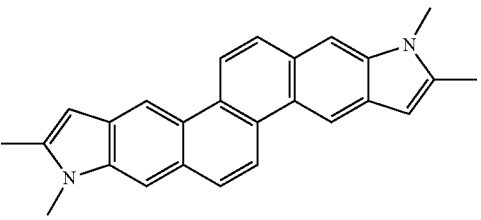
(548)
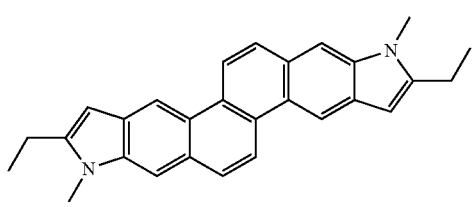
(549)
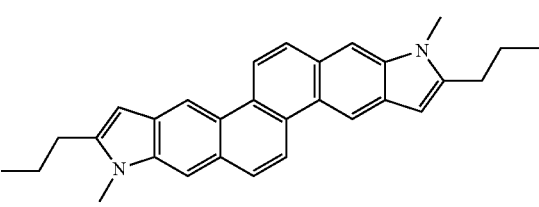
(550)
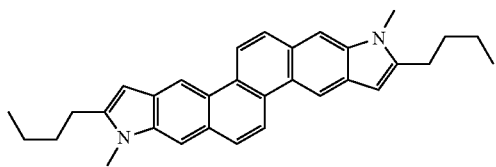
(551)
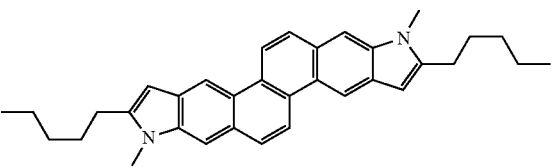

-continued
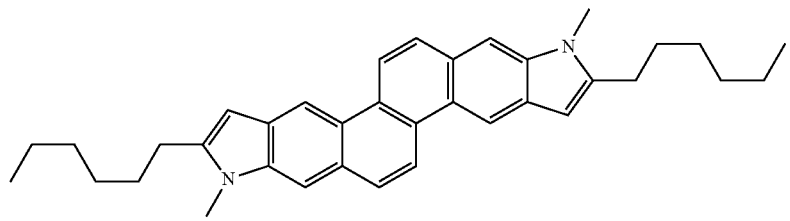
(552)
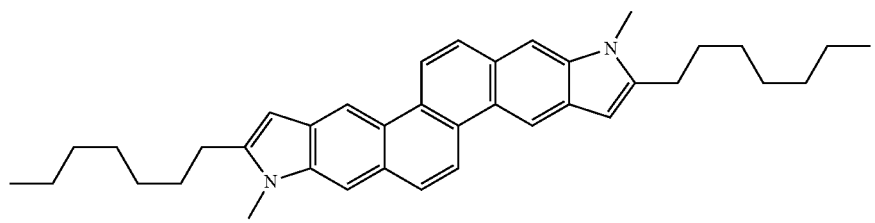
(553)
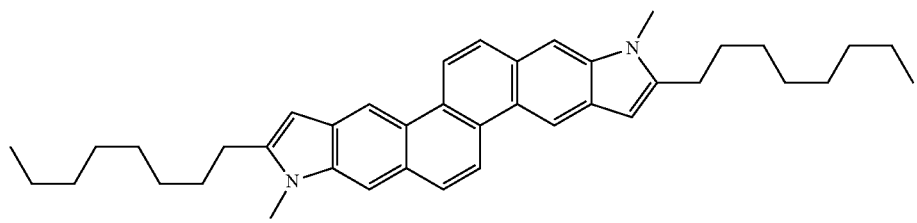
(554)
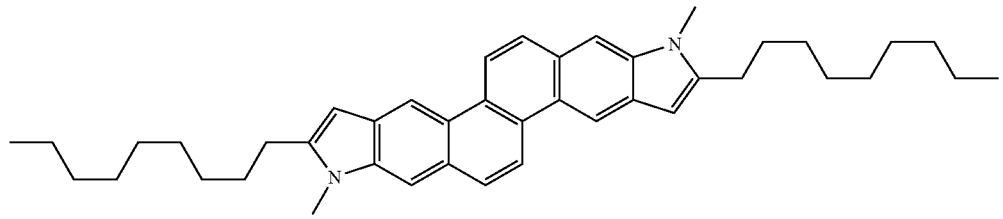
(555)
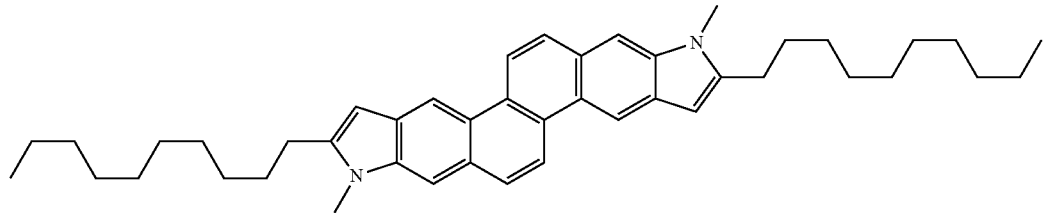
(556)
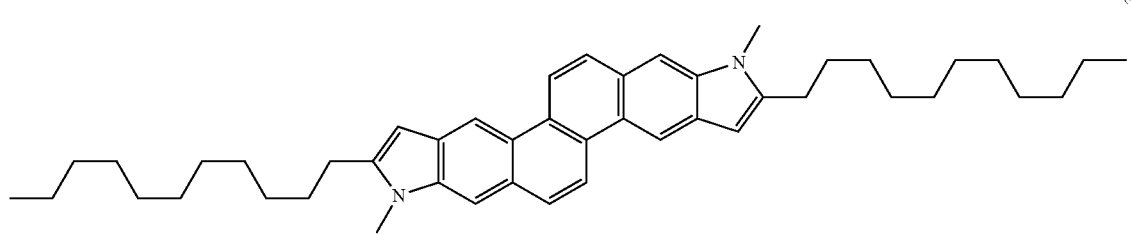
(557)
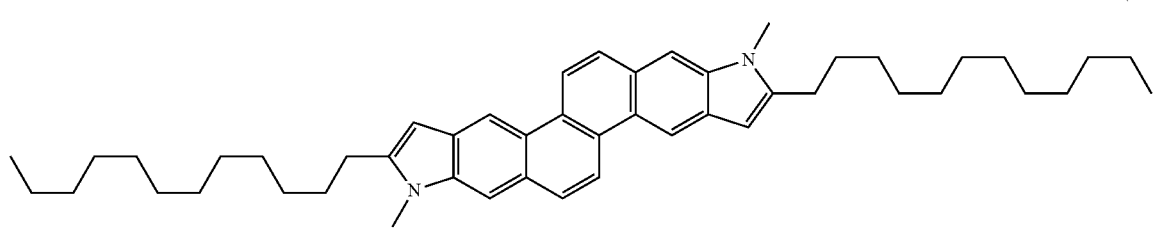
(558)

(559)
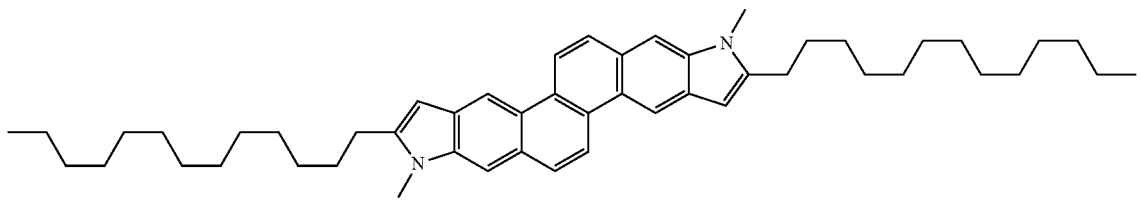
(560)
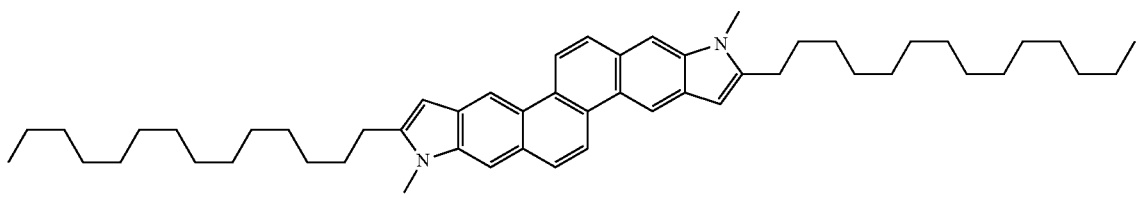
(561)
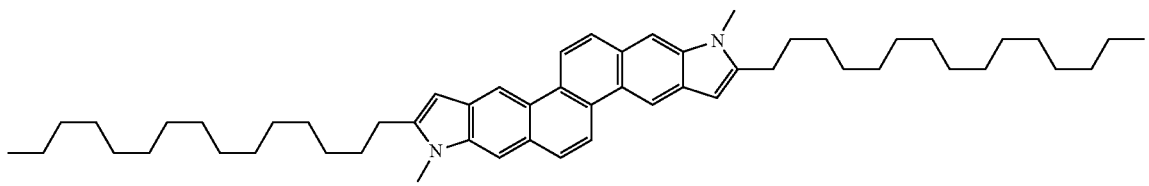
(562)
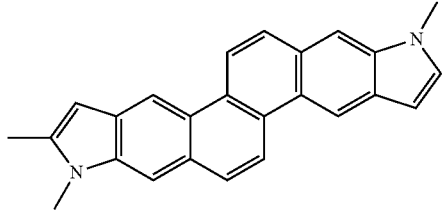
(563)
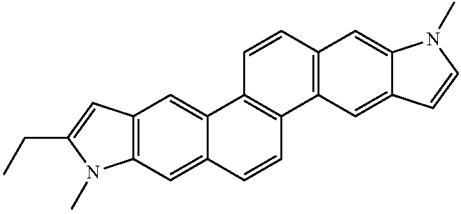
(564)
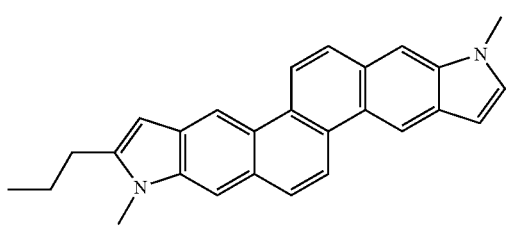
(565)
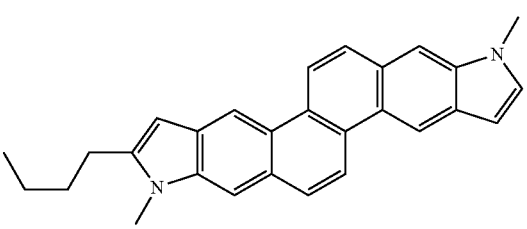
(567)
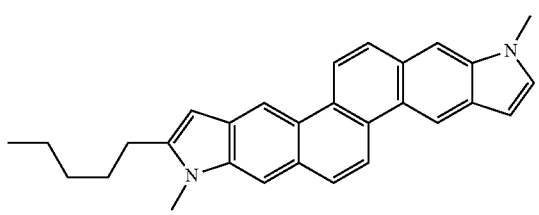
(568)
(569)
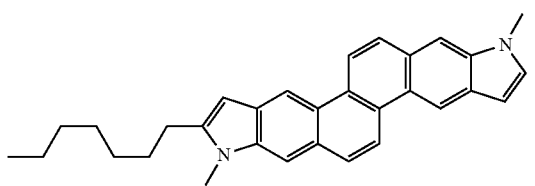
(570)
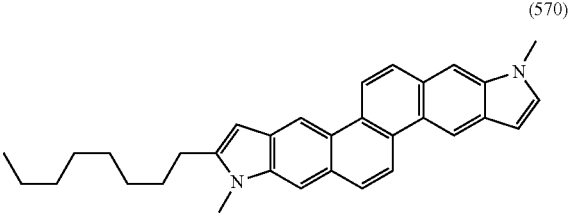

-continued
(571)
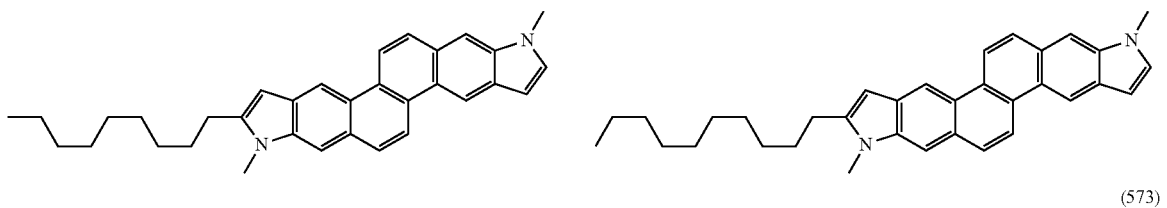
(572)
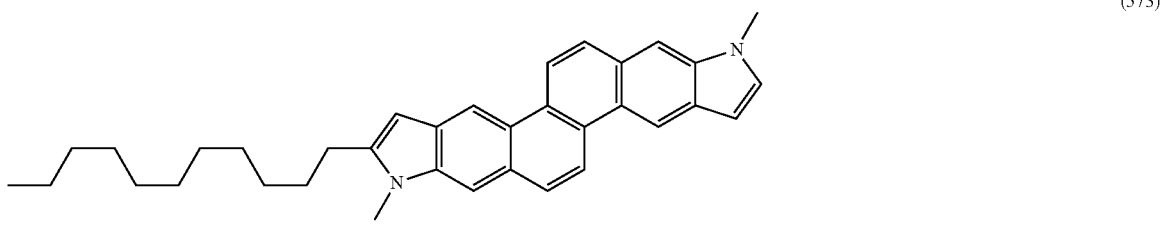
(573)
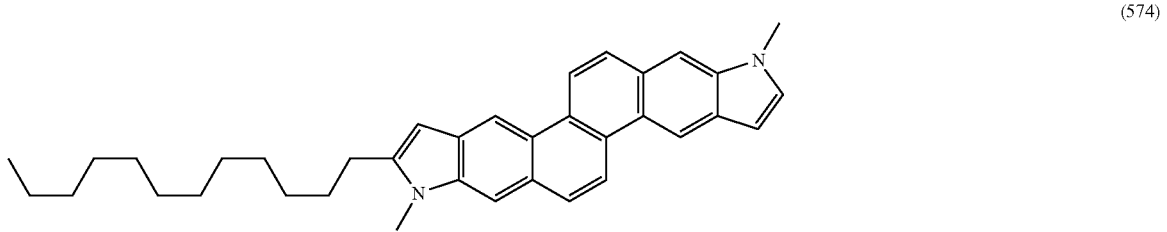
(574)
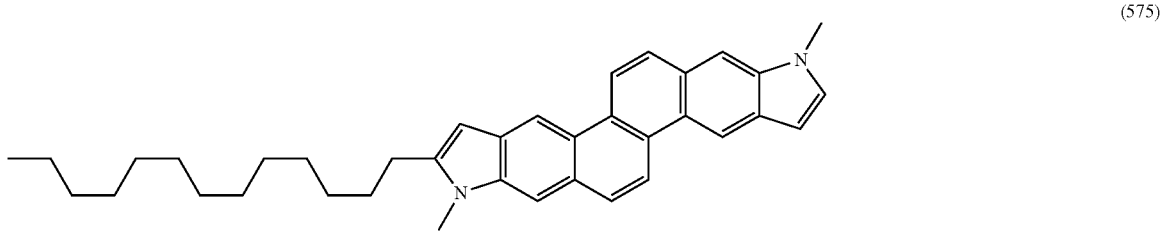
(575)
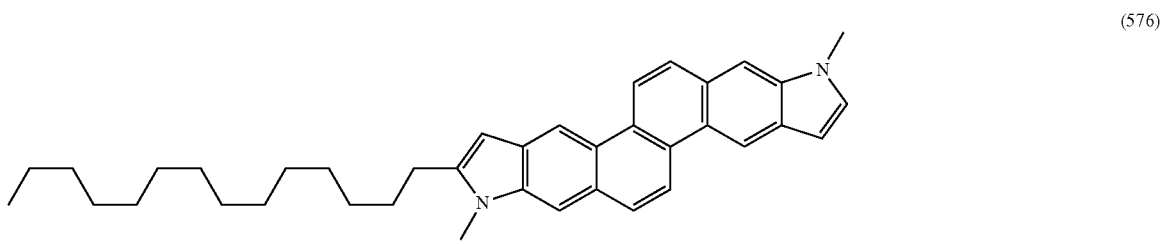
(576)
(577)
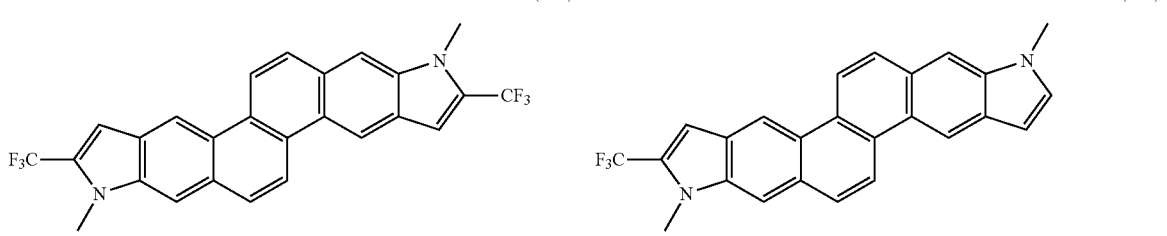
(578)
(579)
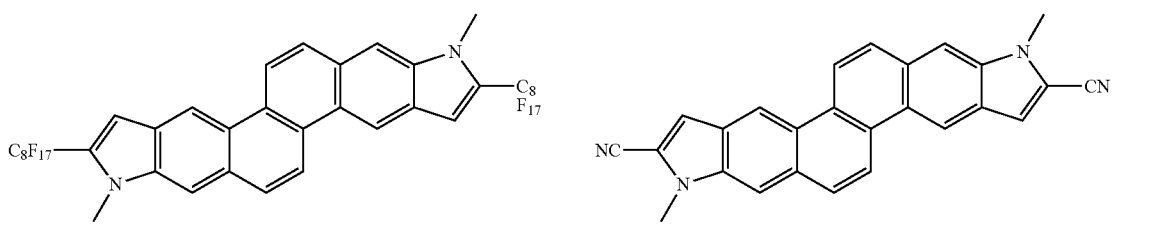
(580)

-continued
(581)
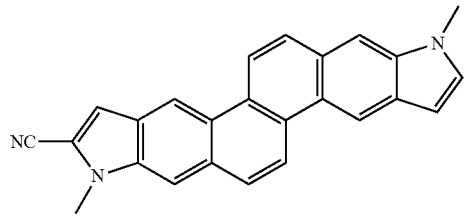
(582)
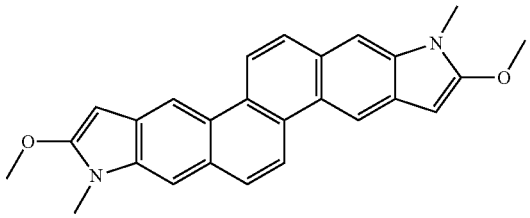
(583)
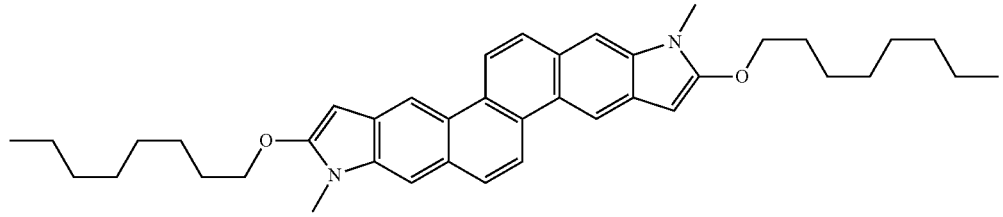
(584)
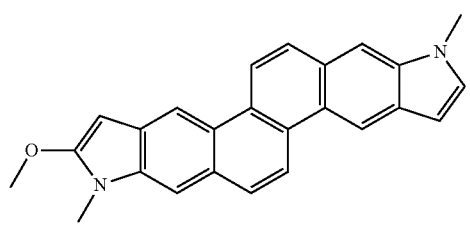
(585)
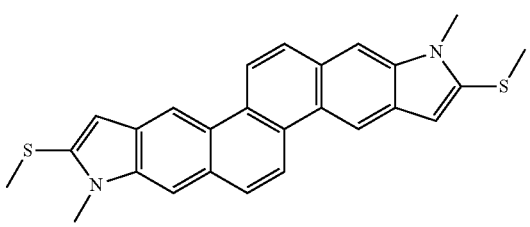
(586)
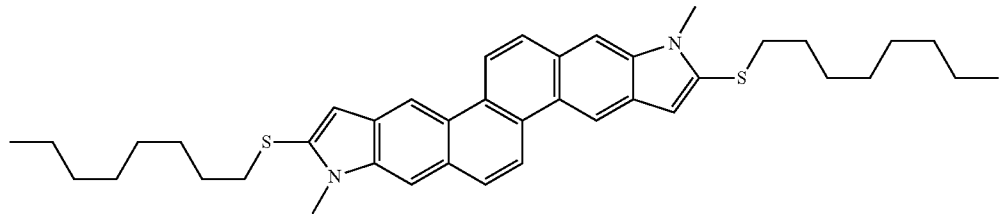
(587)
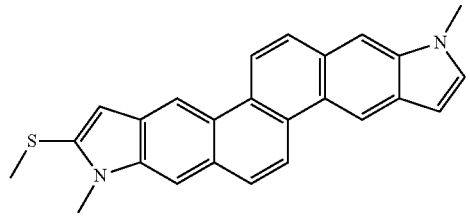
(588)
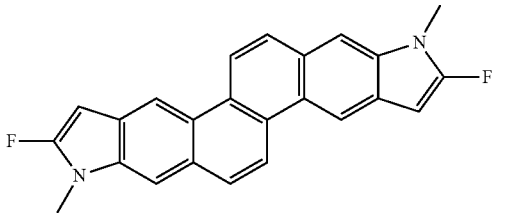
(589)
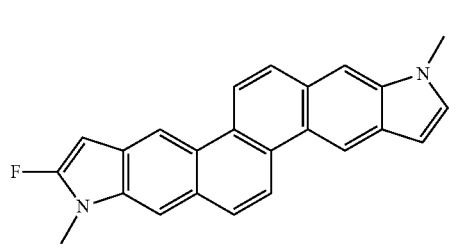
(590)
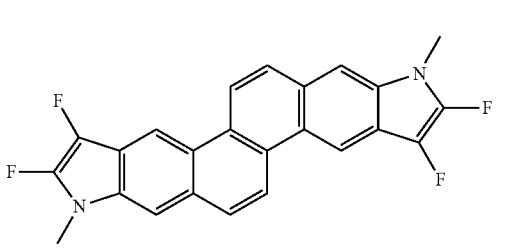
(591)
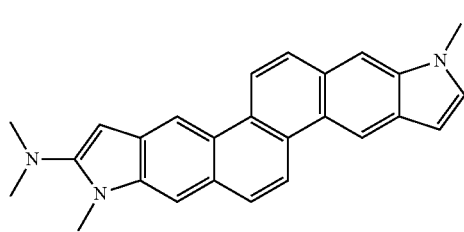

-continued
(592)
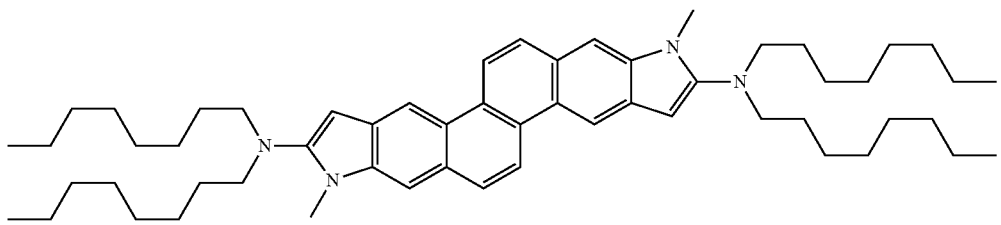
(593)
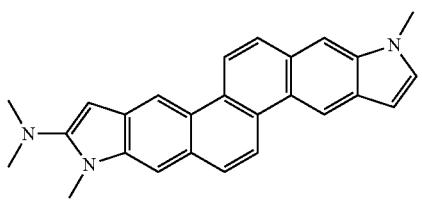
(594)
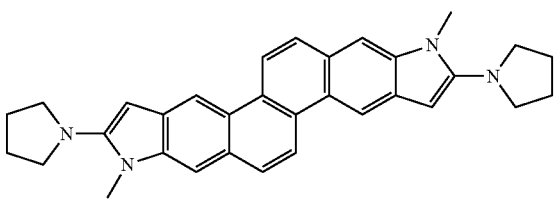
(595)
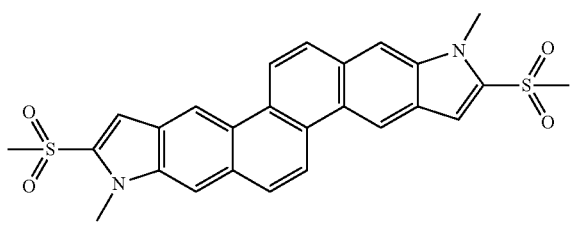
(596)
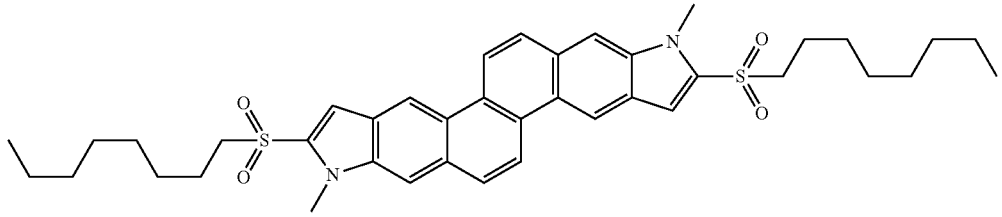
(597)
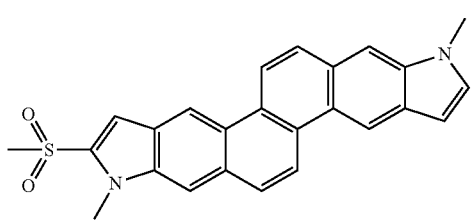
(598)
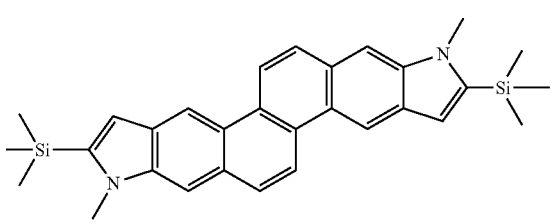
(599)
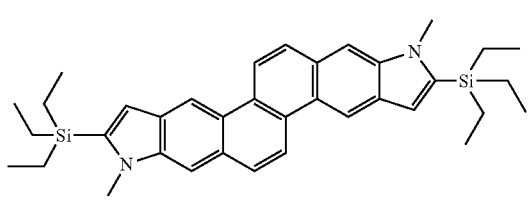
(600)
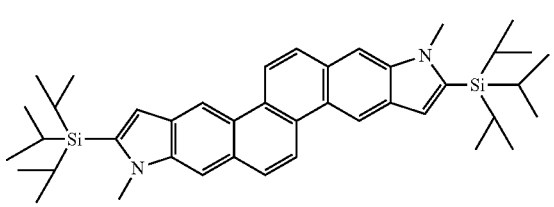
(601)
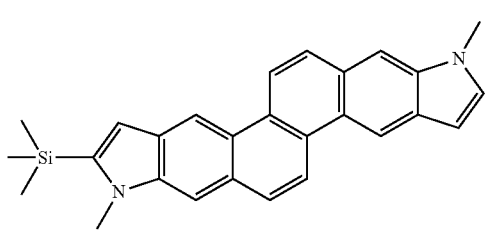
(602)
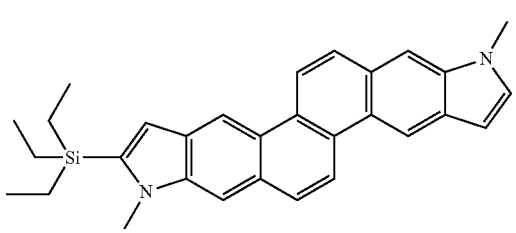

-continued
(603)
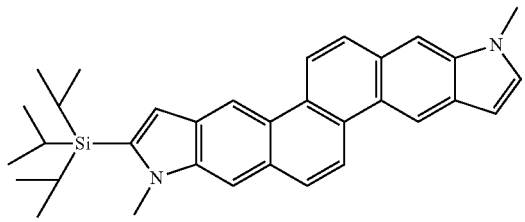
(604)
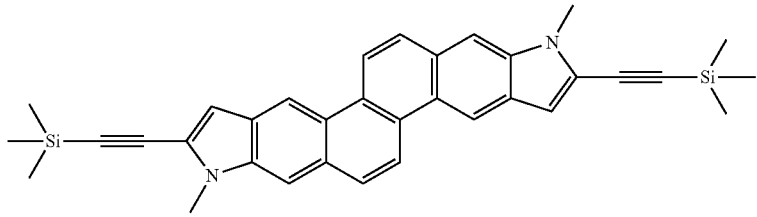
(605)
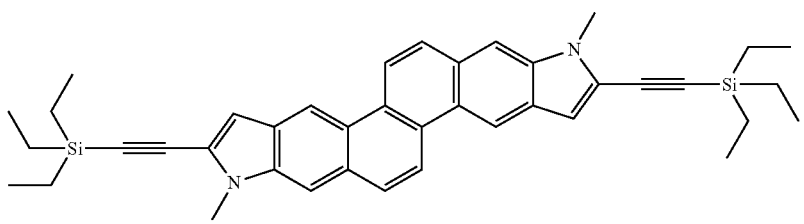
(606)
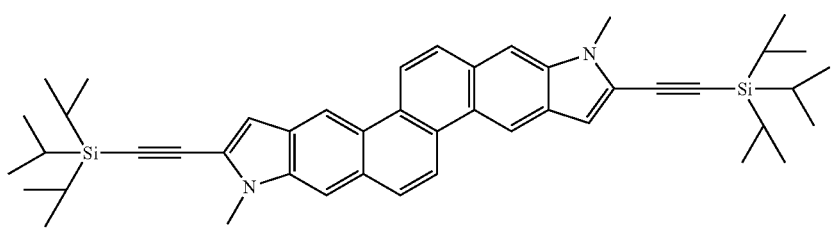
(607)
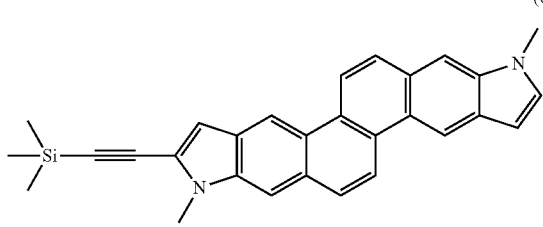
(608)
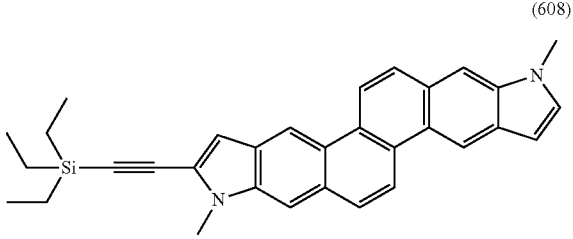
(609)
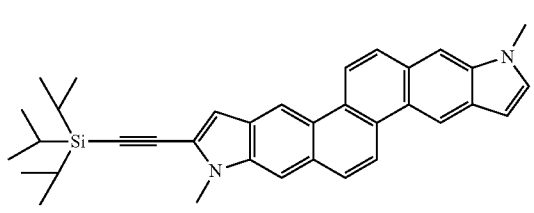
(610)
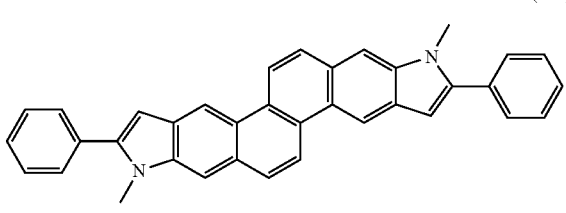
(611)
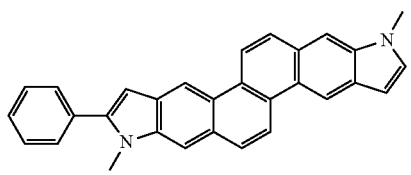
(612)
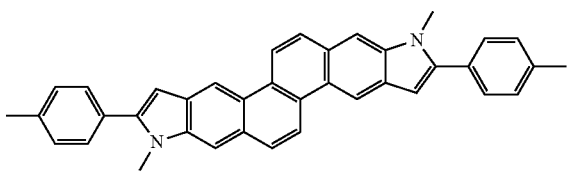

-continued
(613)
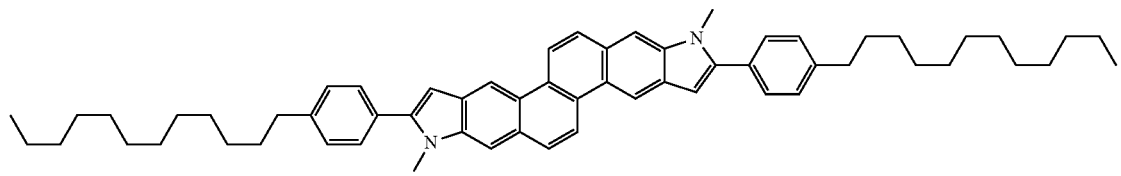
(614)
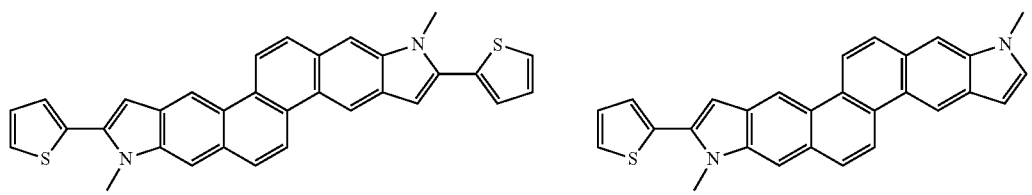
(615)
(616)
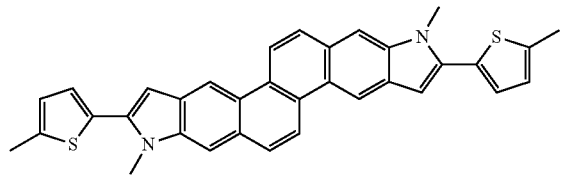
(617)
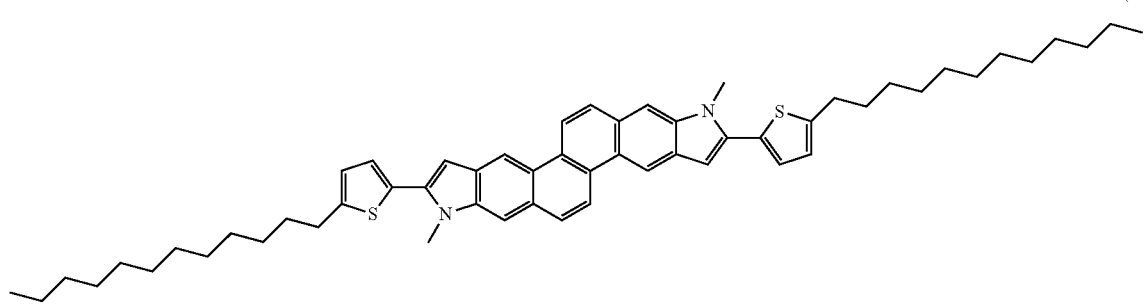
(618)
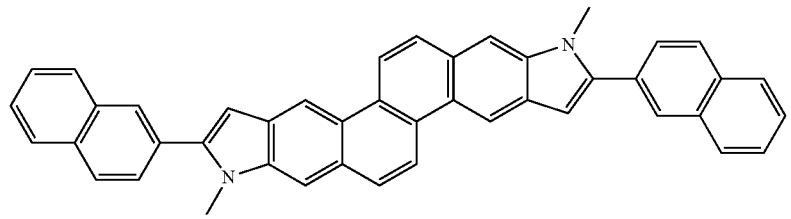
(619)
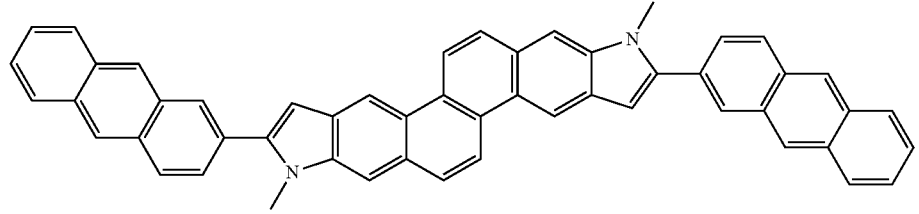
(620)
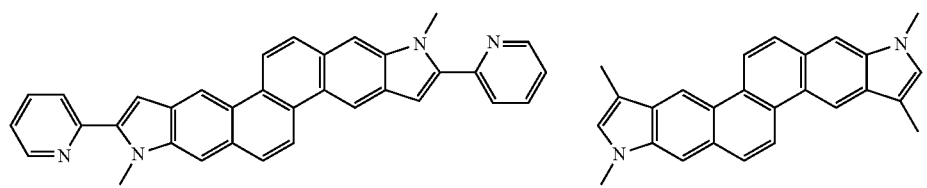
(621)

-continued
(622)
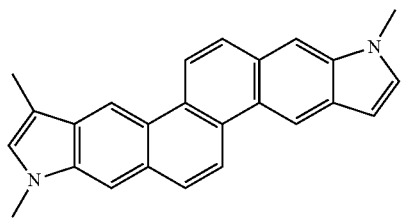
(623)
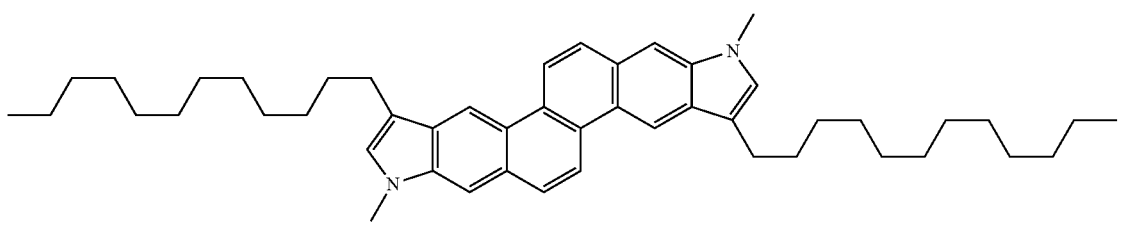
(624)
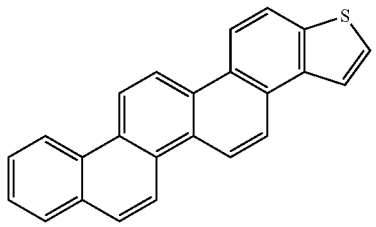
(625)
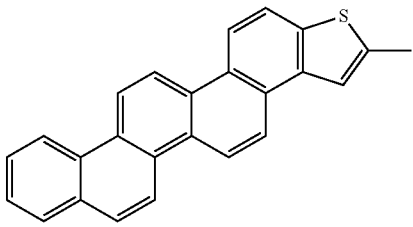
(626)
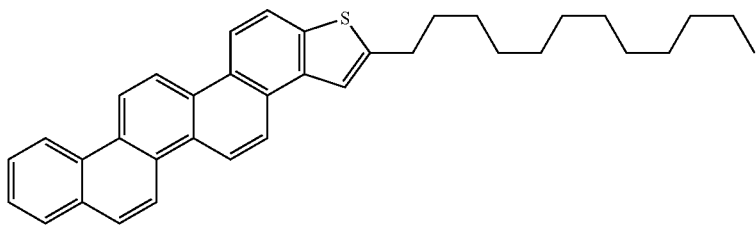
(627)
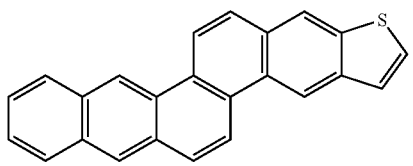
(628)
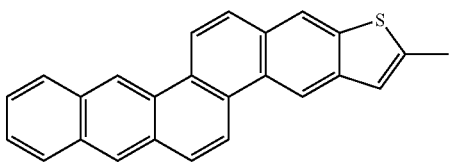
(629)
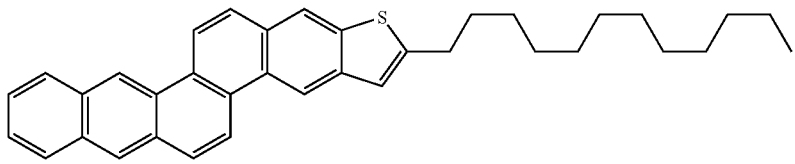
(630)
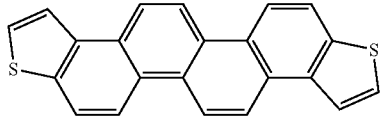
(631)
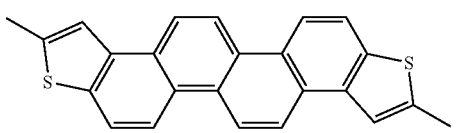
(632)
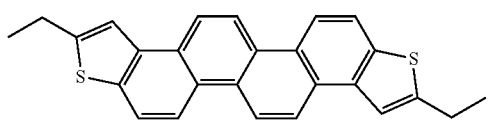
(633)
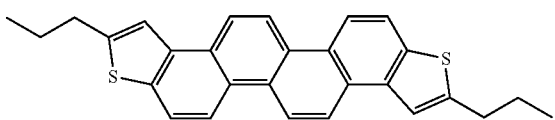

-continued
(634)
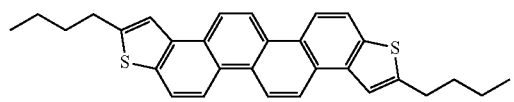
(635)
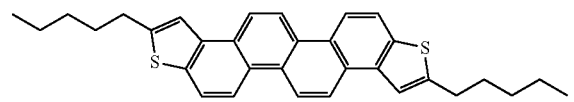
(636)
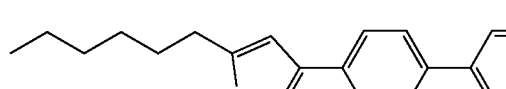
(637)
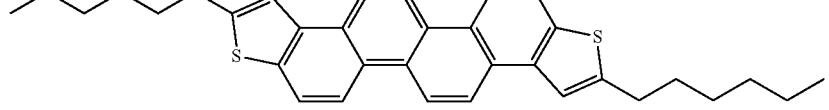
(638)
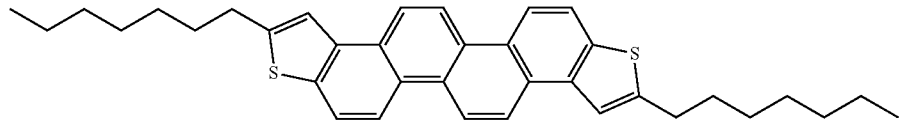
(639)
(640)
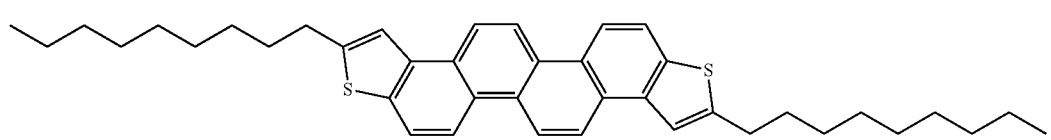
(641)
(642)
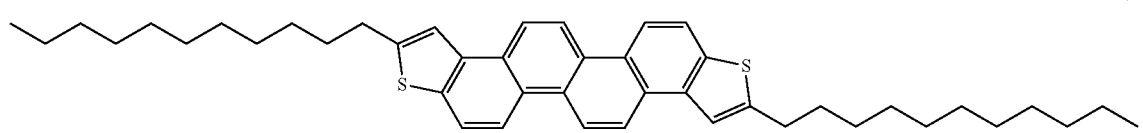
(643)
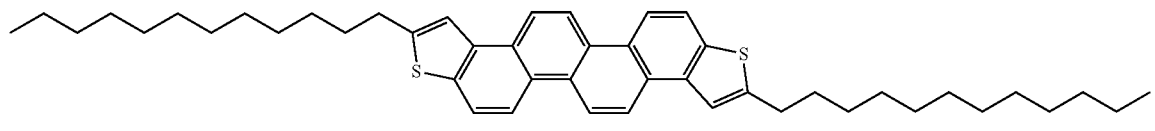
(644)
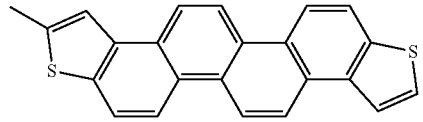
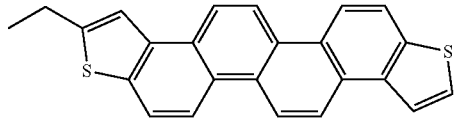
(645)
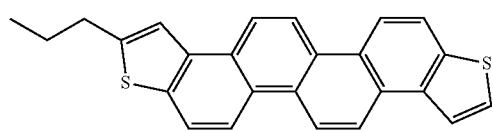
(646)
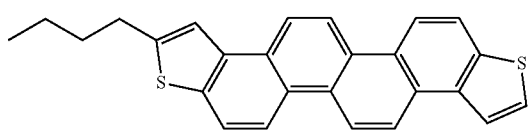
(647)
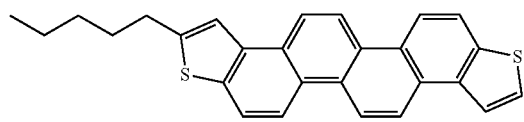
(648)
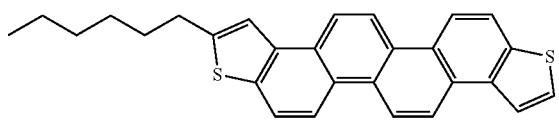

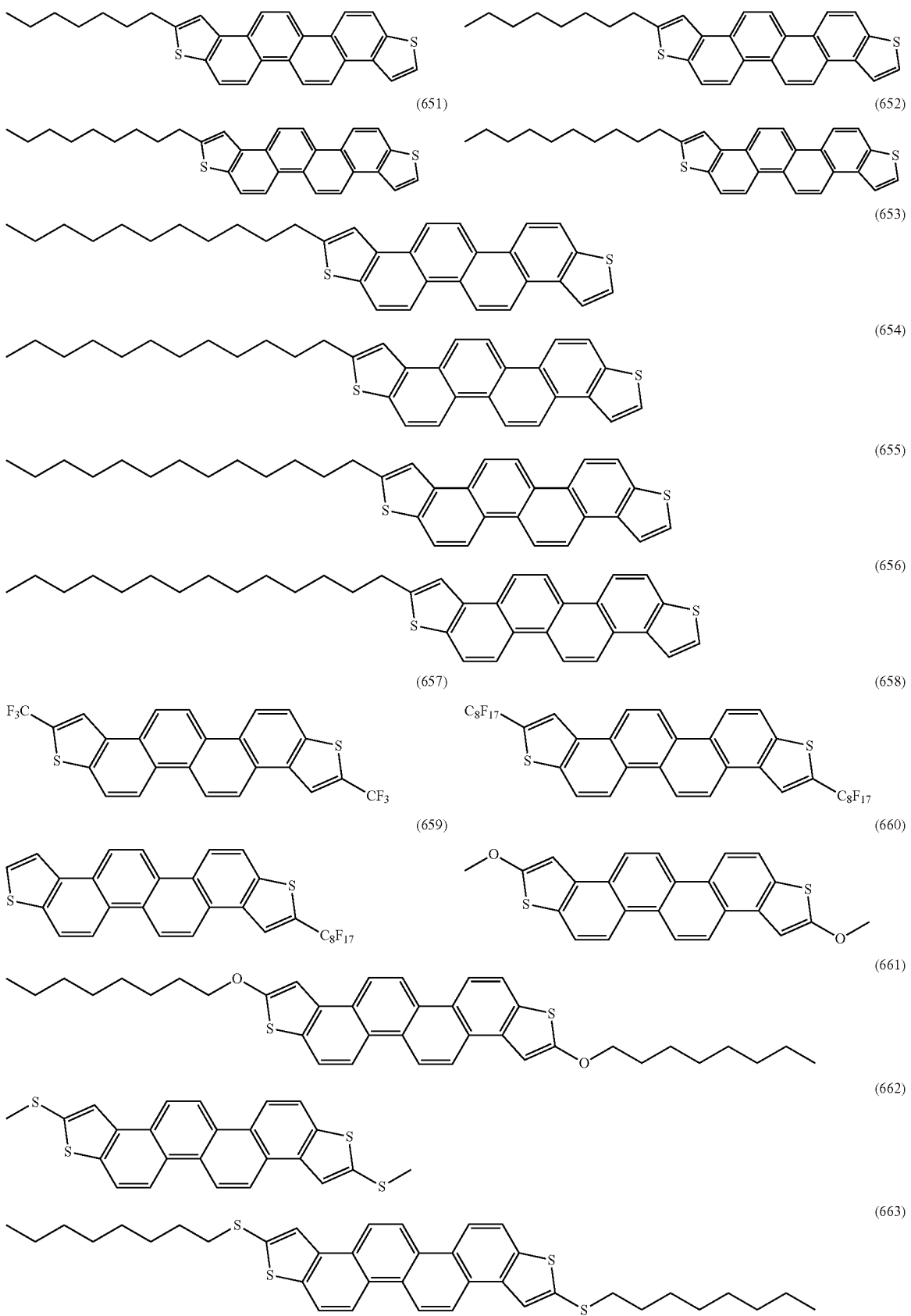

-continued
(664)
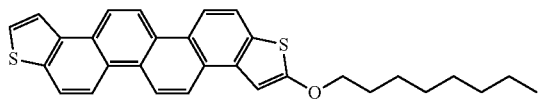
(665)
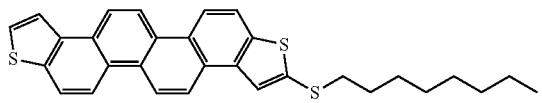
(666)
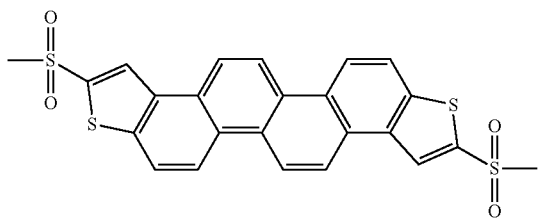
(667)
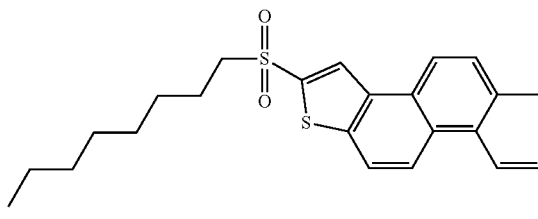
(668)
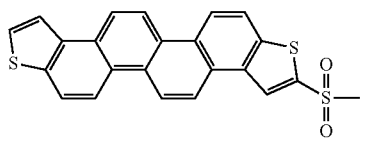
(669)
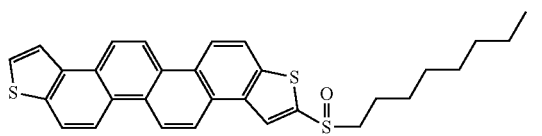
(670)
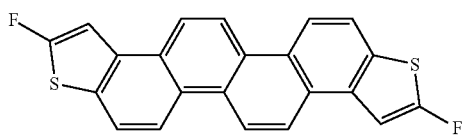
(671)
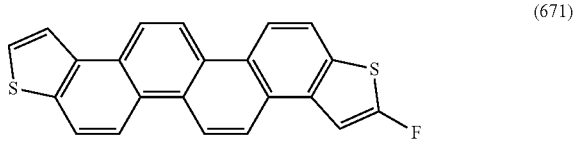
(672)
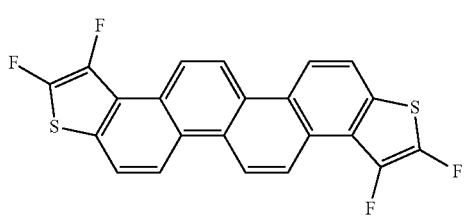
(673)
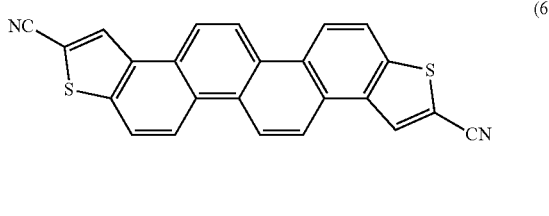
(674)
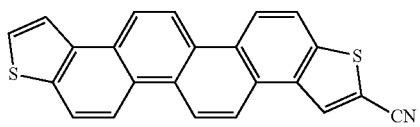
(675)
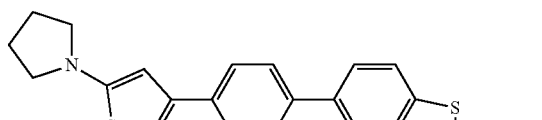
(676)
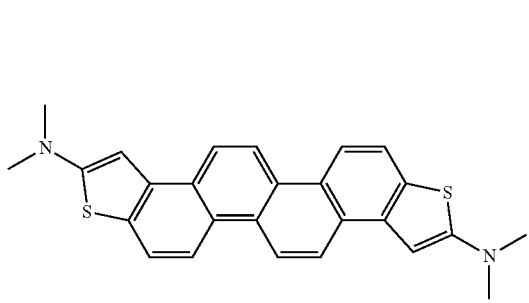

-continued
(677)
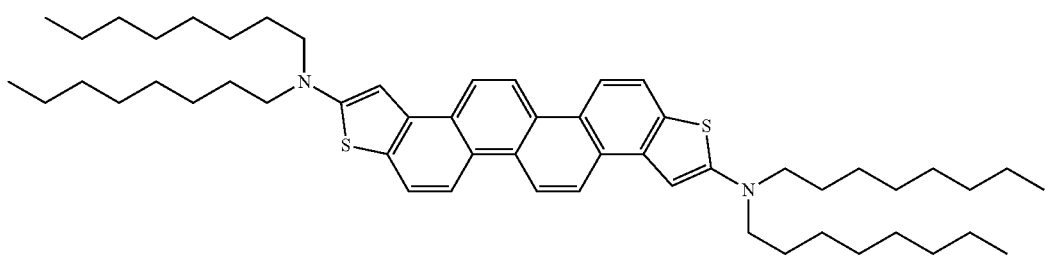
(678)
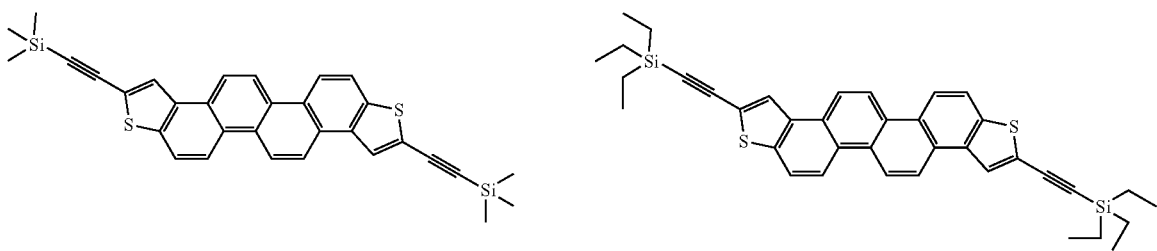
(679)
(680)
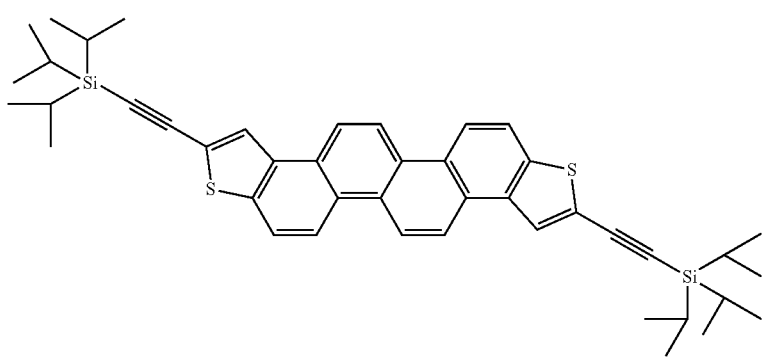
(681)
(682)
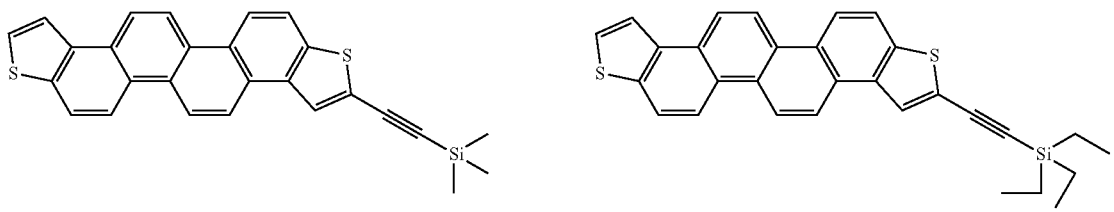
(683)
(684)
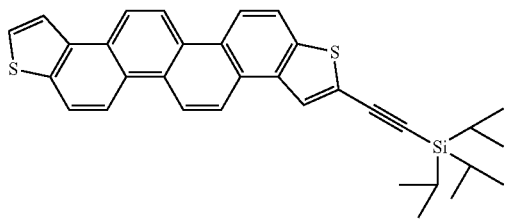
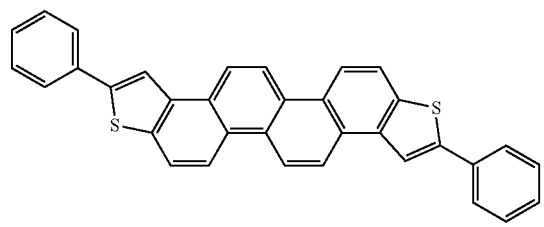
(685)
(686)
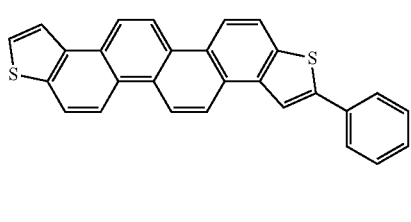
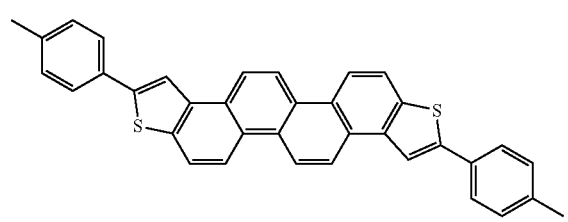

-continued
(687)
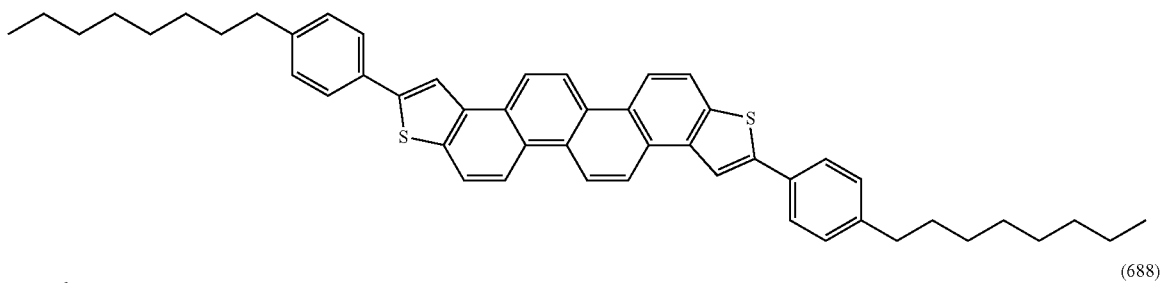
(688)
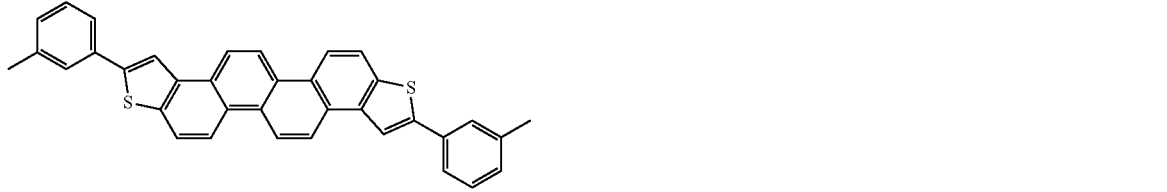
(689)
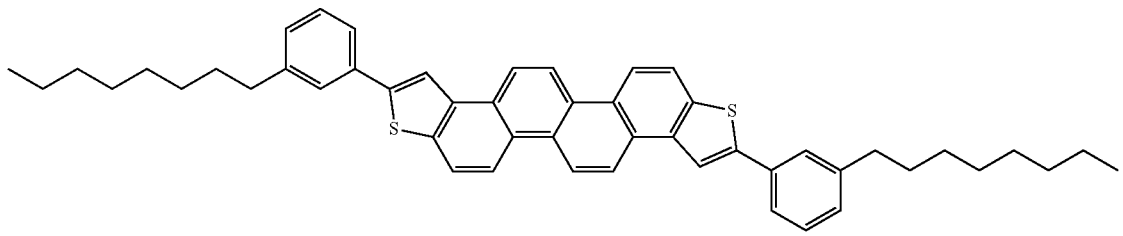
(690)
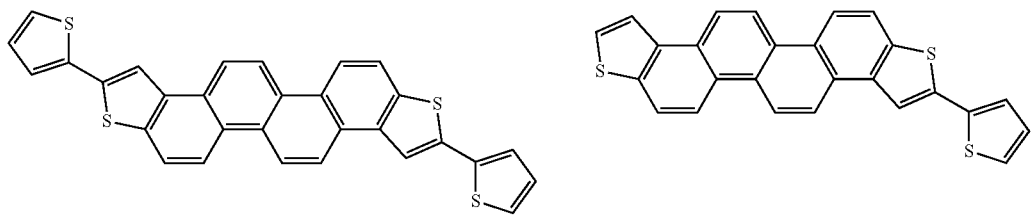
(691)
(692)
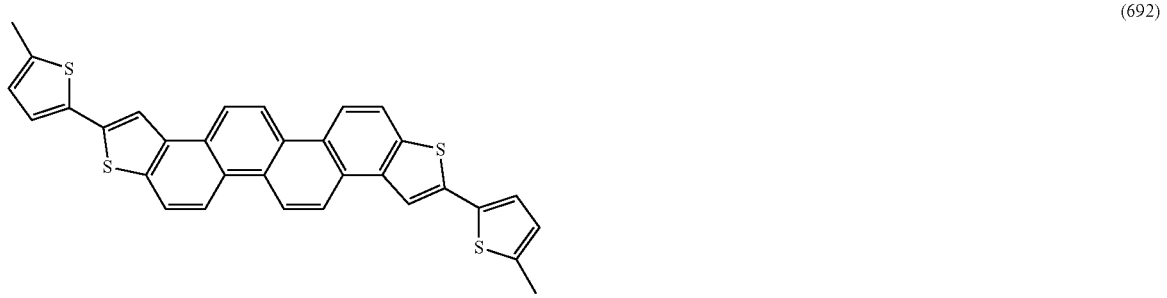
(693)
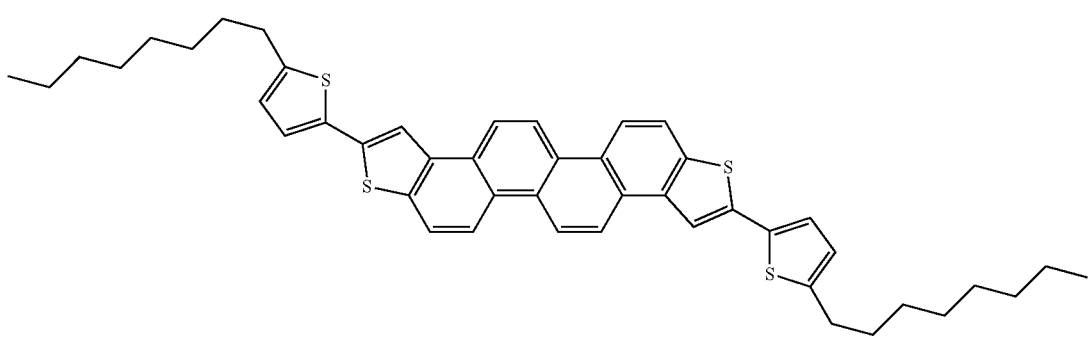

-continued
(694)
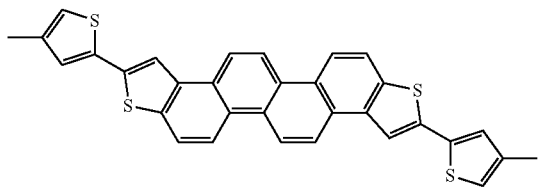
(695)
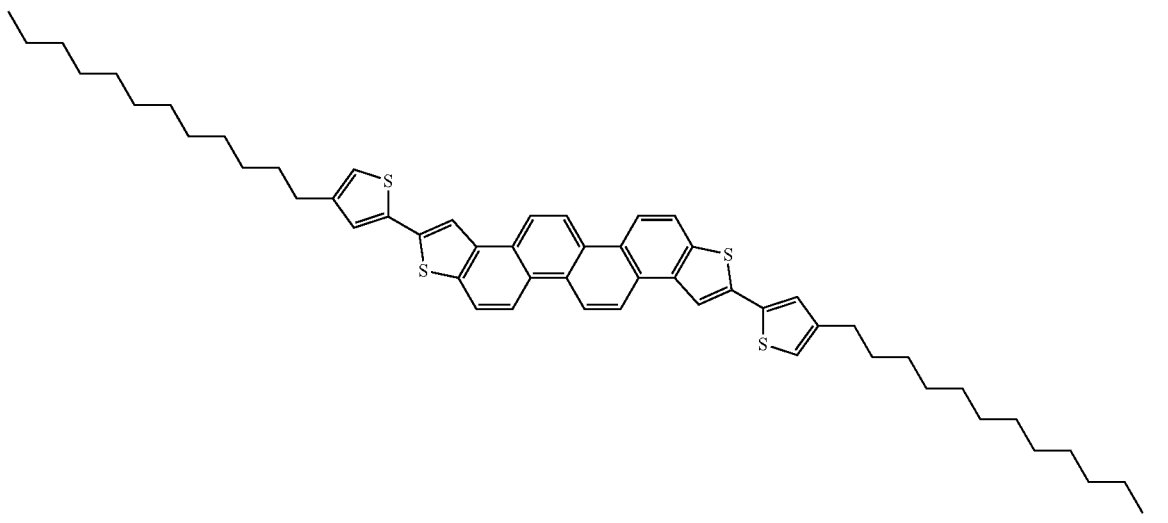
(696)
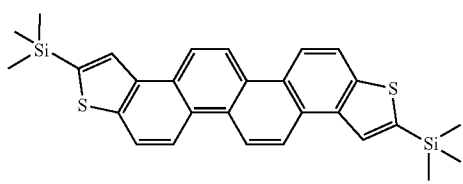
(697)
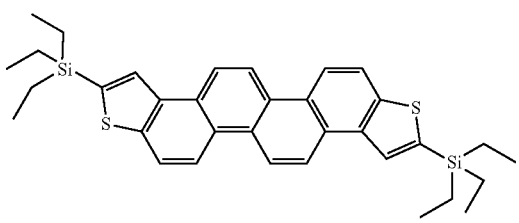
(698)
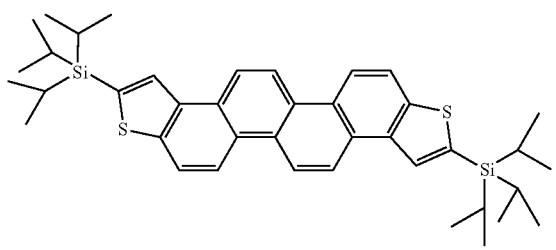
(699)
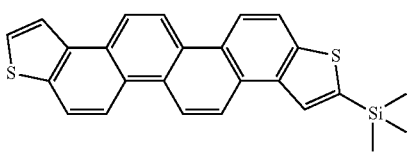
(700)
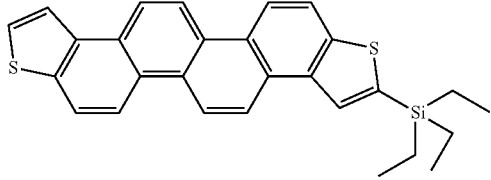
(701)
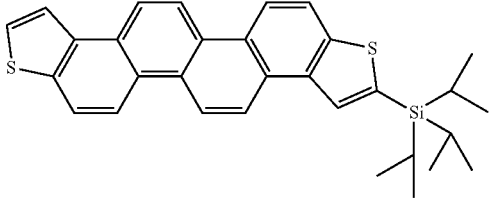

(702)
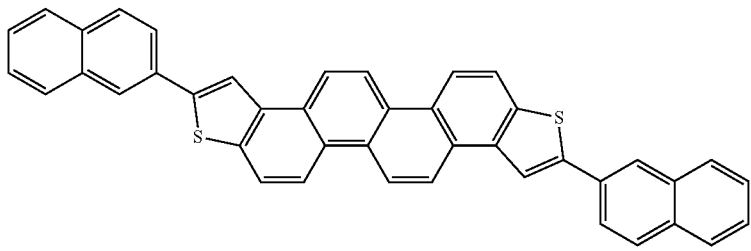
(703)
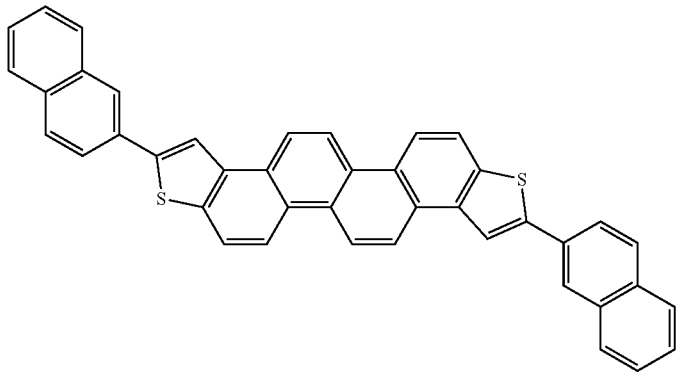
(704)
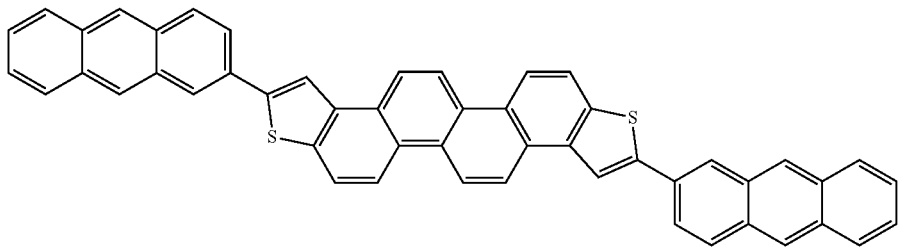
(705)
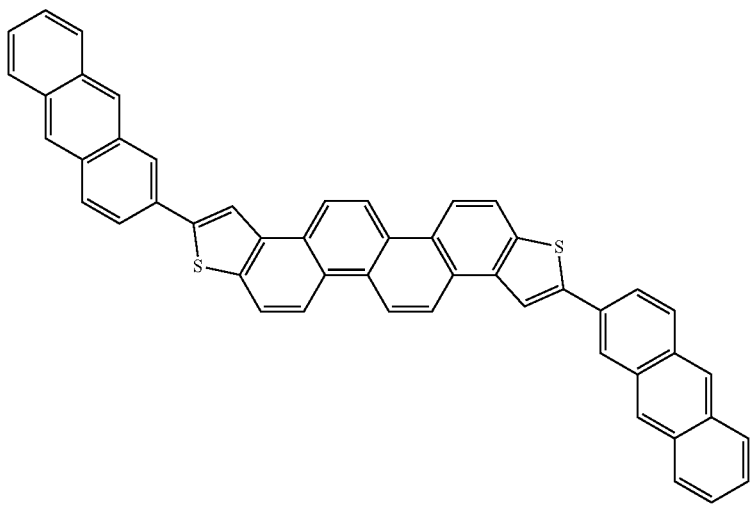
(706)
(707)
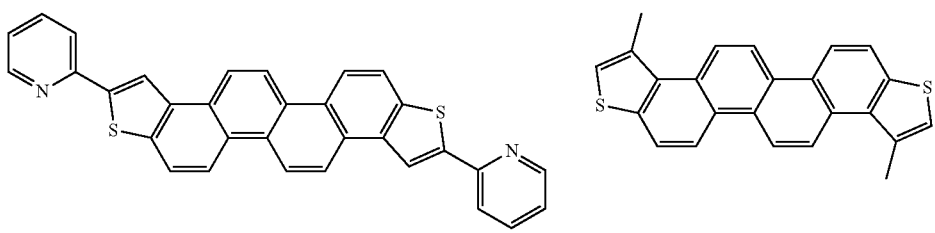

-continued
(708)
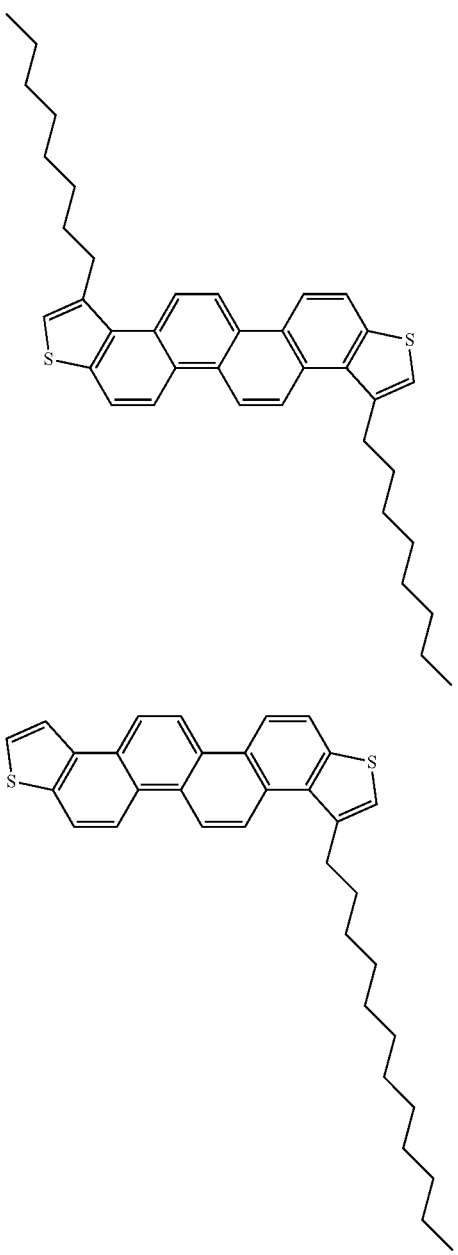
(709)
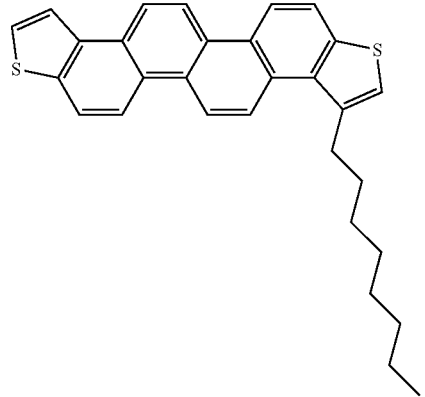
(710)
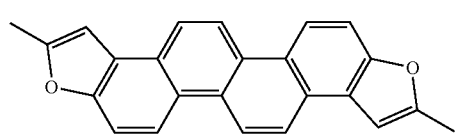
(711)
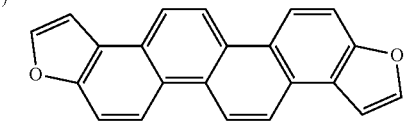
(712)
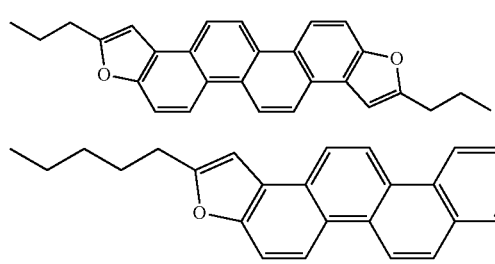
(713)
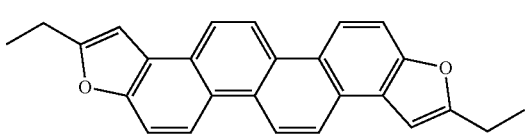
(714)
(715)
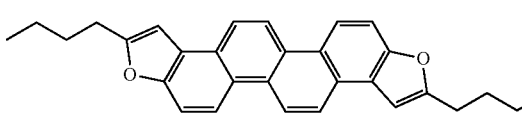
(716)

-continued
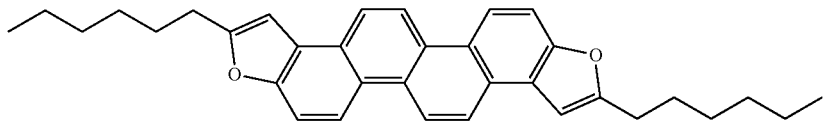
(717)
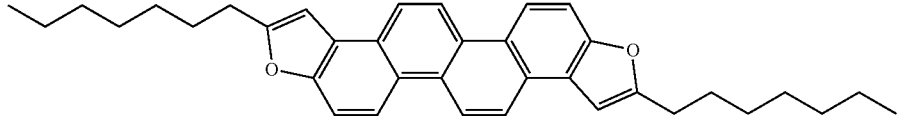
(718)
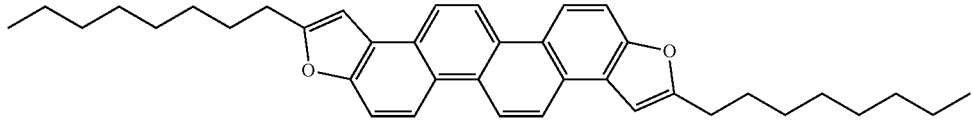
(719)
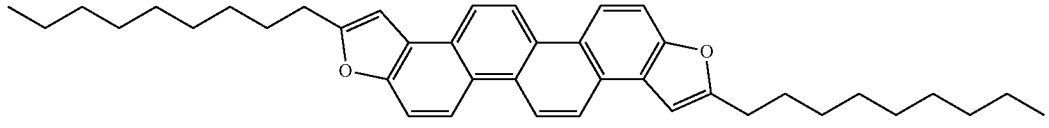
(720)
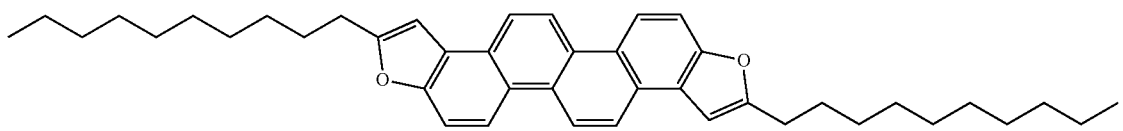
(721)
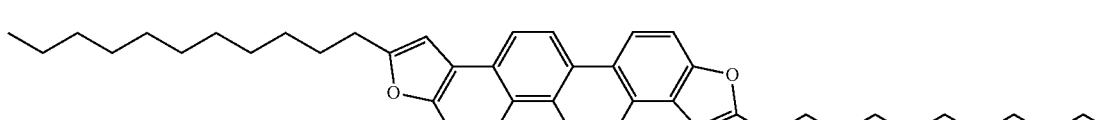
(722)
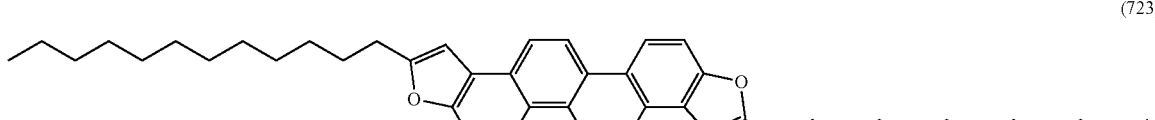
(723)
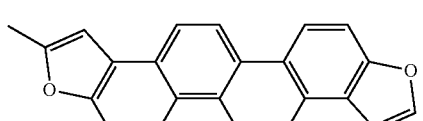
(724)
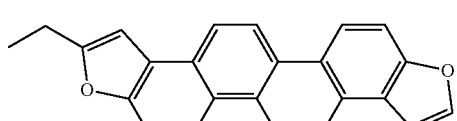
(725)
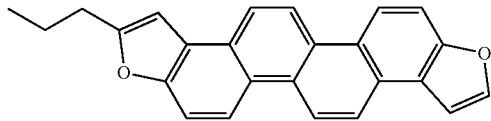
(726)
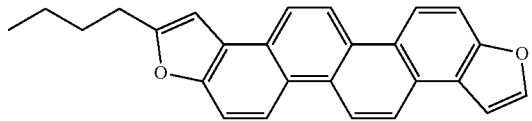
(727)
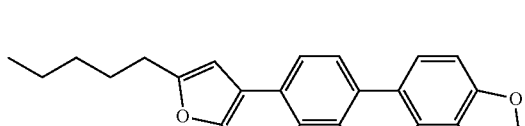
(728)
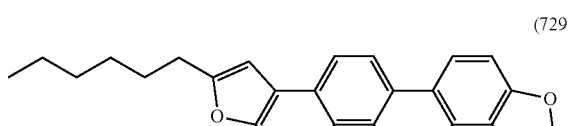
(729)
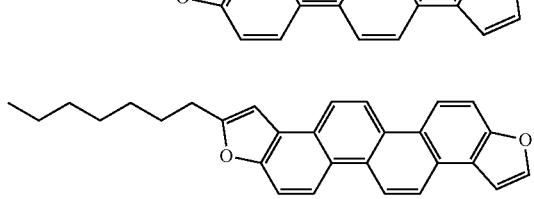
(730)
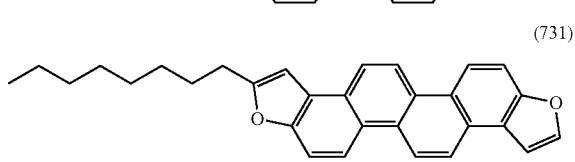
(731)

-continued
(732)
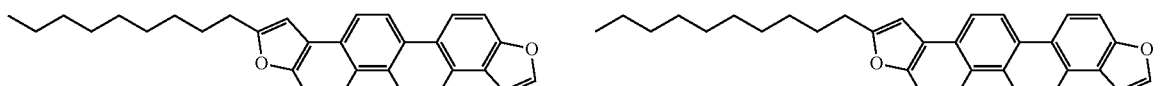
(733)
(734)
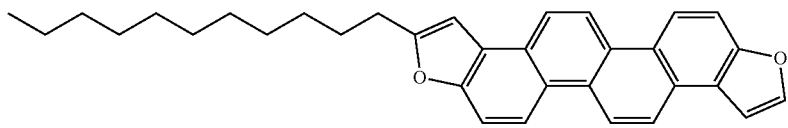
(735)
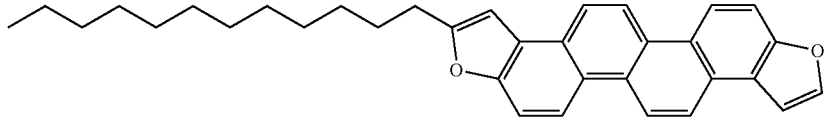
(736)
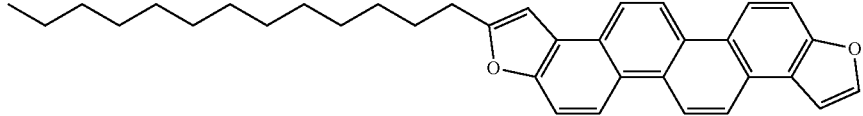
(737)
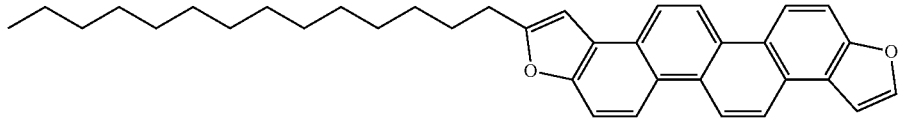
(738)
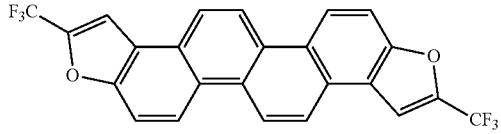
(739)
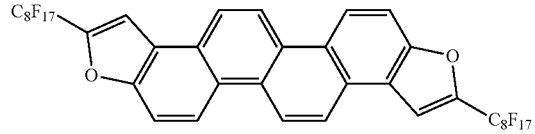
(740)
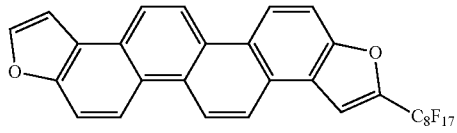
(741)
(742)
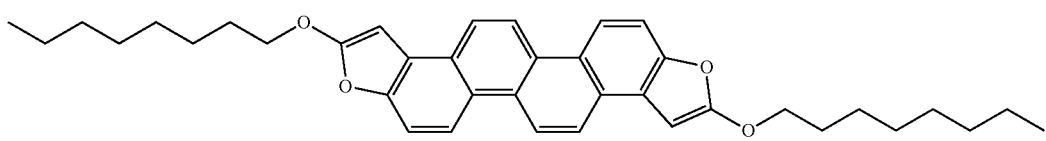
(743)
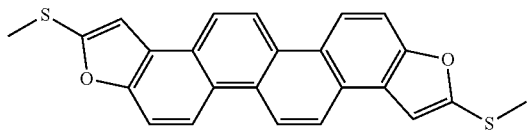
(744)
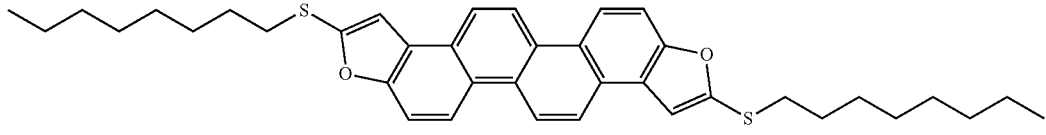
(745)
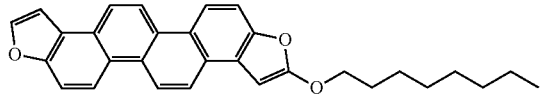
(746)
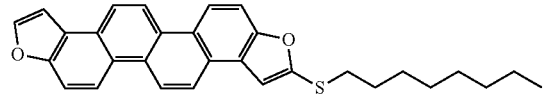

-continued
(747)
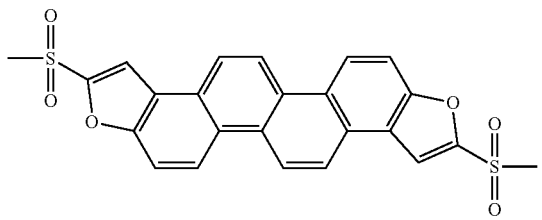
(748)
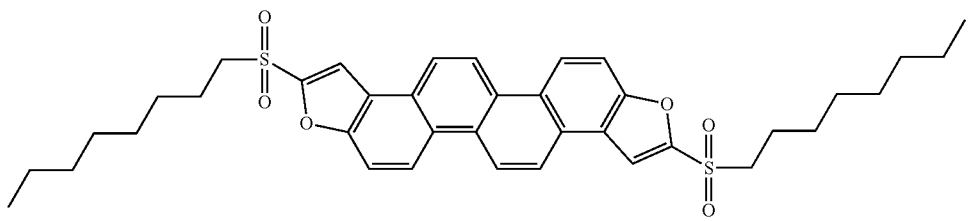
(749)
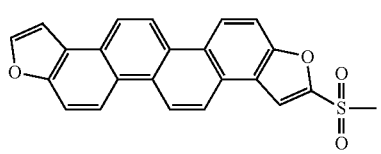
(750)
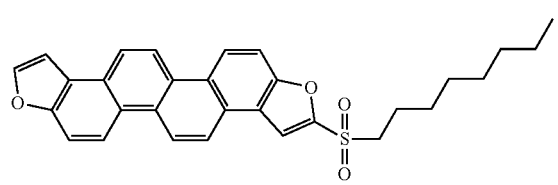
(751)
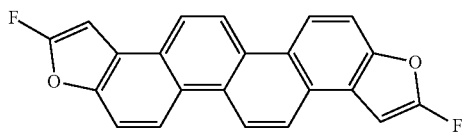
(752)
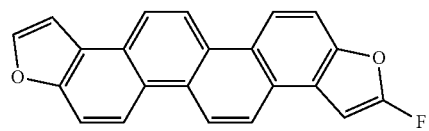
(753)
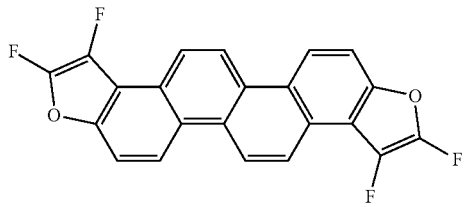
(754)
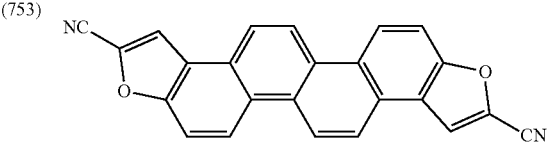
(755)
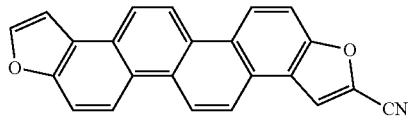
(756)
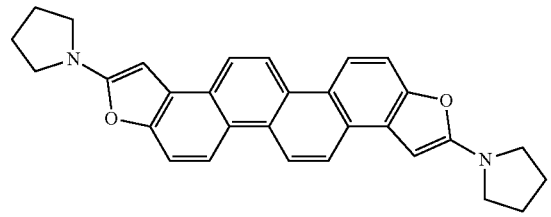
(757)
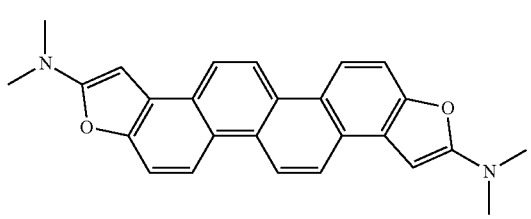

-continued
(758)
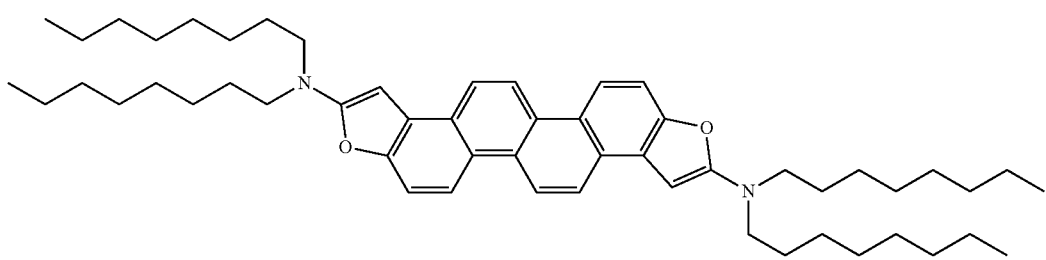
(759) (760)
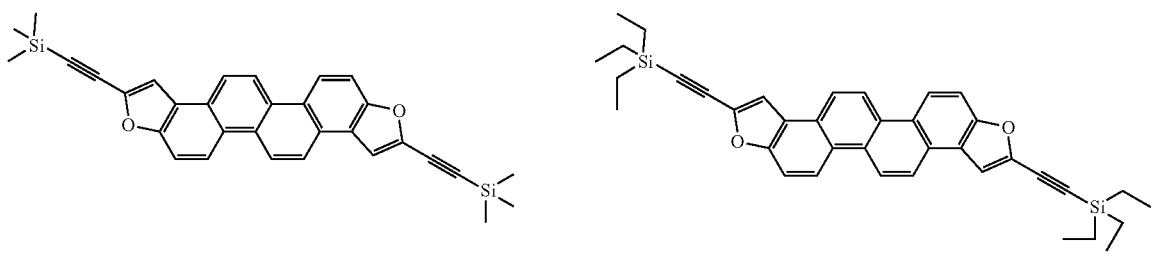
(761)
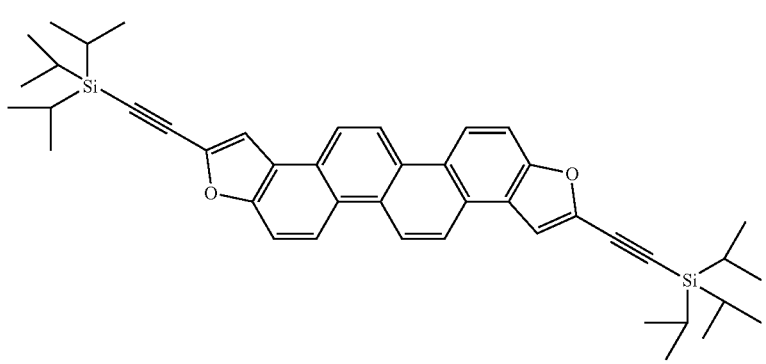
(762) (763)
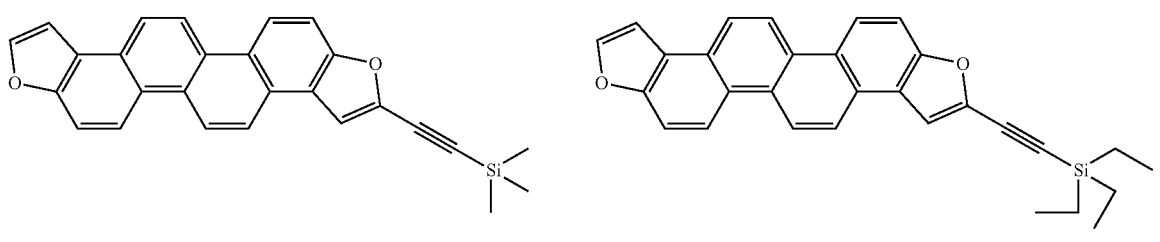
(764)
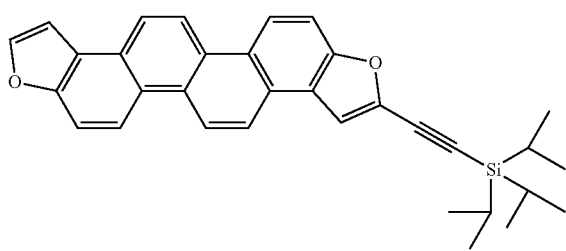
(765) (766)
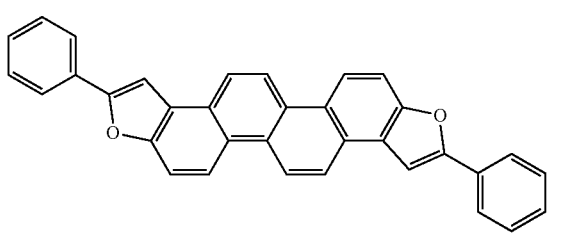 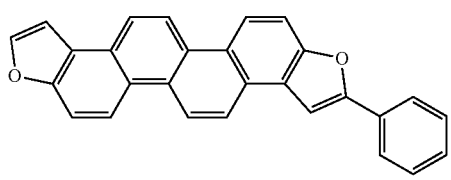

(767)
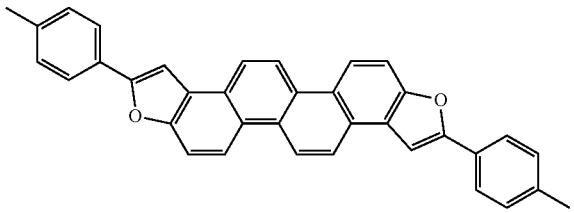
(768)
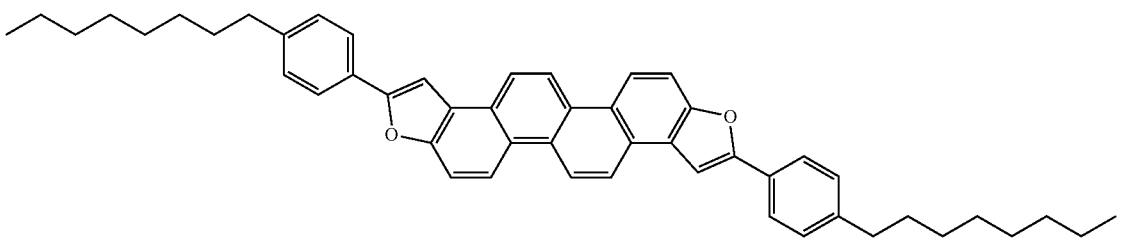
(769)
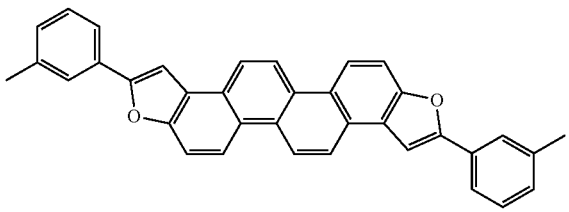
(770)
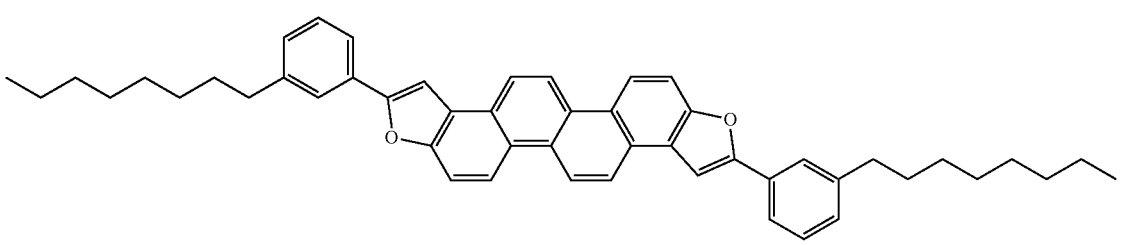
(771)
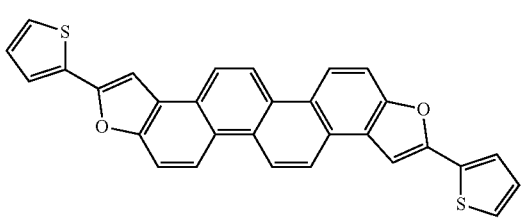
(772)
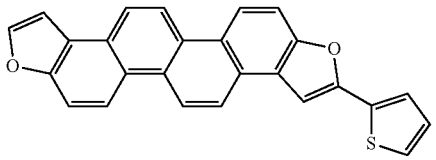
(773)
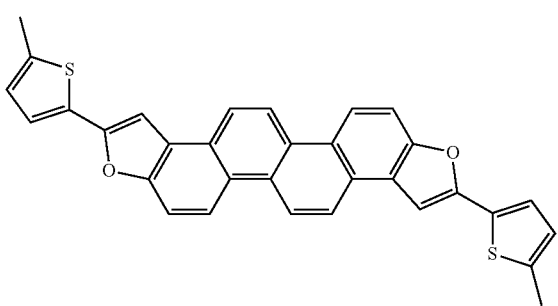

(774)
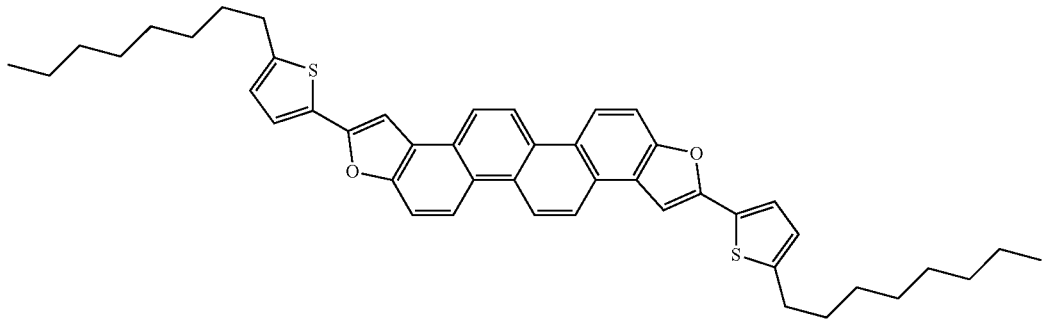
(775)
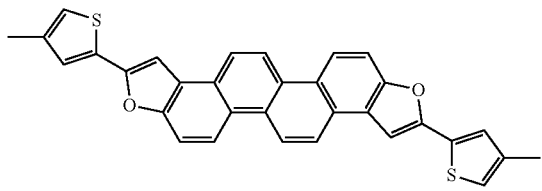
(776)
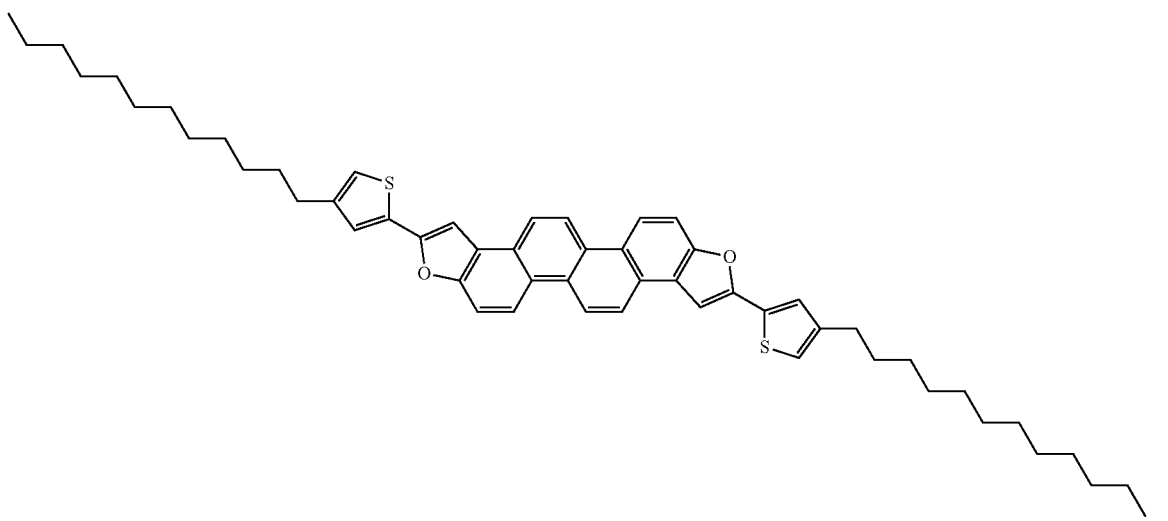
(777)
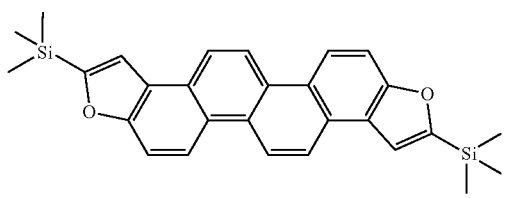
(778)
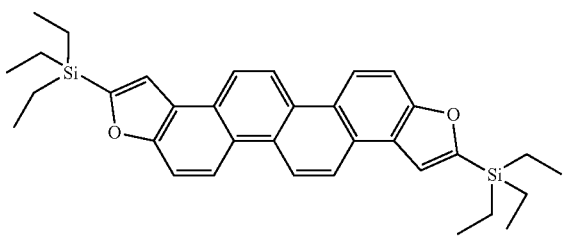
(779)
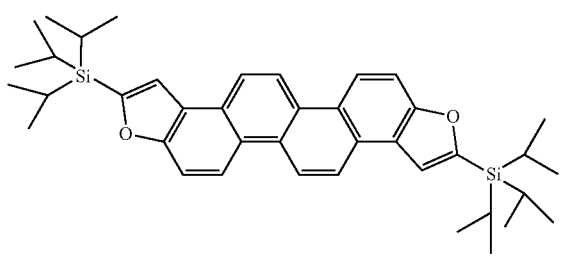
(780)
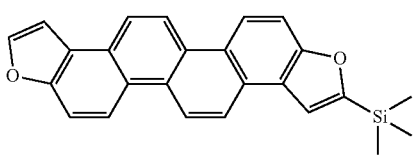

-continued
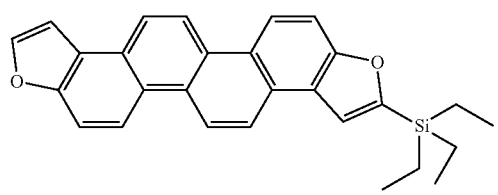
(781)
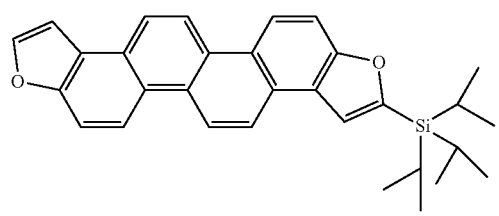
(782)
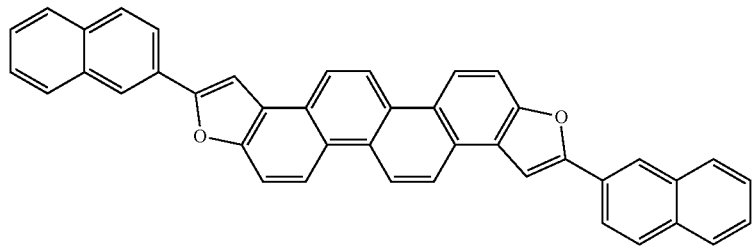
(783)
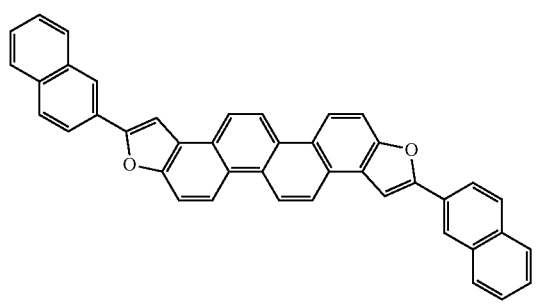
(784)
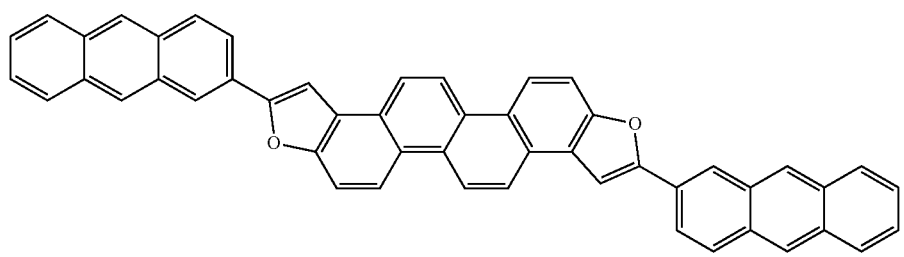
(785)
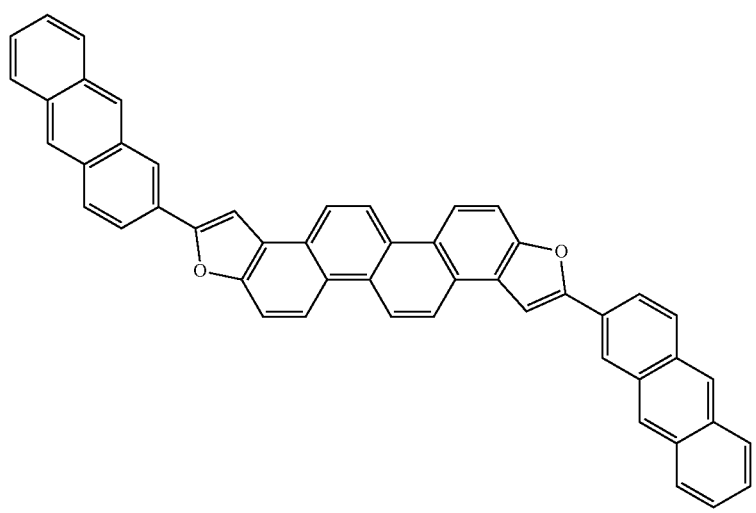
(786)

-continued
(787)
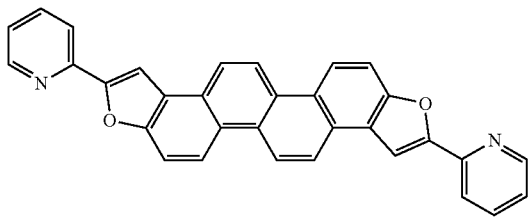
(788)
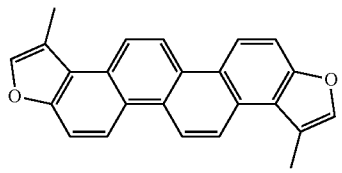
(789)
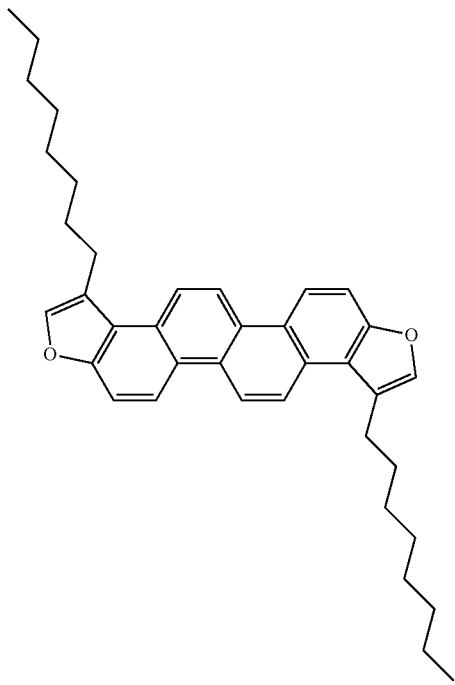
(790)
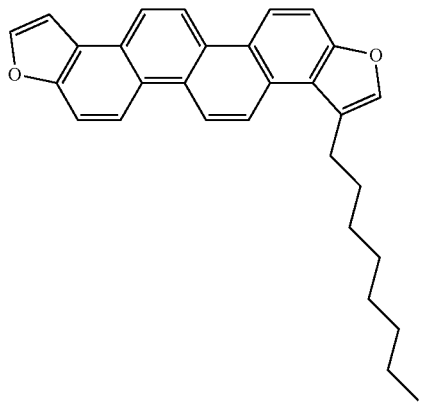
(791)
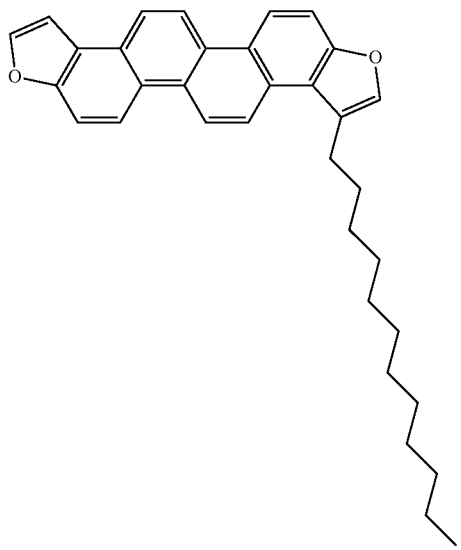
(792)
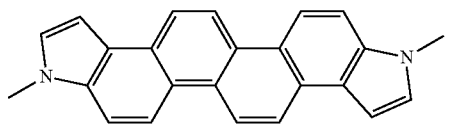
(793)
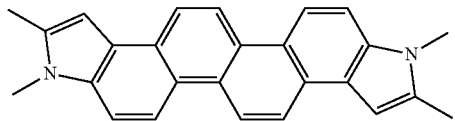
(794)
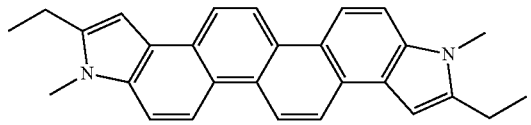

-continued
(795)
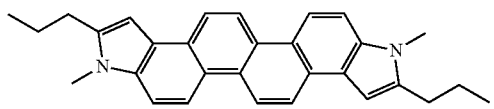
(796)
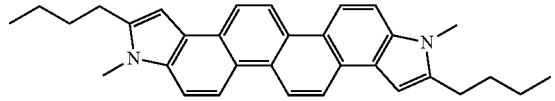
(797)
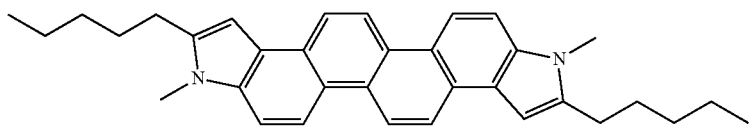
(798)
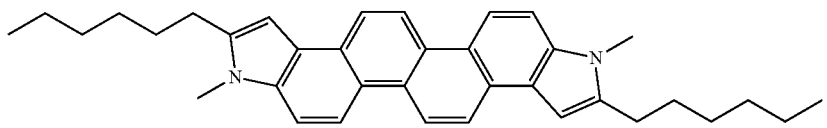
(799)
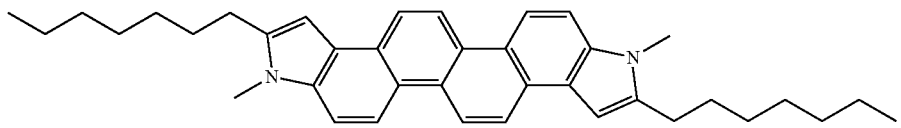
(800)
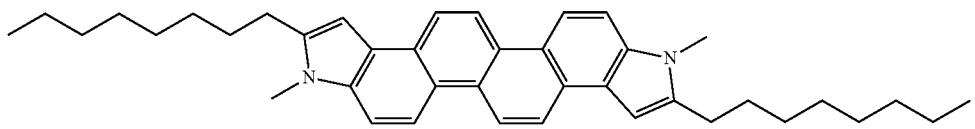
(801)
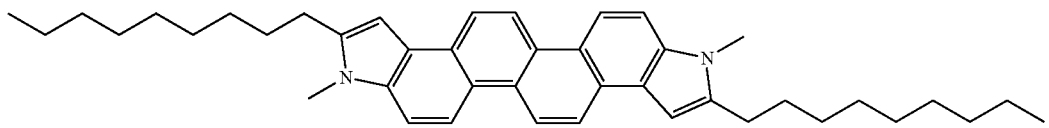
(802)
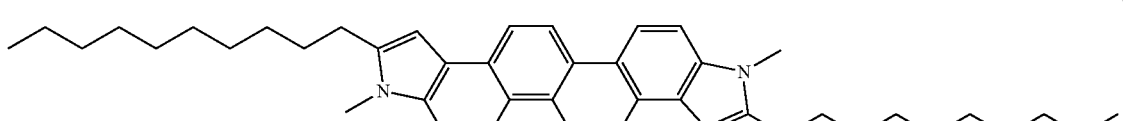
(803)
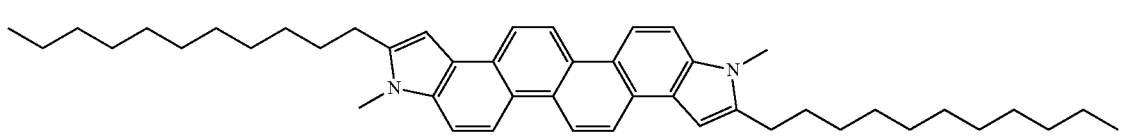
(804)
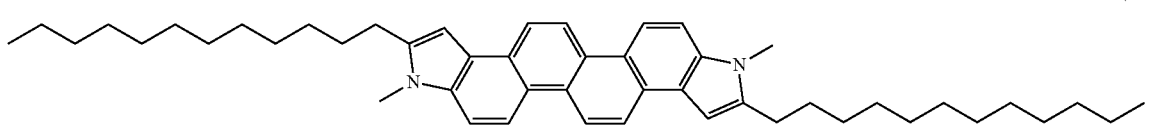
(805)
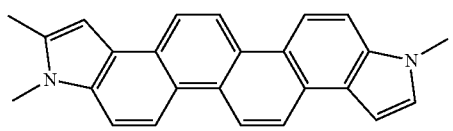
(806)
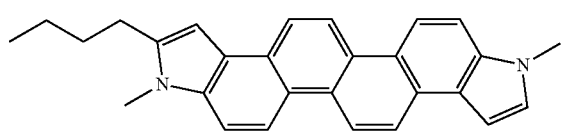
(807)
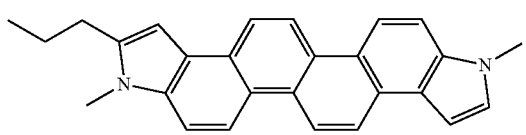
(808)

-continued
(809)
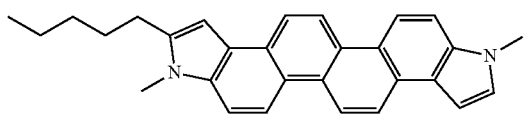
(810)
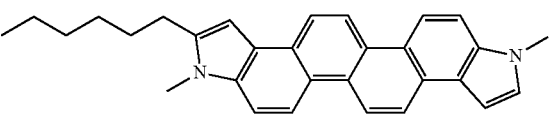
(811)
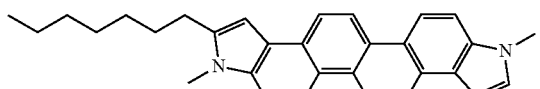
(812)
(813)
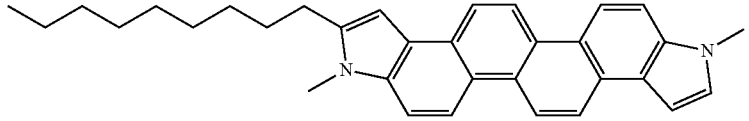
(814)
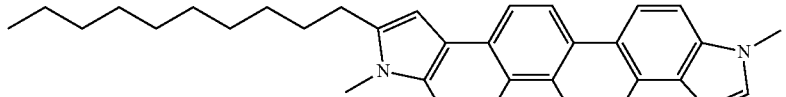
(815)
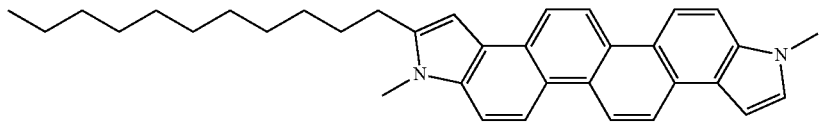
(816)
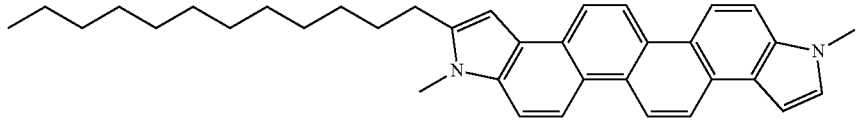
(817)
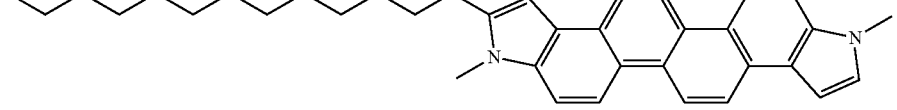
(818)
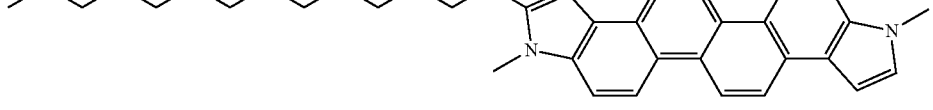
(819)
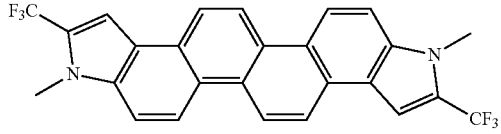
(820)
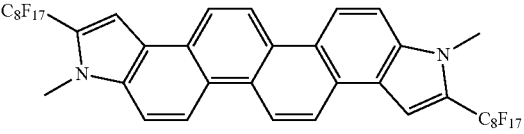
(821)
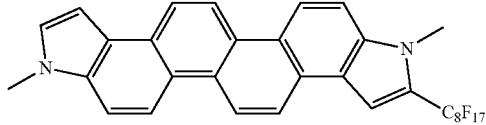
(822)
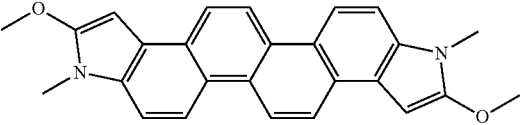
(823)
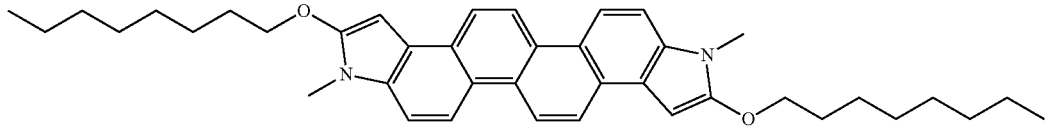

(824)
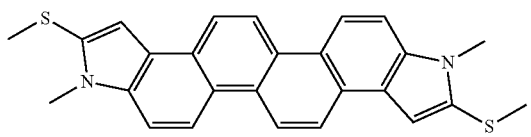
(825)
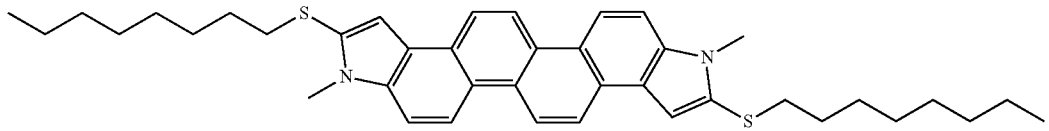
(826)
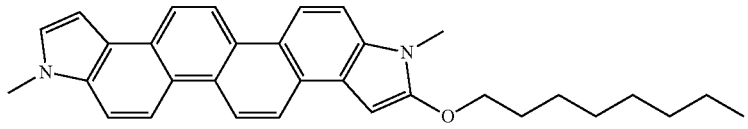
(827)
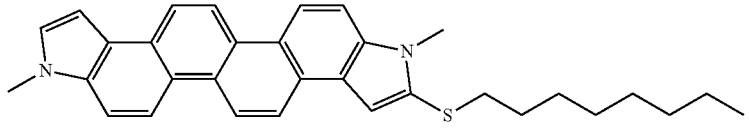
(828)
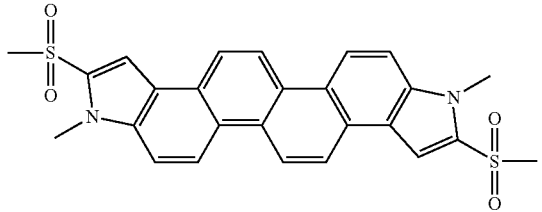
(829)
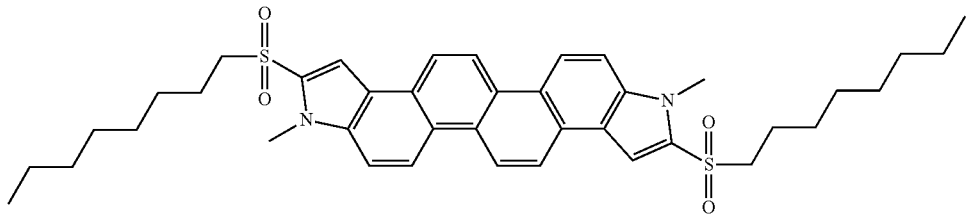
(830)
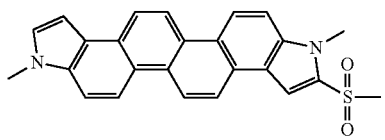
(831)
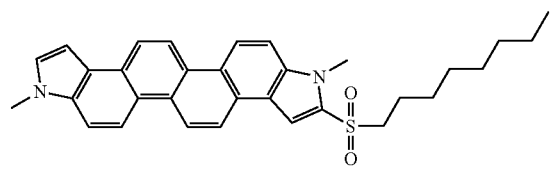
(832)
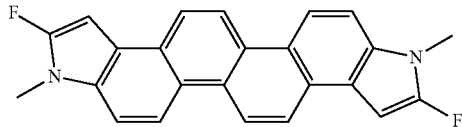
(833)
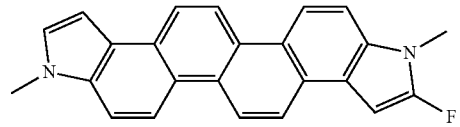
(834)
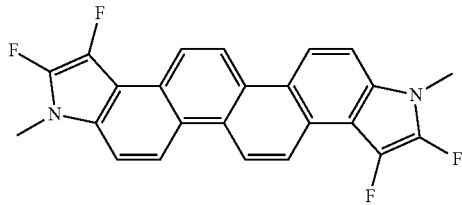
(835)
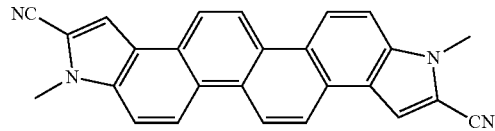

-continued
(836)
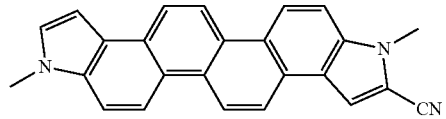
(837)
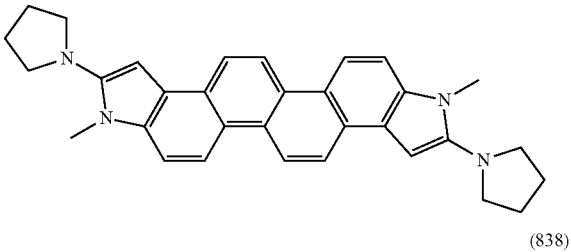
(838)
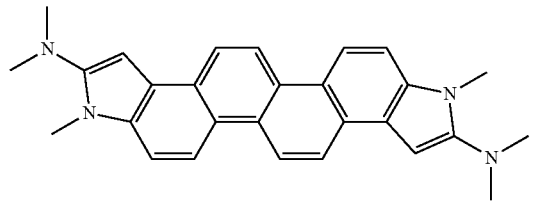
(839)
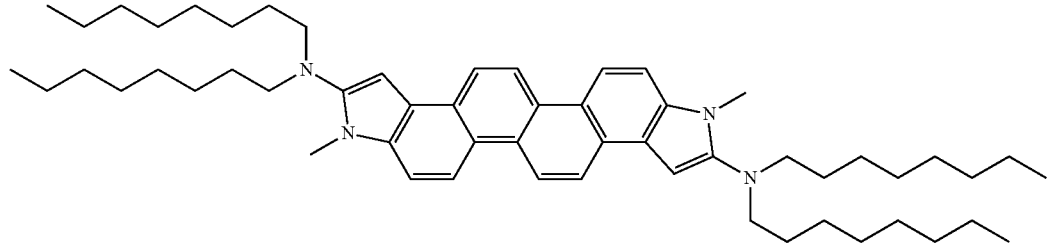
(840)
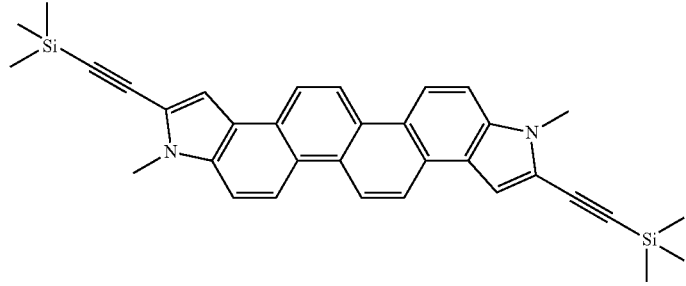
(841)
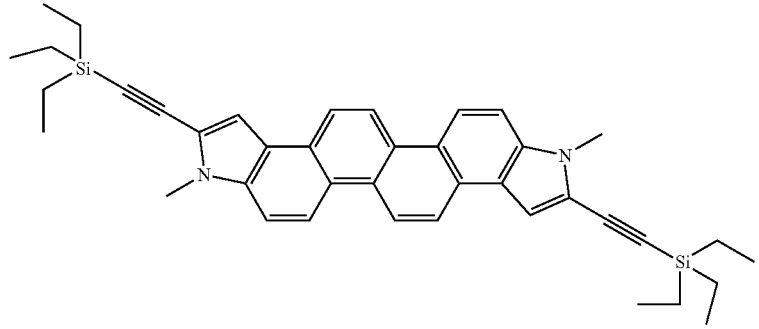

-continued
(842)
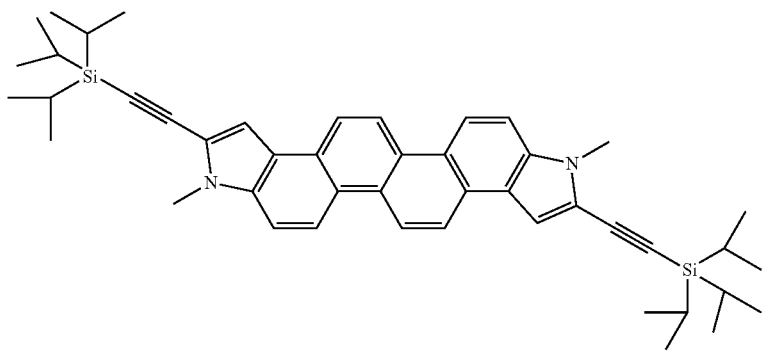
(843)
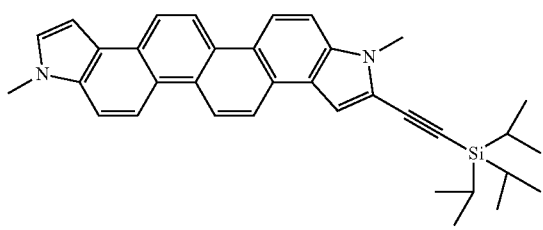
(844)
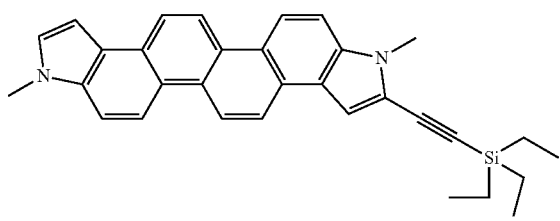
(845)
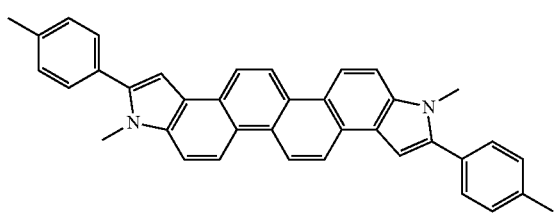
(846)
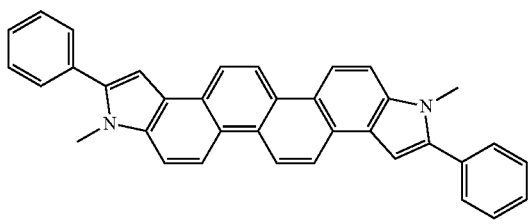
(847)
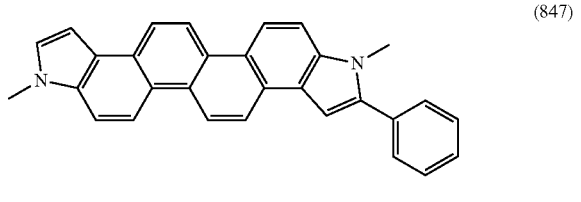
(848)
(849)
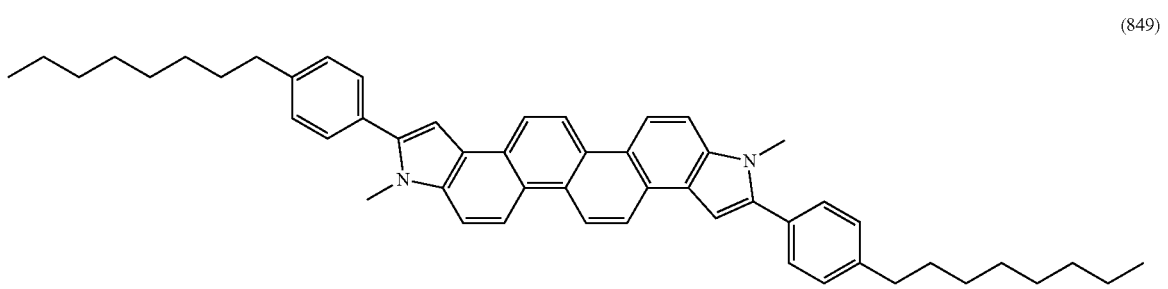

-continued
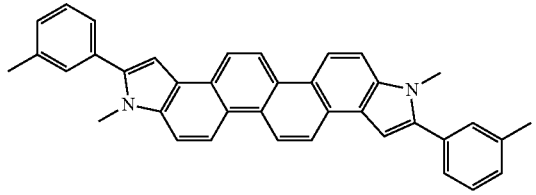
(850)
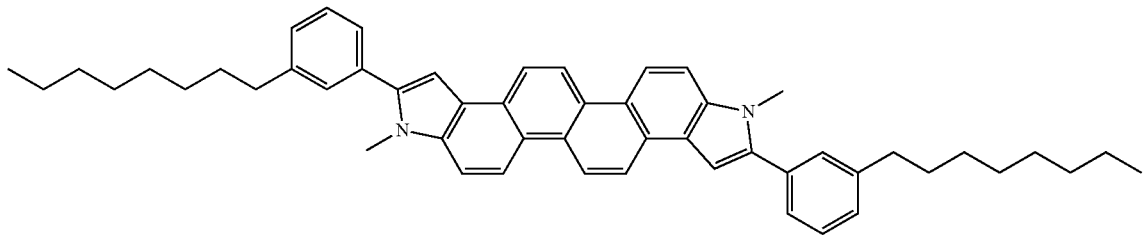
(851)
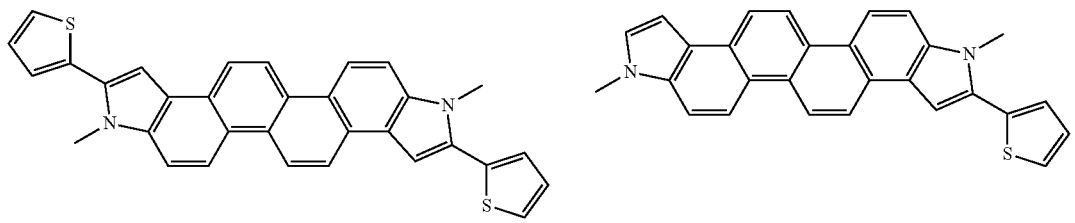
(852)
(853)
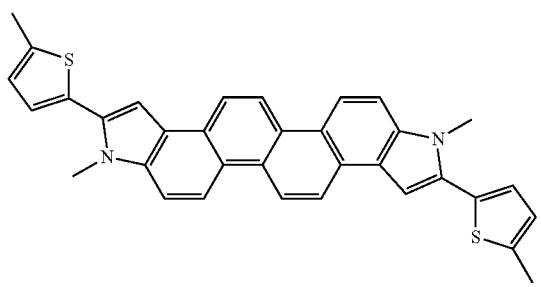
(854)
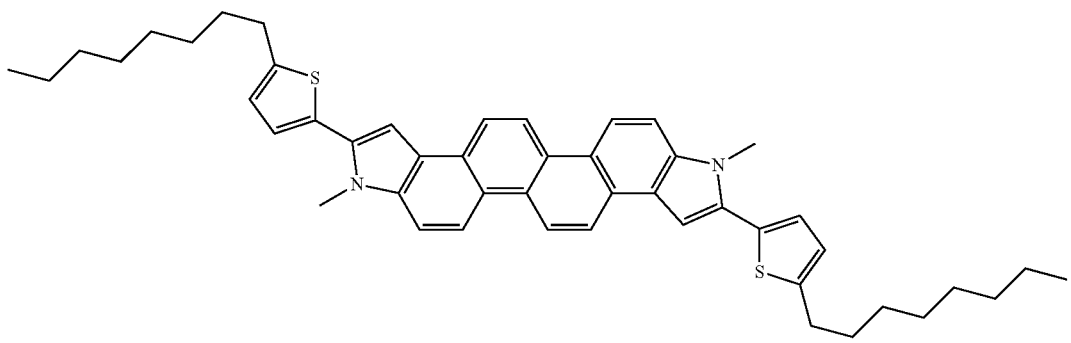
(855)
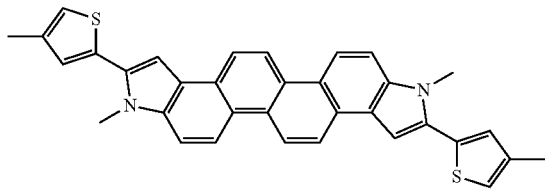
(856)

(857)
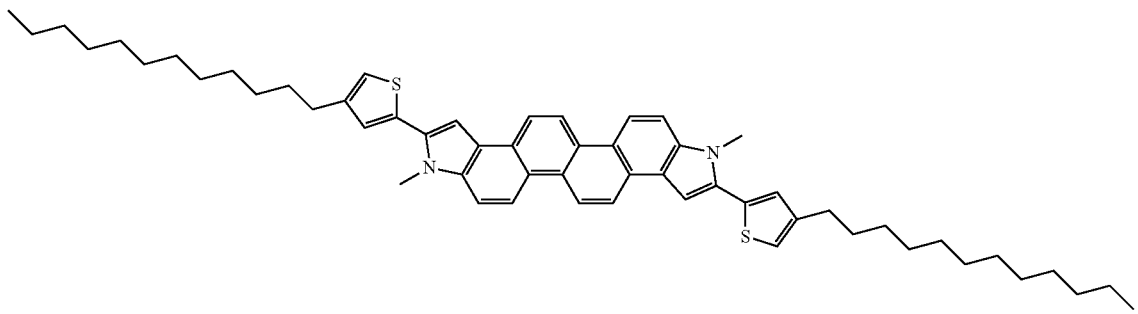
(858)
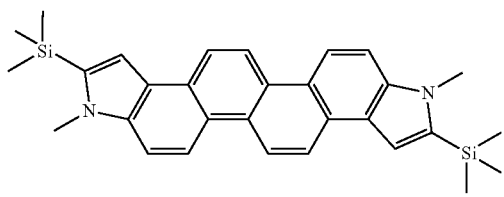
(859)
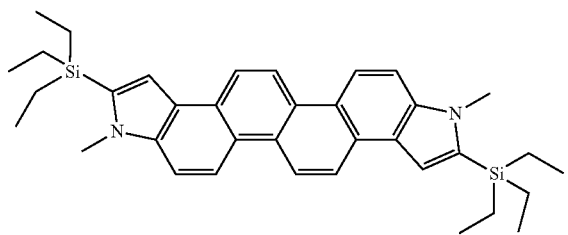
(860)
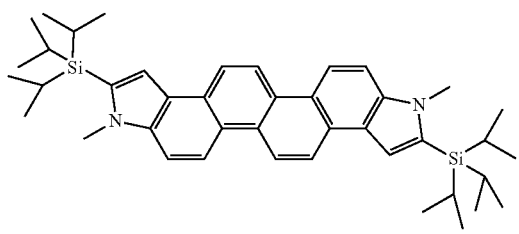
(861)
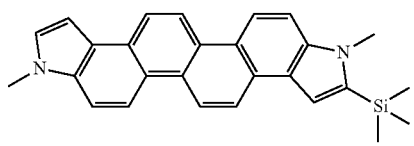
(862)
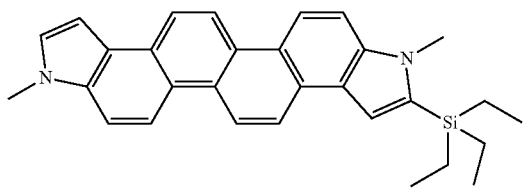
(863)
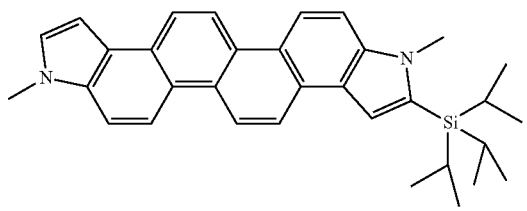
(864)
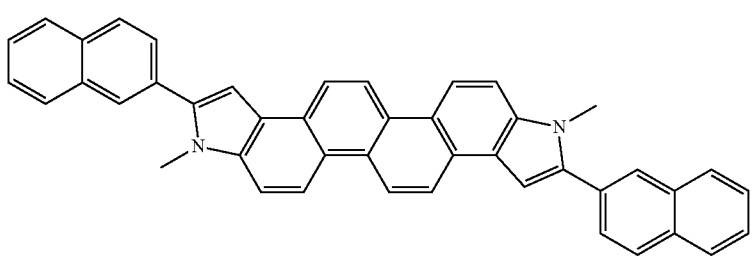

-continued
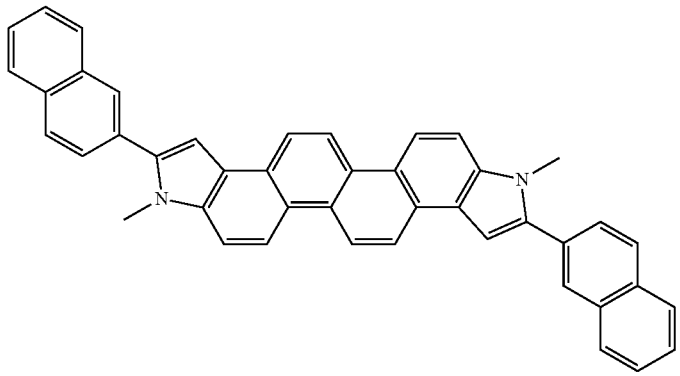
(865)
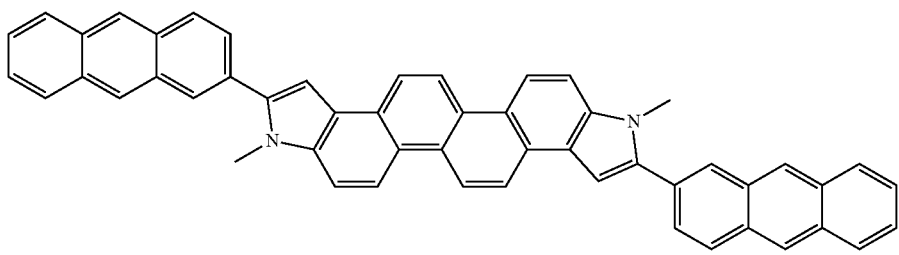
(866)
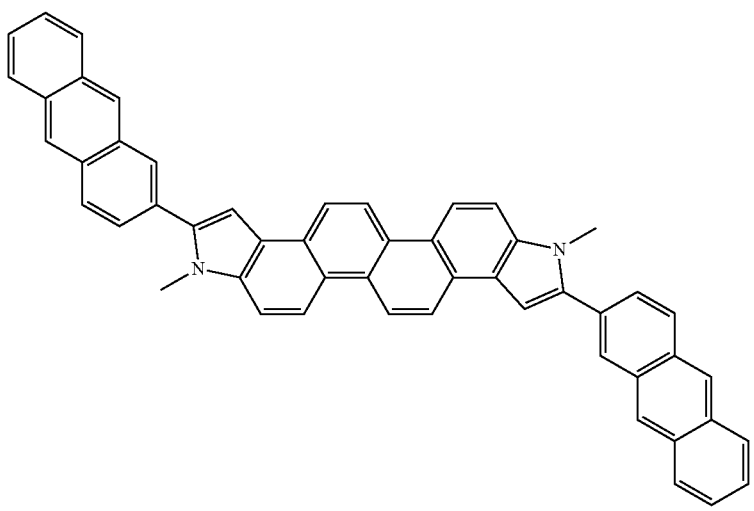
(867)
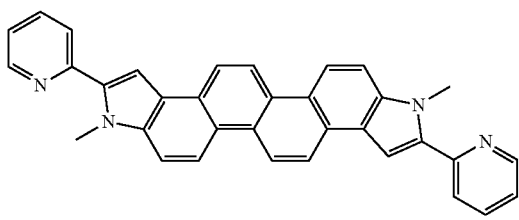
(868)
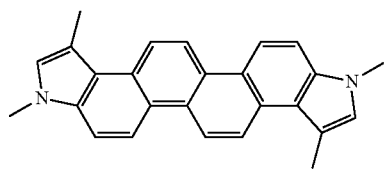
(869)

-continued
(870)
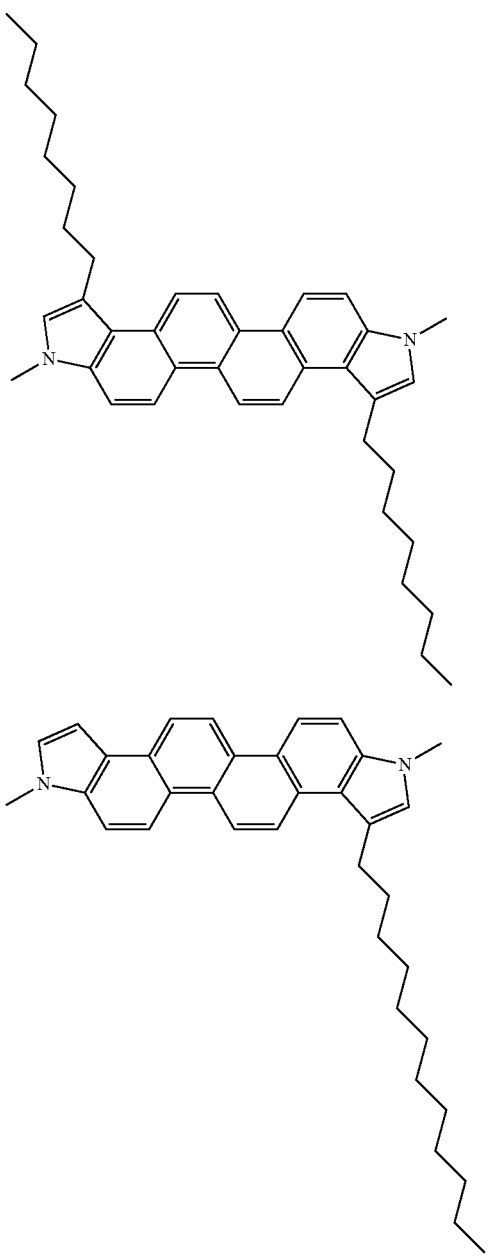
(871)
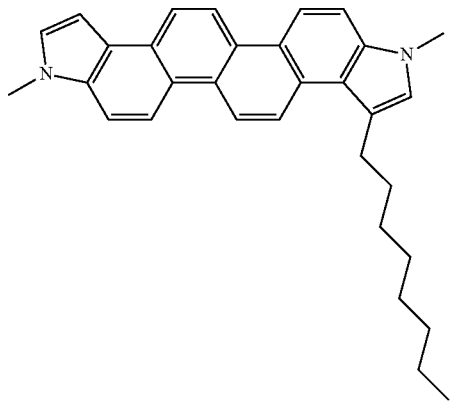
(872)
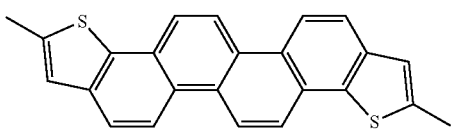
(873)
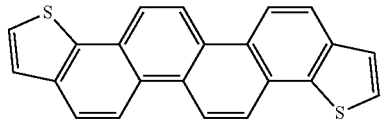
(874)
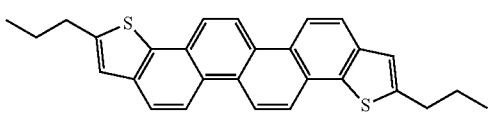
(875)
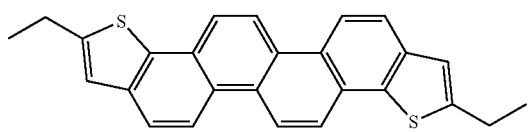
(876)
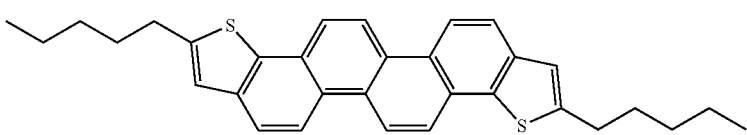
(877)
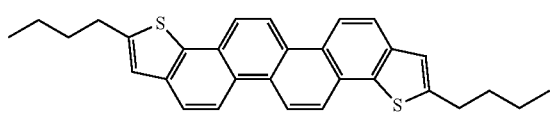
(878)

-continued
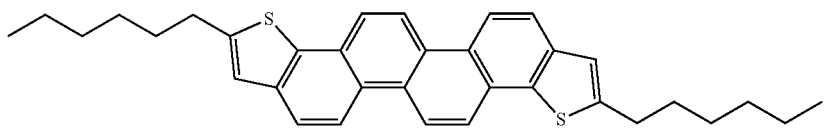 (879)
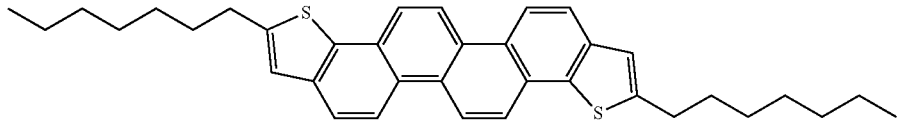 (880)
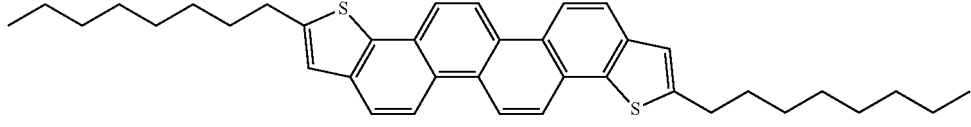 (881)
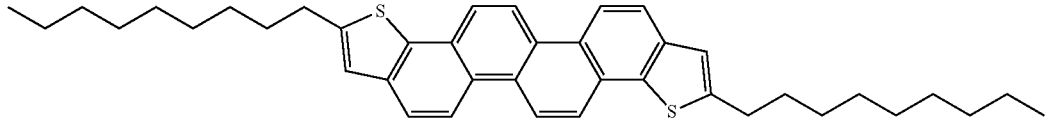 (882)
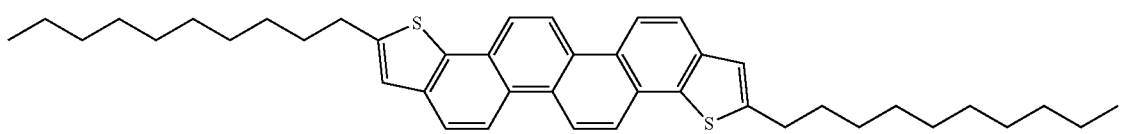 (883)
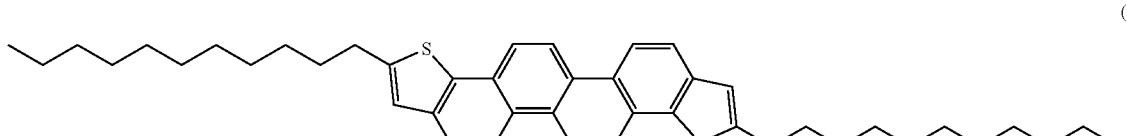 (884)
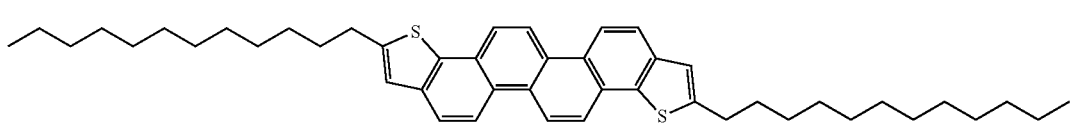 (885)
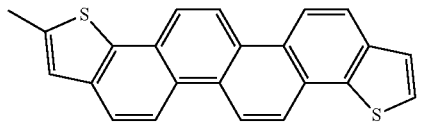 (886)
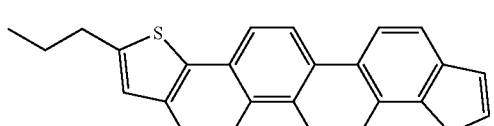 (888)
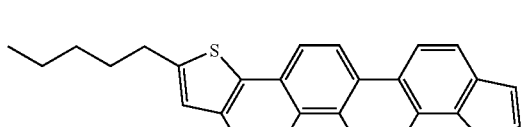 (890)
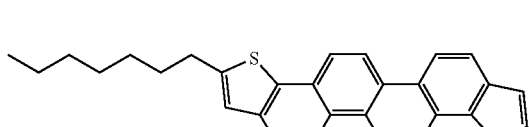 (892)

-continued
(894)
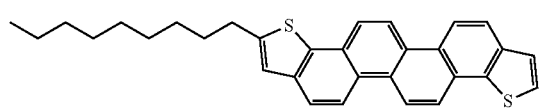
(895)
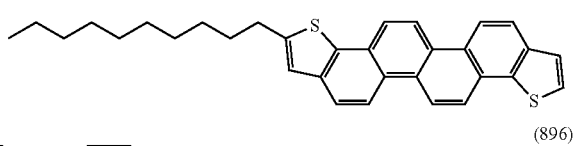
(896)
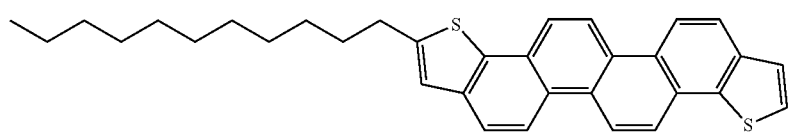
(897)
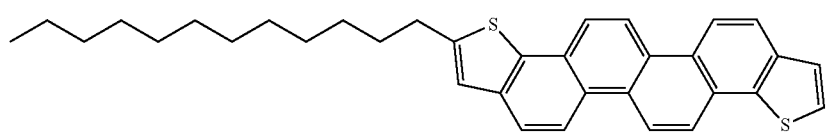
(898)
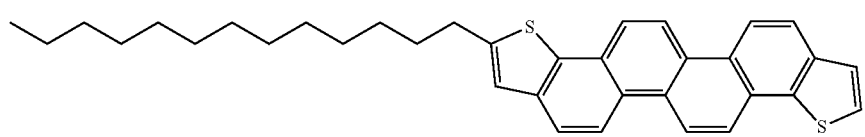
(899)
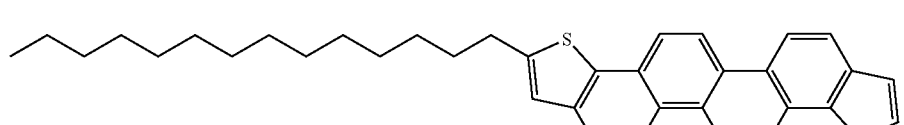
(900)
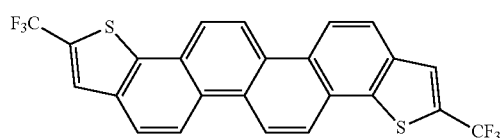
(901)
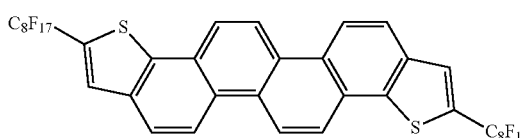
(902)
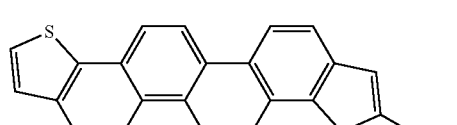
(903)
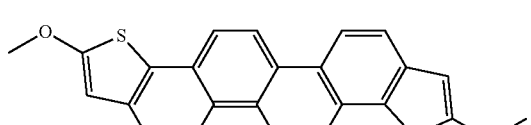
(904)
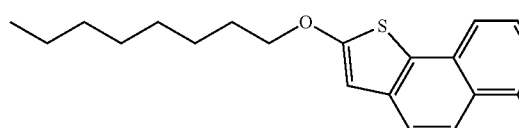
(905)
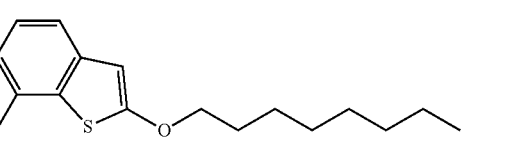
(906)
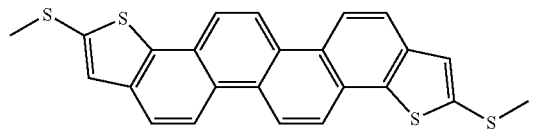
(907)
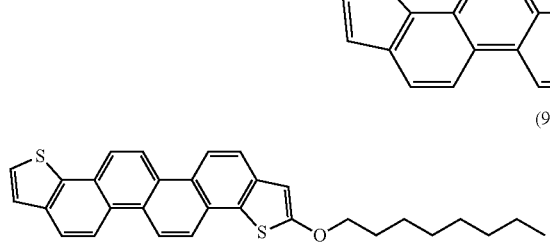
(908)
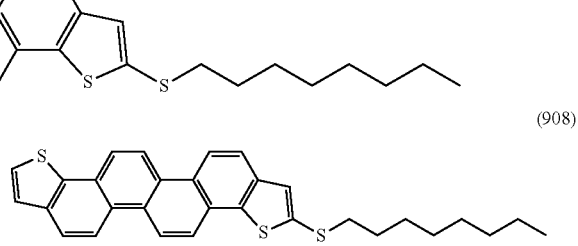

-continued
(909)
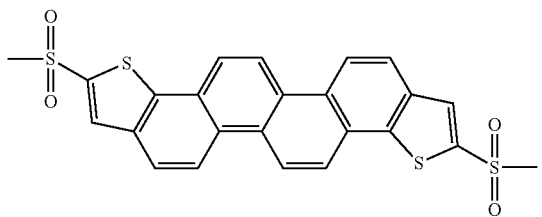
(910)
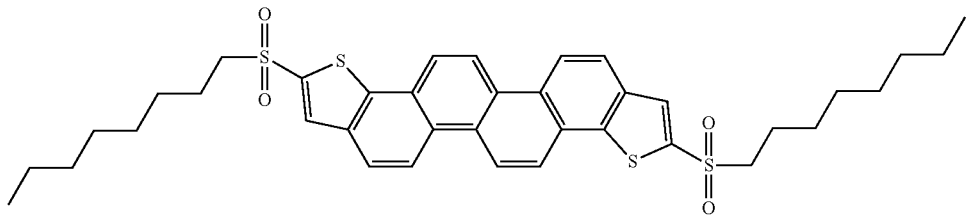
(911)
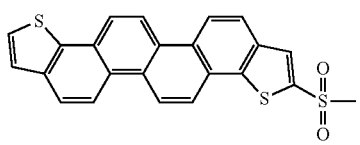
(912)
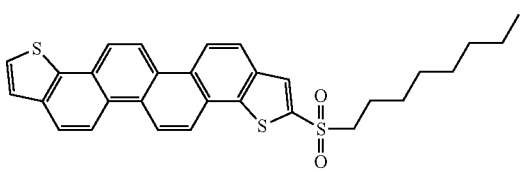
(913)
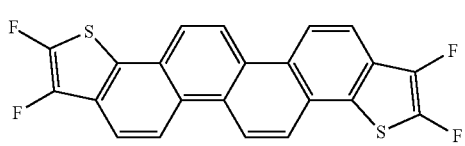
(914)
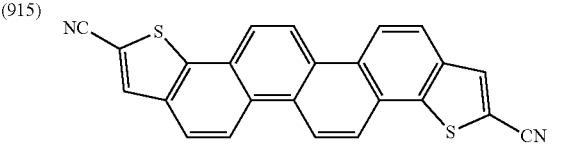
(915)
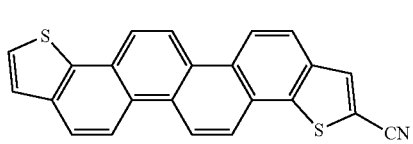
(916)
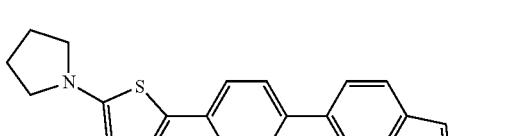
(917)
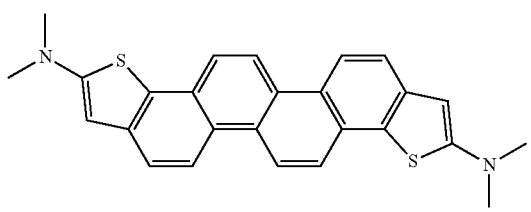
(918)
(919)
(920)
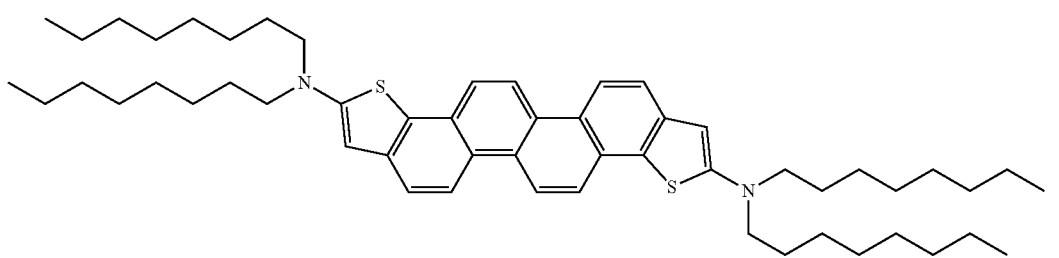

-continued
(921)
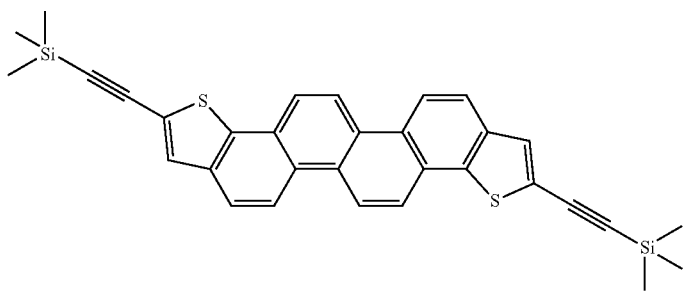
(922)
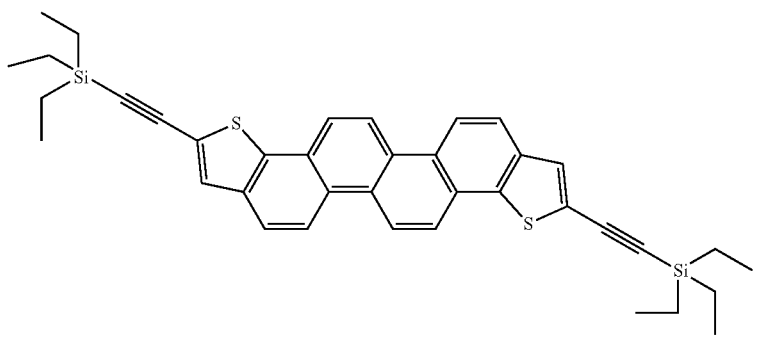
(923)
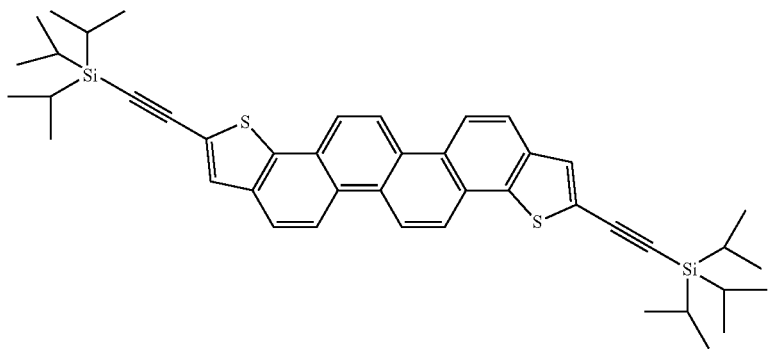
(924)
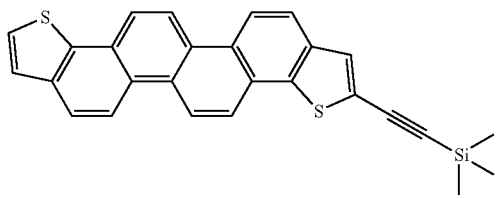
(925)
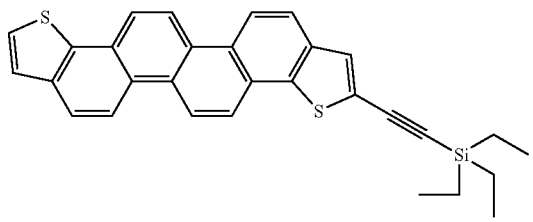
(926)
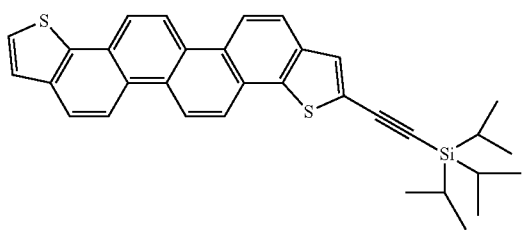

-continued
(927)
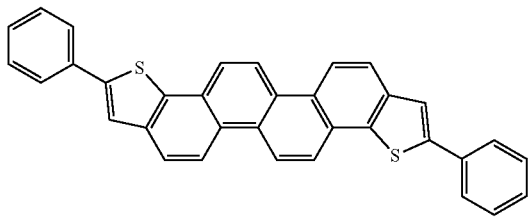
(928)
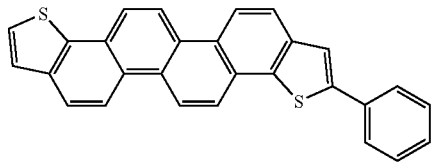
(929)
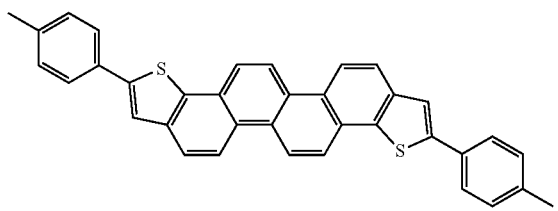
(930)
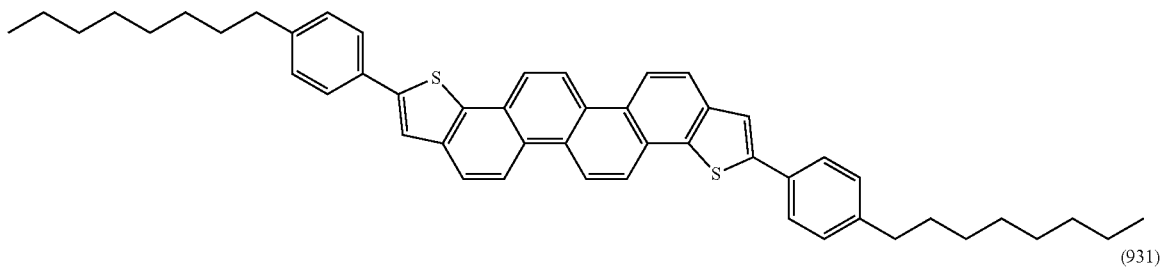
(931)
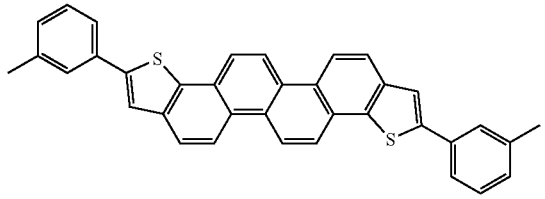
(932)
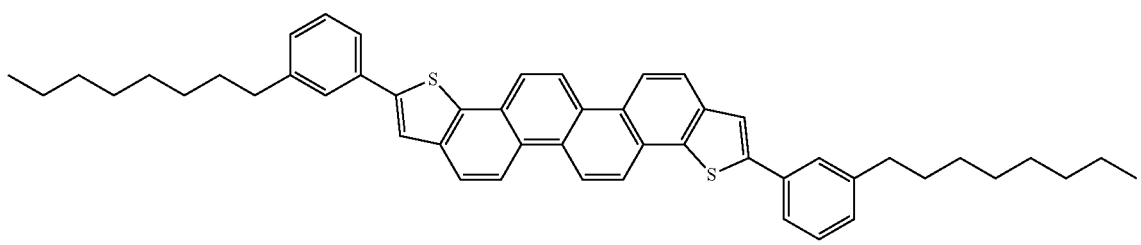
(933)
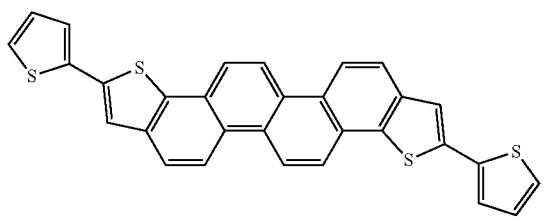
(934)
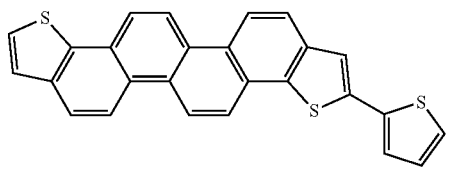
(935)
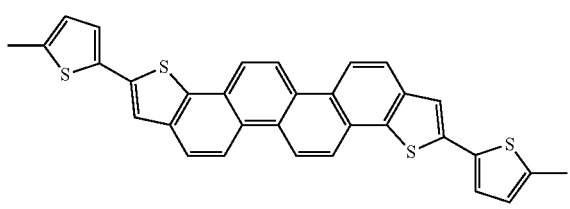

(936)
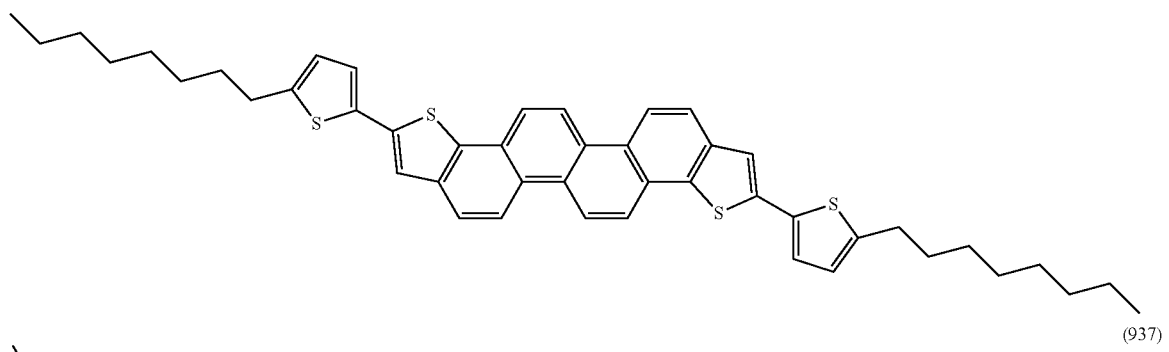
(937)
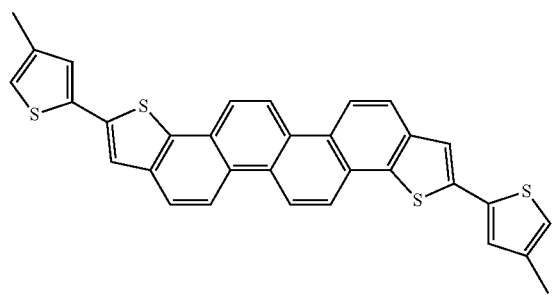
(938)
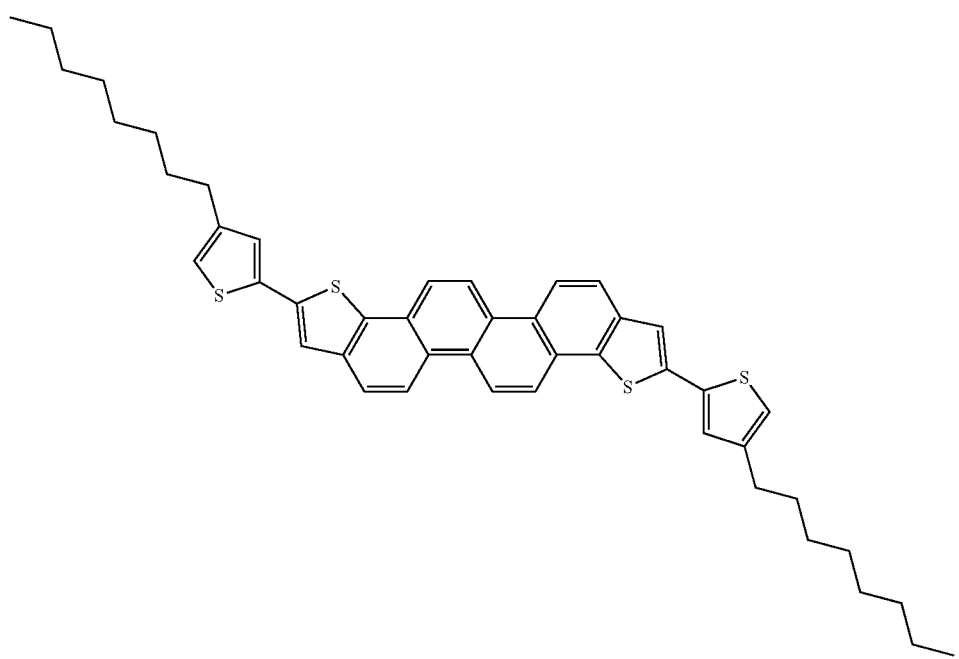
(939)
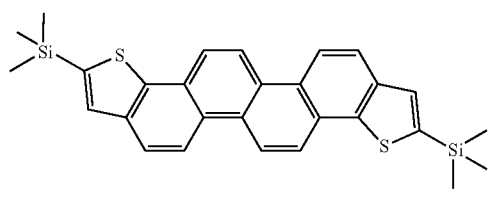
(940)
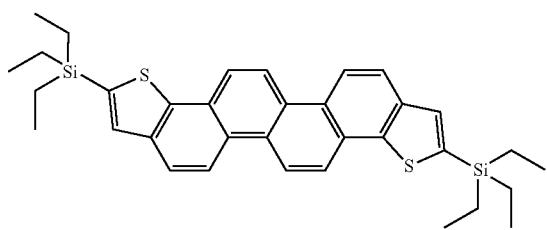

-continued
(941)
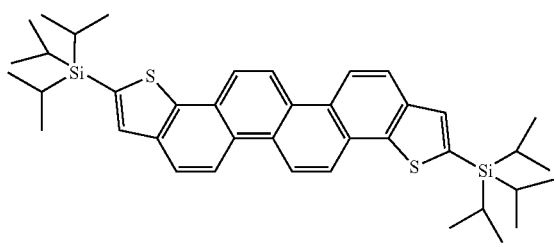
(942)
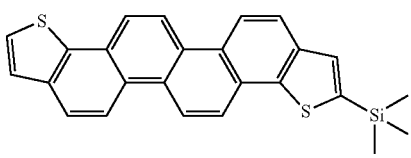
(943)
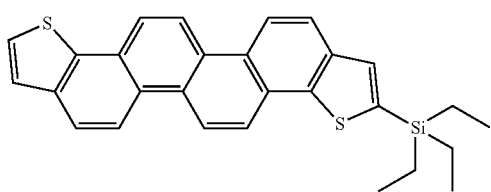
(944)
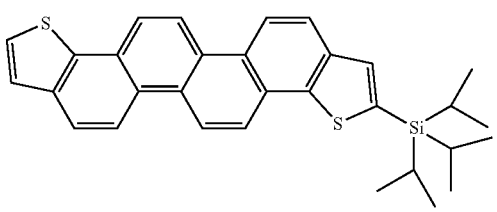
(945)
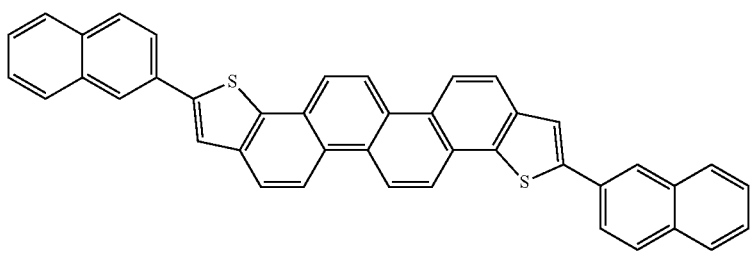
(946)
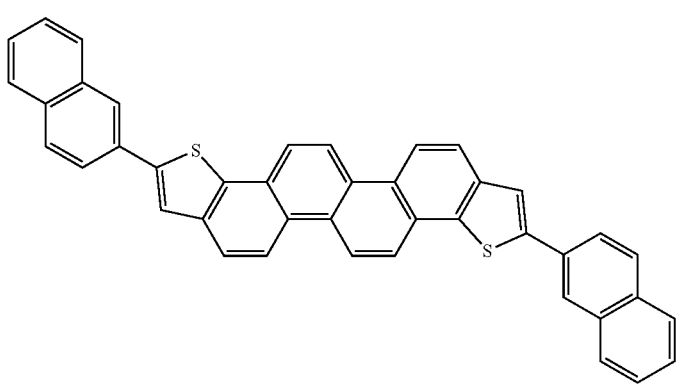
(947)
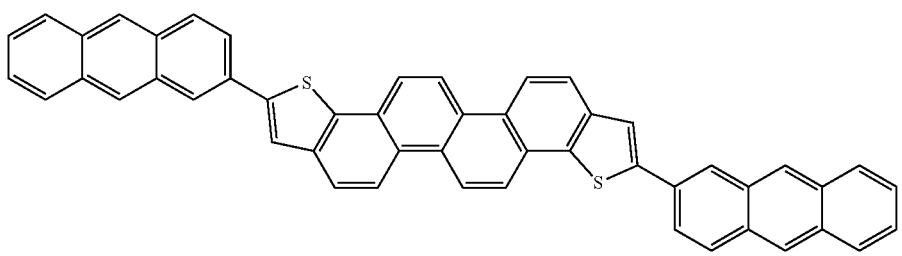

-continued
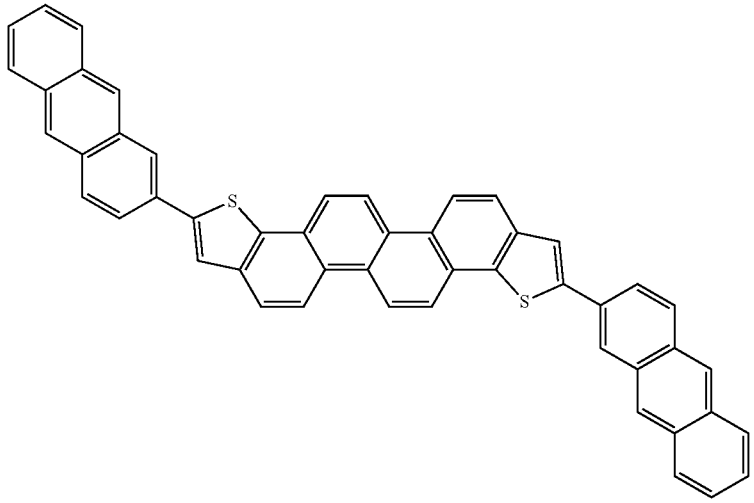
(948)
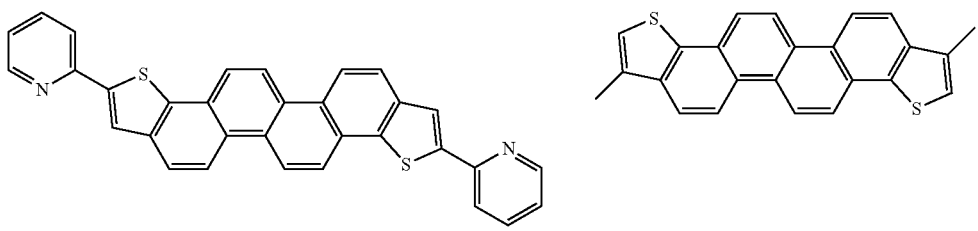
(949)
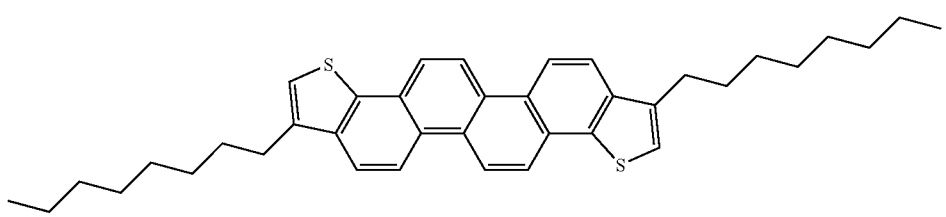
(950)
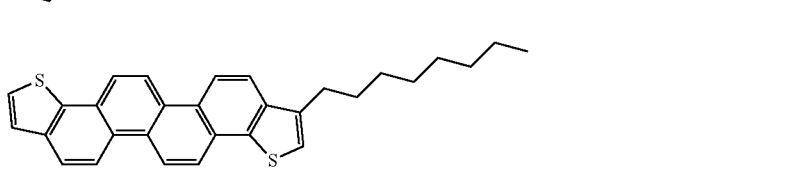
(951)
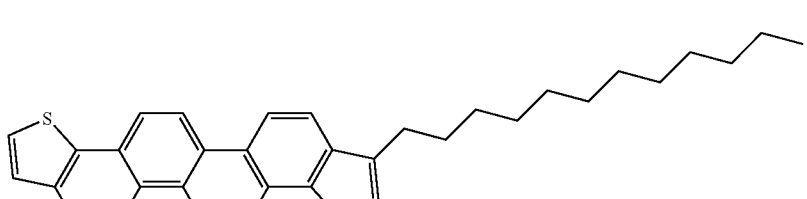
(952)
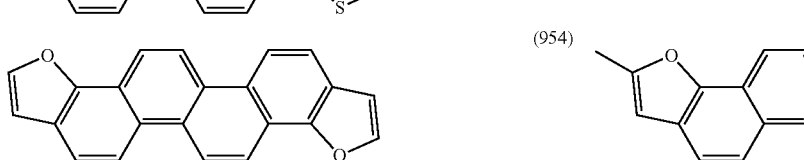
(953)
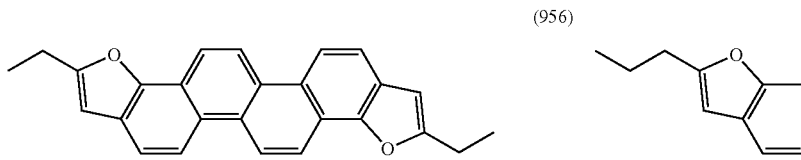
(954) (955)
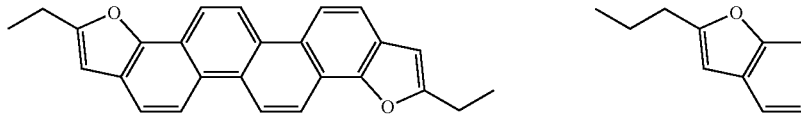
(956) (957)
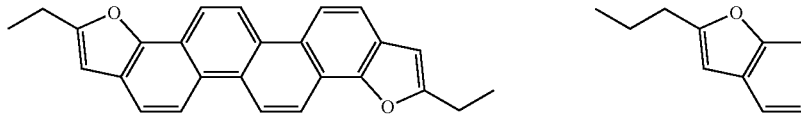

-continued
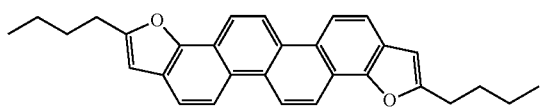
(958)
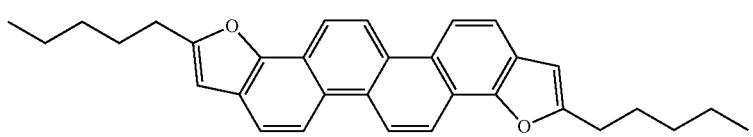
(959)
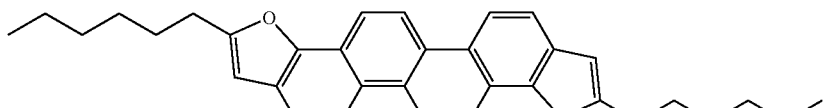
(960)
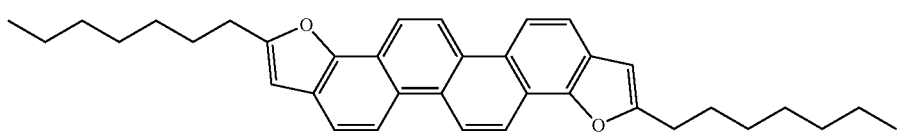
(961)
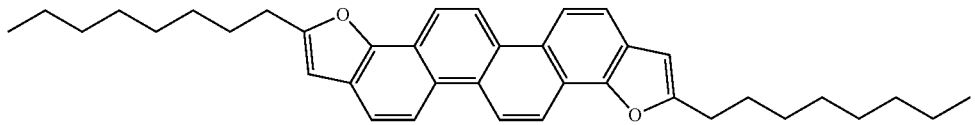
(962)
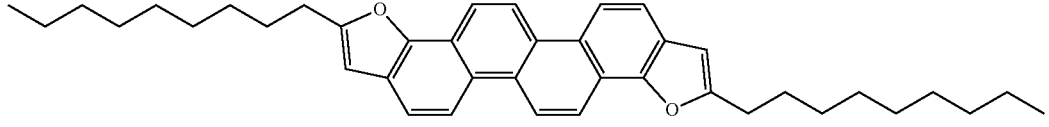
(963)
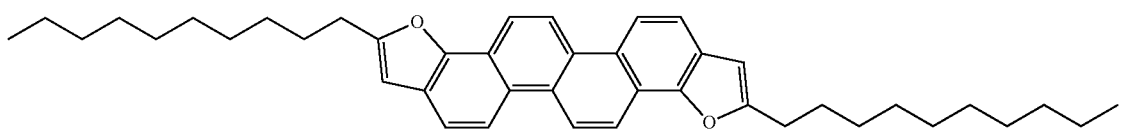
(964)
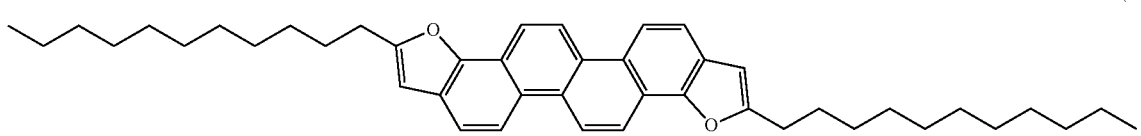
(965)
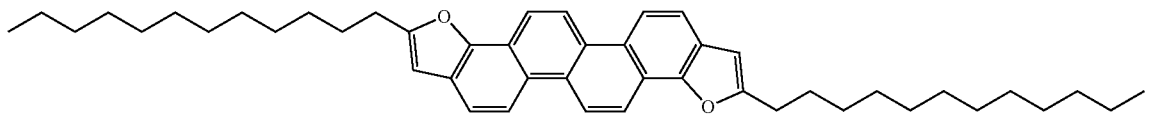
(966)
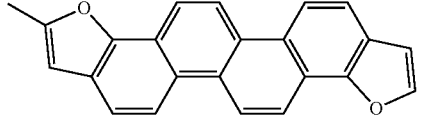
(967)
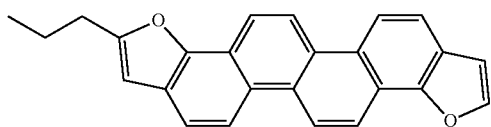
(969)
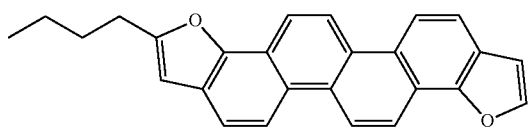
(968)
(970)

-continued
(971)
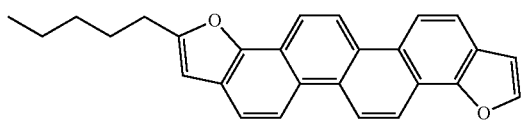
(972)
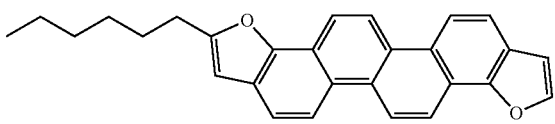
(973)
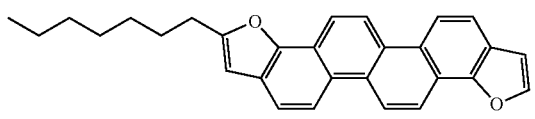
(974)
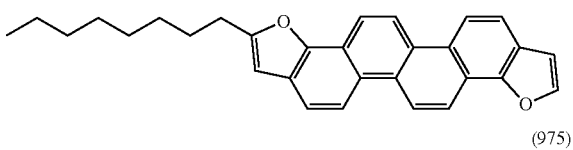
(975)
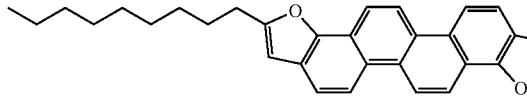
(976)
(977)
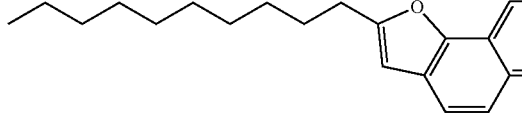
(978)
(979)
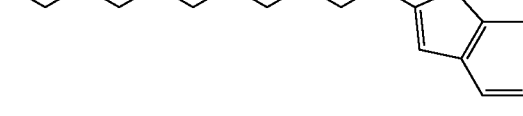
(980)
(981)
(982)
(983)
(984)
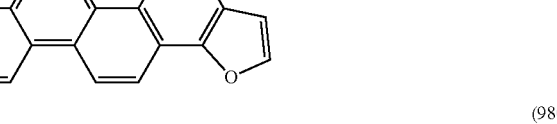
(985)

-continued
(986)
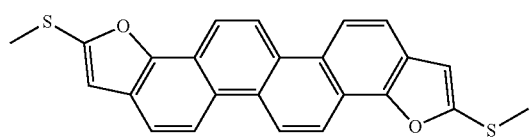
(987)
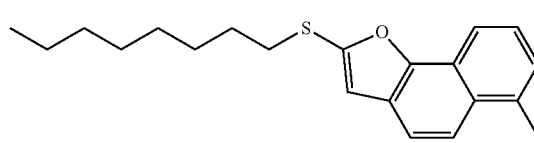
(988)
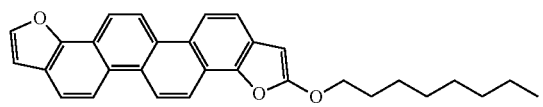
(989)
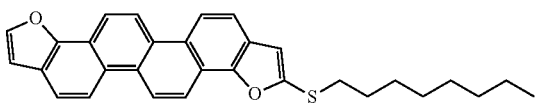
(990)
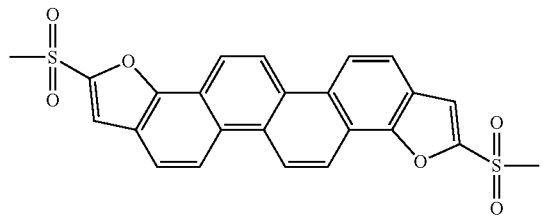
(991)
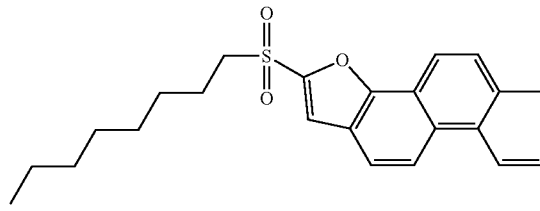
(992)
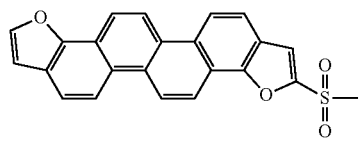
(993)
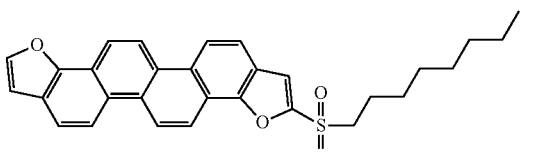
(994)
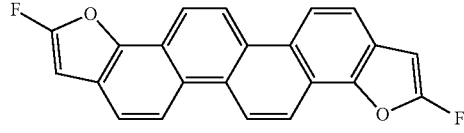
(995)
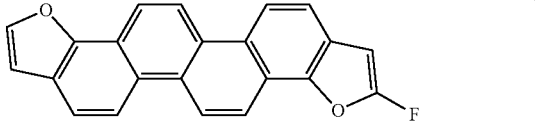
(996)
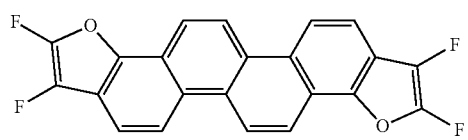
(997)
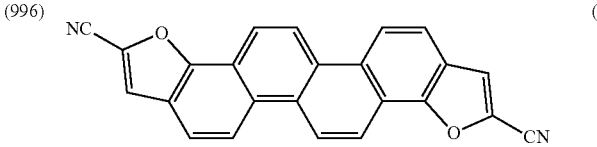
(998)
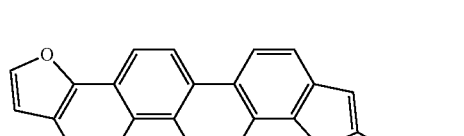
(999)
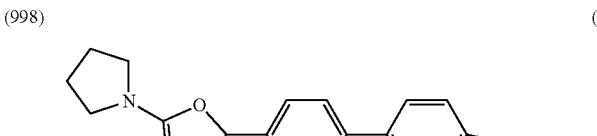

-continued
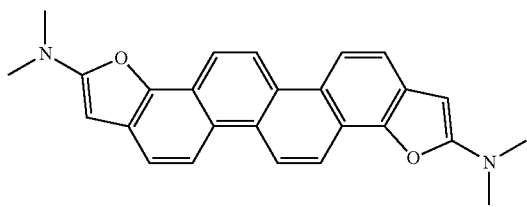
(1000)
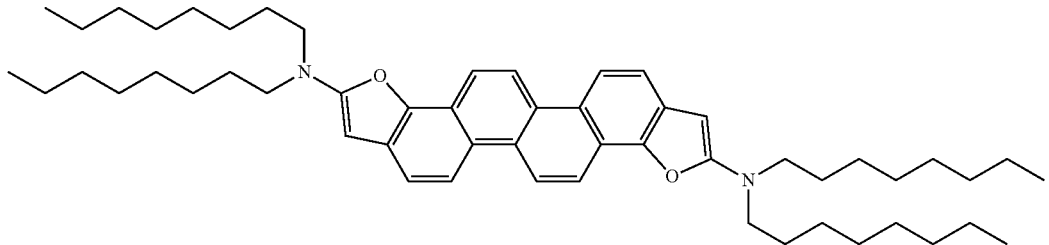
(1001)
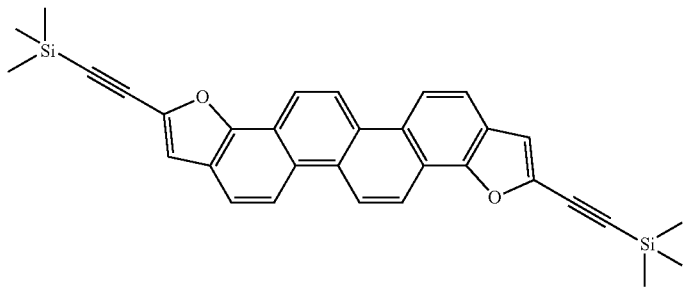
(1002)
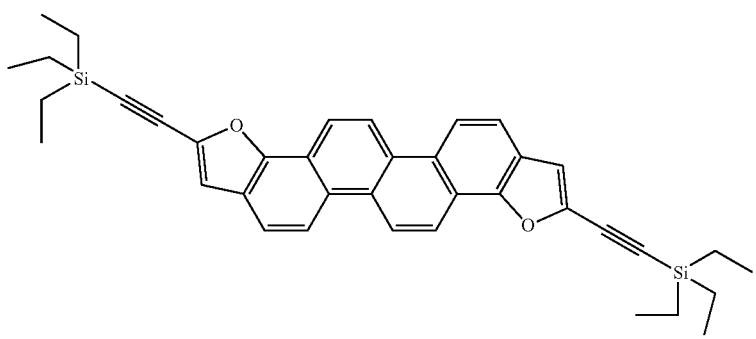
(1003)
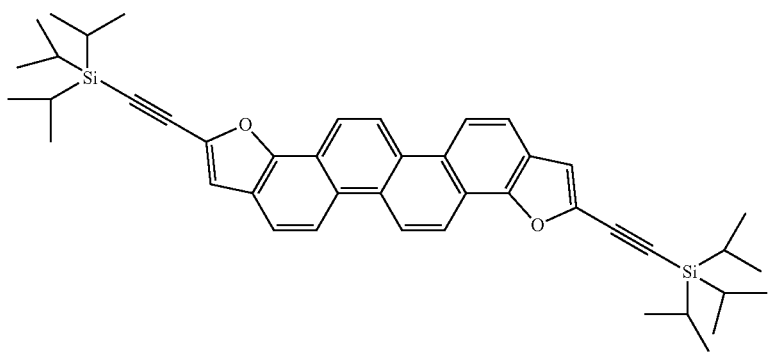
(1004)

-continued
(1005)
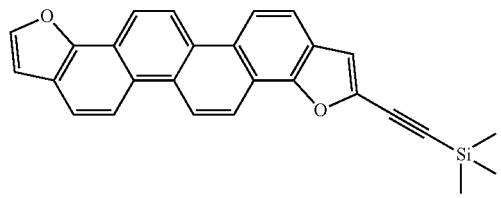
(1006)
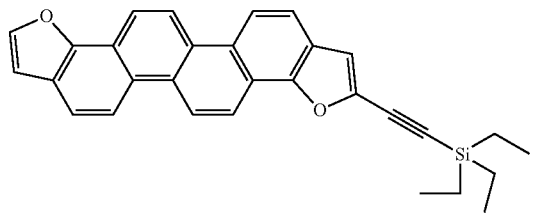
(1007)
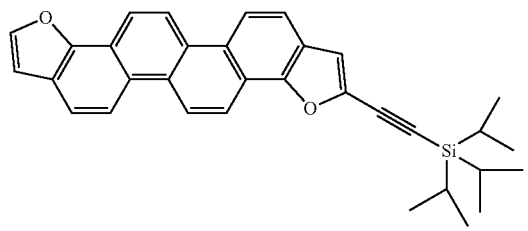
(1008)
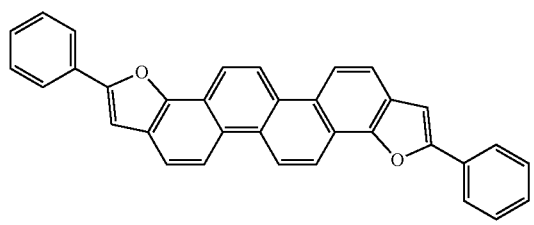
(1009)
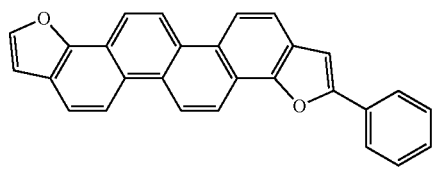
(1010)
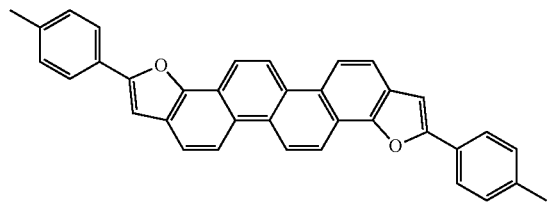
(1011)
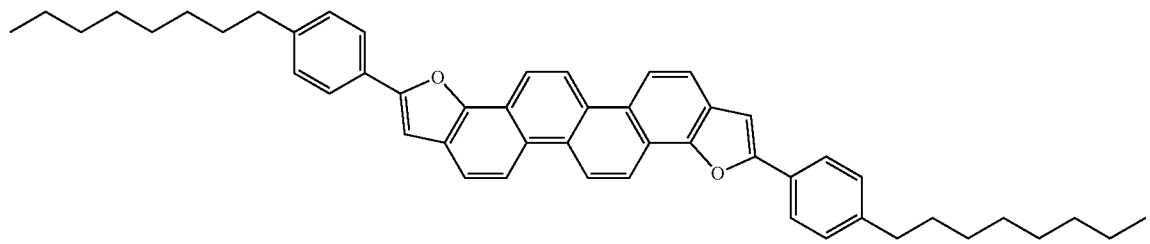
(1012)
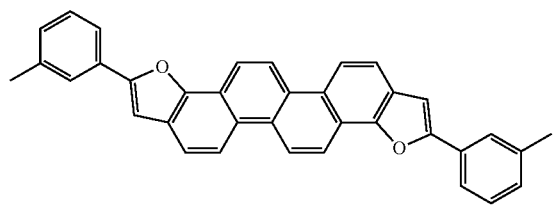

-continued
(1013)
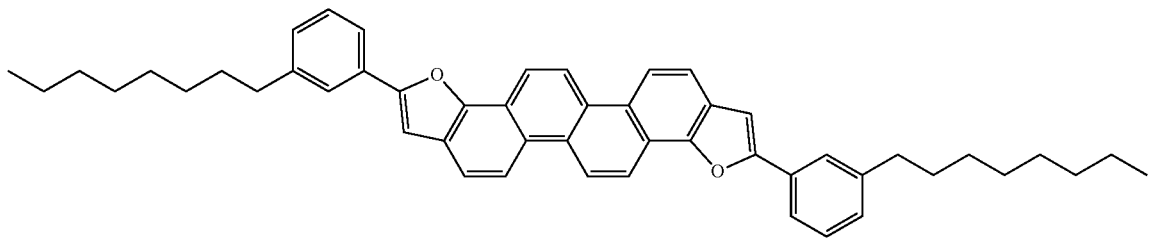
(1014)
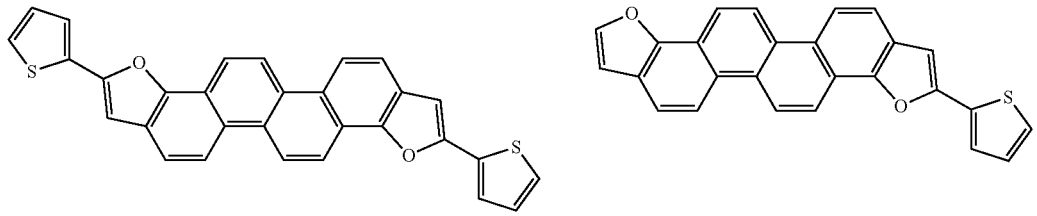
(1015)
(1016)
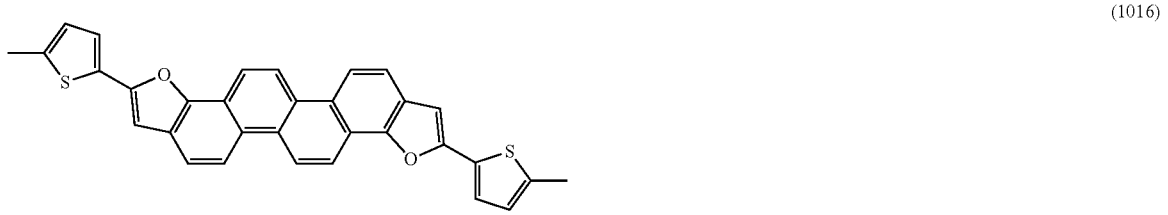
(1017)
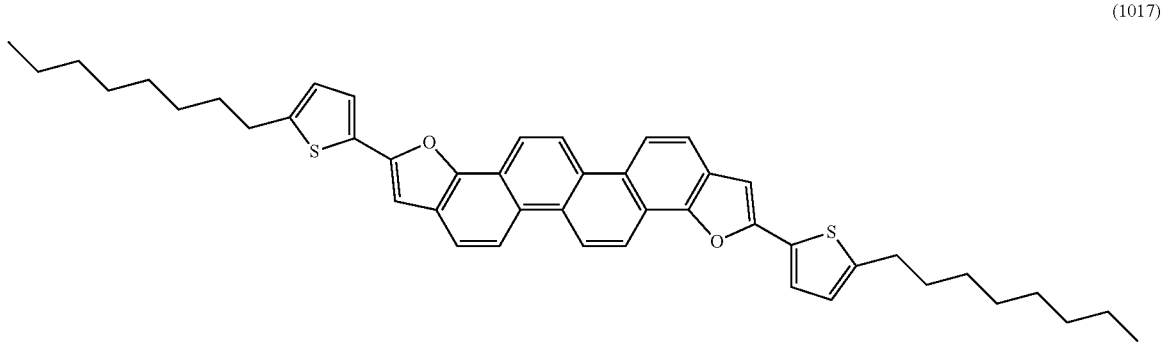
(1018)
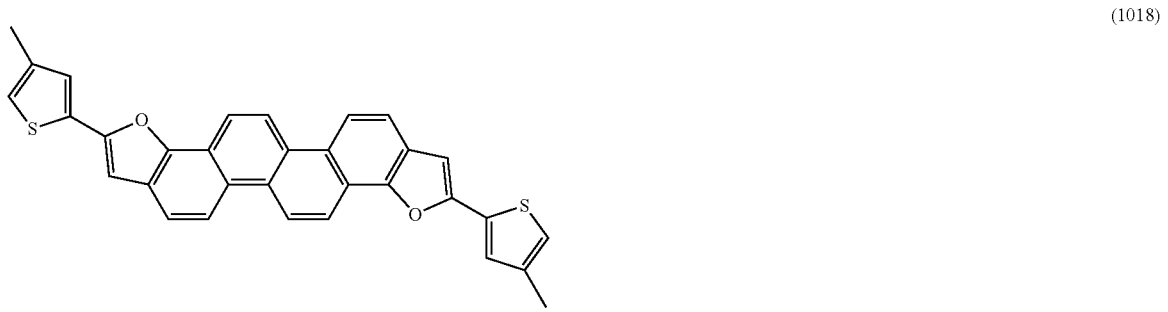

-continued
(1019)
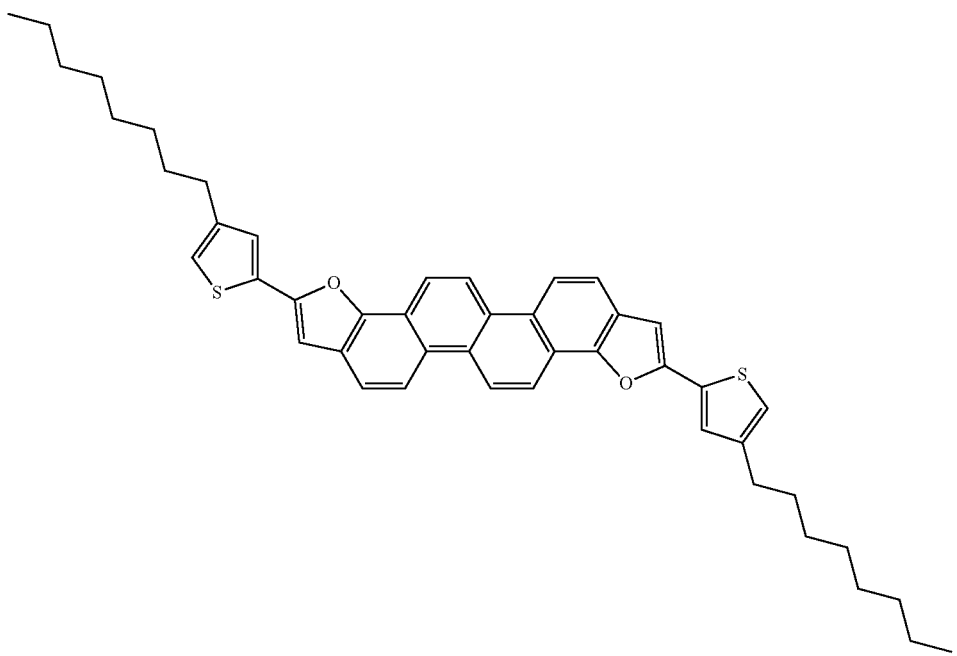
(1020)
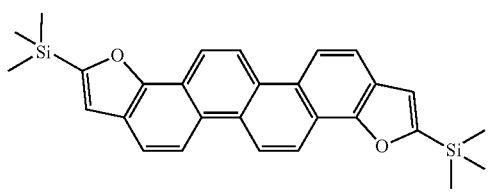
(1021)
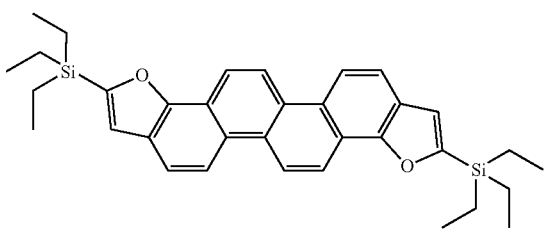
(1022)
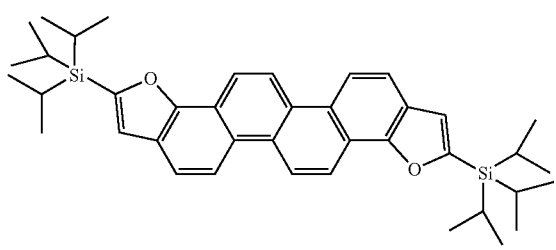
(1023)
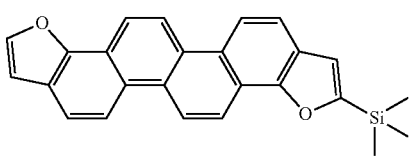
(1024)
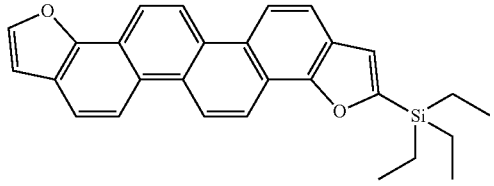
(1025)
(1026)
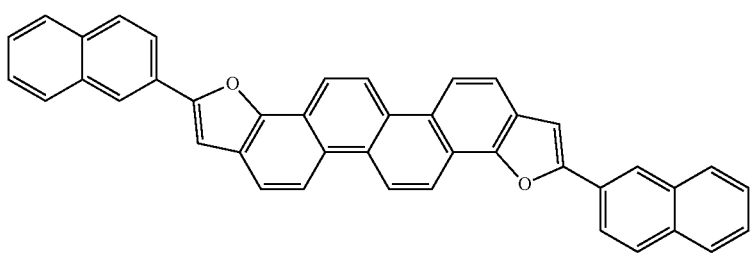

-continued
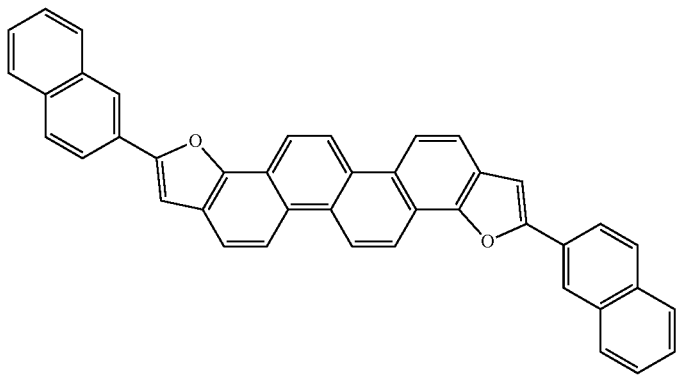
(1027)
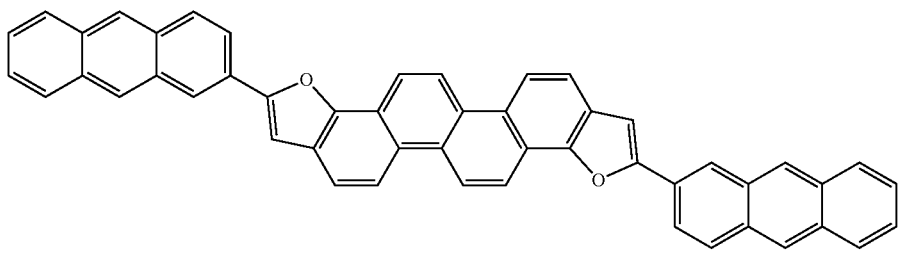
(1028)
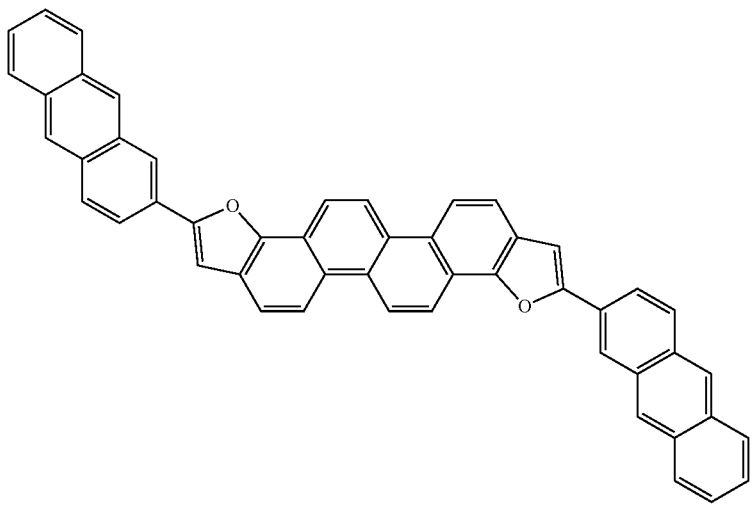
(1029)
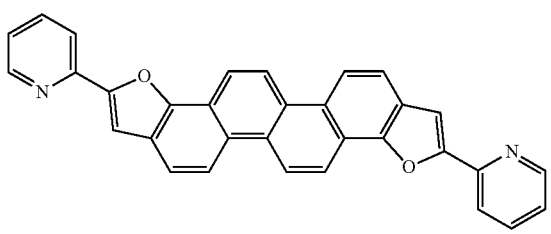
(1030)
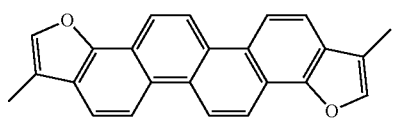
(1031)
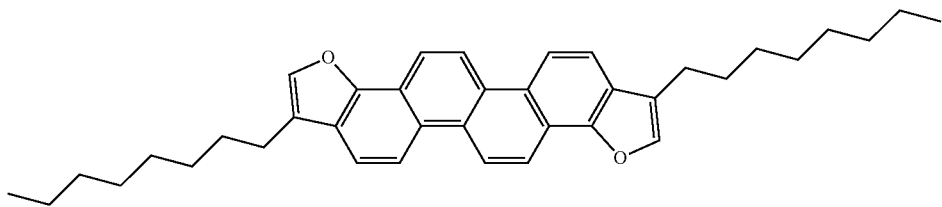
(1032)

(1033)
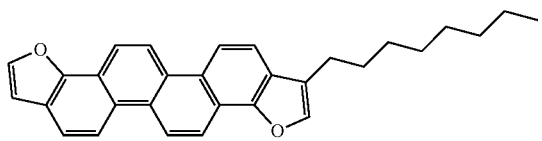
(1034)
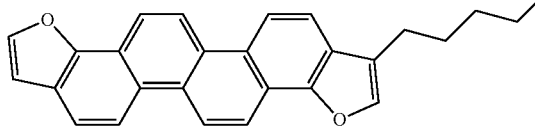
(1035)
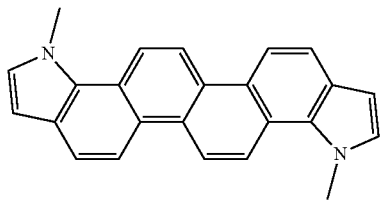
(1036)
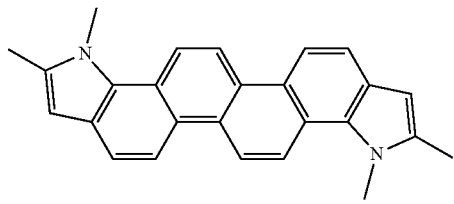
(1037)
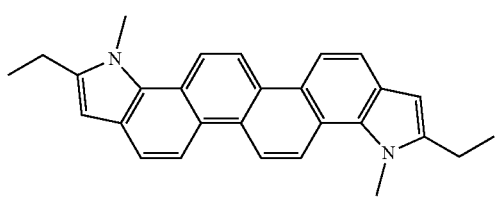
(1038)
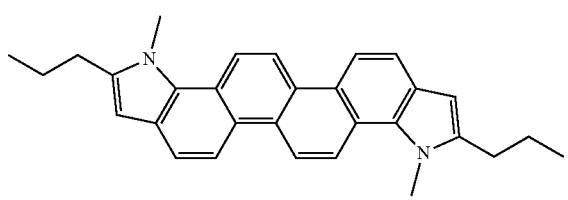
(1039)
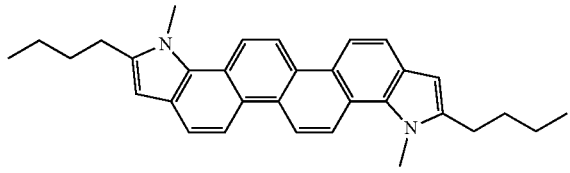
(1040)
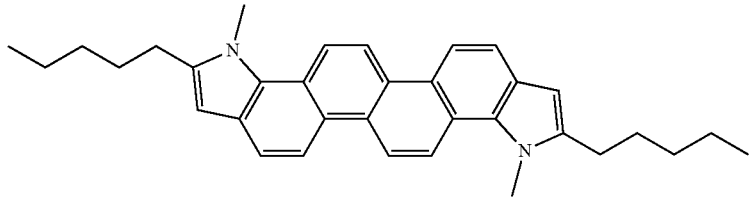
(1041)
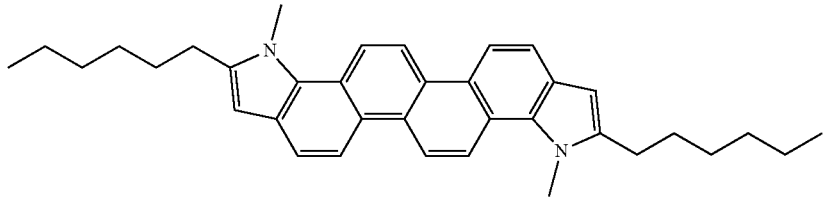
(1042)
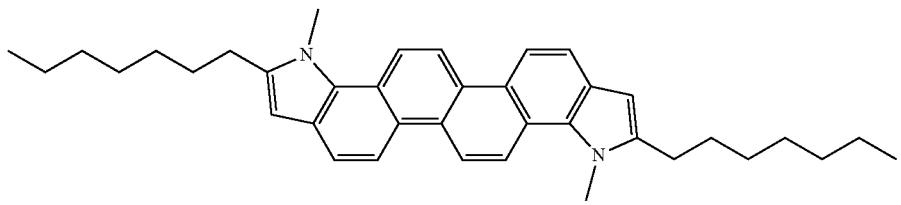

(1043)
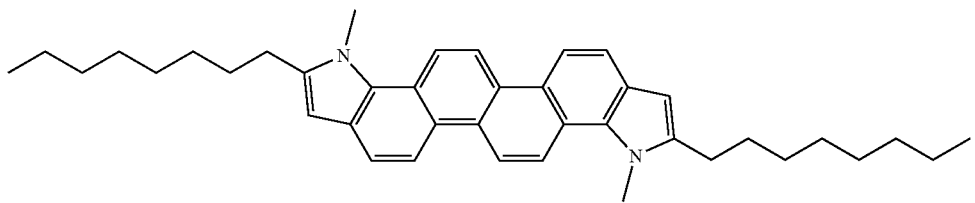
(1044)
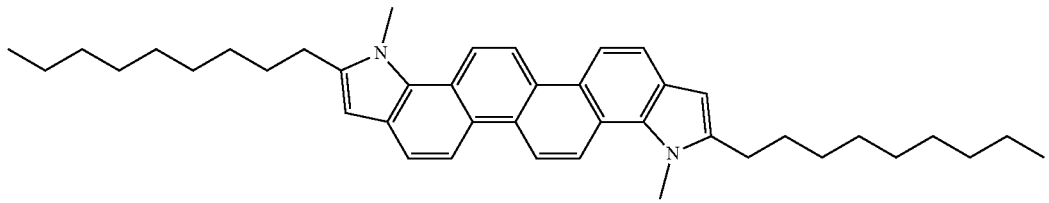
(1045)
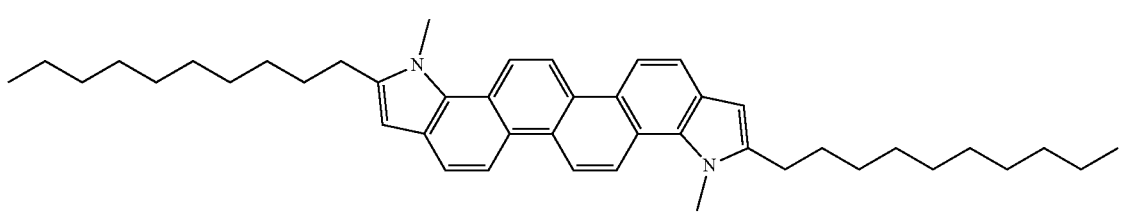
(1046)
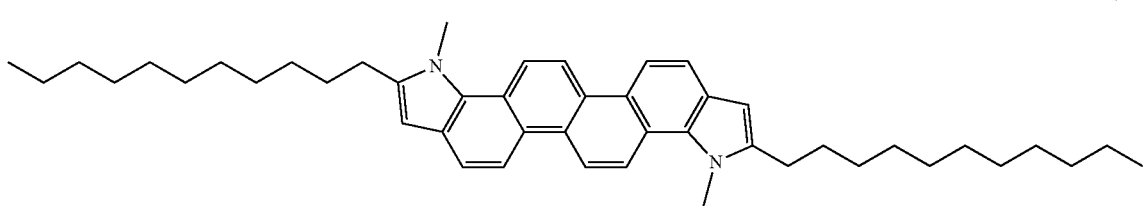
(1047)
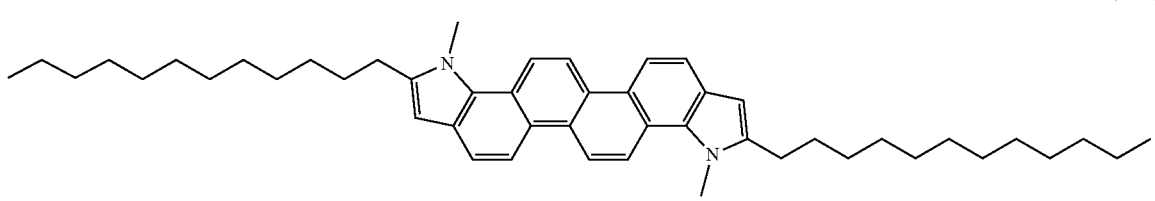
(1048)
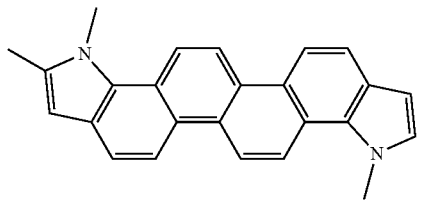
(1049)
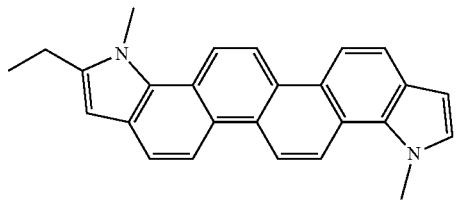
(1050)
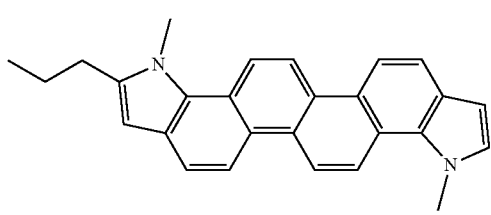
(1051)
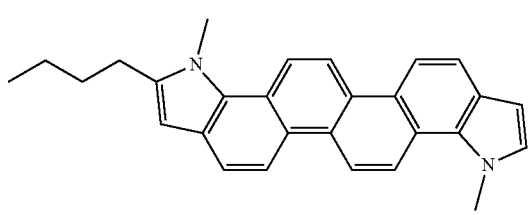

-continued
(1052)
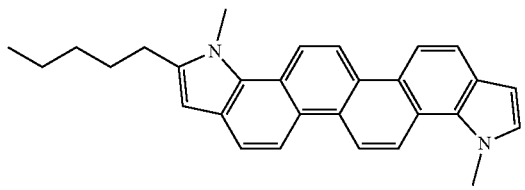
(1053)
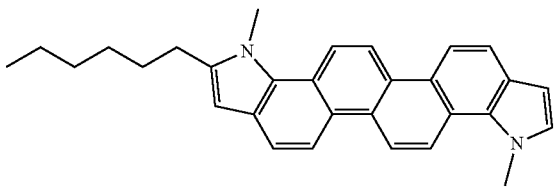
(1054)
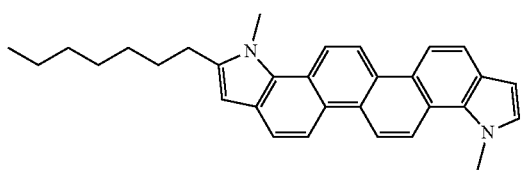
(1055)
(1056)
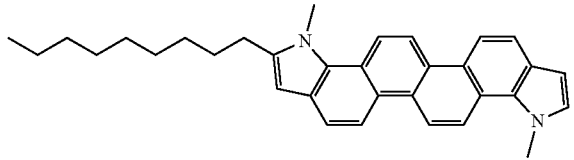
(1057)
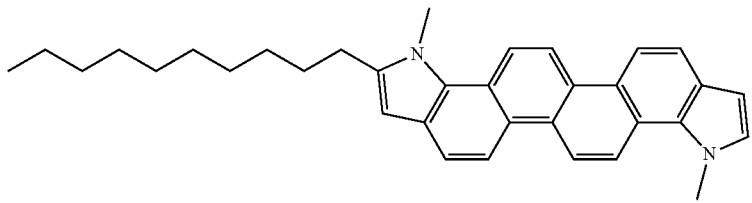
(1058)
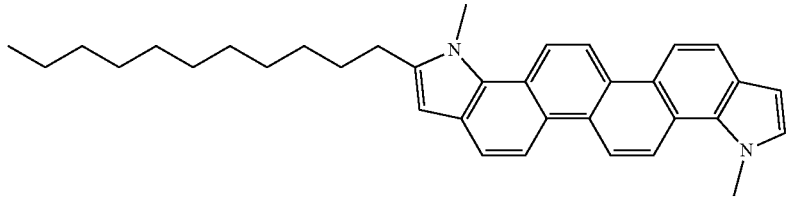
(1059)
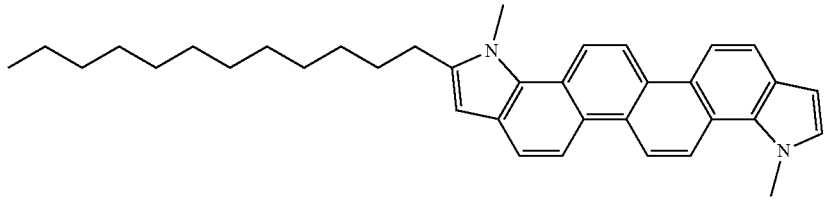
(1060)
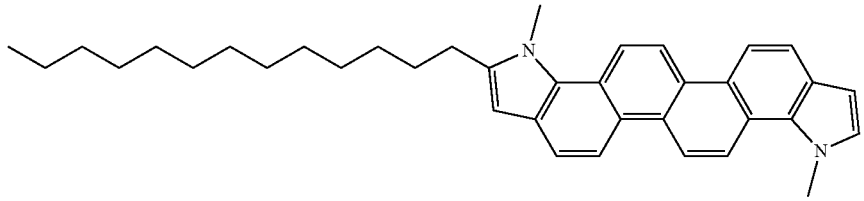
(1061)
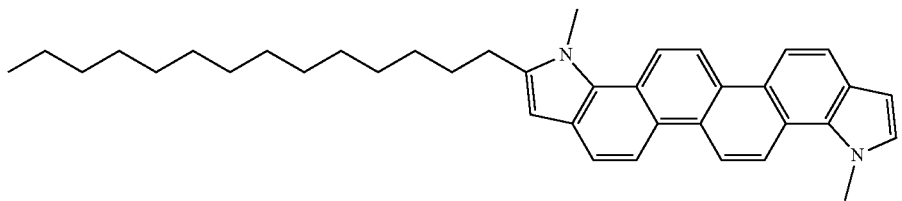

-continued
(1062)
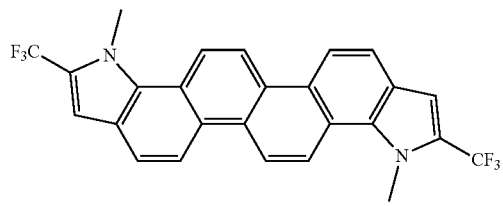
(1063)
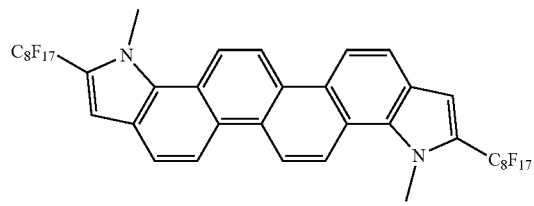
(1064)
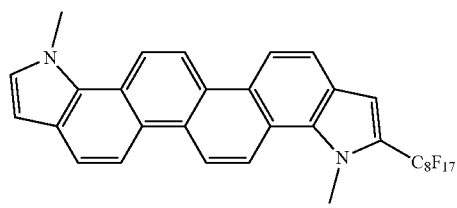
(1065)
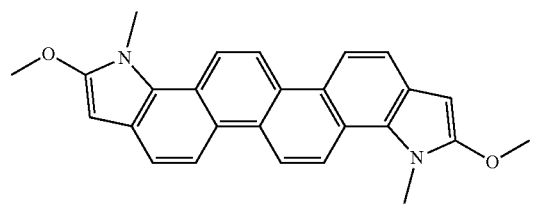
(1066)
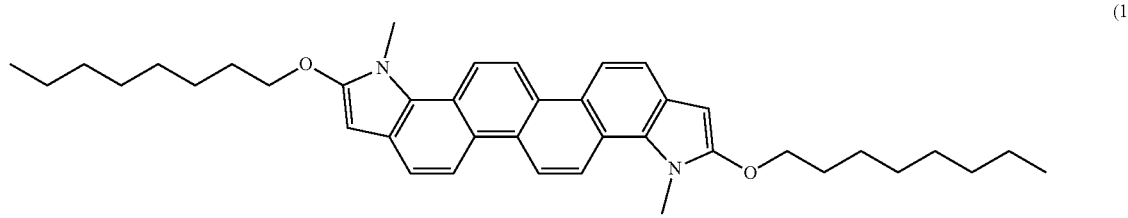
(1067)
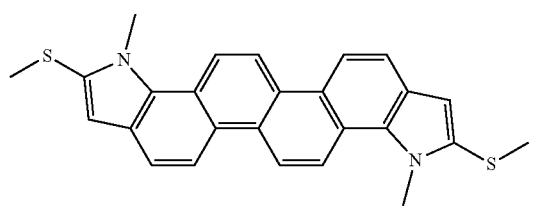
(1068)
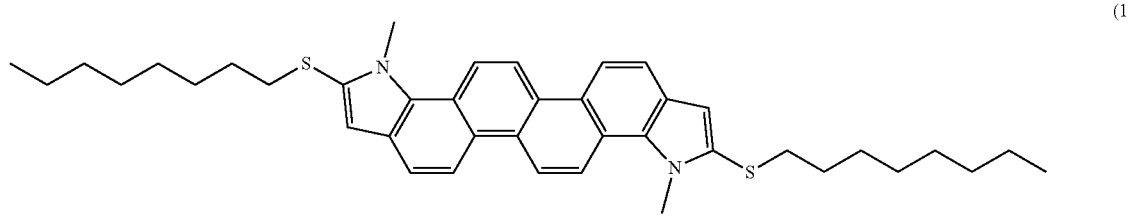
(1069)
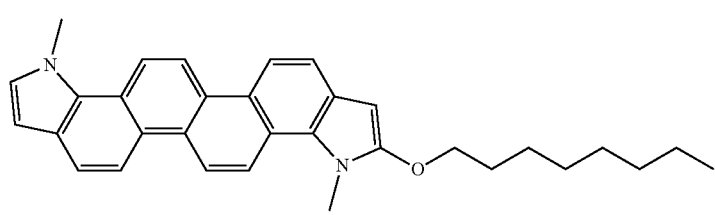
(1070)
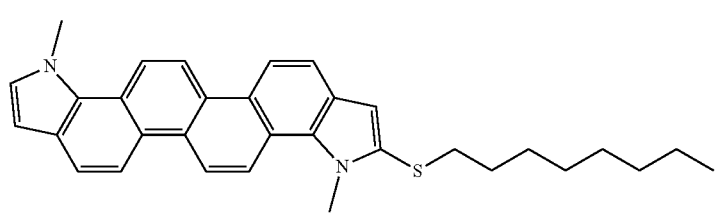

(1071)
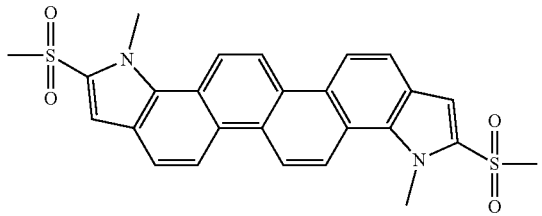
(1072)
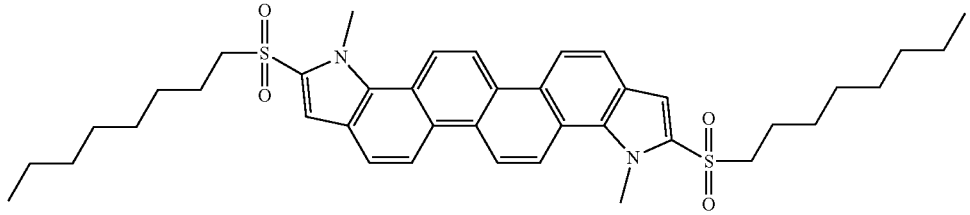
(1073)
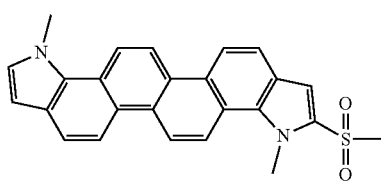
(1074)
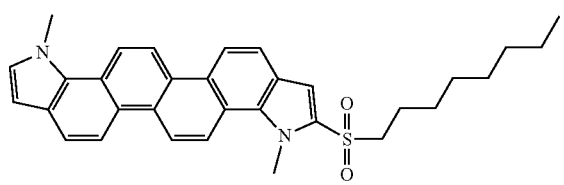
(1075)
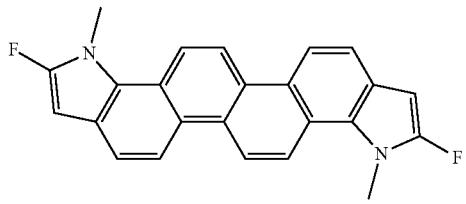
(1076)
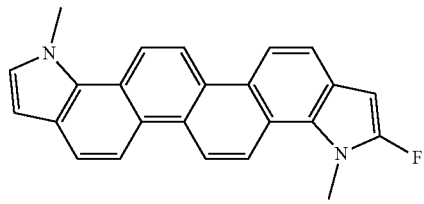
(1077)
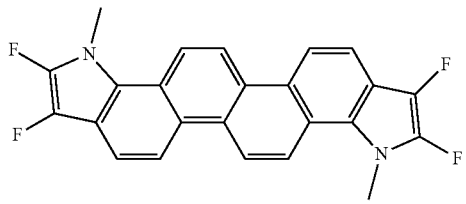
(1078)
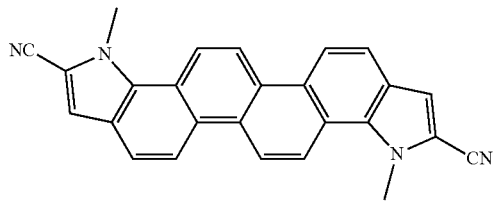
(1079)
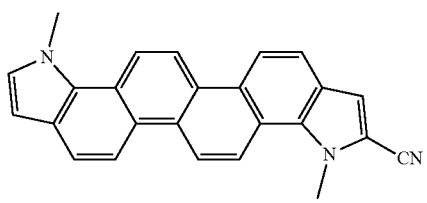
(1080)
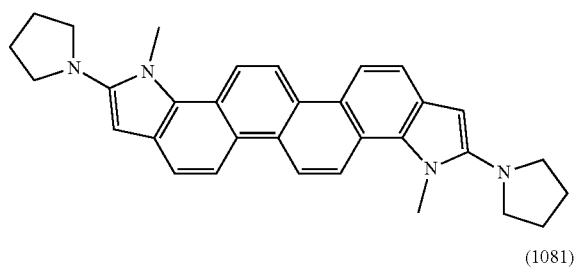
(1081)
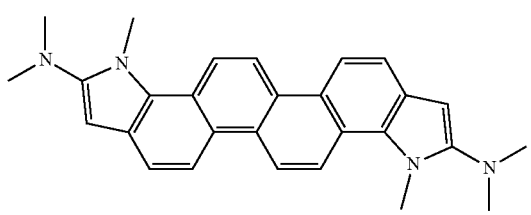

-continued
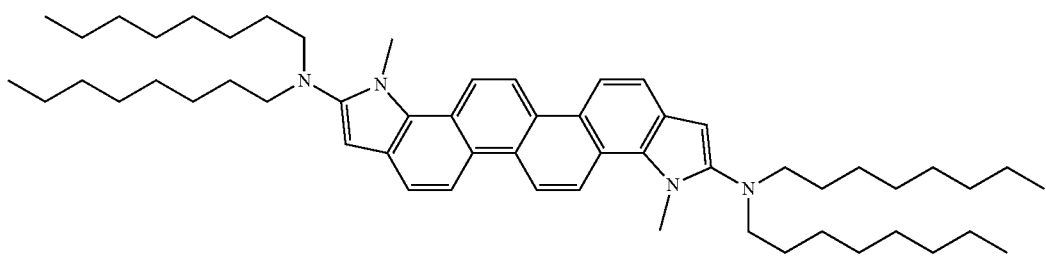
(1082)
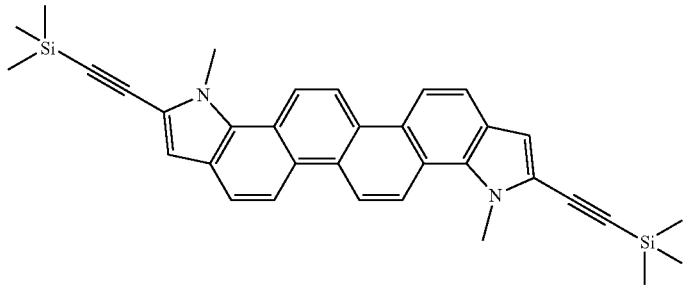
(1083)
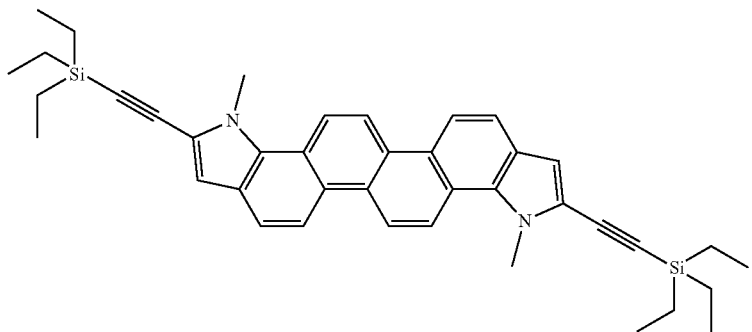
(1084)
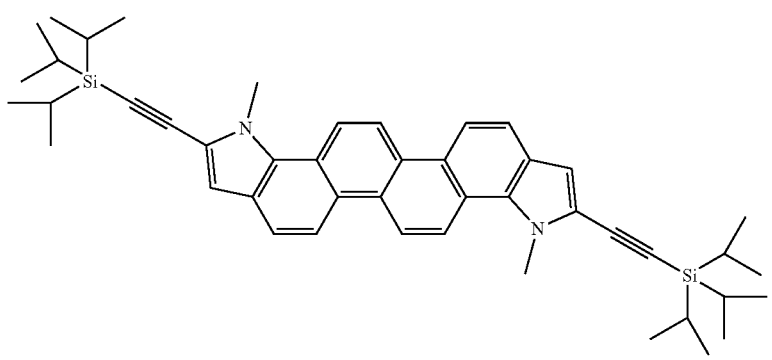
(1085)
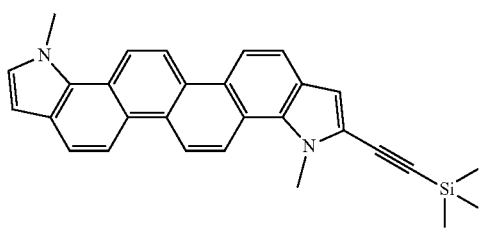
(1086)
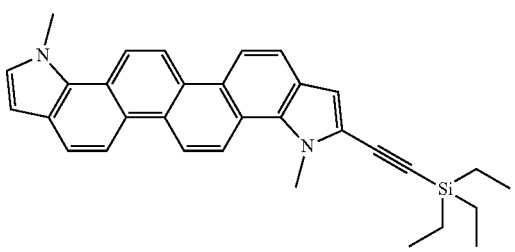
(1087)

-continued
(1088)
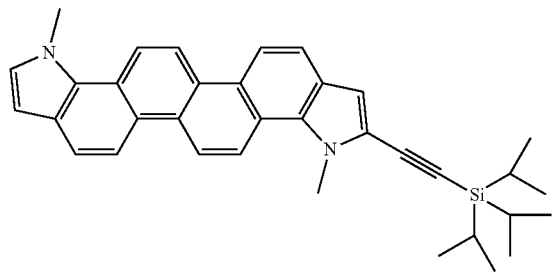
(1089)
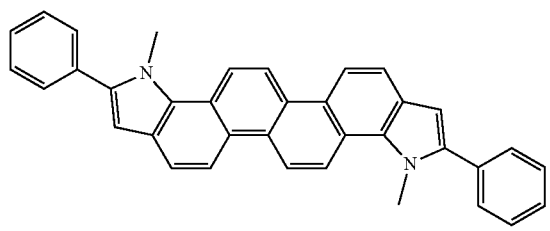
(1090)
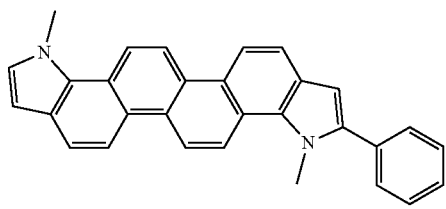
(1091)
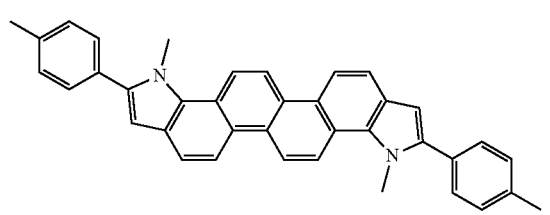
(1092)
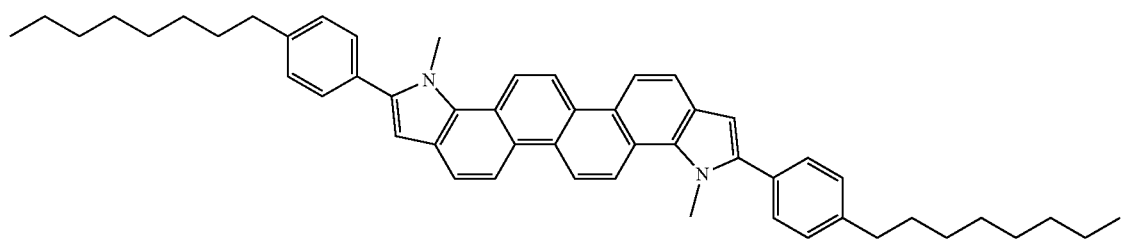
(1093)
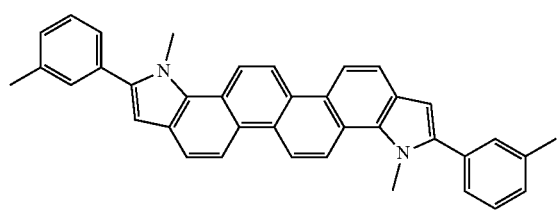

-continued
(1094)
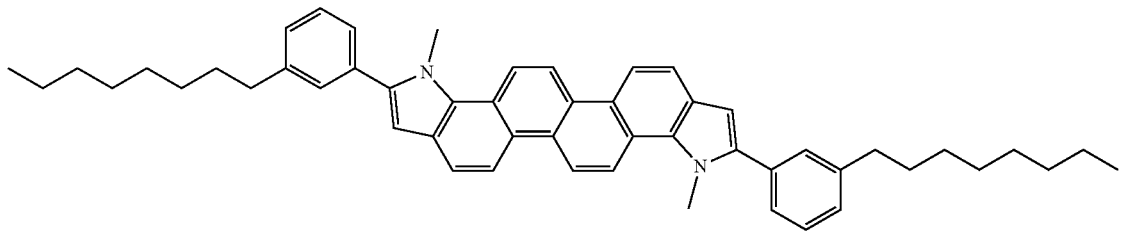
(1095)
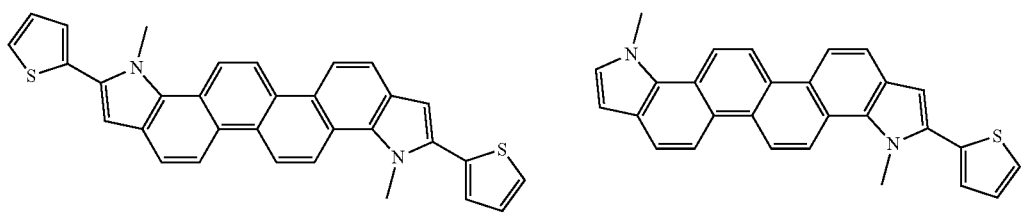
(1096)
(1097)
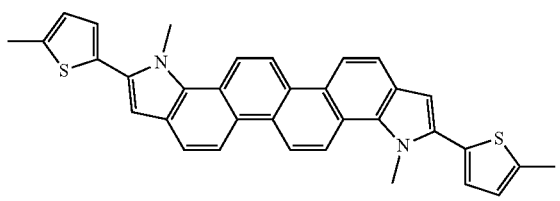
(1098)
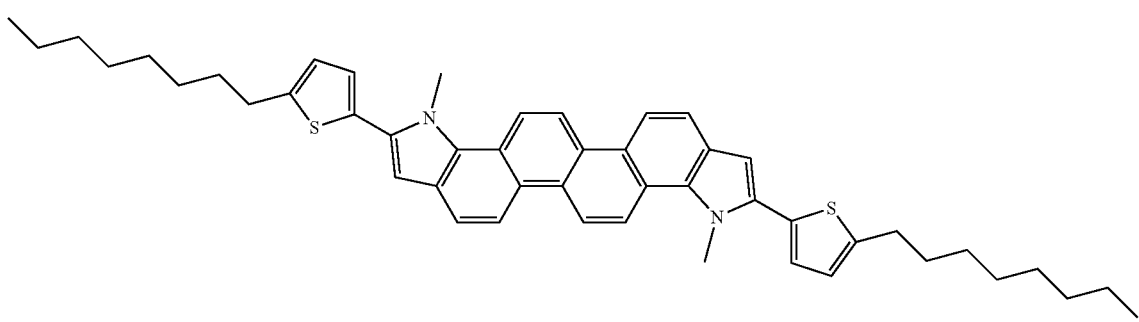
(1099)
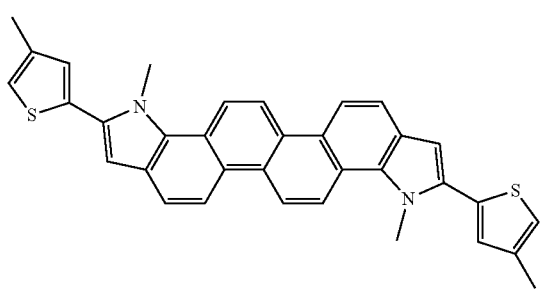

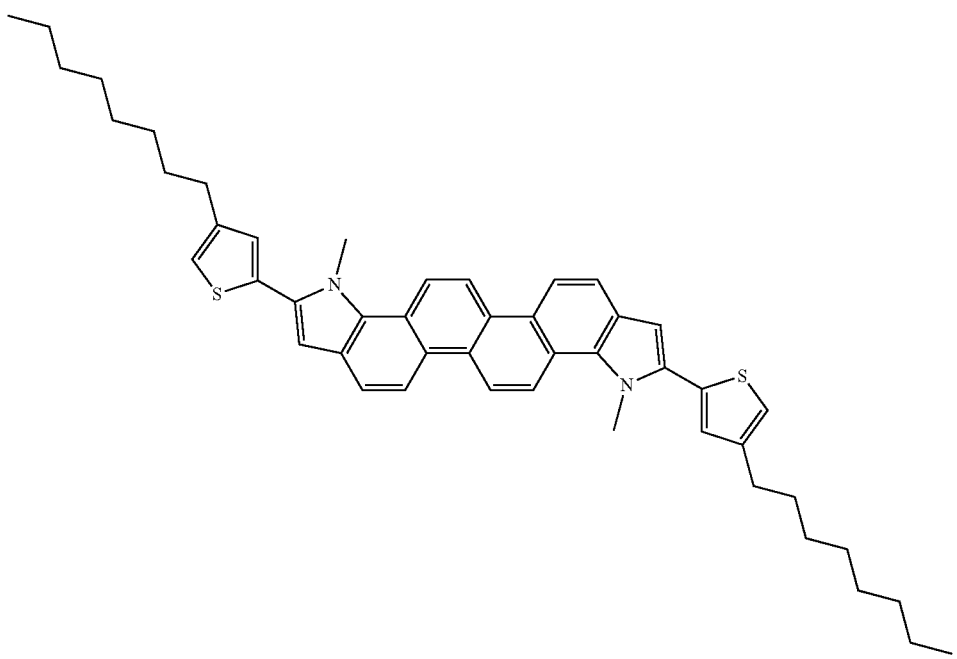
(1100)
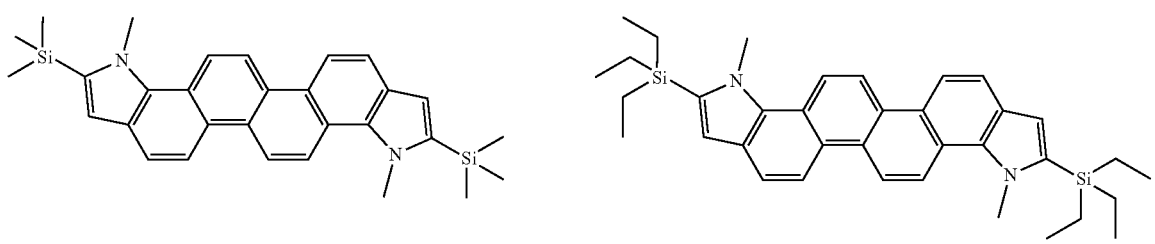
(1101) (1102)
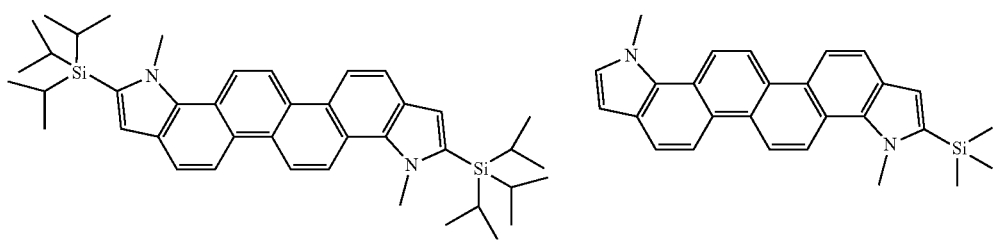
(1103) (1104)
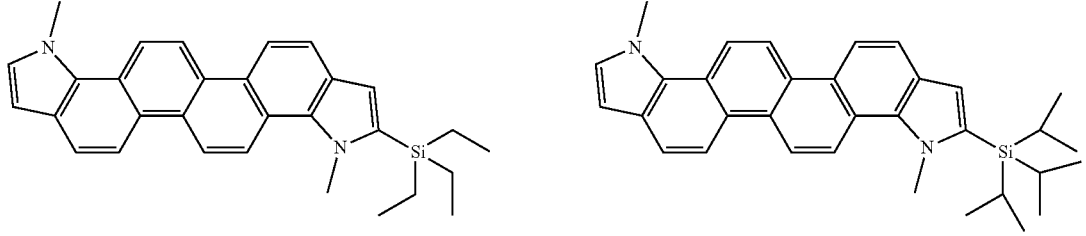
(1105) (1106)

-continued
(1107)
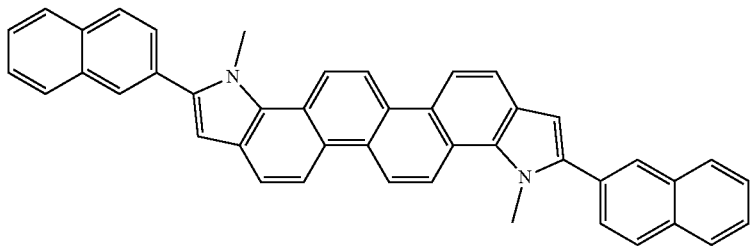
(1108)
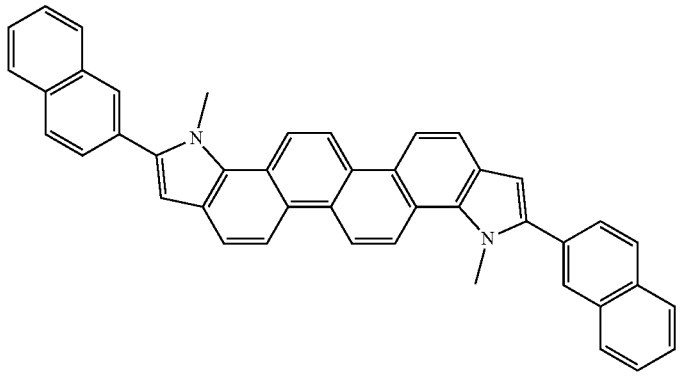
(1109)
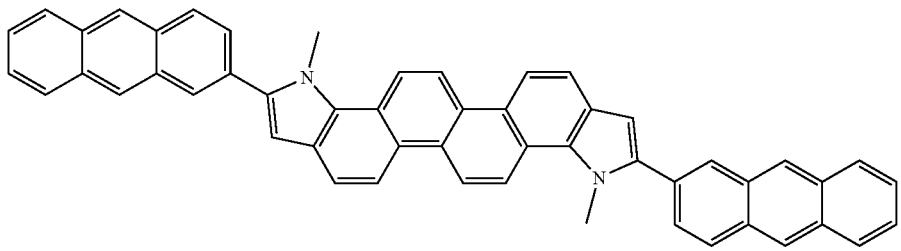
(1110)
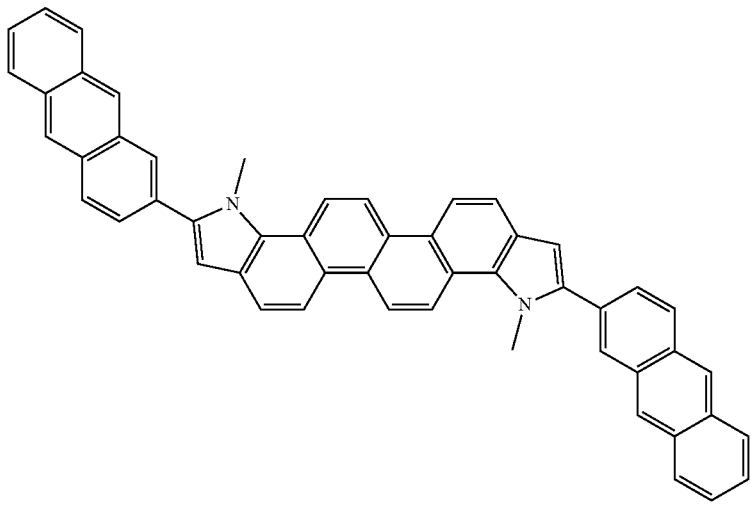
(1111)
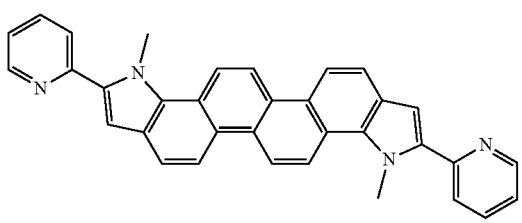
(1112)
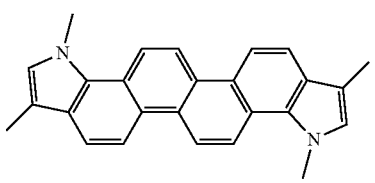

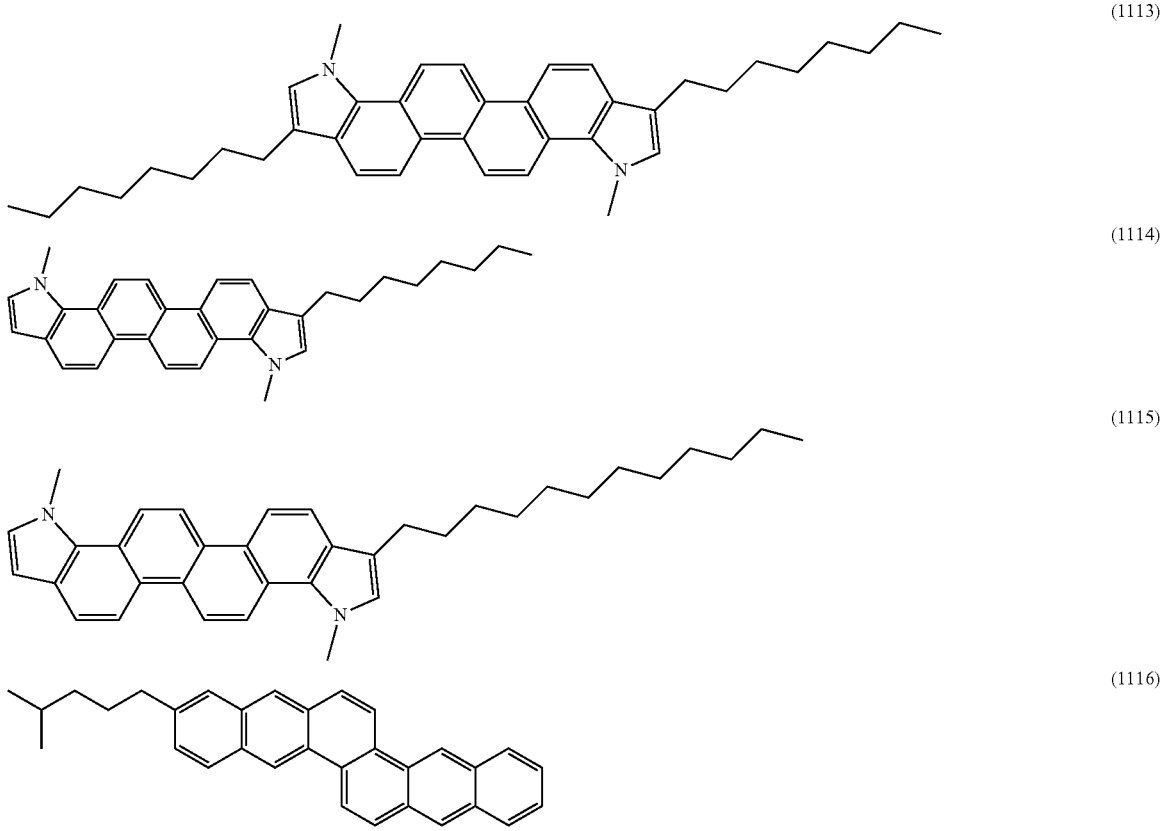

The compound for an organic thin film transistors of the invention can be synthesized by a known method, for example, by a coupling reaction using samarium as shown in (A), a Friedel-crafts reaction as shown in (B), a reduction reaction as shown in (C), a dehydration and oxidation reaction as shown in (D), a coupling reaction using a palladium catalyst as shown in (E), a Diels-Alder reaction as shown in (F), a reduction reaction as shown in (G), methylthioetherification as shown in (H), halogenation as shown in (I), Sonogashira coupling as shown in (J), an annulation reaction as shown in (K), a hydrogenation reaction as shown in (L), a methylthioetherification as shown in (M), a halogenation reaction as shown in (N), a Sonogashira coupling as shown in (O), an annulation reaction as shown in (P), a hydrogenation reaction as shown in (Q), a reaction which forms a phosphonium salt as shown in (R), an iodination reaction or a formylation reaction as shown in (S), a Wittig reaction as shown in (T), a photoannulation reaction as shown in (U), a formylation reaction as shown in (V), an acetalization as shown in (W), halogenation as shown in (X), deacetalization as shown in (Y), Suzuki-Miyaura coupling as shown in (Z), a Wittig reaction as shown in (AA), and an annulation reaction as shown in (AB).

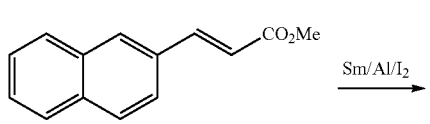

235
-continued
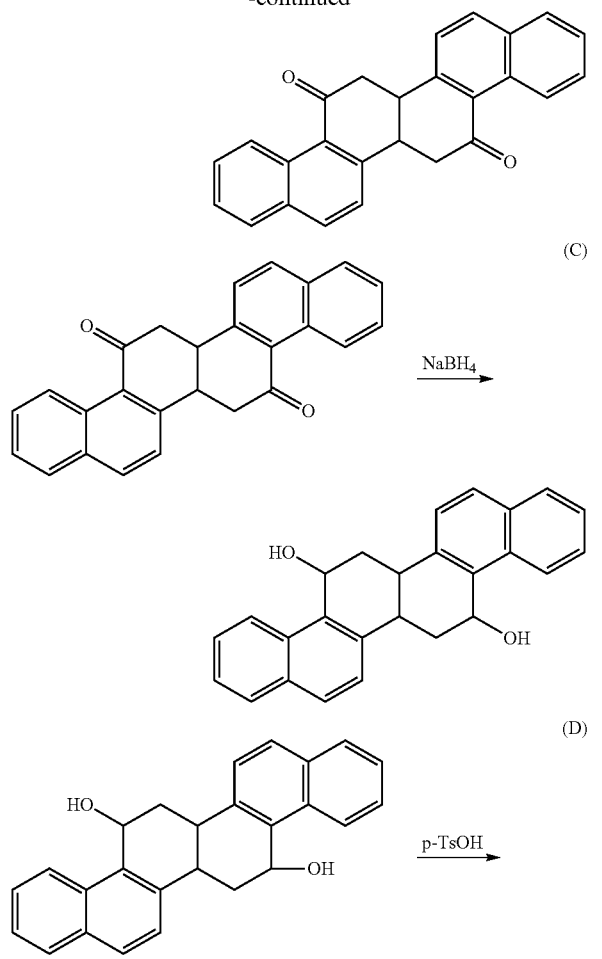
In the above formula, Me is methyl and TsOH is toluenesulfonic acid.
236
-continued
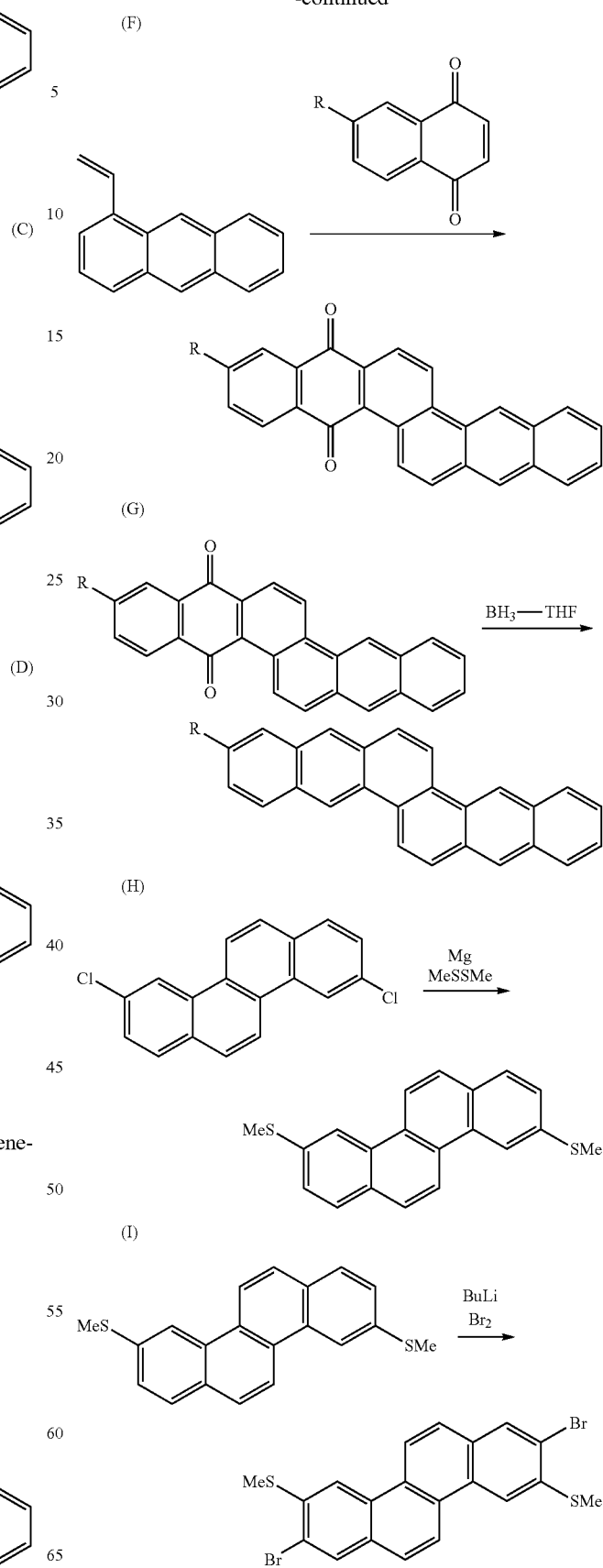

237
-continued
(J)
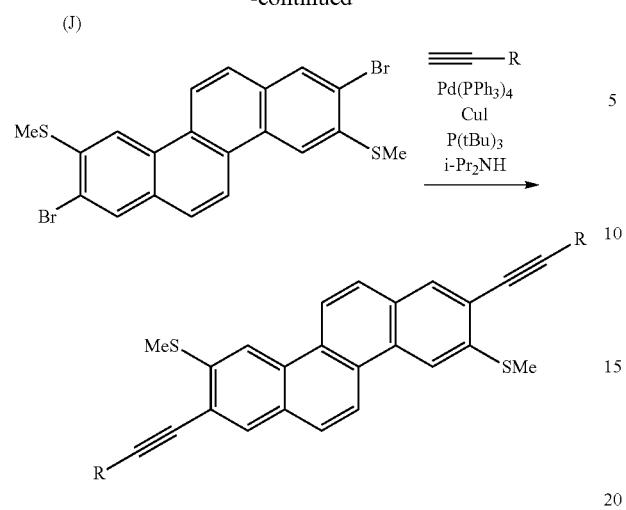
In the above formula, R is an arbitral substituent.
(K)
(L)
(M)
238
-continued
(N)
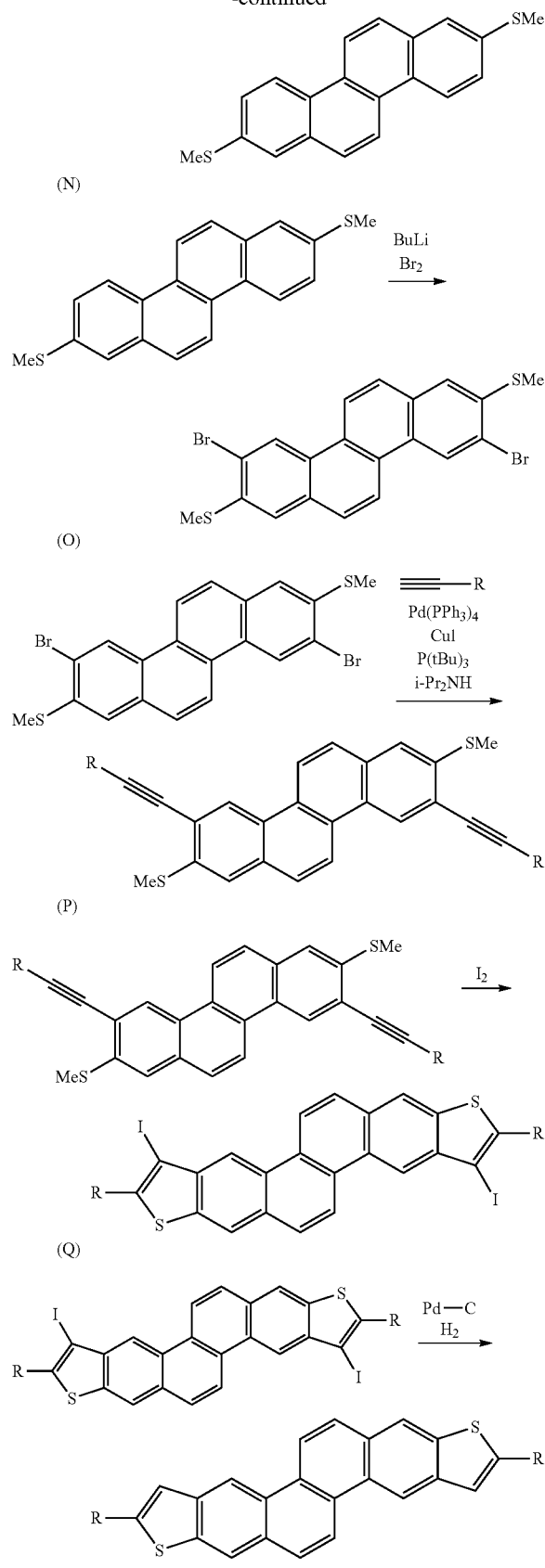
(O)
(P)
(Q)
In the above formula, R is an arbitral substituent.

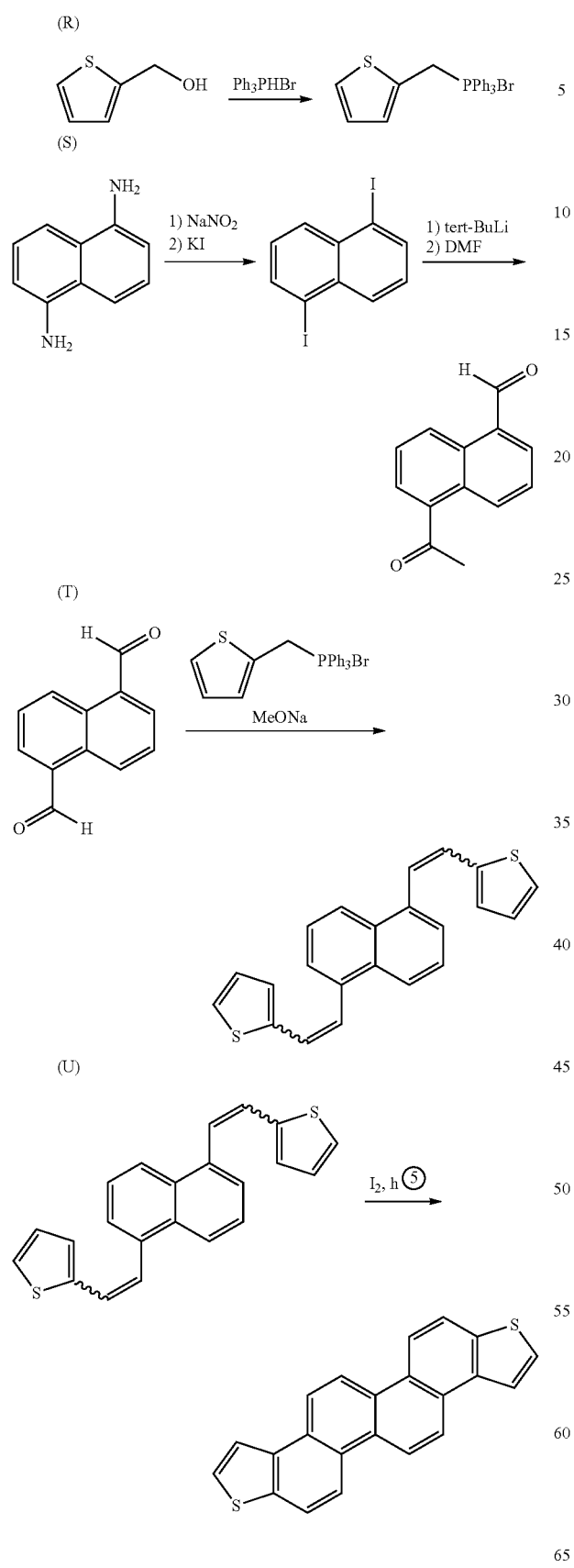
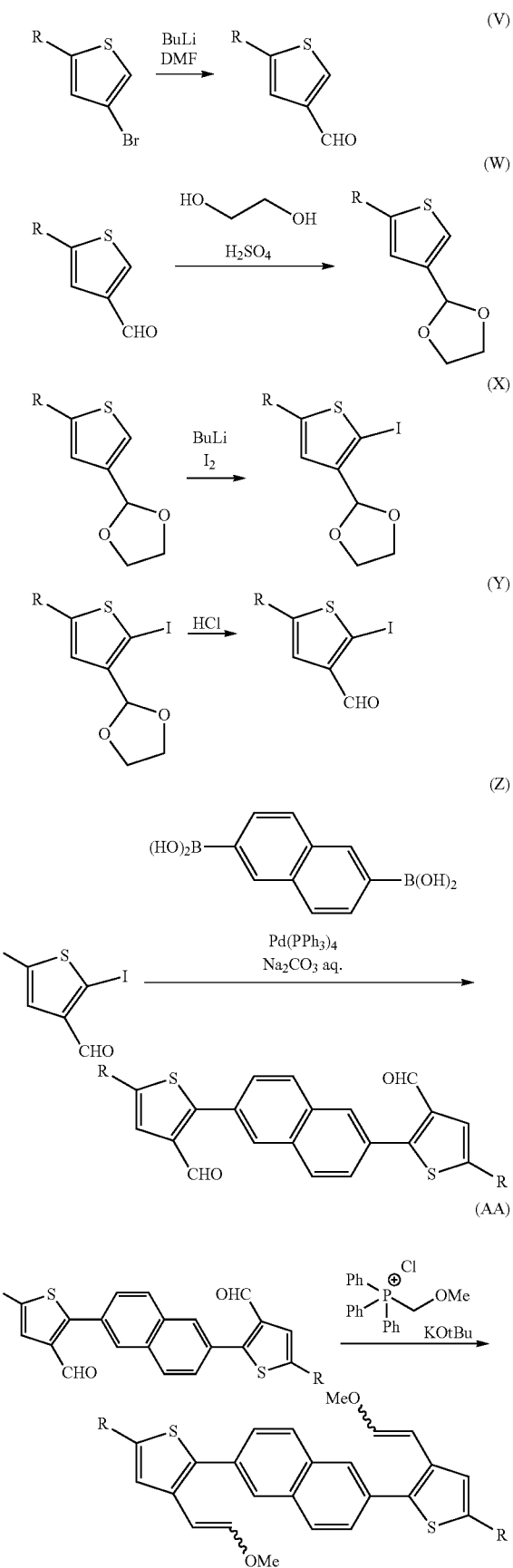
In the above formula, Me is a methyl group, TsOH is a toluenesulfonic acid and DMF is dimethylformamide.

-continued

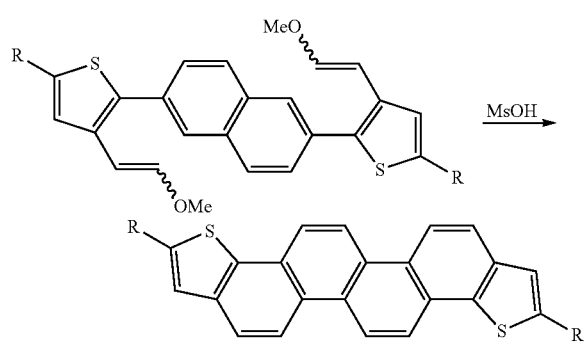

(AB)

In the above formula, R is an arbitral substituent.

A naphthoquinone derivative, 3,9-dichlorochrysene, 2,8-dibromochrysene in the step (F) above and 4-bromo-2-substituted thiophene in the step (V) above can be synthesized with reference to the following documents.
The Journal of Organic Chemistry 1976, vol. 41, page 2625
The Journal of Organic Chemistry 1993, vol. 58, page 4871
Bioorganic & Medicinal Chemistry 2006, vol. 14, page 7231
Synthesis 1977, page 330
Canadian Journal of Chemistry 1972, vol. 50, page 528
Justus Liebigs Annalen der Chemie 1973, page 1112
Synlett 2004, page 177

In an electric device such as a transistor, it is possible to obtain a device with a high field effect mobility or an on-off ratio by using a raw material having a high purity. Therefore, according to need, it is desirable to purify raw materials by techniques such as column chromatography, recrystallization, distillation and sublimation. It is preferably possible to improve the purity by using these purification methods repeatedly or by using a plurality of methods in combination. Further, it is desirable that purification by sublimation be repeated at least twice or more as the final step of the purification. By using these techniques, it is preferable to use a raw material with a purity of 90% or more which is measured by HPLC. By using a raw material with a purity of further preferably 95% or more, particularly preferably 99% or more, it is possible to increase the field effect mobility or the on/off ratio of the organic thin film transistor, and the performance intrinsic to the raw material can be enhanced.

Next, the device structure of the organic thin film transistor of the invention will be explained.

As for the device configuration of the organic thin film transistor of the invention, it is an organic thin film transistor comprising a substrate, three terminals of a gate electrode, a source electrode and a drain electrode, an insulating layer and an organic semiconductor layer being provided on the substrate, source-drain current being controlled by applying a voltage to a gate electrode. The organic thin film transistor of the invention is characterized in that the organic semiconductor layer comprises the above-mentioned compound for an organic thin film transistor of the invention.

There are no particular restrictions on the structure of the transistor. It may have a known device structure except for the component of the organic semiconductor layer. Specific examples of the device structure of the organic thin film transistor will be explained with reference to the drawings.

FIGS. 1 to 4 are each a view showing one example of the device structure of the organic thin film transistor of the invention.

An organic thin film transistor 1 shown in FIG. 1 has a source electrode 11 and a drain electrode 12 which are formed on a substrate 10 so that they are opposed to each other with a predetermined interval. An organic semiconductor layer 13 is formed so as to cover the source electrode 11, drain electrode 12, and the gap between them. Further, an insulating layer 14 is stacked thereon. A gate electrode 15 is formed on the insulating layer 14, and above the gap between the source electrode 11 and the drain electrode 12.

Figure 2:
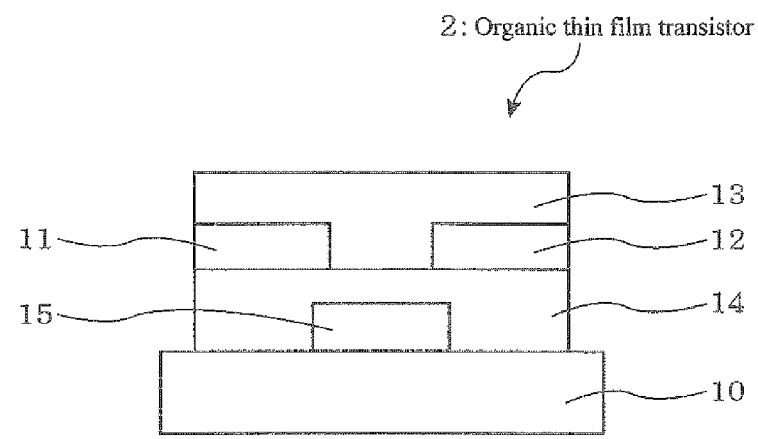
FIG. 2 is a view showing one example of the device structure of the organic thin film transistor of the invention.

An organic thin film transistor 2 shown in FIG. 2 has, on the substrate 10, the gate electrode 15 and the insulating layer 14 in this sequence, and has, on the insulating layer 14, a pair of the source electrode 11 and the drain electrode 12 formed with a predetermined interval. An organic semiconductor layer 13 is formed thereon. The organic semiconductor layer 13 constitutes a channel region, and current flowing between the source electrode 11 and the drain electrode 12 is controlled by a voltage applied to the gate electrode 15, whereby the organic thin film transistor performs an on-off operation.

Figure 3:
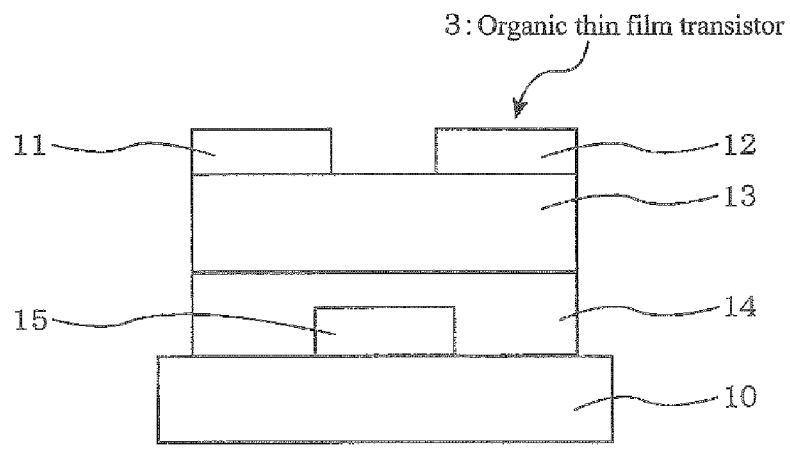
FIG. 3 is a view showing one example of the device structure of the organic thin film transistor of the invention.

An organic thin film transistor 3 shown in FIG. 3 has, on the substrate 10, the gate electrode 15, the insulating layer 14 and the organic semiconductor layer 13 in this sequence, and has, on the organic semiconductor layer 13, a pair of the source electrode 11 and the drain electrode 12 formed with a predetermined interval.

Figure 4:
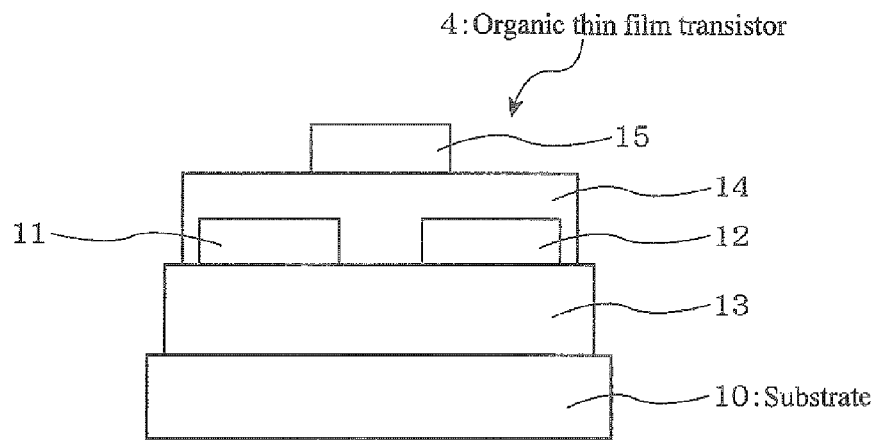
FIG. 4 is a view showing one example of the device structure of the organic thin film transistor of the invention.

An organic thin film transistor 4 shown in FIG. 4 has, on the substrate 10, the organic semiconductor layer 13, and has, on the organic semiconductor layer 13, a pair of the source electrode 11 and the drain electrode 12 formed with a predetermined interval. Further, the insulator layer 14 and the gate electrode 15 are sequentially formed thereon.

The organic thin film transistor of the invention has a field effect transistor (FET: Field Effect Transistor) structure. As mentioned above, several structures can be made by the position of electrodes, the order of stacking the layers or the like. The organic thin film transistor has an organic semiconductor layer (organic compound layer), a source electrode and a drain electrode which are formed so that they are opposed with a predetermined interval, and a gate electrode which is formed with a predetermined interval from each of the source electrode and the drain electrode. By applying a voltage to the gate electrode, current flowing between the source-drain electrodes is controlled. Here, the distance between the source electrode and the drain electrode is determined according to the application where the organic thin film transistor of the invention is used, and is normally 0.1 µm to 1 mm, preferably 1 µm to 100 µm, and further preferably 5 µm to 100 µm.

As for the organic thin film transistor of the invention, in addition to the above-mentioned device structure, various structures as the organic thin film transistor have been proposed. As long as the transistor has a mechanism that effects such as an on-off operation and amplification are exhibited by controlling current flown between the source electrode and the drain electrode due to a voltage applied to the gate electrode, the device structure is not limited to those mentioned above.

Figure 5:
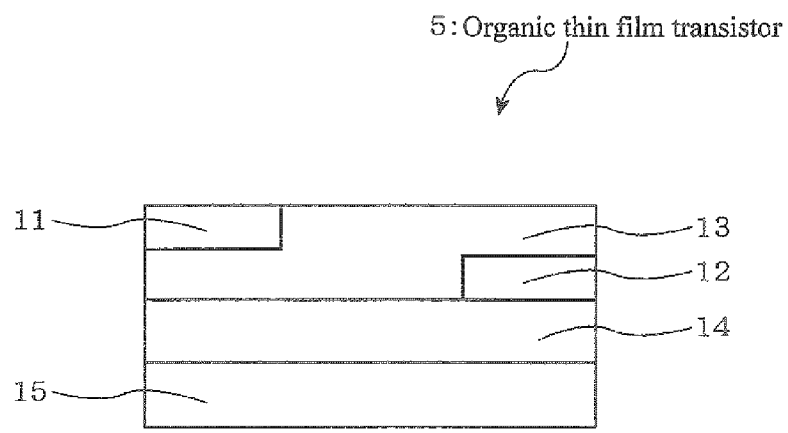
FIG. 5 is a view showing one example of the device structure of the organic thin film transistor of the invention.
Figure 6:
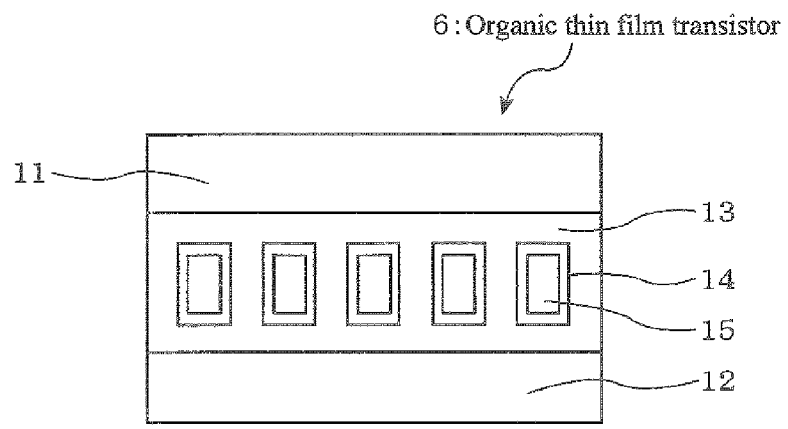
FIG. 6 is a view showing one example of the device structure of the organic thin film transistor of the invention.

For example, it may have a device structure, such as a top and bottom contact type organic thin film transistor (see FIG. 5) proposed in Preprints 27a-M-3 (March, 2002) of the 49th meeting of the Japan Society of Applied Physics and Related Societies by Yoshida, et al. of the National Institute of Advanced Industrial Science and Technology or a vertical type organic thin film transistor (see FIG. 6) proposed on page 1440 of vol. 118-A of the Journal of the Institute of Electrical Engineers of Japan (1998) by Kudo et al. of Chiba University.

The constituting elements of the organic thin film transistor will be mentioned below.

(Organic Semiconductor Layer)

The organic semiconductor layer of the organic thin film transistor of the invention comprises the above-mentioned compound for an organic thin film transistor of the invention. The thickness of the organic semiconductor layer is not particularly limited, but normally 0.5 nm to 1 μm, and preferably 2 nm to 250 nm.

The method for forming the organic semiconductor layer is not particularly restricted, and known methods can be applied. For example, the organic semiconductor layer can be formed from the above-mentioned material for the organic semiconductor layer by, for example, the molecular beam evaporation (MBE) method, the vacuum vapor deposition method, the chemical deposition method, a printing/coating method the dipping method of a solution in which materials are dissolved, the spin coating method, the casting method, the bar coating method, the roll coating method and the ink-jet method, or by baking, electropolymerization, the molecular beam evaporation method, self-assembly from a solution, or by combination of these methods.

Since the field effect mobility is improved by improving the crystallinity of the organic semiconductor layer, it is preferable to perform annealing after the completion of the film formation regardless of the film-formation method. By doing this, a high-performance device can be obtained. The temperature of annealing is preferably 50 to 200° C., further preferably 70 to 200° C., and the duration of annealing is preferably 10 minutes to 12 hours, further preferably 1 to 10 hours.

In the invention, in the organic semiconductor layer, one of the compounds represented by the formula (1) may be used. A plurality of the compounds represented by the formula (1) may be used in combination. The organic semiconductor layer may be formed of a mixed thin film or stacked layers by using a known semiconductor such as pentacene and a thiophene oligomer.

(Substrate)

The substrate in the organic thin film transistor of the invention serves to support the organic thin film transistor structure. As the materials thereof, in addition to glass, inorganic compounds such as metal oxides and metal nitrides, plastic films (PET, PES, PC), a metal substrate or a composite or a stack thereof or the like may be used. If the structure of the organic thin film transistor can be fully supported by constituting elements other than the substrate, the use of a substrate may be omitted. As the material for the substrate, silicon (Si) wafer may be frequently used. In this case, Si itself can be used as a substrate serving also as a gate electrode. Further, $SiO_2$, formed by oxidizing the surface of Si, can be used as an insulator layer. In this case, a metal layer such as an Au layer is often formed on an Si substrate serving also as a gate electrode so as to serve as an electrode for connecting a lead wire.

(Electrode)

The material for the gate electrode, the source electrode and the drain electrode of the organic thin film transistor of the invention is not particularly limited as long as it is a conductive material. Usable materials include platinum, gold, silver, nickel, chromium, copper, iron, tin, antimony, lead, tantalum, indium, palladium, tellurium, rhenium, iridium, aluminum, ruthenium, germanium, molybdenum, tungsten, tin antimony oxide, indium tin oxide (ITO), fluorine-doped zinc oxide, zinc, carbon, graphite, glassy carbon, silver paste and carbon paste, lithium, beryllium, sodium, magnesium, potassium, calcium, scandium, titanium, manganese, zirconium, gallium, niobium, a sodium-potassium alloy, a magnesium/copper mixture, a magnesium/silver mixture, a magnesium/aluminum mixture, a magnesium/indium mixture, an aluminum/aluminum oxide mixture and a lithium/aluminum mixture.

Examples of the method for forming the above-mentioned electrodes include deposition, electron beam deposition, sputtering, atmospheric-pressure plasma method, ion plating, chemical vapor deposition, electrodeposition, electroless plating, spin coating, printing and ink-jetting. As the method for patterning which is conducted if necessary, a method for forming an electrode by photolithography or lift-off, which are known methods, using conductive thin films formed by the above-mentioned methods and a method for forming a resist on metallic foil such as aluminum foil and copper foil, by thermal transfer or ink-jetting, followed by etching, may be mentioned.

Although the film thickness of the electrode thus formed is not particularly limited as long as electric current is passed therethrough, it is preferably 0.2 nm to 10 μm, further preferably 4 nm to 300 nm. If the film thickness falls within this preferable range, there is no case where a thin film causes a rise in resistance and a drop in voltage. If the film thickness is in this preferable range, since the film is not too thick, a shorter time is consumed in film formation, and a stacked film can be formed smoothly without forming a step when another layer such as a protective layer and an organic semiconductor layer is stacked.

In the organic thin film transistor of the invention, as another source electrode, another drain electrode and another gate electrode and the method for forming thereof, it is preferable to use a fluid electrode material, such as a solution, paste, ink or a dispersion liquid, which contains the above-mentioned conductive materials. It is particularly preferable to use a fluid electrode material containing a conductive polymer or fine metal particles containing platinum, gold, silver or copper. In order to prevent damage to the organic semiconductor, as the solvent or the dispersion medium, it is preferable to use a solvent or a dispersion medium which contains 60 mass % or more, preferably 90 mass % or more of water. As the dispersion containing fine metal particles, although a known conductive paste or the like may be used, it is preferable to use a dispersion containing fine metal particles each normally having a particle diameter of 0.5 nm to 50 nm or 1 nm to 10 nm. Examples of the material for the fine metal particles include platinum, gold, silver, nickel, chromium, copper, iron, tin, antimony, lead, tantalum, indium, palladium, tellurium, rhenium, iridium, aluminum, ruthenium, germanium, molybdenum, tungsten and zinc. It is preferable to form electrodes by using a dispersion obtained by dispersing these fine metal particles in a dispersion medium which is water or an arbitral organic solvent by using a dispersion stabilizer composed mainly of an organic material. Examples of the method for producing such dispersion of fine metal particles include a physical production method such as the in-gas evaporation method, the sputtering method and the metal vapor synthesis method, and a chemical production method such as the colloid method and the co-precipitation method, in which metal ions are reduced in the liquid phase to form fine metal particles. It is preferable to use a dispersion of fine metal particles produced by the colloid method disclosed in JP-A-H11-76800, JP-A-H11-80647, JP-A-H11-319538 or JP-A-2000-239853 and by the in-gas evaporation method disclosed in JP-A-2001-254185, JP-A-2001-53028, JP-A-2001-35255, JP-A-2000-124157 or JP-A-2000-123634.

The electrode may be formed by directly performing patterning according to the ink-jet method by using the above-mentioned dispersion containing fine metal particles, or may be formed from a coating film by lithography, laser ablation or the like. Further, it is possible to use a method for patterning according to the printing method such as relief printing, intaglio printing, planographic printing or screen printing. The electrode is shaped, and the solvent is dried. Thereafter, according to need, the electrode is heated along with the shape thereof at a temperature of 100° C. to 300° C., preferably 150° C. to 200° C., whereby fine metal particles are thermally bonded, thus making it possible to form an electrode pattern having an intended shape.

Further, it is also preferable to use known conductive polymers of which the conductivity is improved by doping or the like as the material for another gate electrode, another source electrode and another drain electrode. For example, electroconductive polyaniline, electroconductive polypyrrole, electroconductive polythiophene (e.g. a complex of polyethylene dioxythiophene and polystyrene sulfonic acid) can be preferably used. These materials can reduce contact resistance between the source and drain electrodes, and the organic semiconductor layer. To form the electrode, patterning may be performed according to the inkjet method, and the electrode may be formed from the coating film by lithography, laser ablation, or the like. Further, it is possible to use a method for patterning according to the printing method such as relief printing, intaglio printing, planographic printing or screen printing.

In particular, as the material for forming the source electrode and the drain electrode, of the above-mentioned materials, materials having a low electric resistance in a surface being in contact with the organic semiconductor layer, are preferable. That is, this electric resistance corresponds to a field effect mobility when an electric-current control device is manufactured, and, in order to obtain a high mobility, resistance is required to be as small as possible. Generally, this depends on the magnitude relationship between the work function of electrode materials and the energy level of the organic semiconductor layer.

It is preferred that the following relationship be satisfied, in which a is the work function (W) of materials for the electrodes, b is the ionization potential (Ip) of the organic semiconductor layer, and c is the electron affinity (Af) of the organic semiconductor layer. Herein, a, b, and c are all positive values based on the vacuum level.

In the case of a p-type organic thin film transistor, it is preferred that the relationship b−a<1.5 eV (formula (I)) be satisfied, further preferably b−a<1.0 eV. If this relationship is kept, in the relationship with the organic semiconductor layer, a high-performance device can be obtained. It is preferable to select as large a work function as possible especially for the work function of the electrode materials. It is preferred that the work function of the electrode material be 4.0 eV or more, further preferably 4.2 eV or more. The value of the work function of the metal is described, for example, in Chemistry Manual Basic Edition II, page 493 (Revised third edition, edited by Chemical Society of Japan, issued by Maruzen Co., Ltd., 1983). Selection may be made from the above-mentioned list of effective metals having a work function of 4.0 eV or more. Examples of such metals having a large work function include Ag (4.26, 4.52, 4.64, 4.74 eV), Al (4.06, 4.24, 4.41 eV), Au (5.1, 5.37, 5.47 eV), Be (4.98 eV), Bi (4.34 eV), Cd (4.08 eV), Co (5.0 eV), Cu (4.65 eV), Fe (4.5, 4.67, 4.81 eV), Ga (4.3 eV), Hg (4.4 eV), Ir (5.42, 5.76 eV), Mn (4.1 eV), Mo (4.53, 4. 55, 4.95 eV), Nb (4.02, 4.36, 4.87 eV), Ni (5.04, 5.22, 5.35 eV), Os (5.93 eV), Pb (4.25 eV), Pt (5.64 eV), Pd (5.55 eV), Re (4.72 eV), Ru (4.71 eV), Sb (4.55, 4.7 eV), Sn (4.42 eV), Ta (4.0, 4.15, 4.8 eV), Ti (4.33 eV), V (4.3 eV), W (4.47, 4.63, 5.25 eV) and Zr (4.05 eV).

Of these, noble metals (Ag, Au, Cu, Pt), Ni, Co, Os, Fe, Ga, Ir, Mn, Mo, Pd, Re, Ru, V and W are preferable. In addition to metals, ITO, conductive polymers such as polyanilline and PEDOT:PSS and carbon are preferable. No particular restrictions are imposed on the electrode materials as long as the work function satisfies the formula (I) even if the material contains one or more kinds of the above-mentioned substances having a large work function.

In the case of an n-type organic thin film transistor, it is preferred that the relationship a−c<1.5 eV (formula (II)) be satisfied, further preferably a−c<1.0 eV. If this relationship is kept, in the relationship with the organic semiconductor layer, a high-performance device can be obtained. It is preferable to select as small a work function as possible especially for the work function of the electrode material. It is preferable to select a work function of the electrode material of 4.3 eV or less, further preferably 3.7 eV or less.

As for the specific examples of such metals having a small work function, selection may be made from the list of effective metals having a work function of 4.3 eV or less described in Chemistry Manual Basic Edition II, page 493 (Revised third edition, edited by Chemical Society of Japan, issued by Maruzen Co., Ltd., 1983). Specific examples include Ag (4.26 eV), Al (4.06, 4.28 eV), Ba (2.52 eV), Ca (2.9 eV), Ce (2.9 eV), Cs (1.95 eV), Er (2.97 eV), Eu (2.5 eV), Gd (3.1 eV), Hf (3.9 eV), In (4.09 eV), K (2.28), La (3.5 eV), Li (2.93 eV), Mg (3.66 eV), Na (2.36 eV), Nd (3.2 eV), Rb (4.25 eV), Sc (3.5 eV), Sm (2.7 eV), Ta (4.0, 4.15 eV), Y (3.1 eV), Yb (2.6 eV), and Zn (3.63 eV). Among these metals, preferred metals are Ba, Ca, Cs, Er, Eu, Gd, Hf, K, La, Li, Mg, Na, Nd, Rb, Y, Yb, and Zn. No particular restrictions are imposed on the electrode material as long as the work function thereof satisfies the formula (II) even if the material contains one or a plurality of the above-mentioned substances having a small work function. However, metals having a small work function easily deteriorate when they are brought into contact with moisture or oxygen in the atmosphere, and hence, it is preferable to coat these small-work-function metals with metals, such as Ag or Au, which are stable in the air, if necessary. The film thickness necessary for coating is 10 nm or more, and metals can be more surely protected from oxygen and water in proportion to an increase in film thickness. However, in practical use, it is preferable to set the film thickness to be 1 μm or less from the viewpoint of productivity enhancement or the like.

In the organic thin film transistor according to the invention, a buffer layer may be provided between the organic semiconductor layer and the source and drain electrodes in order to improve injection efficiency, for example. As the buffer layer, for an n-type organic thin film transistor, compounds having an alkaline metal, or alkaline earth metal ionic bonds such as LiF, Li$_2$O, CsF, NaCO$_3$, KCl, MgF$_2$, or CaCO$_3$ used for a cathode of an organic EL device are preferable. In addition, a compound, such as Alq, which is used as an electron-injecting layer or as an electron-transporting layer in an organic EL device may be inserted as the buffer layer.

For a p-type organic thin film transistor, it is desirable to use FeCl$_3$, a cyano compound such as, TCNQ, F$_4$-TCNQ and HAT, CFx, metal oxides other than oxides of alkaline metals and alkaline earth metals such as GeO$_2$, SiO$_2$, MoO$_3$, V$_2$O$_5$, VO$_2$, V$_2$O$_3$, MnO, Mn$_3$O$_4$, ZrO$_2$, WO$_3$, TiO$_2$, In$_2$O$_3$, ZnO, NiO, HfO$_2$, Ta$_2$O$_5$, ReO$_3$, and PbO$_2$, or an inorganic compound such as ZnS or ZnSe. In many cases, these oxides cause oxygen deficiency, and hence is suitable for hole injection. Further, this buffer layer may be made of an amine-based compound, such as TPD or NPD, or a compound, such as CuPc, which is used as a hole-injecting layer or as a hole-transporting layer in an organic EL device. Further, two or more of the above-mentioned compounds may preferably be used in combination.

It is known that the buffer layer has the effect of lowering a threshold voltage by lowering the injection barrier of carriers and the effect of driving the transistor at a low voltage. With respect to the compounds of the invention, we have found that the buffer layer has not only the effect of lowering the voltage but also the effect of improving mobility. The reason therefor is that carrier traps exist in an interface between the organic semiconductor layer and the insulator layer, and, when carrier injection is caused by application of a gate voltage, a carrier that has been injected first is used to bury the traps, and the traps are buried at a low voltage by inserting a buffer layer, whereby mobility is improved. It suffices that the buffer layer be present as a thin film between the electrodes and the organic semiconductor layer, and the thickness thereof is 0.1 nm to 30 nm, and, preferably 0.3 nm to 20 nm.

(Insulator Layer)

No particular restrictions are imposed on materials used for an insulator layer in the organic thin film transistor of the invention as long as these materials have electric insulating properties and can be formed as thin films. It is possible to use materials, such as metallic oxides (including oxides of silicon), metal nitrides (including nitrides of silicon), polymers, or organic low molecules, whose electrical resistivity is 10 Ωcm or more at room temperature. Especially, an inorganic oxide film having a high relative dielectric constant is preferable.

Examples of inorganic oxides include silicon oxide, aluminum oxide, tantalum oxide, titanium oxide, tin oxide, vanadium oxide, barium strontium titanate, barium zirconate titanate, lead zirconate titanate, lead lanthanum titanate, strontium titanate, barium titanate, lanthanum oxide, fluorine oxide, magnesium oxide, bismuth oxide, bismuth titanate, niobium oxide, strontium bismuth titanate, strontium bismuth tantalate, tantalum pentoxide, bismuth tantalate niobate, trioxide yttrium, and combinations of these compounds. Silicon oxide, aluminum oxide, tantalum oxide and titanium oxide are preferable.

Further, inorganic nitrides, such as silicon nitride ($Si_3N_4$, SixNy (x, y>0)) and aluminum nitride, can be preferably used.

The insulator layer may be made of a precursor containing a metal alkoxide. In this case, for example, the substrate is covered with a solution of the precursor, and is subjected to a chemical solution process including a heat treatment, and, as a result, an insulator layer is formed.

The metals forming the metal alkoxide are selected from transition metals, lanthanoids or main group elements. Specific examples of such metals include barium (Ba), strontium (Sr), titanium (Ti), bismuth (Bi), tantalum (Ta), zirconium (Zr), iron (Fe), nickel (Ni), manganese (Mn), lead (Pb), lanthanum (La), lithium (Li), sodium (Na), potassium (K), rubidium (Rb), cesium (Cs), francium (Fr), beryllium (Be), magnesium (Mg), calcium (Ca), niobium (Nb), thallium (Tl), mercury (Hg), copper (Cu), cobalt (Co), rhodium (Rh), scandium (Sc) and yttrium (Y). Examples of alkoxides forming the metal alkoxide include those derived from alcohols including methanol, ethanol, propanol, isopropanol, butanol and isobutanol, and those derived from alkoxy alcohols including methoxyethanol, ethoxyethanol, propoxyethanol, butoxyethanol, pentoxyethanol, heptoxyethanol, methoxypropanol, ethoxypropanol, propoxypropanol, butoxypropanol, pentoxypropanol and heptoxypropanol.

In the invention, if the insulator layer is made of the above-mentioned materials, polarization tends to occur easily in the insulator layer, and the threshold voltage of transistor operation can be reduced. If the insulator layer is made of silicon nitride, in particular, $Si_3N_4$, SixNy, or SiONx (x, y>0) of the above-mentioned materials, a depletion layer tends to be formed more easily, and the threshold voltage of transistor operation can be further decreased.

Examples of materials for the insulator layer using organic compounds include polyimide, polyimide, polyester, polyacrylate, a photo-curable resin such as a photoradical polymerization resin and a photocationic polymerization resin, a copolymer containing acrylonitrile components, polyvinylphenol, polyvinylalcohol, novolac resin and cyanoethylpullulan.

Other examples thereof include wax, polyethylene, polychloropyrene, polyethylene terephthalate, polyoxymethylene, polyvinyl chloride, polyvinylidene fluoride, polysulfone, polyimidecyanoethyl pullulan, poly(vinylphenol) (PVP), poly(methylmethacrylate) (PMMA), polycarbonate (PC), polystyrene (PS), polyolefin, polyacrylamide, poly(acrylic acid), a novolac resin, a resol resin, polyimide, polyxylylene, and an epoxy resin. In addition to these resins, polymer materials having a high dielectric constant such as pullulan can be used.

A particularly suitable organic compound material or polymer material for the insulator layer is a material having water repellency. The use of a material having such water repellency makes it possible to control interaction between the insulator layer and the organic semiconductor layer, and makes it possible to enhance the crystallinity of the organic semiconductor layer by utilizing cohesive properties intrinsic to an organic semiconductor, whereby device performance can be improved. A polyparaxylylene derivative described in Yasuda et al., Jpn. J. Appl. Phys. Vol. 42 (2003) pp. 6614-6618 or a compound described in Janos Veres et al., Chem. Mater., Vol. 16 (2004) pp. 4543-4555 can be mentioned as an example of the organic compound.

When the top gate structure shown in FIG. 1 and FIG. 4 is used, the use of the above-mentioned organic compound as the material for the insulator layer is an effective method, since it makes it possible to form a film while lessening damage exerted on the organic semiconductor layer.

The insulator layer may be a mixed layer in which the above-mentioned inorganic or organic compound materials are used in combination, and may be a stacked layer composed of these materials. In this case, device performance can also be controlled by mixing or stacking a material having a high dielectric constant and a material having water repellency, according to need.

Further, the insulator layer may be formed of an anodic oxidized film, or this anodic oxidized film may be used as a part of the structure of the insulator layer. Preferably, the anodic oxidized film is subjected to a sealing process. The anodic oxidized film is formed by anodizing a metal, which can be anodized, by a known method. Aluminum or tantalum can be mentioned as a metal which can be anodized. No particular restrictions are imposed on the anodizing method, and a known method can be used. An oxidized film is formed by performing an anodizing process. Any type of solution can be used as the electrolytic solution used for the anodizing process as long as a porous oxidized film can be formed. In general, sulfuric acid, phosphoric acid, oxalic acid, chromic acid, boric acid, sulfamic acid, benzenesulfonic acid, or a mixed acid produced by combining two or more kinds of acids of the above-mentioned acids, or salts of the above-mentioned acids are used. Anodizing process conditions cannot be absolutely specified because they variously change depending on an electrolytic solution to be used. In general, appropriate conditions are an electrolyte concentration of 1 to 80 mass %, an electrolyte temperature of 5 to 70° C., an electric current density of 0.5 to 60 A/cm$^2$, a voltage of 1 to 100 volts, and an electrolysis time of 10 seconds to 5 minutes. A preferred anodizing process is to use an aqueous solution of sulfuric acid, phosphoric acid or boric acid as the electrolytic solution and to perform the process by using direct current. Alternating current can also be used instead of direct current. Preferably, the concentration of these acids is 5 to 45 mass %, and the electrolytic process is performed for 20 to 250 seconds under the conditions of an electrolyte temperature of 20 to 50° C. and an electric current density of 0.5 to 20 A/cm$^2$.

As for the thickness of the insulator layer, if the thickness is small, an effective voltage to be applied to the organic semiconductor will be increased, and hence, the driving voltage and threshold voltage of the device itself can be lowered. However, since current leakage between the source electrode and the gate electrode is increased if the thickness is too small, an appropriate film thickness is required to be selected. Normally, the thickness of the insulator layer is 10 nm to 5 μm, and, preferably 50 nm to 2 μm, and more preferably 100 nm to 1 μm.

An arbitrary orientation process may be applied between the insulator layer and the organic semiconductor layer. A preferred example thereof is a method of applying a water-repellent process or the like to the surface of the insulator layer to reduce the interaction between the insulator layer and the organic semiconductor layer, thereby improving the crystallinity of the organic semiconductor layer. Specifically, a method in which a silane coupling agent such as hexamethyldisilazane, octadecyltrichlorosilane and trichloromethylsilazane, or a material for a self-assembled oriented film such as alkanephosphoric acid, alkanesulfonic and alkanecarboxylic acid is brought into contact with the surface of the insulating film in the liquid phase state or the vapor phase state to form a self-assembled film, followed by an appropriate dry process. A method is also preferable in which a film made of, for example, polyimide is formed on the surface of the insulating film as in case of the orientation of liquid crystals, and the surface of the film is subjected to a rubbing process.

Examples of methods employed for forming the insulator layer include dry processes, e.g., the vacuum vapor deposition method, the molecular beam epitaxial growth method, the ion cluster beam method, the low energy ion beam method, the ion plating method, the CVD method, the sputtering method and the atmospheric-pressure plasma method disclosed in JP-A-H11-61406, JP-A-H11-133205, JP-A-2000-121804, JP-A-2000-147209 and JP-A-2000-185362, and wet processes, e.g., the coating method, such as the spray coating method, the spin coating method, the blade coating method, the dip coating method, the casting method, the roll coating method, the bar coating method and the die coating method, and the patterning method such as printing and inkjetting. An adequate process may be used in accordance with materials. For example, as for the wet process, a method of applying and drying a liquid obtained by dispersing fine particles of an inorganic oxide into an arbitrary organic solvent or water by using a dispersion assisting agent, such as a surfactant, as necessary, or the so-called sol-gel method in which an oxide precursor, for example, an alkoxide solution, is applied and dried, are used.

No particular restrictions are imposed on the method for forming the organic thin film transistor of the invention, and a known method can be used. It is preferred that a series of device forming steps consisting of substrate mounting, gate electrode formation, insulator layer formation, organic semiconductor layer formation, source electrode formation, and drain electrode formation be carried out while completely avoiding contact with the atmosphere according to a desired device structure, because device performance can be prevented from being impaired by moisture or oxygen in the atmosphere as a result of contact with the atmosphere. Even when the device must be formed by being unavoidably brought into contact with the atmosphere once, steps subsequent to the step of organic semiconductor layer formation are performed while completely avoiding contact with the atmosphere, and, immediately before the step of organic semiconductor layer formation, a surface on which the organic semiconductor layer is stacked (for example, in device B, a surface in which the source electrode and the drain electrode are partially stacked on the insulator layer) is purified and activated by, for example, ultraviolet light irradiation, ultraviolet light/ozone irradiation, oxygen plasma, argon plasma or the like, and then the organic semiconductor layer is stacked thereon. Some of the materials for a p-type organic thin film transistor can improve the performance thereof by being brought into contact with the atmosphere once so as to absorb oxygen and other gases. Accordingly, contact with the atmosphere is conducted appropriately depending on materials to be used.

Further, a gas barrier layer may be formed on the entire or part of the outer peripheral surface of the organic transistor device, for example, taking into consideration an influence exerted on the organic semiconductor layer by oxygen or water contained in the atmosphere. Materials normally used in this field can be used for forming the gas barrier layer. Examples of such materials include polyvinyl alcohol, an ethylene-vinyl alcohol copolymer, polyvinyl chloride, polyvinylidene chloride and polychlorotrifluoroethylene. Further, inorganic substances having insulation properties exemplified regarding the above-mentioned insulator layer can also be used.

According to the invention, an organic thin film light-emitting transistor which can emit light by using electric current flowing between the source electrode and the drain electrode and can control light emission by applying a voltage to the gate electrode can be provided. That is, the organic thin film transistor can be used as a light-emitting device (organic EL device). Since the transistor for controlling light emission and the light-emitting device can be integrated, cost can be reduced by increasing the aperture ratio of a display and by simplifying the manufacturing process, and as a result, a practically great advantage can be brought about. When the organic thin film transistor is used as an organic light-emitting transistor, a hole is required to be injected from one of the source electrode and the drain electrode whereas an electron is required to be injected from the remaining electrode, and the following conditions are satisfied to improve light-emission performance.

In order to improve hole-injecting properties, in the organic thin film light-emitting transistor of the invention it is preferred that at least one of the source electrode and the drain electrode serve as a hole-injecting electrode. The hole-injecting electrode means an electrode containing a material having a work function of 4.2 eV or more as mentioned above.

In order to improve electron-injection properties, it is preferred that at least one of the source electrode and the drain electrode be an electron-injecting electrode. The electron-injecting electrode means an electrode containing a material having a work function of 4.3 eV or less as mentioned above.

More preferably, the device is an organic thin film light-emitting transistor having one electrode serving as a hole-injecting electrode and the other electrode serving as an electron-injecting electrode.

In order to improve hole-injection properties, it is preferred that a hole-injecting layer be inserted between at least one of the source and drain electrodes and the organic semiconductor layer. For example, an amine-based material, which is used as a hole-injecting material or a hole-transporting material in an organic EL device, can be used in the hole-injecting layer.

In order to improve electron-injecting properties, it is preferred that an electron-injecting layer be inserted between at least one of the source electrode and the drain electrode, and the organic semiconductor layer. As in the case of the hole, an electron-injecting material used in an organic EL device can be used in the electron-injecting layer.

It is more preferred that the device be an organic thin film light-emitting transistor in which one of the electrodes is provided with a hole-injecting layer and the remaining electrode is provided with an electron-injecting layer.

An apparatus using the organic thin film transistor of the invention may be an apparatus which uses the organic thin film transistor of the invention. Examples thereof include a circuit, a personal computer, a display and a mobile phone.

EXAMPLES

The invention will be described in more detail with reference to the Examples.

Example 1

Synthesis of Compound (1)

The compound (1) was synthesized as follows.

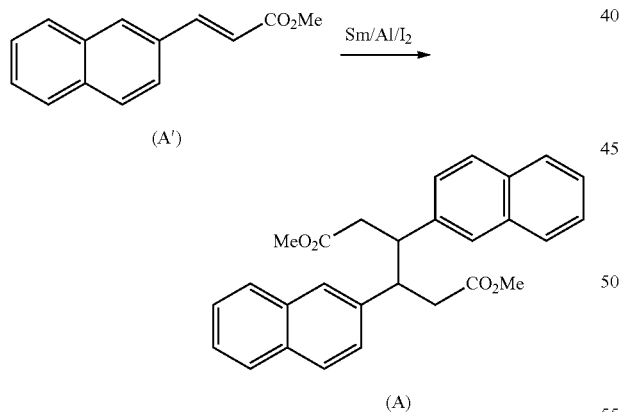

0.32 g of aluminum foil and 20 ml of methanol were put in the reaction container, and 0.60 g of iodine was added thereto. The reaction mixture was stirred for one hour at room temperature. Then, 1.0 g of an ester compound (A') and 0.61 g of samarium were added, and the resultant was refluxed with heating at 60° C. for 6 hours. The reaction mixture was filtered through Celite. The resulting compound was washed with methanol, thereby to obtain a crude product of the compound (A). This crude product was purified by column chromatography (hexane:ethyl acetate), whereby 0.20 g (yield: 19%) of the compound A was obtained.

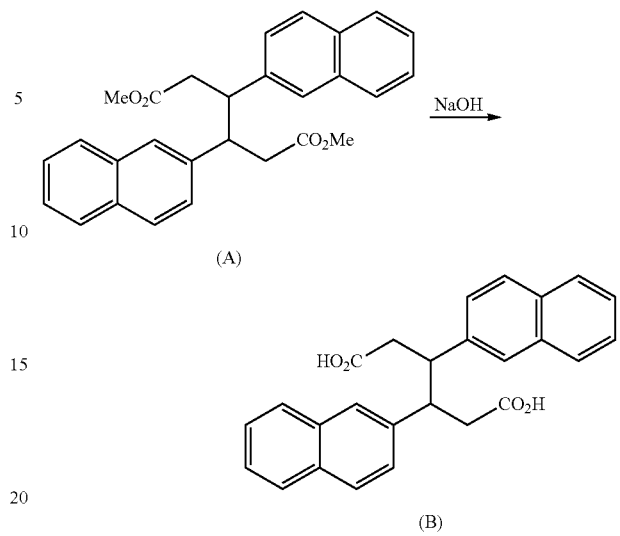

4.68 g (11.0 mmol) of the compound A, 20 ml of tetrahydrofuran and 20 ml of ethanol were put in a reaction container. 30 ml of a 2M aqueous sodium hydroxide solution was added thereto, followed by reflux with heating at 60° C. for 6 hours. The reaction mixture was allowed to be acidic with 2M hydrochloric acid, extracted with ethyl acetate, and the extracted product was distilled off under reduced pressure, whereby 4.30 g (yield 98%) of a crude product of the compound (B) was obtained. This crude product was used as it was in a subsequent reaction.

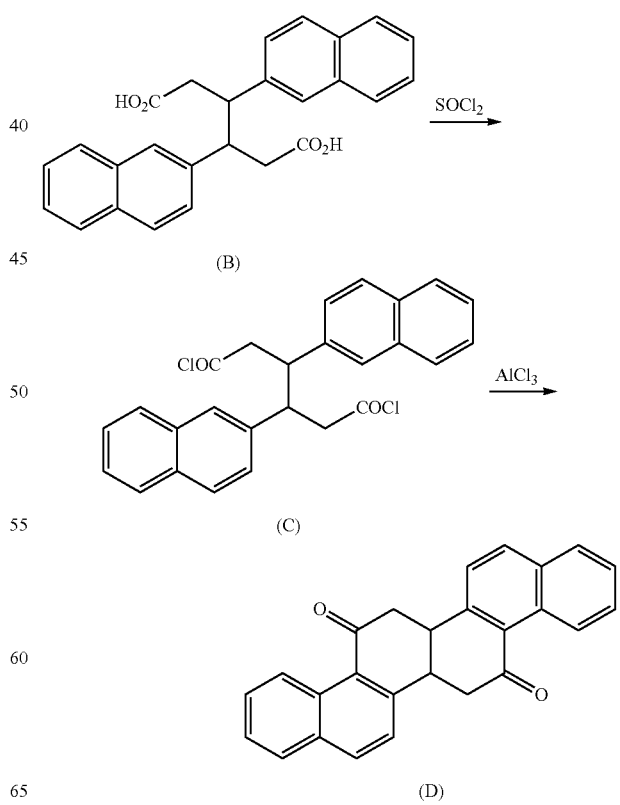

40 ml of chloroform, 5.2 g of thionyl chloride and 0.17 g of pyridine were added to 4.4 g (10.8 mmol) of the compound (B), and the resulting mixture was refluxed with heating at 60° C. for 1 hour. The resultant was distilled off under reduced pressure as it was, whereby the compound (C) was obtained. The compound (C) was added to a reaction container in which 4.4 g of aluminum chloride and 40 ml of methylene chloride had been placed, followed by stirring at room temperature for 8 hours. 20 ml of water was added to the reaction container, and extraction was conducted with ethyl acetate, whereby a crude product of the compound (D) was obtained. This crude product was purified by column chromatography (hexane:ethyl acetate), whereby 0.58 g (yield: 15%) of the compound (D) was obtained.

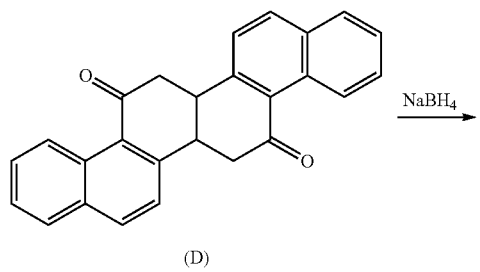

(D)

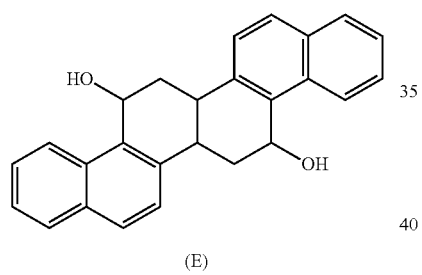

(E)

0.050 g of sodium borohydride was added to a methanol solution of 0.58 g (1.60 mmol) of the compound (D), followed by stirring at room temperature for 3 hours. Water was added to the reaction mixture, and an organic matter was extracted with ethyl acetate, whereby 0.24 g (yield: 41%) of a crude product of the compound (E) was obtained. The crude product was used as it was in a subsequent reaction.

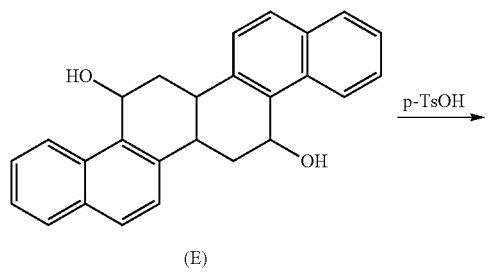

(E)

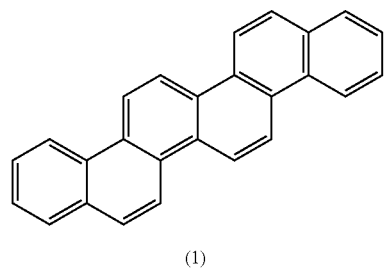

(1)

0.24 g (0.654 mmol) of the compound (E), 0.05 g of p-toluenesulfonic acid monohydrate and 20 ml of toluene were refluxed with heating at 150° C. for 10 hours. The reaction mixture was filtered, washed with methanol and dichloromethane, whereby a crude product was obtained. The resulting crude product was purified by sublimation, whereby 0.16 g (yield 74%) of the compound (1) was obtained.

As a result of the measurement by FD-MS (field desorption mass spectrometry), the compound was confirmed to be an intended product. The measurement results of ED-MS are given below.

FD-MS, calcd for $C_{26}H_{16}$=328, found, m/z=328 (M+, 100)

<FD-MS Measurement>

Apparatus: HX110 (manufactured by JEOL Ltd.)

Conditions: accelerated voltage 8 kV

Scan range m/z=50 to 1500

Example 2

Synthesis of Compound (37)

The compound (37) was synthesized as follows.

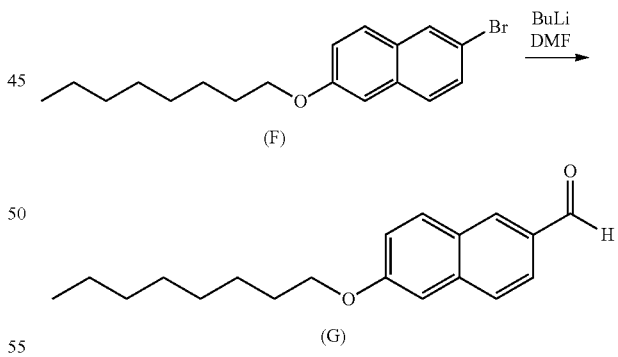

(F)

(G)

A tetrahydrofuran solution of 5.00 g (14.9 mmol) of the compound (F) was cooled to −60° C. A 1.6M hexane solution of butyllithium was added, followed by stirring for 1 hour. N,N-dimethylformamide was added thereto, and stirred at room temperature for 3 hours. Water was added to a reaction mixture. An organic matter was extracted with ethyl acetate, whereby a crude product of the compound (G) was obtained. This crude product was purified by column chromatography (hexane:ethyl acetate), whereby 4.24 g (yield: 70%) of the compound (G) was obtained.

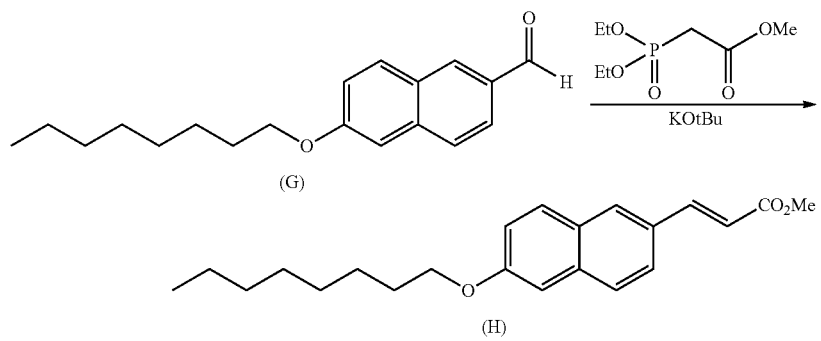

1.93 g of potassium tert-butoxide was added to a tetrahydrofuran solution of 3.28 g (15.6 mmol) of a phosphoric acid ester compound, followed by stirring at room temperature for one hour. 4.24 g (10.4 mmol) of the compound (G) was added thereto, followed by further stirring at room temperature for 3 hours. Water was added to a reaction mixture, and an organic matter was extracted with ethyl acetate, whereby a crude product of the compound (G) was obtained. This crude product was purified by column chromatography (hexane:ethyl acetate), whereby 2.69 g (yield 76%) of the compound (H) was obtained.

The compound (37) was synthesized by treating the compound (H) obtained by the above-mentioned scheme to the same technique as in Example 1.

As a result of the measurement by FD-MS (field desorption mass spectrometry), the resulting compound (37) was confirmed to be an intended product. The measurement results of FD-MS are given below.

FD-MS, calcd for $C_{42}H_{48}O_2$=584, found, m/z=584 (M+, 100)

Example 3

Synthesis of Compound (9)

The compound (9) was synthesized in the same manner as in Example 2, except that 2-bromo-6-octylnaphthalene was used instead of the compound (F) as the starting material.

As a result of the measurement by FD-MS (field desorption mass spectrometry), the compound (9) was confirmed to be an intended product. The measurement results of FD-MS are given below.

FD-MS, calcd for $C_{42}H_{48}$=552, found, m/z=552 (M+, 100)

Example 4

Synthesis of Compound (97)

The compound (97) was synthesized as follows.

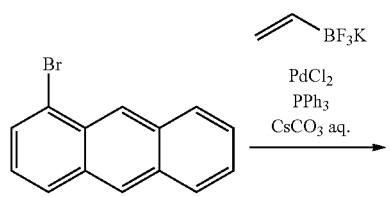

-continued

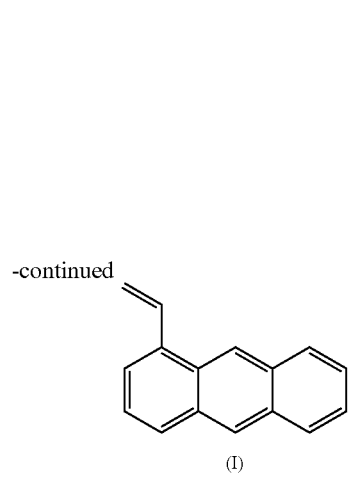

In a reaction container, 5.07 g (19.4 mmol) of 1-bromoanthracene, 2.01 g (19.4 mmol) of potassium vinyltrifluoroborate, 69 ml (0.39 mmol) of palladium (II) chloride, 0.30 g (1.1 mmol) of triphenyl phosphine and 18.9 g (58.1 mmol) of cesium carbonate were weighed, and the atmosphere in the reaction container was replaced with argon. Then, 450 ml of toluene and 50 ml of water were added, and the mixture was refluxed with heating at 85° C. for 20 hours. 30 ml of water was added to the reaction mixture, and an organic phase was extracted with toluene and dried with sodium sulfate. The resulting crude product was re-crystallized from toluene, whereby 2.69 g (yield 68%) of the compound (I) was obtained.

In a reaction container, 2.56 g (12.5 mmol) of the compound (I) and 5.81 g (33.7 mmol) of 6-methylnaphthalene-1,4-dione were weighed. 150 ml of acetic acid was added thereto, and the resulting mixture was stirred at 100° C. for 6 hours. This reaction solution was cooled on ice. Then, 200 ml of water was added, and deposited precipitates were filtered. The powder thus obtained was re-crystallized from acetic acid, whereby 1.45 g (yield 31%) of the compound (J) was obtained.

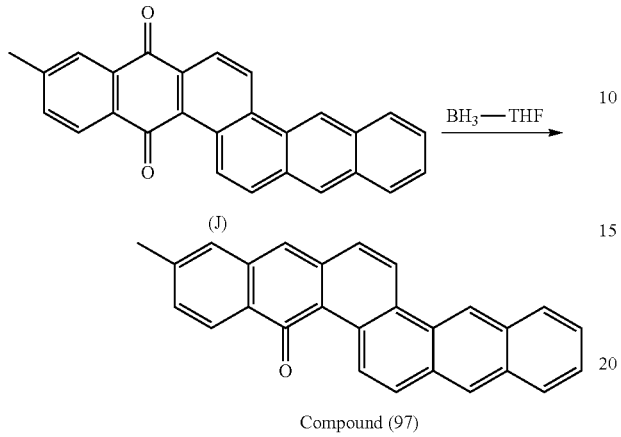

Compound (97)

In a reaction container, 1.40 g (3.76 mmol) of the compound (J) was weighed, and dissolved in 200 ml of tetrahydrofuran anhydride. Then, 12.5 ml (11.3 mmol) of 0.9M solution of a borane-tetrahydrofuran complex was added, followed by stirring at 70° C. for 5 hours. Then, water and toluene were added, and an organic phase was extracted with toluene, and dried with sodium sulfate. The resulting crude product was purified by column chromatography (hexane:toluene) and sublimation, whereby 0.65 g (yield 51%) of the compound (97) was obtained.

As a result of the measurement by FD-MS (field desorption mass spectrometry), the resulting compound (97) was confirmed to be an intended product. The measurement results of FD-MS are given below.

FD-MS, calcd for $C_{27}H_{18}$=342, found, m/z=342 (M+, 100)

Example 5

Synthesis of Compound (98)

The compound (98) was synthesized in the same manner as in Example 4, except that 6-ethylnaphthalene-1,4-dione was used instead of 6-methylnaphthalene-1,4-dione.

As a result of the measurement by FD-MS (field desorption mass spectrometry), the resulting compound (98) was confirmed to be an intended product. The measurement results of FD-MS are given below.

FD-MS, calcd for $C_{28}H_{20}$=356, found, m/z=356 (M+, 100)

Example 6

Synthesis of Compound (104)

The compound (104) was synthesized in the same manner as in Example 4, except that 6-octylnaphthalene-1,4-dione was used instead of 6-methylnaphthalene-1,4-dione.

As a result of the measurement by FD-MS (field desorption mass spectrometry), the resulting compound (104) was confirmed to be an intended product. The measurement results of FD-MS are given below.

FD-MS, calcd for $C_{34}H_{32}$=440, found, m/z=440 (M+, 100)

Example 7

Synthesis of Compound (1116)

The compound (1116) was synthesized in the same manner as in Example 4, except that 6-(4-methylpentyl)naphthalene-1,4-dione was used instead of 6-methylnaphthalene-1,4-dione.

As a result of the measurement by FD-MS (field desorption mass spectrometry), the compound (9) was confirmed to be an intended product. The measurement results of FD-MS are given below.

FD-MS, calcd for $C_{32}H_{28}$=412, found, m/z=412 (M+, 100)

Example 8

Synthesis of Compound (167)

The compound (167) was synthesized as follows.

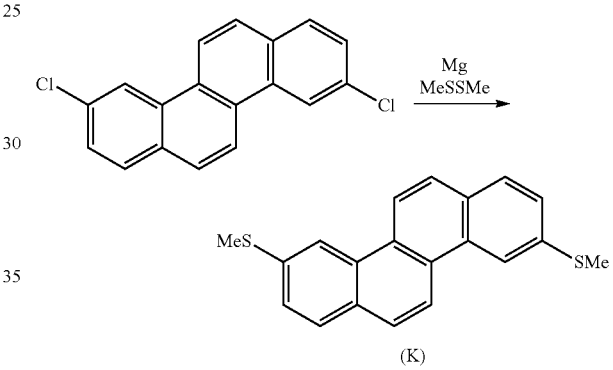

In a reaction container, 0.65 g (27 mmol) of magnesium was weighed, and 50 ml of tetrahydrofuran anhydride was added. One drop of 1,2-dibromoethane was added, followed by reflux with heating for 1 hour. After cooling the reaction solution to room temperature, 50 ml of a tetrahydrofuran anhydride solution of 3.33 g (11.3 mmol) of 3,9-dichlorochrysene was slowly added, and the resulting mixture was refluxed with heating for 10 hours. The reaction mixture was cooled to room temperature again, and 3.0 ml (33.8 mmol) of dimethyl disulfide was added, and stirred for 5 hours. The reaction solution was cooled on ice, methanol was added, and subsequently water and toluene were added. An organic phase was extracted with toluene, and dried with sodium sulfate. The resulting crude product was purified by column chromatography (hexane:toluene), whereby 1.80 g (yield 50%) of the compound (K) was obtained.

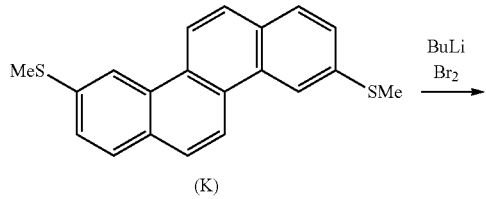

-continued

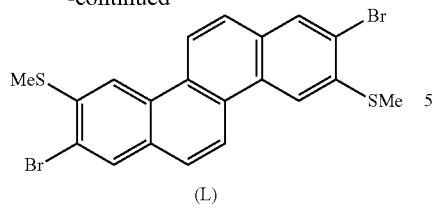

(L)

In a reaction container, 1.80 g (5.62 mmol) of the compound (K) was weighed, and dissolved in 200 ml of tetrahydrofuran anhydride. After cooling the reaction solution to −40° C., 10.5 ml (16.8 mmol) of a 1.6M solution of butyllithium was slowly added, followed by stirring at 0° C. for 5 hours. The reaction solution was cooled to −40° C. again, and 10 ml of a chloroform solution of 2.24 g (14.1 mmol) of bromine was slowly added, and stirred for 3 hours. Water and toluene were added, and an organic phase was extracted with toluene, washed with an aqueous sodium thiosulfate solution, and dried with sodium sulfate. The resulting crude product was purified by column chromatography (hexane:toluene), whereby 1.10 g (yield 41%) of the compound (L) was obtained.

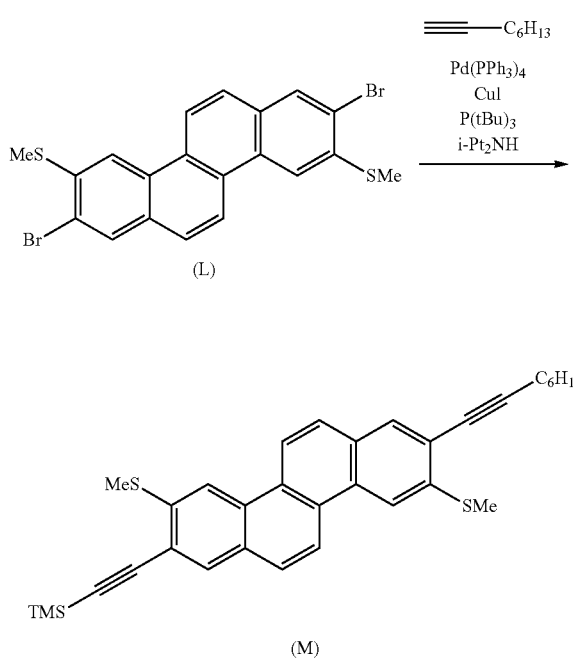

In a reaction container, 1.07 g (2.25 mmol) of the compound (L), 0.26 g (0.23 mol) of tetrakistriphenylphosphine palladium (0) and 0.086 g (0.45 mmol) of copper iodide (I) were weighed, and dissolved in 20 ml of toluene anhydride. 20 ml of diisopropylamine, 1.0 ml (6.75 mmol) of n-octyne and 22 μl (0.18 mmol) of a 66 wt % toluene solution of tris(tert-butyl)phosphine was added, and stirred at 50° C. overnight. Water was added, and an organic phase was extracted with toluene and dried with sodium sulfate. The resulting crude product was purified by column chromatography (hexane:toluene), whereby 0.93 g (yield 77%) of the compound (M) was obtained.

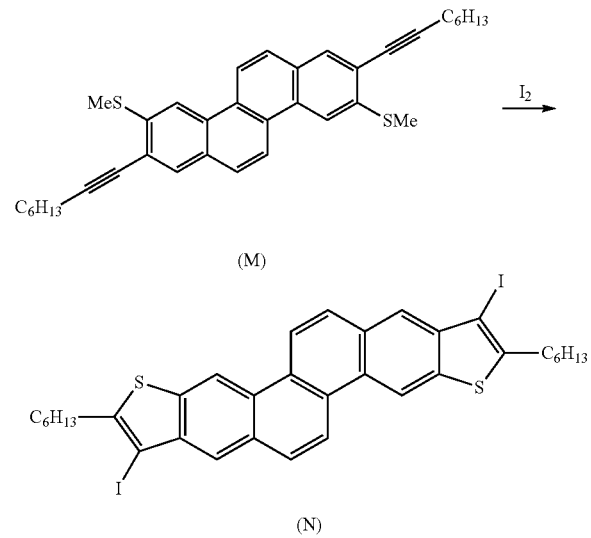

In a reaction container, 0.93 g (1.73 mmol) of the compound (M) was weighed, and dissolved in 20 m of dichloromethane. 1.76 g (6.93 mmol) of iodine was added, and the resulting mixture was refluxed with heating for 12 hours. An aqueous solution of sodium thiosulfate was added, and an organic phase was extracted with chloroform, and dried with sodium sulfate. The resulting crude product was purified by column chromatography (hexane:toluene), whereby 0.84 g (yield 64%) of the compound (N) was obtained.

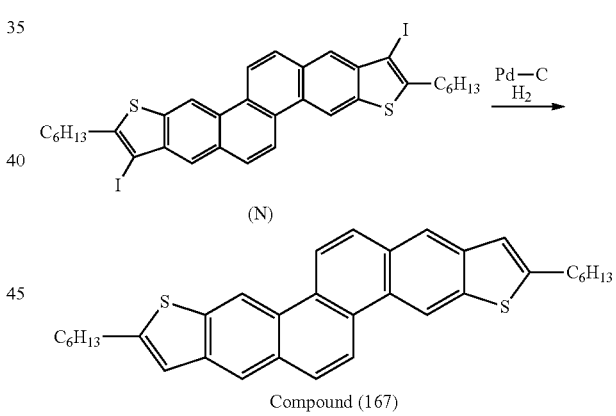

Compound (167)

In a reaction container, 0.84 g (1.73 mmol) of the compound (N) and 0.10 g (0.94 mmol) of palladium/carbon were weighed, and the atmosphere in the reaction system was replaced with hydrogen. 20 ml of toluene anhydride was added, and stirred at 50° C. for 4 hours. The reaction solution was filtered through Celite. The resulting crude product was purified by column chromatography (hexane:toluene) and sublimation, whereby 0.33 g (yield 59%) of the compound (167) was obtained.

As a result of the measurement by FD-MS (field desorption mass spectrometry), the resulting compound (167) was confirmed to be an intended product. The measurement results of FD-MS are given below.

FD-MS, calcd for $C_{34}H_{36}S_2$=508, found, m/z=508 (M+, 100)

Example 9

Synthesis of Compound (250)

The compound (250) was synthesized in the same manner as in Example 8, except that, 2,8-dibromochrysene was used instead of 3,9-dichlorochrysene as the starting material, and Sonogashira coupling was conduced by using n-tetradecine instead of n-octyne which was used in the synthesis of the compound (M) (step (O)).

As a result of the measurement by FD-MS (field desorption mass spectrometry), the resulting compound (250) was confirmed to be an intended product. The measurement results of FD-MS are given below.

FD-MS, calcd for $C_{46}H_{80}S_2=676$, found, m/z=676 (M+, 100)

Example 10

Synthesis of Compound (630)

The compound (630) was synthesized as follows.

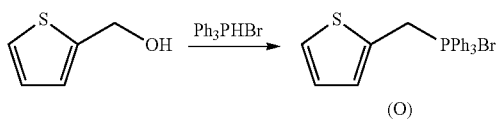

(O)

To a reaction container, 9.10 g (80.0 mmol) of 2-thiophene methanol, 27.4 g (80.0 mmol) of triphenylbromide phosphonium and 300 ml of methanol anhydride were added, and stirred at 45° C. for 7 hours. The solvent of the reaction mixture was removed, and the resulting solids were washed with dichloromethane, whereby 28.4 g (yield 81%) of the compound (O) was obtained.

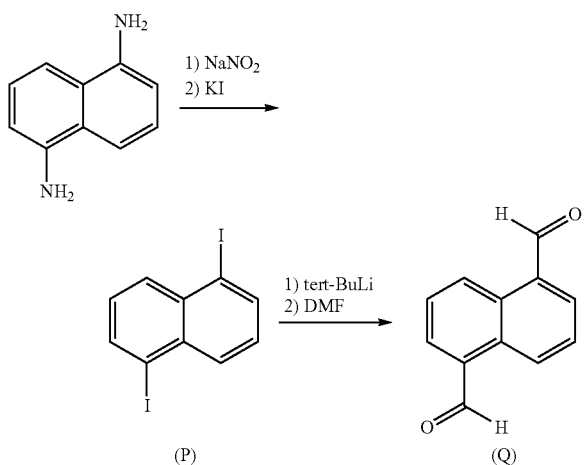

Synthesis of Compound (P)

340 ml of hydrochloric acid and 240 ml of pure water were added to 30.0 g (189 mmol) of 1,5-naphthalenediamine. After cooling the reaction solution to −30° C., 100 ml of an aqueous solution of 28.8 g (417 mmol) of sodium sulfite was added dropwise, and the resulting mixture was stirred at −20° C. for one hour. This reaction mixture was added dropwise to 1 l of an aqueous solution of 31.0 g (1.87 mol) of potassium iodide, and stirred at room temperature for 8 hours. Dichloromethane was added to a reaction product, filtered and extracted to obtain a crude product. The crude product was purified by column chromatography (hexane), whereby 33.0 g (yield 46%) of the compound (P) was obtained.

Synthesis of Compound (Q)

Subsequently, to a reaction container, 15.2 g (40.0 mmol) of the compound (P) and 750 ml of tetrahydrofuran anhydride were added, and the resulting mixture was cooled to −78° C., 100 ml (176 mmol) of 1.76M tert-butyllithium was added dropwise, and stirred for 2 hours. 29.2 g (400 mmol) of dimethylformamide was added dropwise, and stirred at room temperature for 3 hours. After neutralization with hydrochloric acid, the reaction mixture was extracted with toluene, whereby a crude product of the compound (Q) was obtained. The resulting crude product was purified by column chromatography (hexane:ethyl acetate), whereby 5.00 g (yield 70%) of the compound (Q) was obtained.

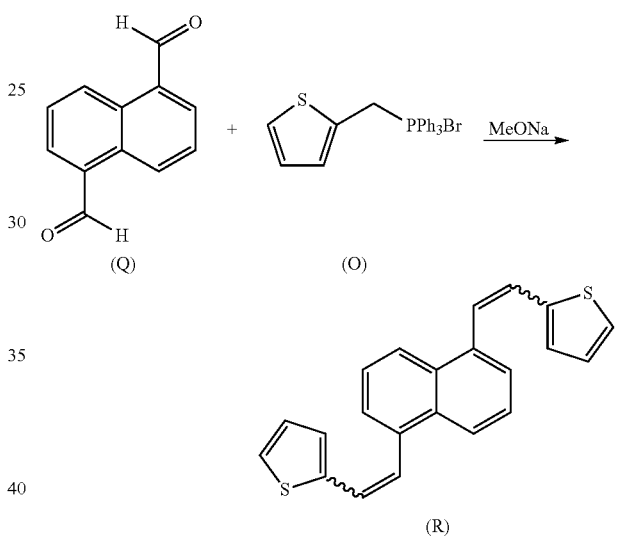

To a reaction container, 9.5 g (22 mmol) of the compound (O), 2.9 g (54 mmol) of sodium methoxide and 400 ml of methanol anhydride were added, followed by stirring at 50° C. for 30 minutes. Then, 100 ml of a methanol anhydride solution of 2.0 g (11 mmol) of the compound (Q) was added, followed by stirring at 65° C. for 7 hours. The solvent in the reaction container was removed and pure water was added. Extraction was conducted with dichloromethane, whereby a crude product of the compound (R) was obtained. The resulting crude product was purified by column chromatography (hexane:dichloromethane), whereby 3.2 g (yield 84%) of the compound (R) was obtained.

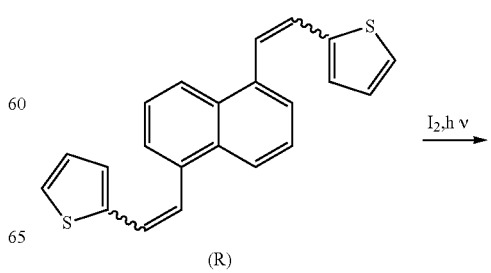

-continued

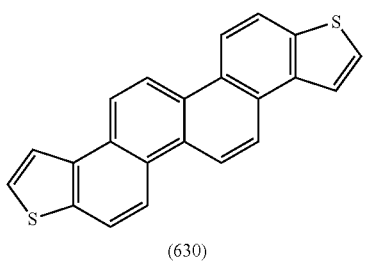

(630)

1.5 g (4.5 mmol) of the compound (R) and 0.57 g (2.2 mmol) of iodine were dissolved in 1.5 l of toluene, and the resultant was irradiated with light for 24 hours by means of a 400 W high-pressure mercury lamp. The reaction product was filtered, whereby a crude product of the compound (630) was obtained. The crude product was purified by sublimation, whereby 0.50 g (yield 32%) of the compound (630) was obtained.

As a result of the measurement by FD-MS (field desorption mass spectrometry), the resulting compound (630) was confirmed to be an intended product. The measurement results of FD-MS are given below.

FD-MS, calcd for $C_{22}H_{12}S_2$=340, found, m/z=340 (M+, 100)

Example 11

Synthesis of Compound (638)

The compound (638) was synthesized as follows.

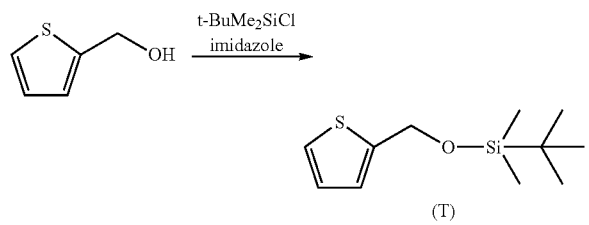

To a reaction container, 100 g (0.66 mol) of tert-butyldimethylchlorosilane and 75 g (1.1 mol) of imidazole were added, and dissolved in 500 ml of anhydrous dimethylformamide. 63 g (0.55 mol) of 2-thiophene methanol was added, and the resulting mixture was further stirred at 40° C. for 8 hours. Pure water was added to the reaction mixture, and extraction was conducted with ethyl acetate, whereby a crude product of the compound (S) was obtained. The resulting crude product was purified by column chromatography (hexane), whereby 101 g (yield 80%) of the compound (S) was obtained.

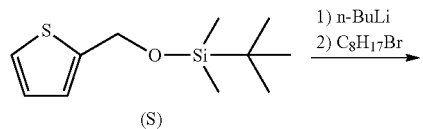

-continued

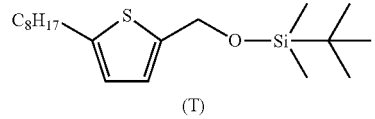

(T)

To a reaction container, 101 g (0.44 mol) of the compound (S) and 300 ml of dehydrated tetrahydrofuran were added. The resulting mixture was cooled to 0° C. Then, 306 ml (0.49 mol) of N-butyl lithium was added dropwise, and stirred at room temperature for 3.5 hours. 94 g (0.49 mol) of N-octylbromide was added, and further stirred at 50° C. for 3 hours. Pure water was added to the reaction mixture, and extraction was conducted with dichloromethane, whereby a crude product of the compound (T) was obtained. The resulting crude product was purified by column chromatography (hexane), whereby 130 g (yield 86%) of the compound (T) was obtained.

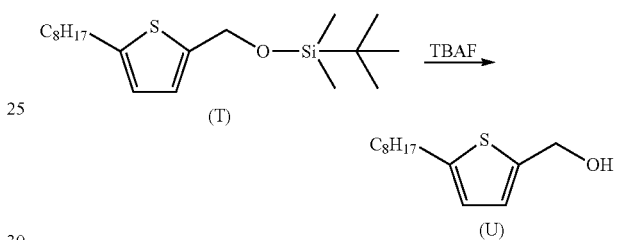

In the above formula, TBAF is tetrabutylammonium fluoride.

To a reaction container, 130 g (0.38 mol) of compound (T), 100 ml of dehydrated tetrahydrofuran, 460 ml (0.46 mol) of tetrabutylammonium fluoride (1.0M) were added, and stirred at room temperature for 4 hours. Pure water was added to the reaction mixture, and extraction was conducted with dichloromethane, whereby a crude product of the compound (U) was obtained. This crude product was purified by column chromatography (hexane:ethyl acetate), whereby 44 g (yield 51%) of the compound (U) was obtained.

A compound (638) was synthesized in the same manner as in Example 10, except that the compound (U) was used instead of 2-thiophene methanol.

As a result of the measurement by FD-MS (field desorption mass spectrometry), the resulting compound (638) was confirmed to be an intended product. The measurement results of FD-MS are given below.

FD-MS, calcd for $C_{38}H_{44}S_2$=564, found, m/z=564 (M+, 100)

Example 12

Synthesis of Compound (881)

The compound (881) was synthesized as follows.

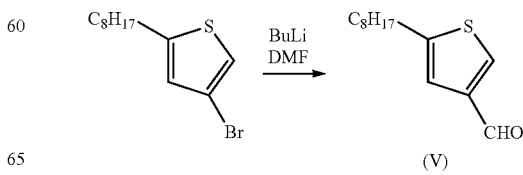

In a reaction container, 2.5 g (9.1 mmol) of 4-bromo-2-octylthiophene was weighed, and dissolved in 50 ml of tetrahydrofuran anhydride. After cooling the reaction solution to −40° C., 9.0 ml (14 mmol) of a 1.6M hexane solution of butyllithium was added. The reaction solution was heated to 0° C., followed by stirring for 2 hours. The reaction solution was cooled to −40° C. again. 1.4 ml (18 mmol) of DMF was added and the mixture was heated to 0° C., and stirred for 3 hours. Then, methanol and water were added, and an organic phase was extracted with ethyl acetate, and dried with sodium sulfate. The resulting crude product was purified by column chromatography (hexane:ethyl acetate), whereby 1.8 g (yield 88%) of the compound (V) was obtained.

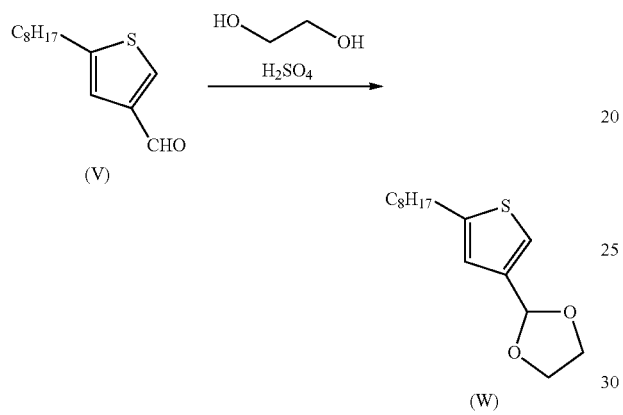

In a reaction container, 1.8 g (8.0 mmol) of the compound (V) and 1.5 g (2.4 mmol) of ethylene glycol were weighed, and dissolved in 40 ml of anhydrous toluene. After adding 3 drops of sulfuric acid, the resulting mixture was refluxed with heating for 3 hours, while dehydrating by means of a Dean-Stark tube. The reaction solution was added slowly to an aqueous saturated sodium hydrocarbonate solution which had been cooled on ice. An aqueous layer was extracted with ethyl acetate, and dried with sodium sulfate. The resulting crude product was purified by column chromatography (hexane:ethyl acetate), whereby 1.9 g (yield 89%) of the compound (W) was obtained.

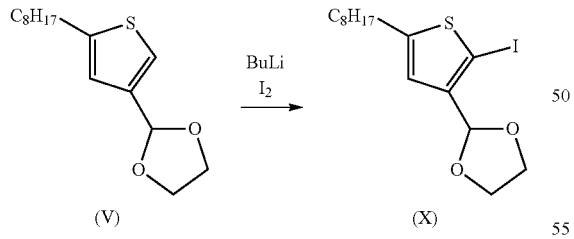

In a reaction container, 1.9 g (7.1 mmol) of the compound (W) was weighed, and dissolved in 35 ml of tetrahydrofuran anhydride. After cooling the reaction solution to −40° C., 6.7 ml (10.7 mmol) of a 1.6M hexane solution of butyllithium was added, followed by stirring for 2 hours. 10 ml of dichloromethane solution of 2.7 g (10.6 mmol) of iodine was added, and the reaction solution was heated to 0° C., followed by stirring for 5 hours. Then, an aqueous sodium thiosulfate solution was added, and an organic phase was extracted with ethyl acetate, and dried with sodium sulfate. The resulting crude product was purified by column chromatography (hexane:ethyl acetate), whereby 2.0 g (yield 72%) of the compound (X) was obtained.

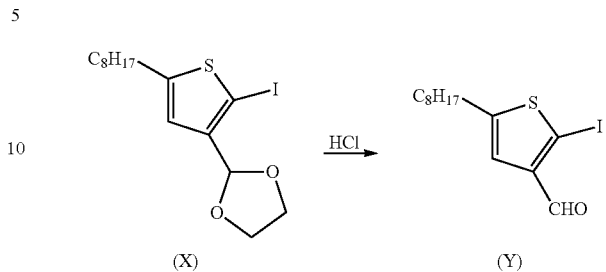

In a reaction container, 2.0 g (5.1 mmol) of the compound (X) was weighed, and dissolved in 25 ml of tetrahydrofuran. 10 ml of 1.0M hydrochloric acid was added, and stirred at 50° C. for 3 hours. The reaction solution was added slowly to an aqueous saturated sodium hydrocarbonate solution which had been cooled on ice. An organic phase was extracted with ethyl acetate, and dried with sodium sulfate. The resulting crude product was purified by column chromatography (hexane:ethyl acetate), whereby 1.6 g (yield 90%) of the compound (Y) was obtained.

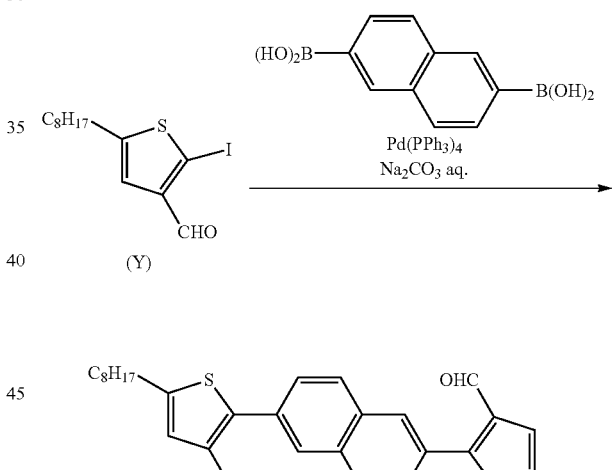

In a reaction container, 1.6 g (4.6 mmol) of the compound (Y), 2.2 g (10 mmol) of 2,6-naphthalene diboronic acid and 0.26 g (0.22 mmol) of tetrakis(triphenylphosphine)palladium (0) were weighed, and 15 ml (30 mmol) of a 2M aqueous sodium carbonate solution and 50 ml of dimethoxyethane were added to allow them to dissolve. The reaction solution was refluxed with heating for 8 hours. Water and toluene were added, and an organic phase was extracted with toluene, and dried with sodium sulfate. The resulting crude product was purified by column chromatography (hexane:ethyl acetate), whereby 1.2 g (yield 91%) of the compound (Z) was obtained.

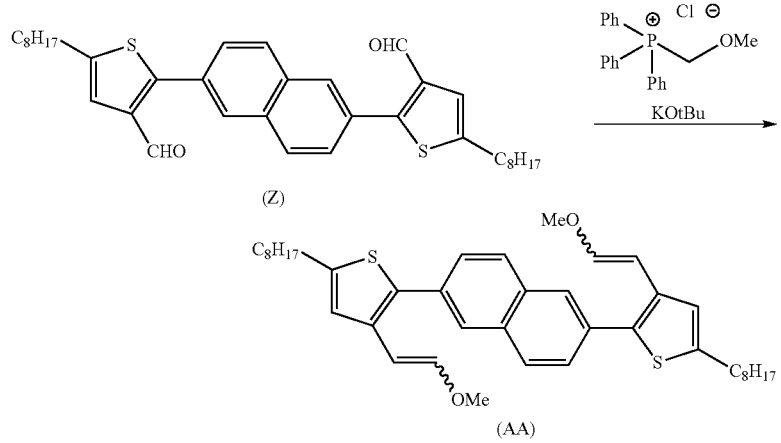
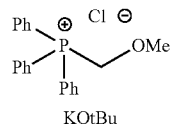

In a reaction container, 4.3 g (13 mmol) of (methoxymethyl)triphenylphosphonium chloride was weighed, and 130 ml of tetrahydrofuran anhydride was added. The reaction solution was cooled on ice, and 1.3 g (12 mmol) of potassium tert-butoxide was added, followed by stirring for 1 hour. 1.2 g (2.1 mmol) of the compound (Z) was added, and the reaction solution was heated to room temperature, followed by stirring for 8 hours. Water was added, and an organic phase was extracted with toluene and dried with sodium sulfate. The resulting crude product was purified by column chromatography (hexane:toluene), whereby 0.78 g (yield 56%) of the compound (AA) was obtained as an isomer mixture.

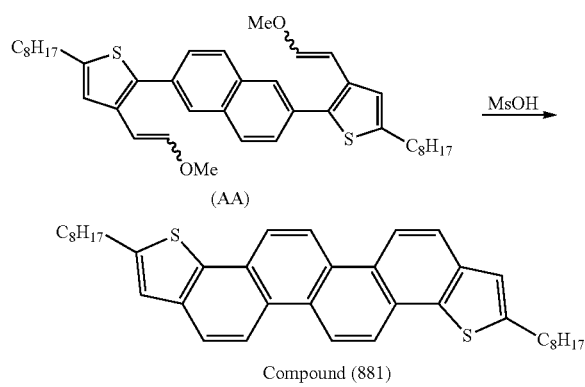

In a reaction container, 0.78 g (1.2 mmol) of the compound (AA) was weighed, and dissolved in 30 ml of anhydrous dichloromethane. The reaction solution was cooled on ice. After adding 5 drops of methanesulfonic acid, the reaction solution was heated to room temperature, and stirred for 6 hours. Generated precipitates were filtered and washed with methanol. The resulting crude product was purified by sublimation, whereby 0.42 g (yield 60%) of the compound (881) was obtained.

As a result of the measurement by FD-MS (field desorption mass spectrometry), the resulting compound (881) was confirmed to be an intended product. The measurement results of FD-MS are given below.

FD-MS, calcd for $C_{38}H_{44}S_2$=564, found, m/z=564 (M+, 100)

Example 13

Production of an Organic Thin Film Transistor

An organic thin film transistor was manufactured through the following steps. First, the surface of an Si substrate (also served as a p-type gate electrode with a specific resistance of 1 Ωcm) was oxidized by the thermal oxidation method, whereby a 300 nm-thick thermally oxidized film was formed on the substrate to form an insulator layer. Further, an $SiO_2$ film formed on one side of the substrate was completely removed by dry etching, and thereafter, chromium was formed into a film of 20 nm by the sputtering method. Further, gold (Au) was formed thereon into a film of 100 nm by the sputtering method, whereby an outcoupling electrode was formed. This substrate was subjected to ultrasonic cleaning for 30 minutes each with a neutral detergent, pure water, acetone and ethanol. The substrate was further subjected to ozone cleaning.

The substrate was then subjected to a surface treatment by heating for 3 hours in the atmosphere of hexamethyldisilazane. The substrate thus surface-treated was mounted in a vacuum vapor deposition apparatus (EX-400, manufactured by ULVAC, Inc.), and, on the insulator layer, the above-mentioned compound (1) was formed into a 50 nm-thick film at a deposition speed of 0.05 nm/s to form an organic semiconductor layer. Subsequently, gold was formed into a film with a thickness of 50 nm through a metal mask, whereby a source electrode and a drain electrode, which were not in contact with each other, were formed such that an interval therebetween (channel length L) became 75 μm. The film formation was conducted such that the width (channel width W) of the source electrode and the drain electrode became 5 mm, whereby an organic thin film transistor was fabricated (see FIG. 3).

A gate voltage ($V_G$) of −70V was applied to the gate electrode of the resulting organic thin film transistor, whereby a voltage was applied between the source electrode and the drain electrode to cause electric current to flow therebetween. In this case, holes were induced in the channel region (a region between the source electrode and the drain electrode), and the transistor was operated as a p-type transistor. The on-off ratio of electric current flowing between the source electrode and the drain electrode in the current saturated region was $2\times10^5$. The field effect mobility (μ) of the hole was calculated from the following formula (A), and it was found to be $1\times10^{-1}$ cm$^2$/Vs.

$$I_D = (W/2L) \cdot C\mu \cdot (V_G - V_T)^2 \qquad (A)$$

In the formula, $I_D$ is source-drain current, W is a channel width, L is a channel length, C is an electric capacitance per unit area of the gate insulator layer, $V_T$ is a gate threshold voltage and $V_G$ is a gate voltage.

Example 14

Production of an Organic Thin Film Transistor Using the Coating Process

The substrate was cleaned, the gate electrode and the insulator layer were formed in the same manner as in Example 3. Subsequently, 0.5 mass % of the above-mentioned compound (37) was dissolved in chloroform, and formed into a film on the substrate on which the gate electrode and the insulating layer had been formed by means of a spin coater (1H-D7, manufactured by Mikasa Co., Ltd.) and dried at 80° C. in the nitrogen atmosphere, thereby to form an organic semiconductor layer. Subsequently, gold (Au) was formed into a film with a thickness of 50 nm through a metal mask in a vacuum vapor deposition apparatus, thereby to form a source electrode and a drain electrode, which were not in contact with each other, whereby an organic thin film transistor was fabricated. The resulting organic thin film transistor was allowed to drive as a p-type transistor by applying a gate voltage $V_G$ of −70V in the same manner as in Example 3. The on/off of the current flowing between the source electrode and the drain electrode was measured, thereby to calculate the field effect mobility μ of the hole. The results are shown in Table 1.

Example 15

Production of an Organic Thin Film Transistor

A glass substrate was subjected to ultrasonic cleaning for 30 minutes each with a neutral detergent, pure water, acetone and ethanol. Then, gold (Au) was formed into a film of 40 nm by sputtering, thereby to form a gate electrode. Subsequently, this substrate was installed on the film-forming part of a thermal CVD apparatus. 250 mg of a polyparaxylene derivative [polyparaxylene chloride (Parylene)] (trade name: diX-C; manufactured by Daisan KASEI CO., LTD.) as a material for an insulator layer was placed in a petri dish and installed in the evaporation part of the raw material. After vacuuming the thermal CVD apparatus by means of a vacuum pump to a pressure of 5 Pa, the evaporation part was heated to 180° C. and a polymerization part was heated to 680° C., and the material was allowed to stand for 2 hours, whereby an insulator layer with a thickness of 1 μm was formed on the gate electrode.

Then, the substrate was installed in a vacuum vapor deposition apparatus (EX-400; manufactured by ULVAC Co.) and the Compound (9) was formed into a film of an organic semiconductor layer with a thickness of 50 nm at a deposition rate of 0.05 nm/second over the insulator layer. Subsequently, a source electrode and a drain electrode which did not contact each other were formed such that the distance between them (channel length: L) became 75 μm by forming gold into a 50 nm-thick film through a metal mask. Film formation was conducted such that the width (channel width W) of the source electrode and the drain electrode become 5 mm, whereby an organic thin film transistor was fabricated.

A gate voltage $V_G$ of −70 V was applied to the gate electrode of the resulting organic thin film transistor to allow it drive as a p-type transistor. The on/off of the current flowing between the source electrode and the drain electrode was measured, thereby to calculate the field effect mobility μ of the hole. The results are shown in Table 1.

Examples 16 to 22

Organic thin film transistors were fabricated and evaluated in the same manner as in Example 15, except that the compounds (97), (98), (167), (250), (630), (638) and (881) were respectively used instead of the compound (9). The results are shown in Table 1.

Example 23

Production of an Organic Thin Film Transistor Using the Coating Process

The substrate was cleaned and the gate electrode and the insulator layer were formed in the same manner as in Example 15. Subsequently, 0.5 wt % of the above-mentioned compound (9) was dissolved in toluene, and formed into a film on the substrate on which the gate electrode and the insulating layer had been formed by means of a spin coater (1H-D7; manufactured by Mikasa Co., Ltd.) and dried at 80° C. in the nitrogen atmosphere, thereby to form an organic semiconductor layer. Subsequently, a source electrode and a drain electrode which did not contact each other were formed such that the distance between them (channel length: L) became 75 μm by forming gold into a 50 nm-thick film through a metal mask. Film formation was conducted such that the width (channel width W) of the source electrode and the drain electrode become 5 mm, whereby an organic thin film transistor was fabricated.

A gate voltage $V_G$ of −70 V was applied to the gate electrode of the resulting organic thin film transistor to allow it drive as a p-type transistor. The on/off of the current flowing between the source electrode and the drain electrode was measured, thereby to calculate the field effect mobility μ of the hole. The results are shown in Table 1.

Examples 24 and 25

Organic thin film transistors were fabricated and evaluated in the same manner as in Example 23, except that the compounds (104) and (638) were respectively used instead of the compound (9). The results are shown in Table 1.

Comparative Example 1

Production of an Organic Thin Film Transistor

An organic thin film transistor was fabricated in the same manner as in Example 13, except that, as the material for the organic semiconductor layer, a comparative compound (1) was used instead of the compound (1). The resulting organic thin film transistor was allowed to drive as a p-type transistor by applying a gate voltage $V_G$ of −70V in the same manner as in Example 13. The on/off ratio of the current flowing between the source electrode and the drain electrode was measured, thereby to calculate the field effect mobility μ of the hole. The results are shown in Table 1.

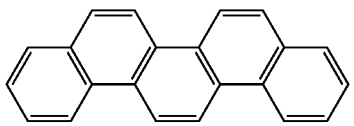

Comparative compound (1)

Comparative Example 2

Production of an Organic Thin Film Transistor Using the Coating Process

Solubility was confirmed by using as the material for an organic semiconductor layer the comparative compound (1) instead of the compound (37). A 0.5 wt % solution could not be obtained when chloroform was used. Therefore, an organic thin film transistor was fabricated in the same manner as in Example 13 by using a suspension. The transistor thus fabricated did not show properties as an organic thin film transistor.

Comparative Example 3

Production of an Organic Thin Film Transistor

An organic thin film transistor was fabricated in the same manner as in Example 15, except that, as the material for the organic semiconductor layer, the above-mentioned comparative compound (1) was used instead of the compound (9). The resulting organic thin film transistor was allowed to drive as a p-type transistor by applying a gate voltage $V_G$ of −70V in the same manner as in Example 13. The on/off of the current flowing between the source electrode and the drain electrode was measured, thereby to calculate the field effect mobility μ of the hole. The results are shown in Table 1.

TABLE 1

| | Organic semiconductor layer | Solubility in chloroform | Type of transistor | Field effect mobility [cm²/Vs] | On-off ratio [—] | Threshold voltage [V] |
|---|---|---|---|---|---|---|
| Example 13 | Compound (1) | — | p type | 1.3 | $3 \times 10^6$ | −55 |
| Example 14 | Compound (37) | ○ | p type | $4 \times 10^{-1}$ | $1 \times 10^5$ | −53 |
| Example 15 | Compound (9) | — | p type | 1.5 | $3 \times 10^6$ | −54 |
| Example 16 | Compound (97) | — | p type | 1.3 | $2 \times 10^6$ | −51 |
| Example 17 | Compound (98) | — | p type | 1.2 | $1 \times 10^5$ | −50 |
| Example 18 | Compound (167) | — | p type | 1.2 | $2 \times 10^6$ | −53 |
| Example 19 | Compound (250) | — | p type | 1.8 | $3 \times 10^6$ | −53 |
| Example 20 | Compound (630) | — | p type | 1.5 | $3 \times 10^6$ | −56 |
| Example 21 | Compound (638) | — | p type | 2.0 | $4 \times 10^5$ | −55 |
| Example 22 | Compound (881) | — | p type | 1.7 | $3 \times 10^6$ | −56 |
| Example 23 | Compound (9) | ○ | p type | 1.2 | $2 \times 10^5$ | −53 |
| Example 24 | Compound (104) | ○ | p type | 1.0 | $1 \times 10^5$ | −50 |
| Example 25 | Compound (638) | ○ | p type | 1.0 | $1 \times 10^5$ | −55 |
| Com. Ex. 1 | Com. compound (1) | — | p type | 1.0 | $1 \times 10^5$ | −67 |
| Com. Ex. 2 | Com. compound (1) | X | — | — | — | — |
| Com. Ex. 3 | Com. compound (1) | — | p type | $1 \times 10^{-1}$ | $1 \times 10^5$ | −62 |

INDUSTRIAL APPLICABILITY

As explained in detail hereinabove, the compound of the invention can be used as a material for an organic semiconductor layer of an organic thin film transistor. By using the compound of the invention in an organic semiconductor layer, an organic thin film transistor which has a high mobility, high response speed (driving speed) and has a high on-off ratio can be obtained. Further, the organic thin film transistor obtained using this compound can also be used as an organic thin film emitting transistor which can emit light.

Although only some exemplary embodiments and/or examples of this invention have been described in detail above, those skilled in the art will readily appreciate that many modifications are possible in the exemplary embodiments and/or examples without materially departing from the novel teachings and advantages of this invention. Accordingly, all such modifications are intended to be included within the scope of this invention.

The documents described in the specification are incorporated herein by reference in its entirety.

The invention claimed is:

1. A compound, which is one of formulas (4) to (7):

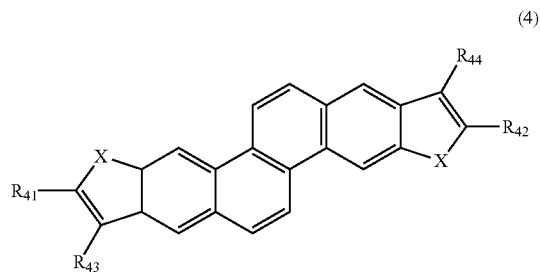

(4)

wherein each X is independently O, S or N—Z and
wherein $R_{41}$ to $R_{44}$ and Z are independently a hydrogen atom, a halogen atom, an alkyl group having 2 to 30 carbon atoms, a haloalkyl group having 1 to 30 carbon atoms, an alkoxyl group having 1 to 30 carbon atoms, a haloalkoxyl group having 1 to 30 carbon atoms, an alkylthio group having 1 to 30 carbon atoms, a haloalkylthio group having 1 to 30 carbon atoms, an alkylamino group having 1 to 30 carbon atoms, a dialkylamino group having 2 to 60 carbon atoms, wherein the alkyl groups are optionally combined with each other to form a ring structure containing the nitrogen atom, an alkylsulfonyl group having 1 to 30 carbon atoms, a haloalkylsulfonyl group having 1 to 30 carbon atoms, an aromatic hydrocarbon group having 6 to 60 carbon atoms, an aromatic heterocyclic group having 3 to 60 carbon atoms, an alkylsilyl group having 3 to 20 carbon atoms, an alkylsilylacetylene group having 5 to 60 carbon atoms or a cyano group, wherein each $R_{41}$ to $R_{44}$ are optionally substituted, and wherein the compound wherein all of $R_{41}$ to $R_{44}$ are hydrogen is excluded;

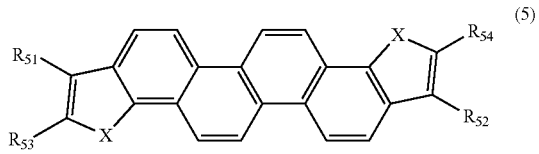

(5)

wherein each X is independently O, S or N—Z and wherein $R_{51}$ to $R_{54}$ and Z are independently a hydrogen atom, a halogen atom, an alkyl group having 2 to 30 carbon atoms, a haloalkyl group having 1 to 30 carbon atoms, an alkoxyl group having 1 to 30 carbon atoms, a haloalkoxyl group having 1 to 30 carbon atoms, an alkylthio group having 1 to 30 carbon atoms, a haloalkylthio group having 1 to 30 carbon atoms, an alkylamino group having 1 to 30 carbon atoms, a dialkylamino group having 2 to 60 carbon atoms, the alkyl groups are optionally combined with each other to form a ring structure containing the nitrogen atom, an alkylsulfonyl group having 1 to 30 carbon atoms, a haloalkylsulfonyl group having 1 to 30 carbon atoms, an aromatic hydrocarbon group having 6 to 60 carbon atoms, an aromatic heterocyclic group having 3 to 60 carbon atoms, an alkylsilyl group having 3 to 20 carbon atoms, an alkylsilylacetylene group having 5 to 60 carbon atoms or a cyano group, wherein each $R_{51}$ to $R_{54}$ are optionally substituted, and wherein the compound wherein all of $R_{51}$ to $R_{54}$ are hydrogen is excluded;

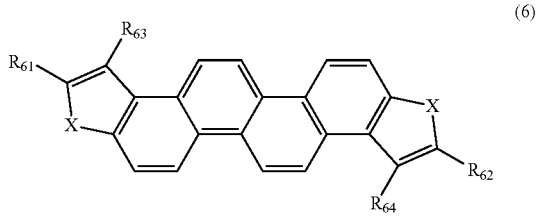

(6)

wherein each X is independently O, S or N—Z and wherein $R_{61}$ to $R_{64}$ and Z are independently a hydrogen atom, a halogen atom, an alkyl group having 1 to 30 carbon atoms, a haloalkyl group having 1 to 30 carbon atoms, an alkoxyl group having 1 to 30 carbon atoms, a haloalkoxyl group having 1 to 30 carbon atoms, an alkylthio group having 1 to 30 carbon atoms, a haloalkylthio group having 1 to 30 carbon atoms, an alkylamino group having 1 to 30 carbon atoms, a dialkylamino group having 2 to 60 carbon atoms, the alkyl groups are optionally combined with each other to form a ring structure containing the nitrogen atom, an alkylsulfonyl group having 1 to 30 carbon atoms, a haloalkylsulfonyl group having 1 to 30 carbon atoms, an aromatic hydrocarbon group having 6 to 60 carbon atoms, an aromatic heterocyclic group having 3 to 60 carbon atoms, an alkylsilyl group having 3 to 20 carbon atoms, an alkylsilylacetylene group having 5 to 60 carbon atoms or a cyano group, wherein each of $R_{61}$ to $R_{64}$ are optionally substituted;

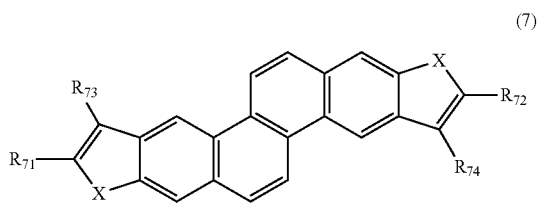

(7)

wherein each X is independently O, S or N—Z and wherein $R_{71}$ to $R_{74}$ and Z are independently a hydrogen atom, a halogen atom, an alkyl group having 1 to 30 carbon atoms, a haloalkyl group having 1 to 30 carbon atoms, an alkoxyl group having 1 to 30 carbon atoms, a haloalkoxyl group having 1 to 30 carbon atoms, an alkylthio group having 1 to 30 carbon atoms, a haloalkylthio group having 1 to 30 carbon atoms, an alkylamino group having 1 to 30 carbon atoms, a dialkylamino group having 2 to 60 carbon atoms, the alkyl groups are optionally combined with each other to form a ring structure containing the nitrogen atom, an alkylsulfonyl group having 1 to 30 carbon atoms, a haloalkylsulfonyl group having 1 to 30 carbon atoms, an aromatic hydrocarbon group having 6 to 60 carbon atoms, an aromatic heterocyclic group having 3 to 60 carbon atoms, an alkylsilyl group having 3 to 20 carbon atoms, an alkylsilylacetylene group having 5 to 60 carbon atoms or a cyano group, wherein each of $R_{71}$ to $R_{74}$ are optionally substituted.

2. A material for an organic thin film transistor which comprises the compound according to claim 1.

3. An organic thin film transistor comprising:

a substrate, three terminals of a gate electrode, a source electrode and a drain electrode, an insulator layer and an organic semiconductor layer being provided on the substrate, source-drain current is controllable by applying a voltage to the gate electrode, the organic semiconductor layer comprising the compound according to claim 1.

4. The organic thin film transistor according to claim 3 which is capable of emitting light by utilizing current flowing between the source electrode and the drain electrode and the light emission is controlled by applying a voltage to the gate electrode.

5. The organic thin film transistor according to claim 4, wherein one of the source electrode and the drain electrode comprises a substance having a work function of 4.2 eV or more and the other of the source electrode and the drain electrode comprises a substance having a work function of 4.3 eV or less.

6. The organic thin film transistor according to claim 3 which further comprises a buffer layer between the source and drain electrodes and the organic semiconductor layer.

7. An apparatus comprising the organic thin film transistor according to claim 3.

8. The compound of claim 1 which is of formula (4).

9. The compound of claim 1 which is of formula (5).

10. The compound of claim 1 which is of formula (6).

11. The compound of claim 1 which is of formula (7).
12. A compound which is one of formulas (4) to (7)

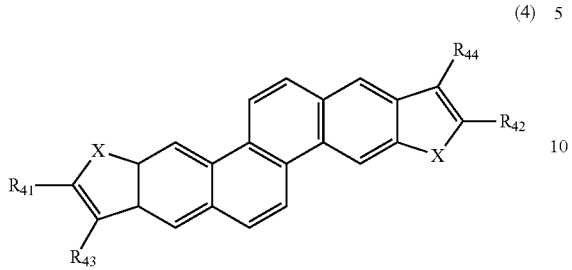
(4)

wherein each X is independently O, S or N—Z and
wherein $R_{41}$ to $R_{44}$ and Z are independently a hydrogen atom, a halogen atom, an alkyl group having 2 to 30 carbon atoms, a haloalkyl group having 1 to 30 carbon atoms, an alkoxyl group having 1 to 30 carbon atoms, a haloalkoxyl group having 1 to 30 carbon atoms, an alkylthio group having 1 to 30 carbon atoms, a haloalkylthio group having 1 to 30 carbon atoms, an alkylamino group having 1 to 30 carbon atoms, a dialkylamino group having 2 to 60 carbon atoms, wherein the alkyl groups are optionally combined with each other to form a ring structure containing the nitrogen atom, an alkylsulfonyl group having 1 to 30 carbon atoms, a haloalkylsulfonyl group having 1 to 30 carbon atoms, an aromatic hydrocarbon group having 6 to 60 carbon atoms, an aromatic heterocyclic group having 3 to 60 carbon atoms, an alkylsilyl group having 3 to 20 carbon atoms, an alkylsilylacetylene group having 5 to 60 carbon atoms or a cyano group, and
wherein the compound wherein all of $R_{41}$ to $R_{44}$ are hydrogen is excluded;

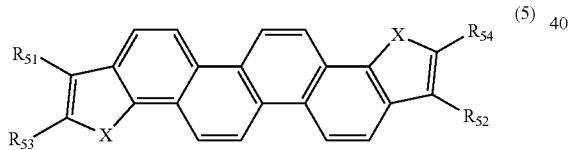
(5)

wherein each X is independently O, S or N—Z and
wherein $R_{51}$ to $R_{54}$ and Z are independently a hydrogen atom, a halogen atom, an alkyl group having 2 to 30 carbon atoms, a haloalkyl group having 1 to 30 carbon atoms, an alkoxyl group having 1 to 30 carbon atoms, a haloalkoxyl group having 1 to 30 carbon atoms, an alkylthio group having 1 to 30 carbon atoms, a haloalkylthio group having 1 to 30 carbon atoms, an alkylamino group having 1 to 30 carbon atoms, a dialkylamino group having 2 to 60 carbon atoms, the alkyl groups are optionally combined with each other to form a ring structure containing the nitrogen atom, an alkylsulfonyl group having 1 to 30 carbon atoms, a haloalkylsulfonyl group having 1 to 30 carbon atoms, an aromatic hydrocarbon group having 6 to 60 carbon atoms, an aromatic heterocyclic group having 3 to 60 carbon atoms, an alkylsilyl group having 3 to 20 carbon atoms, an alkylsilylacetylene group having 5 to 60 carbon atoms or a cyano group, and wherein the compound wherein all of $R_{51}$ to $R_{54}$ are hydrogen is excluded;

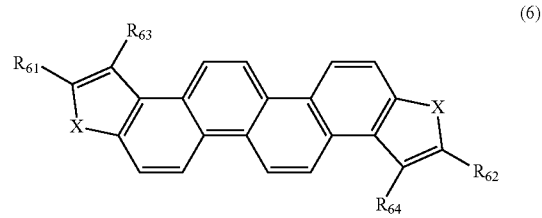
(6)

wherein each X is independently O, S or N—Z and
wherein $R_{61}$ to $R_{64}$ and Z are independently a hydrogen atom, a halogen atom, an alkyl group having 1 to 30 carbon atoms, a haloalkyl group having 1 to 30 carbon atoms, an alkoxyl group having 1 to 30 carbon atoms, a haloalkoxyl group having 1 to 30 carbon atoms, an alkylthio group having 1 to 30 carbon atoms, a haloalkylthio group having 1 to 30 carbon atoms, an alkylamino group having 1 to 30 carbon atoms, a dialkylamino group having 2 to 60 carbon atoms, the alkyl groups are optionally combined with each other to form a ring structure containing the nitrogen atom, an alkylsulfonyl group having 1 to 30 carbon atoms, a haloalkylsulfonyl group having 1 to 30 carbon atoms, an aromatic hydrocarbon group having 6 to 60 carbon atoms, an aromatic heterocyclic group having 3 to 60 carbon atoms, an alkylsilyl group having 3 to 20 carbon atoms, an alkylsilylacetylene group having 5 to 60 carbon atoms or a cyano group;

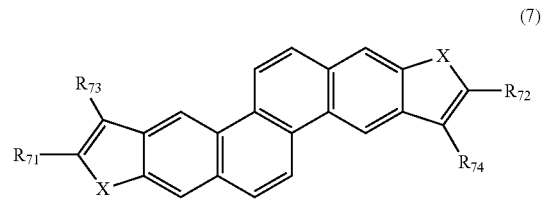
(7)

wherein each X is independently O, S or N—Z and
wherein $R_{71}$ to $R_{74}$ and Z are independently a hydrogen atom, a halogen atom, an alkyl group having 1 to 30 carbon atoms, a haloalkyl group having 1 to 30 carbon atoms, an alkoxyl group having 1 to 30 carbon atoms, a haloalkoxyl group having 1 to 30 carbon atoms, an alkylthio group having 1 to 30 carbon atoms, a haloalkylthio group having 1 to 30 carbon atoms, an alkylamino group having 1 to 30 carbon atoms, a dialkylamino group having 2 to 60 carbon atoms, the alkyl groups are optionally combined with each other to form a ring structure containing the nitrogen atom, an alkylsulfonyl group having 1 to 30 carbon atoms, a haloalkylsulfonyl group having 1 to 30 carbon atoms, an aromatic hydrocarbon group having 6 to 60 carbon atoms, an aromatic heterocyclic group having 3 to 60 carbon atoms, an alkylsilyl group having 3 to 20 carbon atoms, an alkylsilylacetylene group having 5 to 60 carbon atoms or a cyano group.

* * * * *